US005643932A

United States Patent [19]

Chihiro et al.

[11] Patent Number: 5,643,932

[45] Date of Patent: Jul. 1, 1997

[54] SUPEROXIDE RADICAL INHIBITOR

[75] Inventors: Masatoshi Chihiro, Naruto; Hajime Komatsu; Michiaki Tominaga, both of Itano-gun; Yoichi Yabuuchi, Tokushima, all of Japan

[73] Assignee: Otsuka Pharmaceutical Co., Ltd., Tokyo, Japan

[21] Appl. No.: 444,728

[22] Filed: May 19, 1995

Related U.S. Application Data

[63] Continuation of Ser. No. 916,082, Jul. 29, 1992, abandoned.

[30] Foreign Application Priority Data

Nov. 30, 1990 [JP] Japan .................................... 2-337727

[51] Int. Cl.$^6$ ....................... C07D 413/04; A61K 31/425

[52] U.S. Cl. .............................. 514/365; 544/35; 544/39; 544/52; 544/165; 544/366; 546/135; 546/269.7; 548/169; 548/181; 548/203; 548/204; 514/342

[58] Field of Search .................................... 548/203, 204, 548/164, 181; 514/365, 342; 546/135, 280; 544/35, 39, 52, 165, 366

[56] References Cited

U.S. PATENT DOCUMENTS

| | | | |
|---|---|---|---|
| 1,970,656 | 8/1934 | Johnson .................................... | 260/44 |
| 3,244,703 | 4/1966 | Yates et al. . | |
| 3,320,270 | 5/1967 | Grogan et al. . | |
| 4,001,420 | 1/1977 | Malen et al. . | |
| 4,259,341 | 3/1981 | Baldwin et al. . | |
| 4,282,364 | 8/1981 | Amato et al. . | |
| 4,298,743 | 11/1981 | Cragol .................................... | 548/203 |
| 4,329,459 | 5/1982 | McCall et al. . | |
| 4,791,200 | 12/1988 | Press et al. . | |

FOREIGN PATENT DOCUMENTS

| | | |
|---|---|---|
| 0018080A1 | 10/1980 | European Pat. Off. . |
| 0037274 | 7/1981 | European Pat. Off. . |
| 0159677A2 | 10/1985 | European Pat. Off. . |
| 0423632A | 4/1991 | European Pat. Off. . |
| 8018 | 6/1970 | France . |
| 2082164 | 12/1971 | France . |
| 2023425 | 10/1970 | Germany . |
| 1670383A | 10/1970 | Germany . |
| 3002595A1 | 8/1980 | Germany . |
| 204094 | 11/1983 | Germany . |
| 3601411A1 | 7/1987 | Germany . |
| 47-1469 | 1/1972 | Japan . |
| 47-784 | 1/1972 | Japan . |
| 47-7368 | 3/1972 | Japan . |
| 54-14970 | 2/1979 | Japan . |
| 54-61936 | 5/1979 | Japan . |
| 54-66674 | 5/1979 | Japan . |
| 55-11579 | 1/1980 | Japan . |
| 55-111418 | 8/1980 | Japan . |
| 55-111478 | 8/1980 | Japan . |
| 55-133366 | 10/1980 | Japan . |
| 55-149263 | 11/1980 | Japan . |
| 56-154472 | 11/1981 | Japan . |
| 59-25381 | 2/1984 | Japan . |
| 59-25380 | 2/1984 | Japan . |
| 60-58981 | 4/1985 | Japan . |
| 60-222481 | 11/1985 | Japan . |
| 60-230147 | 11/1985 | Japan . |
| 61-33186 | 2/1986 | Japan . |
| 61-167688 | 7/1986 | Japan . |
| 61-200985 | 9/1986 | Japan . |
| 62-22493 | 1/1987 | Japan . |
| 62-252780 | 11/1987 | Japan . |
| 63-60978 | 3/1988 | Japan . |
| 63-192755 | 8/1988 | Japan . |
| 2-171280 | 2/1990 | Japan . |
| 6715532 | 5/1968 | Netherlands . |
| 6905474 | 10/1969 | Netherlands . |
| 1381860 | 1/1975 | United Kingdom . |
| 1574583 | 9/1980 | United Kingdom . |
| 2133007 | 7/1984 | United Kingdom . |

OTHER PUBLICATIONS

Khadse Indian J. Chem. Sect B 26B 856 (1987).
Sawheny, Ind. J. Chem 15B 727 (1977).
Chemical Abstracts, vol. 75, (21), 129708g (1971).
Chemical Abstracts, vol. 89, (17), 89:197388z (1978).
Chemical Abstracts, vol. 92, (13), 92:110908j (1980).
Chemical Abstracts, vol. 81, (15), 91408a (1974).
Chemical Abstracts, vol. 85, (25), 85:192614c (1976).
Chemical Abstracts, vol. 88, (25), 88:190657g (1978).
Chemical Abstracts, vol. 94, (3), 94: 15628a (1981).
Chemical Abstracts, vol. 103, (3), 103: 22508u (1985).
Chemical Abstracts, vol. 104, (9), 104: 68782c (1986).

(List continued on next page.)

*Primary Examiner*—Robert Gerstl
*Attorney, Agent, or Firm*—Finnegan, Henderson, Farabow, Garrett & Dunner

[57] ABSTRACT

A superoxide radical inhibitor containing, as an effective ingredient, an azole derivative represented by the general formula (1),

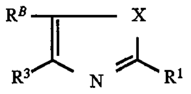

(1)

[wherein $R^1$ represents a phenyl group which may have 1–3 lower alkoxy groups as substituent(s) on the phenyl ring, a phenyl group having a lower alkylenedioxy group, or the like; $R^2$ represents a hydrogen atom, a phenyl group, a halogen atom, a lower alkoxycarbonyl group, a lower alkyl group, an amino-lower alkyl group which may have a lower alkyl group as a substituent, a dihydrocarbostyril group, or the like; $R^3$ represents a group of the formula,

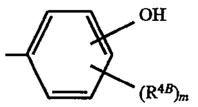

($R^{4B}$ represents a hydroxyl group, a carboxy group, a lower alkenyl group or a lower alkyl group. m represents 0, 1 or 2); X represents a sulfur atom or an oxygen atom] or a salt thereof.

11 Claims, No Drawings

OTHER PUBLICATIONS

Chemical Abstracts, vol. 73, (15), 77117h (1970).
Chemical Abstracts, vol. 87, (3), 87:16437e (1977).
Chemical Abstracts, vol. 87, (9), 87:68218d (1977).
Chemical Abstracts, vol. 85, (21), 85:159962e (1976).
Chemical Abstracts, vol. 84, (13), 90050c (1976).
Chemical Abstracts, vol. 69, (11), 43837v (1968).
Chemical Abstracts, vol. 60, (3), (29219) (1964).
Chemical Abstracts, vol. 96, (15), 96:122757e (1982).
Chemical Abstracts, vol. 96, (15), 96:122675b (1982).
Chemical Abstracts, vol. 96, (9), 96: 68881a (1982).
Chemical Abstracts, vol. 86, (23), 86:171308m (1977).
Chemical Abstracts, vol. 86, (17), 86:121232m (1977).
Chemical Abstracts, vol. 82, (9), 57594u (1975).
Chemical Abstracts, vol. 87, (7), 87: 53142a (1977).
Chemical Abstracts, vol. 87, (13), 87: 96735p (1977).
Chemical Abstracts, vol. 87, (13), 87: 96736g (1977).
Chemical Abstracts, vol. 85, (25), 85:192613b (1976).
J. Med. Chem., 1988, vol. 31, pp. 1778–1785 (1984).
Chemical Abstracts, vol. 101, (1), 101: 7145p.
Chemical Abstracts, vol. 100, (9), 100: 68214m (1984).
Chemical Abstracts, vol. 106, (15), 106: 116059n (1987).
Chemical Abstracts, vol. 91, (23), 91: 186442c (1987).
Chemical Abstracts, vol. 90, (13), 90: 103886f (1979).
Chemical Abstracts, vol. 87, (19), 87:152066Zk (1977).
Chemical Abstracts, vol. 89, (17), 89: 146824f (1978).
Chemical Abstracts, vol. 109, (3), 109:22883m (1988).
Chemical Abstracts, vol. 66, (22), 96203e (1967).
Chemical Abstracts, vol. 86, (9), 86:55326 (1977).
Chemical Abstracts, vol. 96, (3), 96:20015u (1982).

SUPEROXIDE RADICAL INHIBITOR

This application is a continuation of application Ser. No. 07/916,082, filed as PCT/JP91/01659, Nov. 29, 1991, now abandoned.

TECHNICAL FIELD

The present invention relates to a superoxide radical inhibitor containing an azole derivative as the effective ingredient.

1. Background Art

It is thought that neutrophilic leukocytes show a germicidal activity to foreign invaders in living bodies by a wondering reaction, a feeding action, generation of superoxide radical ($O_2^-$) and release of lysosomal enzyme and play an important role in protection of living body. While neutrophilic leukocytes have the above reaction for living body protection, it has been made clear that the superoxide radical released by tissues or neutrophilic leukocytes during ischemia of tissues and subsequent blood re-perfusion or during acute inflammation at early stage destroys cells, causing functional disturbances of tissues [B. R. Lucchesi: Annual Review of Pharmacology and Toxicology, Vol. 26, p. 201 (1986); B. A. Freeman et al.: Laboratory Investigation, Vol. 47, p. 412 (1982); E. Braunwald, R. A. Kloner: Journal of Clinical Investigation, Vol. 76, p. 1713 (1985); J. L. Romson et al.: Circulation, Vol. 67, p. 1016 (1983)].

2. Disclosure of the Invention

Based on the thought that the major cause for the above-mentioned disturbances in cells, in particular the disturbances after ischemia and re-perfusion in heart, brain, kidney, lung and digestive tract lies in the superoxide radical released by neutrophilic leukocytes, the present invention has an object of providing a new drug for inhibiting the release of the superoxide radical.

The present inventors made study for the above object and, as a result, found that certain azole derivatives show a very strong inhibitory activity for release of superoxide radical in living bodies. Further study based on the finding has led to the completion of the present invention.

Therefore, the present invention relates to a superoxide radical inhibitor containing, as the effective ingredient, at least one of the azole derivatives represented by the following general formula (1).

Azole derivatives represented by the general formula (1),

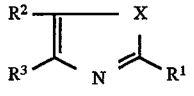
(1)

{wherein $R^1$ and $R^3$ which may be the same or different, each represent a phenyl group which may have 1 to 5 substituents on the phenyl ring, selected from the group consisting of an alkoxy group, a tri-lower alkyl group-substituted silyloxy group, a lower alkyl group, a hydroxyl group, a lower alkenyloxy group, a lower alkylthio group, a phenyl group which may have a group selected from the group consisting of a thiazolyl group having, as a substituent on the thiazolyl ring, a phenyl group which may have a lower alkoxy group on the phenyl ring, a carboxyl group and a hydroxyl group, a lower alkylsulfinyl group, a lower alkylsulfonyl group, a halogen atom, a nitro group, a group of the formula,

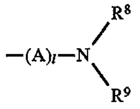

{wherein A represents a lower alkylene group or a group of the formula

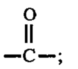

l represents 0 or 1; $R^8$ and $R^9$, which may be the same or different, each represent a hydrogen atom, a lower alkyl group, a lower alkanoyl group, an amino-lower alkyl group which may have a lower alkyl group as a substituent, or a piperidinyl-lower alkyl group, further $R^8$ and $R^9$ as well as the adjacent nitrogen atom being bonded thereto, together with or without other nitrogen atom or oxygen atom may form a five- to six-membered saturated or unsaturated heterocyclic group; said five- to six-membered heterocyclic group may have a lower alkanoyl group or a lower alkyl group as a substituent.], a lower alkanoyl group, a lower alkanoyloxy group, an alkoxycarbonyl group, a cyano group, a tetrahydropyranyloxy group which may have 1–4 substituents selected from the group consisting of a hydroxyl group, a lower alkoxycarbonyl group, a phenyl-lower alkoxy group, a hydroxyl group- or lower alkanoyloxy group-substituted lower alkyl group and a lower alkanoyloxy group, an amidino group, a hydroxysulfonyloxy group, a lower alkoxycarbonyl-substituted lower alkoxy group, a carboxy-substituted lower alkoxy group, a mercapto group, a lower alkoxy-substituted lower alkoxy group, a lower alkyl group having hydroxyl groups, a lower alkenyl group, an aminothiocarbonyloxy group which may have a lower alkyl group as a substituent, an aminocarbonylthio group which may have a lower alkyl group as a substituent, a lower alkanoyl-substituted lower alkyl group, a carboxy group, a group of the formula,

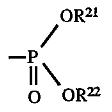

($R^{21}$ and $R^{22}$ which may be the same or different, each represent a hydrogen atom or a lower alkyl group.), a phenyl-lower alkoxycarbonyl group, a cycloalkyl group, a lower alkynyl group, a lower alkoxycarbonyl-substituted lower alkyl group, a carboxy-substituted lower alkyl group, a lower alkoxycarbonyl-substituted lower alkenyl group, a carboxy-substituted lower alkenyl group, a lower alkylsulfonyloxy group which may have a halogen atom, a lower alkoxy-substituted lower alkoxycarbonyl group, a lower alkenyl group having halogen atoms and a phenyl-lower alkoxy group; a phenyl group having a lower alkylenedioxy group; a 5- to 15-membered monocyclic, bicyclic or tricyclic heterocyclic residual group having 1 to 2 hetero atoms selected from the group consisting of a nitrogen atom, an oxygen atom and a sulfur atom [said heterocyclic residual group may have 1 to 3 substituents selected from the group consisting of an oxo group, an alkyl group, a benzoyl group, a lower alkanoyl group, a hydroxyl group, a carboxy group, a lower alkoxycarbonyl group, a lower alkylthio group, a group of the formula,

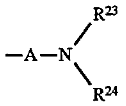

(A is the same as defined above. $R^{23}$ and $R^{24}$, which may be the same or different, each represent a hydrogen atom or a lower alkyl group; further, $R^{23}$ and $R^{24}$ as well as the adjacent nitrogen atom being bonded thereto, together with or without other nitrogen atom or oxygen atom may form a five- to six-membered saturated heterocyclic group; said five- to six-membered heterocyclic group may have a lower alkyl group as a substituent.), a cyano group, a lower alkyl group having hydroxyl groups, a phenylaminothiocarbonyl group and an amino-lower alkoxycarbonyl group which may have a lower alkyl group as a substituent.]; a lower alkyl group; a lower alkoxycarbonyl-lower alkyl group; a lower alkoxycarbonyl group; a carbamoyl-lower alkyl group; a 2,3-dihydroindenyl group which may have an oxo group or/and a hydroxyl group as substituent(s); a phenyl-lower alkyl group which may have a lower alkoxy group as a substituent on the phenyl ring or may have a hydroxyl group as a substituent on the lower alkyl group; a benzoyl group which may have a lower alkoxy group as a substituent on the phenyl ring; a phenyl-lower alkenyl group which may have a lower alkoxy group as a substituent on the phenyl ring; a piperazinyl-lower alkyl group which may have a lower alkyl group on the piperazine ring; or an adamantyl group; $R^3$ may represent, besides the above, a hydrogen atom; $R^2$ represents a hydrogen atom, a phenyl group, a halogen atom, a lower alkoxycarbonyl group, a lower alkyl group, an amino-lower alkyl group (which may have a lower alkyl group as a substituent), or a dihydrocarbostyril group; $R^2$ and $R^3$ may bond to each other to form a group of the formula,

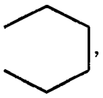

, a group of the formula,

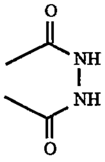

or a group of the formula,

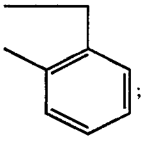

;

X represents a sulfur atom or an oxygen atom.}, and salts thereof.

The compounds of the present invention have an activity of inhibiting the release of superoxide radical from neutrophilic leukocytes or of removing the superoxide radical. Accordingly, they have an action of preventing or lowering the in vivo production of peroxidized lipids. Hence, the compounds are useful as an agent for preventing and treating various disturbances and diseases caused by excessive generation of superoxide radical, in vivo accumulation of peroxidized lipids, or defect of protective organizations therefor. More specifically, the drugs of the present invention are useful in a pharmaceutical field as a drug for protecting various tissue cells from disturbances associated with ischemia and blood re-perfusion, for example, a remedy for ulcers of the digestive tract (e.g. stress ulcer), a remedy for ischemic heart disease (e.g. myocardial infarction, arrhythmia), a remedy for cerebrovascular diseases (e.g. cerebral hemorrhage, cerebral infarction, temporal cerebral ischemic attack), and a hepatic and renal function improver for disturbances caused by transplant, microcirculation failure, etc., or as an agent for inhibiting various cell function disturbances believed to be caused by the superoxide radical abnormally generated by factors other than ischemia, for example, a remedy for Bechcet disease, dermatovascular inflammation, ulcerative colitis, malignant rheumatoid, arthritis, arteriosclerosis, diabetes mellitus, etc.

It is described in Japanese Patent Publication No. 15935/1971 that the compounds represented by the following general formula,

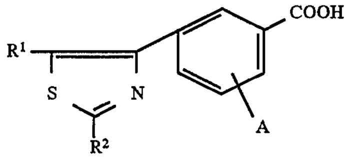

(wherein $R^1$ is a group selected from the group consisting of a hydrogen atom and a straight-chain or branched-chain lower alkyl group of 1 to 5 carbon atoms; $R^2$ is a group selected from the group consisting of a lower alkyl group having 1 to 5 carbon atoms, a phenylalkyl group which may be substituted with a lower alkyl or lower alkoxy group having 1 to 5 carbon atoms, or substituted with one or more halogen atoms, and a phenyl group; and A is a group selected from the group consisting of a hydrogen atom, a halogen atom, a hydroxyl group and a lower alkyl or lower alkoxy group having 1 to 5 carbon atoms.) have properties which are advantageous for fibrinolysis, platelet stickiness, ulcers and immunological treatments and can be used for prevention and treatment of thrombosis, arteriosclerosis, gastric ulcer and hypersecretion.

Among the compounds of the present invention, the thiazole derivatives represented by the following general formula (A), (A)

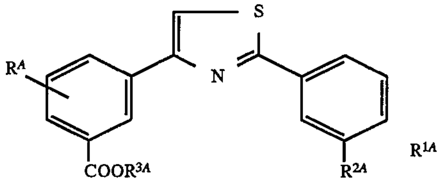

[wherein $R^A$ represents a hydrogen atom or a hydroxyl group; $R^{1A}$ and $R^{2A}$ each represent a methoxy group or an ethoxy group; $R^{3A}$ represents a hydrogen atom or a lower alkyl group; $R^A$ is substituted at the 4- or 6-position in the phenyl ring; $R^{1A}$ and $R^{2A}$ should not be a methoxy group simultaneously] and their salts contain some compounds which are similar to the compounds of the above prior art in chemical structure; however, the compounds of the present invention are not disclosed in said prior art. Further, the compounds of the present invention, as shown in the pharmacological tests given later in Table 16, exhibit very strong inhibitory activities for releasing superoxide radical, even though as compared with the most similar compounds.

Among the compounds of the present invention, preferable are:

thiazole derivatives represented by the general formula (B),

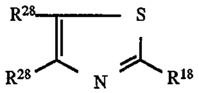

(B)

{wherein $R^{1B}$ represents a phenyl group which may have 1 to 3 lower alkoxy groups as substituent(s) on the phenyl ring; a phenyl group having a lower alkylenedioxy group; a pyridyl group which may have an oxo group; a thienyl group; a carbostyril group; a pyrazyl group; a pyrrolyl group; a quinolyl group which may have an oxo group; or a 3,4-dihydrocarbostyril group; $R^{2B}$ represents a hydrogen atom; $R^{3B}$ represents a group of the formula,

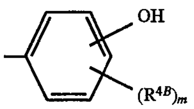

[$R^{4B}$ represents an alkoxy group; a tri-lower alkyl group-substituted silyloxy group; a lower alkyl group; a hydroxyl group; a lower alkenyloxy group; a lower alkylthio group; a phenyl group which may have a group selected from the group consisting of a thiazolyl group having, as a substituent on the thiazolyl ring, a phenyl group which may have a lower alkoxy group on the phenyl ring, a carboxyl group and a hydroxyl group; a lower alkylsulfinyl group; a lower alkylsulfonyl group; a halogen atom; a nitro group; a group of the formula,

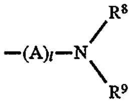

(wherein A represents a lower alkylene group or a group

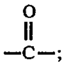

l represents 0 or 1; $R^8$ and $R^9$, are each the same or different, and are each a hydrogen atom, a lower alkyl group, a lower alkanoyl group, an amino-lower alkyl group which may have a lower alkyl group as a substituent, or a piperidinyl-lower alkyl group; further $R^8$ and $R^9$ well as the adjacent nitrogen atom being bonded thereto, together with or without other nitrogen atom or oxygen atom may form a five- to six-membered saturated or unsaturated heterocyclic group; said five- to six-membered heterocyclic group may have a lower alkanoyl group or a lower alkyl group as a substituent.); a lower alkanoyl group; a lower alkanoyloxy group; an alkoxycarbonyl group; a cyano group; a tetrahydropyranyloxy group which may have 1–4 substituents selected from the group consisting of a hydroxyl group, a lower alkoxycarbonyl group, a phenyl-lower alkoxy group, a lower alkanoyloxy group-substituted lower alkyl group and a lower alkanoyloxy group; an amidino group; a hydroxysulfonyloxy group; a lower alkoxycarbonyl-substituted lower alkoxy group; a carboxy-substituted lower alkoxy group; a mercapto group; a lower alkoxy-substituted lower alkoxy group; a lower alkyl group having hydroxyl groups; a lower alkenyl group; an aminothiocarbonyloxy group which may have a lower alkyl group as a substituent; an aminocarbonylthio group which may have a lower alkyl group as a substituent; a lower alkanoyl-substituted lower alkyl group; a carboxy group; a group of the formula,

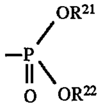

($R^{21}$ and $R^{22}$ which may be the same or different, each represent a hydrogen atom or a lower alkyl group.); a phenyl-lower alkoxycarbonyl group; a cycloalkyl group; a lower alkynyl group; a lower alkoxycarbonyl-substituted lower alkyl group; a carboxy-substituted lower alkyl group; a lower alkoxycarbonyl-substituted lower alkenyl group; a carboxy-substituted lower alkenyl group; a lower alkylsulfonyloxy group which may have a halogen atom; a lower alkoxy-substituted alkoxycarbonyl group; a lower alkenyl group having halogen atoms; or a phenyl-lower alkoxy group. m represents 0, 1 or 2.]; or, a phenyl group having 1–3 substituents, on the phenyl ring, selected from the group consisting of a lower alkanoyloxy group, a hydroxysulfonyloxy group, a cyano group, an amidino group, a nitro group, a lower alkylthio group, a lower alkylsulfonyl group, a tetrahydropyranyloxy group which may have 1 to 4 substituents selected from the group consisting of a hydroxyl group, a lower alkoxycarbonyl group, a phenyl-lower alkoxy group, a hydroxyl group- or lower alkanoyloxy group-substituted lower alkyl group and a lower alkanoyloxy group, a phenyl group which may have a group selected from the group consisting of a thiazolyl group which may have, as a substituent on the thiazolyl ring, a phenyl group which may have a lower alkoxy group on the phenyl ring, a carboxyl group and a hydroxyl group, a lower alkyl group having hydroxyl groups, and a group of the formula,

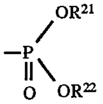

($R^{21}$ and $R^{22}$ are the same as defined above); a phenyl group having a lower alkylenedioxy group; a lower alkyl group; a lower alkoxycarbonyl-lower alkyl group; a lower alkoxycarbonyl group; a carbamoyl-lower alkyl group; a 2,3-dihydroindenyl group which may have an oxo group or/and a hydroxyl group as substituent(s); a phenyl-lower alkyl group which may have a lower alkoxy group as a substituent on the phenyl ring or may have a hydroxyl ring as a substituent on the lower alkyl group; a benzoyl group which may have a lower alkoxy group as a substituent on the phenyl ring; a phenyl-lower alkenyl group which may have a lower alkoxy group as a substituent on the phenyl ring; a piperazinyl-lower alkyl group which may have a lower alkyl group as a substituent on the piperazinyl ring; or an adamantyl group. When $R^{4B}$ represents a lower alkoxycarbonyl group-substituted lower alkyl group or a carboxy-substituted lower alkyl group, then, m represents 2}, and their salts;

thiazole derivatives represented by the general formula (C),

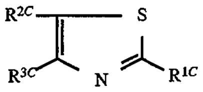

(C)

[wherein $R^{1C}$ represents a phenyl group which may have 1 to 3 lower alkoxy groups as substituent(s) on the phenyl ring; $R^{2C}$ represents a hydrogen atom; $R^{3C}$ represents a group of the formula,

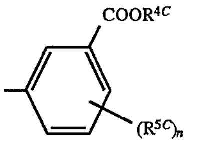

(wherein $R^{4C}$ represents a hydrogen atom, a lower alkyl group, a phenyl-lower alkyl group or a lower alkoxy-substituted lower alkyl group; $R^{5C}$ represents an amino group, a lower alkoxy group-substituted lower alkyl group, a lower alkyl group, a nitro group, a lower alkenyl group, a lower alkanoyl group, a lower alkenyl group having halogen atoms, a phenyl-lower alkoxy group, a halogen atom or a hydroxyl group-substituted lower alkyl group; n represents 2)], and their salts;

thiazole derivatives represented by the general formula (D),

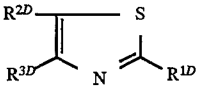

(D)

[wherein $R^{1D}$ represents a phenyl group which may have 1 to 3 lower alkoxy groups as substituent(s) on the phenyl ring; $R^{2D}$ represents a hydrogen atom; $R^{3D}$ represents a group of the formula,

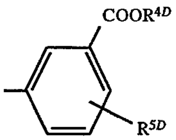

(wherein $R^{4D}$ represents a hydrogen atom or a lower alkyl group; $R^{5D}$ represents an amino group, a lower alkoxycarbonyl-lower alkoxy group, a nitro group, a lower alkenyloxy group, a lower alkoxy-substituted lower alkoxy group, a mercapto group, a lower alkanoyloxy group, an aminocarbonylthio group which may have a lower alkyl group as a substituent, an aminothiocarbonyloxy group which may have a lower alkyl group as a substituent, a carboxy-substituted lower alkoxy group or a lower alkyl-sulfoniumoxy group which may have a halogen atom)], and their salts;

thiazole derivatives represented by the general formula,

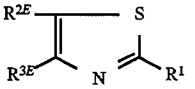

(E)

{wherein $R^1$ is the same as defined above; $R^{2E}$ represents a hydrogen atom; $R^{3E}$ represents a 5- to 15-membered monocyclic, bicyclic or tricyclic heterocyclic residual group having 1 to 2 hetero atoms selected from the group consisting of a nitrogen atom, an oxygen atom and a sulfur atom [said heterocyclic residual group may have 1 to 3 substituents selected from the group consisting of an oxo group, an alkyl group, a benzoyl group, a lower alkanoyl group, a hydroxyl group, a carboxy group, a lower alkoxycarbonyl group, a lower alkylthio group, a group of the formula,

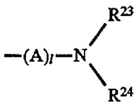

(A and l are the same as defined above; $R^{23}$ and $R^{24}$, are each the same or different, and are each represents a hydrogen atom or a lower alkyl group; further $R^{23}$ and $R^{24}$ as well as the adjacent nitrogen atom being bonded thereto, together with or without other nitrogen atom or oxygen atom may form a five- to six-membered saturated heterocyclic group; said five- to six-membered heterocyclic group may have a lower alkyl group as a substituent), a cyano group, lower alkyl group having hydroxy groups, a phenylamino- thiocarbonyl group and an amino-lower alkoxycarbonyl group which may have a lower alkyl group as a substituent]}, and their salts; and thiazole derivatives represented by the general formula (F),

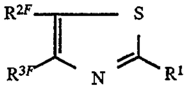

(F)

[wherein $R^1$ is the same as defined above; $R^{2F}$ represents a hydrogen atom, $R^{3F}$ represents a group of the formula,

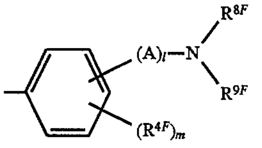

(wherein A, l and m are the same as defined above; $R^{8F}$ and $R^{9F}$ which may be the same or different, each represent a lower alkanoyl group, an amino-lower alkyl group which may have a lower alkyl group as a substituent, or a piperidinyl-lower alkyl group; further $R^{8F}$ and $R^{9F}$ as well as the adjacent nitrogen atom being bonded thereto, together with or without other nitrogen atom or oxygen atom may form a five- to six-membered saturated or unsaturated heterocyclic group; said five- to six-membered heterocyclic group may have a lower alkanoyl group or a lower alkyl group as a substituent); $R^{4F}$ is the same as the above-mentioned $R^{4B}$ other than a hydroxyl group)], or their salts.

BEST MODE FOR CARRYING OUT THE INVENTION

Each group shown in the present specification is specifically as follows.

The alkoxy group can be exemplified by straight-chain or branched-chain alkoxy groups having 1 to 18 carbon atoms such as methoxy, ethoxy, propoxy, isopropoxy, butoxy, tert-butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy and the like.

The lower alkyl group can be exemplified by straight-chain or branched-chain alkyl groups having 1 to 6 carbon atoms such as methyl, ethyl, propyl, isopropyl, butyl, tert-butyl, pentyl, hexyl and the like.

The lower alkylthio group can be exemplified by straight-chain or branched-chain alkylthio groups having 1 to 6 carbon atoms such as methylthio, ethylthio, propylthio, isopropylthio, butylthio, tert-butylthio, pentylthio, hexylthio and the like.

The lower alkylsulfonyl group can be exemplified by straight-chain or branched-chain alkylsulfonyl groups having 1 to 6 carbon atoms such as methylsulfonyl, ethylsulfonyl, isopropylsulfonyl, butylsulfonyl, tert-butylsulfonyl, pentylsulfonyl, hexylsulfonyl and the like.

As the halogen atom, there can be mentioned, for example, a fluorine atom, a chlorine atom, a bromine atom and an iodine atom.

As the lower alkanoyl group, there can be mentioned straight-chain or branched-chain alkanoyl groups having 1 to 6 carbon atoms such as formyl, acetyl, propionyl, butyryl, isobutyryl, pentanoyl, tert-butylcarbonyl, hexanoyl and the like.

The lower alkoxycarbonyl group can be exemplified by straight-chain or branched-chain alkoxycarbonyl groups having 1 to 6 carbon atoms such as methoxycarbonyl, ethoxycarbonyl, propoxycarbonyl, isopropoxycarbonyl, butoxycarbonyl, tert-butoxycarbonyl, pentyloxycarbonyl, hexyloxycarbonyl and the like.

As to the lower alkylenedioxy group, there can be mentioned straight-chain or branched-chain alkylenedioxy groups having 1 to 3 carbon atoms such as methylenedioxy, ethylenedioxy, trimethylenedioxy, tetramethylenedioxy and the like.

As to the alkyl group, there can be mentioned, in addition to the lower alkyl groups mentioned above, straight-chain or branched-chain alkyl groups having 1 to 18 carbon atoms such as heptyl, octyl, nonyl, decyl, undecyl, dodecyl, tridecyl, tetradecyl, pentadecyl, hexadecyl, octadecyl and the like.

As to the lower alkoxycarbonyl-lower alkyl group, there can be mentioned straight-chain or branched-chain alkoxycarbonylalkyl groups having 1 to 6 carbon atoms whose alkyl moieties are each a straight-chain or branched-chain alkyl group having 1 to 6 carbon atoms, such as methoxycarbonylmethyl, 3-methoxycarbonyl-propyl, ethoxycarbonylmethyl, 4-ethoxycarbonylbutyl, 6-propoxycarbonylhexyl, 5-isopropoxycarbonylpentyl, 1,1-dimethyl-2-butoxycarbonylethyl, 2-methyl-3-tert-butoxycarbonylpropyl, 2-pentyloxycarbonylethyl, hexyloxycarbonylmethyl and the like.

As to the carbamoyl-lower alkyl group, there can be mentioned carbamoylalkyl groups whose alkyl moieties are each a straight-chain or branched-chain alkyl group having 1 to 6 carbon atoms, such as carbamoylmethyl, 2-carbamoylethyl, 1-carbamoylethyl, 3-carbamoylpropyl, carbamoylpropyl, 4-carbamoylbutyl, 5-carbamoylpentyl, 6-carbamoylhexyl, 1,1-dimethyl-2-carbamoylethyl, 2-methyl-3-carbamoylpropyl and the like.

The 2,3-dihydroindenyl group which may have an oxo group or/and a hydroxyl group as substituent(s), can be exemplified by 2,3-dihydroindenyl groups which may each have an oxo group or/and a hydroxyl group as substituent(s), such as 1-oxo-7-hydroxy-2,3-dihydroindenyl, 1-oxo-6-hydroxy-2,3-dihydroindenyl, 1-oxo-5-hydroxy-2,3-dihydroindenyl, 1-oxo-4-hydroxy-2,3-dihydroindenyl, 1-oxo-2,3-dihydroindenyl, 2-oxo-2,3-dihydroindenyl, 2-oxo-7-hydroxy-2,3-dihydroindenyl and the like.

The phenyl group which may have, on the phenyl ring, 1 to 5 substituent(s) selected from the group consisting of an alkoxy group, a tri-lower alkyl group-substituted silyloxy group, a lower alkyl group, a hydroxyl group, a lower alkenyloxy group, a lower alkylthio group, a phenyl group, a lower alkylsulfonyl group, a lower alkylsulfinyl group, a halogen atom, a nitro group, a group of the formula,

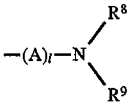

(wherein A, l, $R^8$ and $R^9$ are the same as defined above), a lower alkanoyl group, a lower alkanoyloxy group, a lower alkoxycarbonyl group, a cyano group, a tetrahydropyranyloxy group which may have 1 to 4 substituents selected from the group consisting of a hydroxyl group, a lower alkoxycarbonyl group, a phenyl-lower alkoxy group, a lower alkanoyloxy group-substituted lower alkyl group and a lower alkanoyloxy group, an amidino group, a hydroxysulfonyloxy group, a lower alkoxycarbonyl-substituted lower alkoxy group, a carboxy-substituted lower alkoxy group, a mercapto group, a lower alkoxy-substituted lower alkoxy group, a lower alkyl group having hydroxyl groups, a lower alkenyl group, an aminothiocarbonyloxy group which may have a lower alkyl group as a substituent, an aminocarbonylthio group which may have a lower alkyl group as a substituent, a lower alkanoyl-substituted lower alkyl group, a carboxy group, a group of the formula,

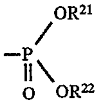

($R^{21}$ and $R^{22}$, are each the same or different, and are each represents a hydrogen atom or a lower alkyl group), a phenyl-lower alkoxycarbonyl group, a cycloalkyl group, a lower alkynyl group, a lower alkoxycarbonyl-substituted lower alkyl group, a carboxy-substituted lower alkyl group, a lower alkoxycarbonyl-substituted lower alkenyl group, a carboxy-substituted lower alkenyl group, a halogen-substituted or unsubstituted lower alkylsulfonyloxy group which may have a halogen atom, a lower alkoxy-substituted lower alkoxycarbonyl group, a lower alkenyl group having halogen atoms and a phenyl-lower alkoxy group, or the phenyl group having a lower alkylenedioxy group can be exemplified by, for example, phenyl groups which may each have, on the phenyl ring, 1 to 5 substituents selected from the group consisting of a $C_{1-18}$ straight-chain or branched-chain alkoxy group, a silyloxy group substituted with three straight-chain or branched-chain alkyl groups having 1 to 6 carbon atoms, a $C_{1-6}$ straight-chain or branched-chain alkyl group, a hydroxyl group, a $C_{2-6}$ straight-chain or branched-chain alkenyloxy group, a $C_{1-6}$ straight-chain or branched-chain alkylthio group, a phenyl group, a $C_{1-6}$ straight-chain or branched-chain alkylsulfonyl group, a $C_{1-6}$ straight-chain or branched-chain alkylsulfinyl group, a halogen atom, a nitro group, a group of the formula,

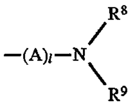

[wherein A represents a $C_{1-6}$ straight-chain or branched-chain alkylene group or a group of the formula

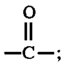

l represents 0 or 1; $R^8$ and $R^9$, are each the same or different, and are each represents a hydrogen atom, a $C_{1-6}$ straight-chain or branched-chain alkyl group, a $C_{1-6}$ straight-chain or branched-chain alkanoyl group or a $C_{1-6}$ straight-chain or branched-chain alkyl group having an amino group which may have, as substituent(s), one to two $C_{1-6}$ straight-chain or branched-chain alkyl groups, further $R^8$ and $R^9$ as well as the adjacent nitrogen atom being bonded thereto, together with or without other nitrogen atom or oxygen atom may form a five- to six-membered saturated or unsaturated heterocyclic ring. The heterocyclic ring may have a $C_{1-6}$ straight-chain or branched-chain alkanoyl group or a $C_{1-6}$ straight-chain or branched-chain alkyl group as a substituent]; a $C_{1-6}$ straight-chain or branched-chain alkanoyl group, a $C_{1-6}$ straight-chain or branched-chain alkoxycarbonyl group, a cyano group, a tetrahydropyranyloxy group which may have, as substituent(s), 1 to 4 groups selected from the group consisting of a hydroxyl group, a $C_{1-6}$ straight-chain or branched-chain alkoxycarbonyl group, a phenylalkoxy group whose alkoxy moiety is a $C_{1-6}$ straight-chain or branched-chain phenylalkoxy group, a $C_{1-6}$ straight-chain or branched-chain alkyl group having one to three hydroxy groups or $C_{2-6}$ straight-chain or branched-chain alkanoyloxy groups, and a $C_{2-6}$ straight-chain or branched-chain alkanoyloxy group, an amidino group, a hydroxysulfonyloxy group, a $C_{1-6}$ straight-chain or branched-chain alkoxycarbonylalkoxy group whose alkoxy moiety is a $C_{1-6}$ straight-chain or branched-chain alkoxy group, a carboxyalkoxy group whose alkoxy moiety is a $C_{1-6}$ straight-chain or branched-chain alkoxy group, a mercapto group, a alkoxyalkoxy group whose alkoxy moiety is a $C_{1-6}$ straight-chain or branched-chain alkoxy group, a $C_{1-6}$ straight-chain or branched-chain alkyl group having 1 to 3 hydroxyl groups, a $C_{2-6}$ straight-chain or branched-alkenyl group, a thiocarbonyloxy group having an amino group which may have one to two $C_{1-6}$ straight-chain or branched-chain alkyl groups as substituent(s), a carbonylthio group having an amino group which may have one to two $C_{1-6}$ straight-chain or branched-chain alkyl groups as substituent (s), a $C_{1-6}$ straight-chain or branched-chain alkyl group having one to three $C_{1-6}$ straight-chain or branched-chain alkanoyl group, a carboxy group, a group of the formula,

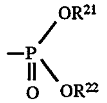

($R^{21}$ and $R^{22}$, are each the same or different, and are each represents a hydrogen atom or a $C_{1-6}$ straight-chain or branched-chain alkyl group), a phenylalkoxy group whose alkoxy moiety is a $C_{1-6}$ straight-chain or branched-chain alkoxy group, a $C_{2-6}$ straight-chain or branched-chain alkynyl group, an alkoxycarbonylalkyl group having a $C_{1-6}$ straight-chain or branched-chain alkoxy moiety and a $C_{1-6}$ straight-chain or branched-chain alkyl moiety, a carboxyalkyl group whose alkyl moiety is a $C_{1-6}$ straight-chain or branched-chain alkyl group, an alkoxycarbonyl-alkenyl group having a $C_{1-6}$ straight-chain or branched-chain alkoxy moiety and a $C_{2-6}$ straight-chain or branched-chain alkenyl moiety, a carboxyalkenyl group whose alkenyl moiety is a $C_{2-6}$ straight-chain or branched-chain alkenyl group, a $C_{1-6}$ straight-chain or branched-chain alkylsulfonyloxy group which may have 1 to 3 halogen atoms, an alkoxyalkoxycarbonyl group whose alkoxy moiety is a $C_{1-6}$ straight-chain or branched-chain alkoxy group, a $C_{2-6}$ straight-chain or branched-chain alkenyl group having 1 to 3 halogen atoms, and a phenylalkoxy group having a $C_{1-6}$ straight-chain or branched-chain alkoxy moiety, or phenyl groups each having a $C_{1-4}$ straight-chain or branched-chain alkylenedioxy group, such as phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3-ethoxy-4-methoxyphenyl, 2,3-dimethoxyphenyl, 3,4-diethoxyphenyl, 3,5-dimethoxyphenyl, 2,5-dimethoxyphenyl, 2,6-dimethoxyphenyl, 3,4,5-trimethoxyphenyl, 3,4-dipentyloxyphenyl, 2-methylphenyl, 3-methylphenyl, 4-methylphenyl, 2-ethylphenyl, 3-ethylphenyl, 4-ethylphenyl, 3-butylphenyl, 4-isopropylphenyl, 4-pentylphenyl, 4-hexylphenyl, 3,4-dimethylphenyl, 3,4-diethylphenyl, 2,5-dimethylphenyl, 2,6-dimethylphenyl, 3,4,5-trimethylphenyl, 2-hydroxyphenyl, 3-hydroxyphenyl, 4-hydroxyphenyl, 3,4-dihydroxyphenyl, 3,5-dihydroxyphenyl, 2,5-dihydroxyphenyl, 2,4-dihydroxyphenyl, 2,6-dihydroxyphenyl, 3,4,5-trihydroxyphenyl, 2-methylthiophenyl, 3-methylthiophenyl, 4-methylthiophenyl, 2-ethylthiophenyl, 3-ethylthiophenyl, 4-ethylthiophenyl, 4-isopropylthiophenyl, 4-pentylthiophenyl, 4-hexylthiophenyl, 3,4-dimethylthiophenyl, 3,4-diethylthiophenyl, 2,5-dimethylthiophenyl, 2,6-dimethylthiophenyl, 3,4,5-trimethylthiophenyl, 2-phenylphenyl, 3-phenylphenyl, 4-phenylphenyl, 2-methylsulfonylphenyl, 3-methylsulfonylphenyl, 4-methylsulfonylphenyl, 2-ethylsulfonylphenyl, 4-isopropylsulfonylphenyl, 4-pentylsulfonylphenyl, 4-hexylsulfonylphenyl, 3,4-dimethylsulfonylphenyl, 3,4-diethylsulfonylphenyl, 2,5-dimethylsulfonylphenyl, 2,6-dimethylsulfonylphenyl, 3,4,5-trimethylsulfonylphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3-dichlorophenyl, 2,4-dichlorophenyl, 3,4-difluorophenyl, 3,5-dibromophenyl, 3,4,5-trichlorophenyl, 2,3,4,5,6-pentafluorophenyl, 2-nitrophenyl, 3-nitrophenyl, 4-nitrophenyl, 3,4-dinitrophenyl, 2,5-dinitrophenyl, 2,6-dinitrophenyl, 3,4,5-trinitrophenyl, 2-aminophenyl, 3-aminophenyl, 4-aminophenyl, 2-methylaminophenyl, 3-ethylaminophenyl, 4-propylaminophenyl, 2-isopropylaminophenyl, 3-butylaminophenyl, 4-pentylamino-phenyl, 2-hexylaminophenyl, 4-dimethylaminophenyl, 3-(N-methyl-N-ethylamino)phenyl, 3-dihexylaminophenyl, 2-(N-methyl-N-acetylamino)phenyl, 4-(N-acetylamino)phenyl, 3-(N-acetylamino)phenyl, 4-(N-formylamino)phenyl, 4-(N-isobutyrylamino)phenyl, 2-(N-pentanoylamino)phenyl, 3,4-di(N-acetylamino)phenyl, 3,4-diaminophenyl, 3,4,5-triaminophenyl, 2,6-diaminophenyl, 2,5-diaminophenyl, 2-carbamoylphenyl, 3-carbamoylphenyl, 4-carbamoylphenyl, 2-acetylphenyl, 3-acetylphenyl, 4-acetylphenyl, 2-formylphenyl, 3-propionylphenyl, 4-isobutyrylphenyl, 2-pentanoylphenyl, 3-hexanoylphenyl, 3,4-diacetylphenyl, 2,5-diacetylphenyi, 3,4,5-triacetylphenyl, 2-methoxycarbonylphenyl, 2-ethoxycarbonylphenyl, 3-ethoxycarbonylphenyl, 4-ethoxycarbonylphenyl, 3-propoxycarbonylphenyl, 4-butoxycarbonylphenyl, 4-pentyloxycarbonylphenyl, 4-hexyloxycarbonylphenyl, 3,4-diethoxycarbonylphenyl, 2,5-diethoxycarbonylphenyl, 2,6-diethoxycarbonylphenyl, 3,4,5-triethoxycarbonylphenyl, 2-carboxyphenyl, 3-carboxyphenyl, 4-carboxyphenyl, 3,4-dicarboxyphenyl, 2,5-dicarboxyphenyl, 2,6-dicarboxyphenyl, 3,4,5-tricarboxyphenyl, 3,4-methylenedioxyphenyl, 3,4-ethylenedioxyphenyl, 2,3-trimethylenedioxyphenyl, 3,4- tetramethylenedioxyphenyl, 3,5-di-tert-butyl-4-hydroxyphenyl, 3-hydroxy-4-pentyloxyphenyl, 2-hydroxy-5-tert-butylphenyl, 3,5-dichloro-4-aminophenyl, 3-(N-acetylamino)-4-hydroxyphenyl, 3-amino-4-hydroxyphenyl, 3-(N-methyl-N-acetylamino)-4-methoxyphenyl, 3-nitro-4-(N-acetylamino)phenyl, 3-nitro-4-chlorophenyl, 3-chloro-4-methylphenyl, 3-methoxy-4-hydroxyphenyl, 3-hydroxy-4-methoxyphenyl, 3-methoxy-4-hydroxy-5-iodophenyl, 3,4-dimethoxy-5-bromophenyl, 3,5-diiodo-4-hydroxyphenyl, 4-(dimethyl-tert-butylsilyloxy)phenyl, 3-(tri-tert-butylsilyloxy)phenyl, 2-(trimethylsilyloxy)phenyl, 3-amino-4-(dimethyl-tert-butylsilyloxy)phenyl, 4-allyloxyphenyl, 2-vinyloxyphenyl, 3-(2-butenyloxy)-phenyl, 2-(3-butenyloxy)phenyl, 3-(1-methylallyloxy)-phenyl, 4-(2-pentenyloxy)phenyl, 2-(2-hexenyloxy)phenyl, 3-methyl-4-allyloxyphenyl, 3-methoxy-4-octadecyloxy-phenyl, 4-dimethylamidophenyl, 2-methylamidophenyl, 3-ethylamidophenyl, 4-propylamidophenyl, 2-isopropyl-amidophenyl, 3-butylamidophenyl, 4-pentylamidophenyl, 2-hexylamidophenyl, 3-diethylamidophenyl, 4-(N-methyl-N-propylamido)phenyl, 2-methylsulfinylphenyl, 3-methylsulfinylphenyl, 4-methylsulfinylphenyl, 2-ethylsulfinylphenyl, 3-ethylsulfinylphenyl, 4-ethylsulfinylphenyl, 4-isopropylsulfinylphenyl, 4-pentylsulfinylphenyl, 4-hexylsulfinylphenyl, 3,4-dimethylsulfinylphenyl, 3,4-diethylsulfinylphenyl, 2,5-dimethylsulfinylphenyl, 2,6-dimethylsulfinylphenyl, 3,4,5-trimethylsulfinylphenyl, 3-methoxy-4-methylsulfinylphenyl, 2-acetyloxyphenyl, 3-acetyloxyphenyl, 4-acetyloxyphenyl, 2-formyloxyphenyl, 3-propionyloxyphenyl, 4-isobutyryloxyphenyl, 2-pentanoyloxyphenyl, 3-hexanoyloxyphenyl, 3,4-diacetyloxyphenyl, 2,5-diacetyloxyphenyl, 3,4,5-triacetyloxyphenyl, 3,5-bis(acetylamino)phenyl, 2-amidinophenyl, 4-amidinophenyl, 3-amidinophenyl, 4-(4-methyl-1-piperazinyl)-3-nitriophenyl, 4-hydroxysulfonyloxyphenyl, 3-hydroxysulfonyloxyphenyl, 2-hydroxysulfonyloxyphenyl, 4-hydroxy-3-acetylaminophenyl, 4-(2,3,4,6-tetra-o-acetyl-β-D-glucopyranosyloxy)phenyl, 4-(β-D-glucopyranosyloxy) phenyl, 4-(2,3,4,6-tetra-o-benzyl-β-D-glucopyranosyloxy) phenyl, 3,5-bis(dimethylamino)phenyl, 4-chloro-3-nitrophenyl, 4-(4-methyl-1-piperazinyl)-3-nitrophenyl, 4-cyanophenyl, 3-acetylamino-4-(methyl-1-piperazinyl) phenyl, 3-nitro-4-morpholinophenyl, 4-(1-piperazinyl)-3-nitrophenyl, 4-(1-piperazinyl)-3-nitrophenyl, 4-hydroxy-3-carboxyphenyl, 4-morpholino-3-aminophenyl, 4-hydroxy-3-aminophenyl, 4-hydroxy-3-(2-dimethylaminoethylamino) phenyl, 4-methoxy-3-(4-acetyl-1-piperazinyl)phenyl, 4-methoxy-3-(1-piperazinyl)phenyl, 4-methoxy-3-(4-methyl-1-piperazinyl)phenyl, 4-methoxy-3-(4-ethyl-1-piperazinyl)phenyl, 4-hydroxy-3-aminophenyl, 4-hydroxy-3-[(4-methyl-1-piperazinyl)methyl]phenyl, 4-methoxy-3-[(1-pyrrolidinyl)methyl]phenyl, 3,5-diacetyloxyphenyl, 3-methoxy-5-methoxycarbonylphenyl, 3-methoxy-5-carboxyphenyl, 3-methoxy-5-[(4-methyl-1-piperazinyl) carbonyl]phenyl, 3-methoxy-5-[(1-pyrrolidinyl)-carbonyl] phenyl, 3-methoxy-5-[(4-methyl-1-piperazinyl)methyl] phenyl, 3-amino-4-carboxyphenyl, 3-carbamoyl-4-hydroxyphenyl, 4-hydroxy-3-dimethylamido-phenyl, 3-methoxycarbonyl-4-methoxycarbonylmethoxy-phenyl, 4-allyloxy-3-methoxycarbonylphenyl, 3-carboxy-4-carboxymethoxyphenyl, 4-hydroxy-4-allyl-3-methoxy-carbonylphenyl, 3-carboxy-4-allyloxyphenyl, 4-hydroxy-3-carboxy-5-allylphenyl, 4-mercapto-3-carboxyphenyl, 5-nitro-4-hydroxy-3-methoxycarbonylphenyl, 5-nitro-3-methoxycarbonylphenyl, 3-methoxycarbonyl-4-methoxy-methoxyphenyl, 3-methoxycarbonyl-5-aminophenyl, 3-carboxy-5-aminophenyl, 5-methoxycarbonyl-3-bromo-2-aminophenyl, 2-cyanophenyl, 4-cyanophenyl, 3-cyanophenyl, 3-methoxycarbonyl-4-hydroxyphenyl, 3-carboxy-4-hydroxy-5-(1,1-dimethyl-2-propenyl)phenyl, 2-hydroxy-3-carboxyphenyl, 3-carboxy-4-hydroxy-5-(2-isopropenyl)phenyl, 3-carboxy-4-hydroxy-5-methylphenyl, 3-methoxycarbonyl-4-methoxyphenyl, 3-methoxycarbonyl-4-hydroxy-5-aminophenyl, 3-carboxy-4-hydroxy-5-propylphenyl, 3-carboxy-4-hydroxy-5-aminophenyl, 3-carboxy-4-hydroxy-5-chlorophenyl, 3-carboxy-6-hydroxyphenyl, 4-ethoxyphenyl, 3,4-dibutoxyphenyl, 3,4-dipropoxyphenyl, 3-methoxy-4-ethoxyphenyl, 3-propoxy-4-methoxyphenyl, 3-ethoxy-4-methoxyphenyl, 3,4-didecyloxyphenyl, 2,4-diethoxyphenyl, 3-ethoxy-4-propoxyphenyl, 3-carboxy-4-hydroxy-5-isobutylphenyl, 3-carboxy-4-acetylaminophenyl, 3-carboxy-4-hydroxy-5-(2-hydroxyethyl)phenyl, 3-carboxy-4-amino-6-hydroxyphenyl, 3-carboxy-4-hydroxy-5-(2,3-dihydroxypropyl)phenyl, 3-carboxy-4-aminophenyl, 3-carboxy-4-acetyloxyphenyl, 3-ethyl-4-hydroxyphenyl, 3-carboxy-5-hydroxyphenyl, 4-carboxy-3,5-dihydroxyphenyl, 3-carboxy-4,6-dihydroxyphenyl, 5-methoxycarbonyl-3-amino-2-hydroxyphenyl, 2-allyloxy-5-methoxycarbonylphenyl, 3-carboxy-6-methoxyphenyl, 3-methoxycarbonyl-6-hydroxyphenyl, 3-carbonyl-6-allyloxyphenyl, 3-carboxy-5-nitro-6-hydroxyphenyl, 3-carboxy-5-allyl-6-hydroxyphenyl, 3-carboxy-6-hydroxyphenyl, 3-carboxy-5-amino-6-hydroxyphenyl, 3-methoxycarbonyl-4-dimethyl-aminothiocarbonyloxyphenyl, 3-methoxycarbonyl-4-dimethylaminocarbonylthiophenyl, 3-methoxycarbonyl-4-hydroxy-5-(2,3-dihydroxypropyl)phenyl, 3-methoxycarbonyl-4-hydroxy-5-formylmethylphenyl, 3-methoxycarbonyl-4-hydroxy-5-(2-hydroxyethyl)phenyl, 3-ethoxycarbonyl-4-acetylaminophenyl, 3-methoxycarbonyl-5-hydroxyphenyl, 3-methoxycarbonyl-4-acetylamino-6-hydroxyphenyl, 3-methoxycarbonyl-6-methoxyphenyl, 4-propoxy-3-ethoxyphenyl, 3-methoxycarbonyl-5-allyl-6-hydroxyphenyl, 3-methoxycarbonyl-4-(2-butenyloxy)phenyl, 3-methoxycarbonyl-4-hydroxy-5-(1-methyl-2-propenyl)-phenyl, 3-methoxycarbonyl-4-(2-isopentenyloxy)phenyl, 3-methoxycarbonyl-4-hydroxy-5-(1,1-dimethyl-2-propenyl)-phenyl, 3-methoxycarbonyl-4-(2-methyl-2-propenyloxy)-phenyl, 3-methoxycarbonyl-4-hydroxy-5-(2-methyl-2-propenyl)phenyl, 5-chloro-4-hydroxy-3-methoxycarbonyl-phenyl, 3-methoxycarbonyl-4-hydroxy-5-methylphenyl, 3,5-dinitro-4-hydroxyphenyl, 4-hydroxy-3-nonyloxycarbonyl-phenyl, 4-hydroxy-3-benzyloxycarbonylphenyl, 4-hydroxy-3-(2-methyl-2-propenyl)-5-benzyloxycarbonyl, 4-hydroxy-3-(2-methyl-2-propenyl)-5-nonyloxycarbonylphenyl,

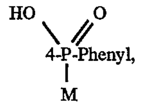

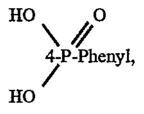

4-[2-(1-piperidinyl)ethylamino]-3-carboxyphenyl, 4-methoxy-3-carboxyphenyl, 2-methyl-4-hydroxy-5-carboxyphenyl, 3-ethyl-4-hydroxy-3-carboxyphenyl, 3-(4- ethyl-1-piperazinyl)-4-hydroxyphenyl, 4-(2-hydroxy-3-carboxyphenyl)phenyl, 4-[2-(3,4-diethoxyphenyl)-4-thiazolyl]-3-hydroxy-2-carboxyphenyl, 4-hydroxy-3-hydroxymethylphenyl, 4-ethoxy-3-carboxyphenyl, 4-n-butoxy-3-n-butoxycarbonylphenyl, 4-n-butoxy-3-carboxyphenyl, 3-acetylmethyl-4-hydroxy-3-carboxyphenyl, 3-n-butyl-4-hydroxy-3-carboxyphenyl, 3-allyl-4-hydroxy-3-carboxyphenyl, 3-hydroxymethyl-4-hydroxy-3-carboxyphenyl, 3-formyl-4-hydroxy-5-carboxyphenyl, 5-(2-carboxyethyl)-4-hydroxy-3-carboxyphenyl, 5-(2-methoxycarboxyethyl)-4-hydroxy-3-carboxyphenyl, 5-methylaminomethyl-4-hydroxy-3-carboxyphenyl, 5-(2-carboxyvinyl)-4-hydroxy-3-carboxyphenyl, 5-(2-methoxycarboxyvinyl)-4-hydroxy-3-carboxyphenyl, 5-acetyl-4-hydroxy-3-carboxyphenyl, 5-phenyl-4-hydroxy-3-carboxyphenyl, 5-bromo-4-hydroxy-3-carboxyphenyl, 5-cyano-4-hydroxy-3-carboxyphenyl, 4,5-hydroxy-3-carboxy-phenyl, 5-methoxy-4-hydroxy-3-carboxyphenyl, 5-ethylamino-4-hydroxy-3-carboxyphenyl, 5-acetylamino-4-hydroxy-3-carboxyphenyl, 3,5-dicarboxy-4-hydroxyphenyl, 4-methoxy-3-carboxyphenyl, 4-ethoxy-3-carboxyphenyl, 4-n-butyoxy-3-carboxyphenyl, 4-dimethylamino-3-hydroxyphenyl, 4-dimethylamino-3-hydroxymethylphenyl, 4-dimethylamino-3-methoxycarboxyphenyl, 4-trifluoro-methylsulfonyloxy-3-methoxycarbonylphenyl, 3-methoxymethoxycarbonyl-4-methoxymethoxy-5-(1-propenyl)-phenyl, 3-methoxymethoxycarbonyl-4-methoxymethoxy-5-formylphenyl, 3-methoxymethoxycarbonyl-4-methoxymethoxy-5-acetylmethylphenyl, 5-(2-methyl-2-propenyl)-4-methoxymethoxy-3-methoxymethoxycarbonylphenyl and the like.

The 5- to 15-membered monocylic, bicyclic or tricyclic heterocyclic residual group having 1 to 2 hetero atoms selected from the group consisting of a nitrogen atom, an oxygen atom and a sulfur atom can be exemplified by pyrrolidinyl, piperidinyl, pierazinyl, morpholino, pyridyl, 1,2,5,6-tetrahydropyridylthienyl, quinolyl, 1,4-dihydroquinolyl, benzothiazolyl, pyrazyl, pyrimidyl, pyridazylthienyl, pyrrolyl, carbostyril, 3,4-dihydrocarbostyril, 1,2,3,4-tetrahydroquinolyl, indolyl, isoindolyl, indolinyl, benzoimidazolyl, benzoxazolyl, imidazolidinyl, isoquinolyl, quinazolidinyl, quinoxalinyl, cinnolinyl, phthalazinyl, carbazolyl, acrydinyl, chromanyl, isoindolinyl, isochromanyl, pyrazolyl, imidazolyl, pyrazolidinyl, phenothiazinyl, benzofuryl, 2,3-dihydrobenzo[b]furyl, benzothienyl, phenoxthinyl, phenoxazinyl, 4H-chromenyl, 1H-indazolyl, phenazinyl, xanthenyl, thianthrenyl, isoindolinyl, 2-imidazolinyl, 2-pyrrolinyl, furyl, oxazolyl, isooxazolyl, thiazolyl, isothiazolyl, pyranyl, pyrazolidinyl, 2-pyrazolinyl, quinuclidinyl, 1,4-benzoxazinyl, 3,4-dihydro-2H-1,4-benzoxazinyl, 3,4-dihydro-2H-1,4-benzothiazinyl, 1,4-benzothiazinyl, 1,2,3,4-tetrahydroquinoxalinyl, 1,3-dithia-2,4-dihydronaphthalenyl, phenanthridinyl, 1,4-dithianaphthalenyl, dibenzo[b,e]azepine and 6,11-dihydro-5H-dibenzo[b,e]azepine.

The heterocyclic ring having 1 to 3 groups selected from the group consisting of an oxo group, an alkyl group, a benzoyl group, a lower alkanoyl group, a hydroxyl group, a carboxy group, a lower alkoxycarbonyl group, a lower alkylthio group, a group

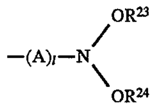

(A and l are the same as defined above; $R^{23}$ and $R^{24}$ are each the same or different, and are each represents a hydrogen atom or a lower alkyl group; further $R^{23}$ and $R^{24}$ as well as the adjacent nitrogen atom being bonded thereto, together with or without other nitrogen atom or oxygen atom may form a five- to six-membered saturated heterocyclic group; said five- to six-membered heterocyclic group may have a lower alkyl group as a substituent.), a cyano group, a lower alkyl group having hydroxyl groups, a phenylaminothiocarbonyl group and an amino-lower alkoxycarbonyl group which may have lower alkyl groups as substituents, can be exemplified by heterocyclic rings each having 1 to 3 groups selected from the group consisting of an oxo group, a $C_{1-18}$ straight-chain or branched-chain alkyl group, a benzoyl group, a $C_{1-6}$ straight-chain or branched-chain alkanoyl group, a hydroxyl group, a carboxy group, a $C_{1-6}$ straight-chain or branched-chain alkoxycarbonyl group, a $C_{1-6}$straight-chain or branched-chain alkylthio group, a group of the formula,

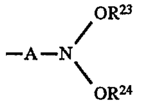

(A is the same as defined above; $R^{23}$ and $R^{24}$, are each the same or different, and are each represent a hydrogen atom or a $C_{1-6}$ straight-chain or branched-chain alkyl group, further $R^{23}$ and $R^{24}$ as well as the adjacent nitrogen atom being bonded thereto, together with or without other nitrogen atom or oxygen atom may form a five- to six-membered saturated heterocyclic ring, said heterocyclic ring may have a $C_{1-6}$ straight-chain or branched-chain alkyl group as a substituent.), a cyano group, a $C_{1-6}$ straight-chain or branched-chain alkyl group having 1 to 3 hydroxyl groups, a phenylaminothiocarbonyl group and a $C_{1-6}$ straight-chain or branched-chain alkoxycarbonyl group having an amino group which may have one to two $C_{1-6}$ straight-chain or branched-chain alkyl groups as substituent(s), such as dibenzo[b,e]-azepin-3-yl-6-one, 4-oxo-1,4-dihydroquinolyl, 1-oxopyridyl, 2-oxo-pyridyl, 1-methyl-3,4-dihydrocarbostyril, 1-ethylcarbostyril, 1-butyl-3,4-dihydrocarbostyril, 1-hexylcarbostyril, 1-octadecyl-3,4-dihydrocarbostyril, 3-oxo-4-methyl-3,4-dihydro-2H-1,4-benzothiazinyl, 3-oxo-3,4-dihydro-2H-1,4-benzothiazinyl, 1-benzoyl-1,2,3,4-tetrahydroquinolyl, 1-octadecyl-1,2,3,4-tetrahydroquinolyl, 1-benzoylcarbostyril, 4-benzoyl-3,4-dihydro-2H-1,4-benzothiazolyl, 4-methyl-1,2,3,4-tetrahydroquinoxalinyl, 4-benzoyl-1,2,3,4-tetrahydroquinoxalinyl, 1-acetyl-1,2,3,4-tetrahydroquinolyl, 1-acetyl-3,4-dihydrocarbostyril, 4-acetyl-3,4-dihydro-2H-1,4-benzothiazolyl, 4-benzoyl-3,4-dihydro-2H-1,4-benzoxazinyl, 4-acetyl-3,4-dihydro-2H-1,4-benzoxazinyl, 4-acetyl-1,2,3,4-tetrahydro-quinoxalinyl, 1-methyl-1,2,3,4-tetrahydroquinolyl, 7-hydroxy-3,4-dihydrocarbostyril, 8-hydroxy-3,4-dihydrocarbostyril, 2-methylthiobenzothiazolyl, 3-oxo-3,4-dihydro-2H-1,4-benzoxazinyl, 1-acetylindolinyl, 2-oxobenzoimidazolyl, 4-methyl-3,4-dihydro-2H-1,4-benzoxazinyl, 10-acetylphenothiazinyl, 2-oxobenzothiazolyl, 2-oxobenzoxazolyl, 2-oxo-3-methyl-benzothiazolyl, 1,3- dimethyl-2-oxobenzoimidazolyl, 6-hydroxy-3,4-dimethylquinolyl, 4-oxopyridyl, 1-propyl-1,2,3,4-tetrahydroquinolyl, 4-pentyl-1,2,3,4-tetrahydroquinoxalinyl, 1-propanoyl-1,2,3,4-tetrahydroquinolyl, 1-butylcarbostyril, 4-pentanoyl-3,4-dihydro-2H-1,4-benzothiazolyl, 4-hexanoyl-3,4-dihydro-2H-1,4-benzoxazinyl, 2-ethylthiobenzoxazolyl, 2-propylthiobenzoimidazolyl, 2-butylthiobenzothiazolyl, 6-pentylcarbostyril, 7-hexylthio-3,4-dihydrocarbostyril, 2-carboxypyridyl, 2-carboxypyrrolyl, 2-ethoxycarbonylpyridyl, 2-methoxycarbonylpyrrolyl, 1-methylpyridinum, 1-methyl-1,2,5,6-tetrahydropyridyl, 2-methoxycarbonylfuryl, 2-carboxyfuryl, 2-dimethylaminocarbonylpyridyl, 2-acetylpyrrolyl, 2-hydroxymethylpyridyl, 2-ethoxycarbonyl-4-methylpyridyl, 2-carboxy-4-methylpyridyl, 2-(4-methyl-1-piperazinyl)carboxypyridyl, 2-(2-dimethylaminoethoxycarbonyl)pyridyl, 2-dimethylaminomethylpyridyl, 2-ethoxycarbonylthienyl, 2-methyl-7-carboxybenzofuryl, 2-carboxythienyl, 4-ethoxycarbonylthiazolyl, 4-carboxythiazolyl, 4-methyl-5-carboxythiazolyl, 3-carboxypyridyl, 2,2-dimethyl-7-carboxy-2,3-dihydrobenzo[b]furyl, 4-carboxypyridyl, 2-methyl-4-carbamoylpyridyl, 2,6-dimethyl-3-carbamoylpyridyl, 2-phenylaminothiocarbonylpyridyl, 2-methyl-3-carboxypyridyl, 2,6-dimethyl-3-carboxypyridyl and the like.

As to the lower alkenyloxy group, there can be mentioned $C_{2-6}$ straight-chain or branched-chain alkenyloxy groups such as vinyloxy, allyloxy, 2-butenyloxy, 3-butenyloxy, 1-methylallyloxy, 2-pentenyloxy, 2-hexenyloxy and the like.

The lower alkylsulfinyl group can be exemplifed by $C_{1-6}$ straight-chain or branched-chain alkylsulfinyl groups such as methylsulfinyl, ethylsulfinyl, isopropylsulfinyl, butylsulfinyl, tert-butylsulfinyl, pentylsulfinyl, hexylsulfinyl and the like.

As to the lower alkanoyloxy group, there can be mentioned $C_{1-6}$ straight-chain or branched-chain alkanoyloxy groups such as formyloxy, acetyloxy, propionyloxy, butyryloxy, isobutyryloxy, pentanoyloxy, tert-butylcarbonyloxy, hexanoyloxy and the like.

The tri-lower alkyl group-substituted silyloxy group can be exemplified by silyloxy groups each substituted with three $C_{1-6}$ straight-chain or branched-chain alkyl groups, such as trimethylsilyloxy, triethylsilyloxy, triisopropylsilyloxy, tributylsilyloxy, tri-tert-butylsilyloxy, tripentylsilyloxy, trihexylsilyloxy, dimethyl-tert-butylsilyloxy and the like.

The phenyl-lower alkyl group which may have a lower alkoxy group as a substituent on the phenyl ring and a hydroxyl group as a substituent on the lower alkyl group, can be exemplified by phenylalkyl groups each having a $C_{1-6}$ straight-chain or branched-chain alkyl group moiety, which may each have one to three $C_{1-6}$ straight chain or branched chain alkoxy groups as substituent(s) on the phenyl ring and a hydroxyl group as a substituent on the lower alkyl group, such as benzyl, 2-phenylethyl, 1-phenylethyl, 3-phenylpropyl, 4-pehnylbutyl, 1,1-dimethyl-2-phenylethyl, 5-phenylpentyl, 6-phenylhexyl, 2-methyl-3-phenylpropyl, 2-methoxybenzyl, 2-(3-methoxyphenyl)ethyl, 1-(4-methoxyphenyl)ethyl, 3-(2-ethoxyphenyl)propyl, 4-(3-ethoxyphenyl)butyl, 1,1-dimethyl-2-(4-isopropoxyphenyl) ethyl, 5-(4-pentyloxyphenyl)pentyl, 6-(4-hexyloxyphenyl) hexyl, 3,4-dimethoxybenzyl, 2,5-dimethoxybenzyl, 2,6-dimethoxybenzyl, 3,4,5-trimethoxybenzyl, 1-phenyl-1-hydroxymethyl, 2-phenyl-1-hydroxyethyl, 1-phenyl-2-hydroxyethyl, 3-phenyl-1-hydroxypropyl, 4-phenyl-4-hydroxybutyl, 5-phenyl-5-hydroxypentyl, 6-phenyl-6-hydroxyhexyl, 2-methyl-3-phenyl-3-hydroxypropyl, 1-(2-methothyphenyl)-1-hydroxymethyl, 2-(3-methoxyphenyl)-1-hydroxyethyl, 3-(2-ethoxyphenyl)-2-hydroxypropyl, 4-(3-ethoxyphenyl)-3-hydroxybutyl, 5-(4-pentyloxyphenyl)-4-hydroxypentyl, 6-(4-hexyloxyphenyl)-5-hydroxyhexyl, 6-(4-hexyloxyphenyl)-1-hydroxhexyl, 1-(3,4-dimethoxyphenyl)-1-hydroxymethyl, 1-(3,4,5-trimethoxyphenyl)-1-hydroxymethyl and the like.

The benzoyl group which may have lower alkoxy groups as substituents on the phenyl ring, can be exemplified by benzoyl groups which may each have one to three $C_{1-6}$ straight-chain or branched-chain alkoxy groups as substituent(s) on the phenyl ring, such as benzoyl, 2-methoxybenzoyl, 3-methoxybenzoyl, 4-methoxybenzoyl, 2-ethoxybenzoyl, 3-ethoxybenzoyl, 4-isopropoxybenzoyl, 4-pentyloxybenzoyl, 4-hexyloxybenzoyl, 3,4-dimethoxybenzoyl, 3-ethoxy-4-methoxybenzoyl, 2,3-dimethoxybenzoyl, 3,4-diethoxybenzoyl, 2,5-dimethoxybenzoyl, 2,6-dimethoxybenzoyl, 3,5-dimethoxybenzoyl, 3,4-dipentyloxybenzoyl, 3,4,5-trimethoxybenzoyl and the like.

The phenyl-lower alkenyl group which may have lower alkoxy groups as substituents on the phenyl group, can be exemplified by phenylalkenyl groups each having a $C_{3-6}$ straight chain or branched chain alkenyl moiety, which may each have one to three $C_{1-6}$ straight chain or branched chain alkoxy groups as substituents on the phenyl ring, such as cinnamyl, styryl, 4-phenyl-3-butenyl, 4-phenyl-2-butenyl, 5-phenyl-4-pentenyl, 5-phenyl-3-pentenyl, 5-phenyl-2-pentenyl, 6-phenyl-5-hexenyl, 6-phenyl-4-hexenyl, 6-phenyl-3-hexenyl, 6-phenyl-2-hexenyl, 2-methyl-4-phenyl-3-butenyl, 2-methylcinnamyl, 1-methylcinnamyl, 2-methoxystyryl, 3-methoxycinnamyl, 4-methoxystyryl, 2-ethoxycinnamyl, 3-ethoxystyryl, 4-ethoxystyryl, 2-propoxystyryl, 3-propoxystyryl, 4-propoxycinnamyl, 3-(tert-butoxy)styryl, 4-pentyloxycinnamyl, 3-hexyloxystyryl, 3,4-dimethoxystyryl, 3,5-dimethoxystyryl, 2,6-dimethoxystyryl, 3,4-diethoxystyryl, 3,5-diethoxystyryl, 3,4,5-trimethoxystyryl, 4-ethoxyphenyl-3-butenyl, 4-(3-tertbutoxyphenyl)- 2-butenyl, 5-(4-hexyloxyphenyl)-4-pentenyl, 6-(3,4-dimethoxyphenyl)-5-hexenyl, 6-(3,4,5-triethoxyphenyl)-3-hexenyl and the like.

The amino-lower alkyl group which may have lower alkyl groups as substituents, can be exemplified by amino group-containing $C_{1-6}$ straight-chain or branched-chain alkyl groups which may each have one to two $C_{1-6}$ straight-chain or branched-chain alkyl groups as substituent(s), such as aminomethyl, 2-eminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, (N-ethyl-N-propylamino)methyl, 2-(N-methyl-N-hexylamino)ethyl and the like.

The five- or six-membered saturated or unsaturated heterocyclic ring which $R^8$ and $R^9$ as well as the adjacent nitrogen atom bonded thereto may form together with or without other nitrogen atom or oxygen atom, can be exemplified by piperazinyl, pyrrolidinyl, morpholinyl, piperidinyl, pyrrolyl, imidazolyl, pyrazolyl, 2-pyrrolinyl, 2-imidazolinyl, imidazolidinyl, 2-piperazolinyl, pyrazolidinyl, 1,2,5,6-tetrahydropyridyl, etc.

The above heterocyclic ring substituted with a lower alkanoyl group or a lower alkyl group can be exemplified by above heterocyclic rings each substituted with a $C_{1-6}$ straight-chain or branched-chain alkanoyl group or a $C_{1-6}$ straight-chain or branched-chain alkyl group, such as 4-acetylpiperazinyl, 3-formylpyrrolidinyl, 2-propionylpyrrolidinyl, 4-butyrylpiperidinyl, 3-pentanoylpiperazinyl, 2-hexanoylmorpholino, 4-methylpiperazinyl, 4-ethylpiprazinyl, 3-ethylpyrrolidinyl, 2-propylpyrrolidinyl, 4-butylpiperidinyl, 3-pentylmorpholino, 2-hexylpiprazinyl, 2-acetylpyrrolyl and the like.

The phenyl-lower alkoxy group can be exemplified by phenylalkoxy groups each having a $C_{1-6}$ straight-chain or branched-chain alkoxy moiety, such as benzyloxy, 2-phenylethoxy, 1-phenylethoxy, 3-phenylpropoxy, 4-phenylbutoxy, 1,1-dimethyl-2-phenylethoxy, 5-phenylpentyloxy, 6-phenylhexyloxy, 2-methyl-3-phenylpropoxy and the like.

As to the hydroxyl group- or lower alkanoyloxy group-substituted lower alkyl group, there can be mentioned $C_{1-6}$ straight-chain or branched-chain alkyl groups each having one to three hydroxyl groups or one to three $C_{1-6}$ straight-chain or branched-chain alkanoyloxy groups, such as hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, acetyloxymethyl, 2-propionyloxyethyl, 1-butyryloxyethyl, 3-acetyloxypropyl, 2,3-diacetyloxypropyl, 4-isobutyryloxybutyl, 5-pentanoyloxypentyl, 6-tert-butylcarbonyloxyhexyl, 1,1-dimethyl-2-hexanoyloxyethyl, 5,5,4-triacetyloxypentyl, 2-methyl-3-acetyloxypropyl and the like.

The tetrahydropyranyloxy group which may have, as substituent(s), one to four groups selected from the group consisting of a hydroxyl group, a lower alkoxycarbonyl group, a phenyl-lower alkoxy group, a hydroxyl group- or lower alkanoyloxy group-substituted lower alkyl group and a lower alkanoyloxy group, can be exemplified by tetrahydropyranyloxy groups which may each have, as substituent (s), one to four groups selected from the group consisting of a hydroxyl group, a $C_{1-6}$ straight-chain or branched-chain alkoxycarbonyl group, a phenylalkoxy group having a $C_{1-6}$ straight-chain or branched-chain alkoxy moiety, a $C_{1-6}$ straight-chain or branched-chain alkyl group having one to three hydroxyl groups or one to three $C_{1-6}$ straight-chain or branched-chain alkanoyloxy groups, and a $C_{2-6}$ straight-chain or branched-chain alkanoyloxy group, such as 2-, 3- or 4-tetrahydropyranyloxy, 3,4,5-trihydroxy-6-methoxycarbonyl-2-tetrahydropyranyloxy, 3,4,5-tribenzyloxy-6-hydroxymethyl-2-tetrahydropyranyloxy, 3,4,5-triacetyloxy-6-acetyloxymethyl-2-tetrahydropyranyloxy, 3,4,5-trihydroxy-6-hydroxymethyl-2-tetrahydropyranyloxy, 3-hydroxy-2-tetrahydropyranyloxy, 2,4-dihydroxy-3-tetrahydropyranyloxy, 2,3,5-trihydroxy-4-tetrahydropyranyloxy, 3-(2,3-dihydroxypropyl)-2-tetrahydropyranyloxy, 6-methoxycarbonyl-2-tetrahydropyranyloxy, 6-(5,5,4-trihydroxypentyl)-2-tetrahydropyranyloxy, 4-ethoxycarbonyl-3-tetrahydropyranyloxy, 4,6-dimethoxycarbonyl-4-tetrahydropyranyloxy, 4,5,6-trimethoxycarbonyl-2-tetrahydropyranyloxy, 2-propoxycarbonyl-3-tetrahydropyranyloxy, 6-butoxycarbonyl-4-tetrahydrypyranyloxy, 6-pentyloxycarbonyl-2-tetrahydropyranyloxy, 4-hexyloxycarbonyl-3-tetrahydropyranyloxy, 3,4,5,6-tetrahydroxy-2-tetrahydropyranyloxy, 6-benzyloxy-2-tetrahydropyranyloxy, 4-(2-phenylethoxy)-3-tetrahydropyranyloxy, 4,6-dibenzyloxy-4-tetrahydropyranyloxy, 4,5,6-tribenzyloxy-2-tetrahydropyranyloxy, 2-(3-phenylpropoxyl-3-tetrahydropyranyloxy, 6-(4-phenylbutoxy)-4-tetrahydropyranyloxy, 6-(5-phenylpentyloxy)-2-tetrahydropyranyloxy, 4-(6-phenylhexyloxy)-3-tetrahydropyranyloxy, 3,4,5-trihydroxy-6-benzyloxy-2-tetrahydropyranyloxy, 6-acetyloxy-2-tetrahydropyranyloxy, 4-propionyloxy-3-tetrahydropyranyloxy, 4,6-diacetyloxy-4-tetrahydropyranyloxy, 4,5,6-triacetyloxy-2-tetrahydropyranyloxy, 2-butyryloxy-3-tetrahydropyranyloxy, 6-pentanoyloxy-3-tetrahydropyranyloxy, 4-hexanoyloxy-3-tetrahydropyranyloxy, 3,4,5-trihydroxy-6-acetyloxy-2-tetrahydropyranyloxy, 6-hydroxymethyl-2-tetrahydropyranyloxy, 4-(2-hydroxyethyl)-2-tetrahydropyranyloxy, 4,6-dihydroxymethyl-4-tetrahydropyranyloxy, 4,5,6-dihydroxymethyl-2-tetrahydropyranyloxy, 2-(3-hydroxypropyl)-3-tetrahydropyranyloxy, 6-acetyloxyethyl-2-tetrahydropyranyloxy, 4-(2-acetyloxyethyl)-2-tetrahydropyranyloxy, 4,6-diacetyloxymethyl-4-tetrahydropyranyloxy, 4,5,6-triacetyloxymethyl-2-tetrahydropyranyloxy, 2-(3-propionyloxypropyl)-3-tetrahydropyranyloxy, 6-(4-butyryloxybutyl)-4-tetrahydropyranyloxy, 6-(5-hydroxypentyl)-2-tetrahydropyranyloxy, 4-(6-hexanoyloxyhexyl)-3-tetrahydropyranyloxy, 3,4,5-trihydroxymethyl-6-acetyloxymethyltetrahydropyranyloxy and the like.

The piperazinyl-lower alkyl group which may have lower alkyl groups as substituents on the piperazine ring, can be exemplified by piperazinylalkyl groups each having a $C_{1-6}$ straight-chain or branched-chain lower alkyl moiety, which may each have one to three $C_{1-6}$ straight-chain or branched-chain alkyl groups as substituent(s) on the piperazine ring, such as (1-piperazinyl)methyl, 2-(1-piperazinyl)ethyl, 1-(1-piperazinyl)ethyl, 3-(1-piperazinyl)propyl, 4-(1-piperazinyl) butyl, 5-(1-piperazinyl)pentyl, 6-(1-piperazinyl)hexyl, 1,1-dimethyl-2-(1-piperazinyl)ethyl, 2-methyl-3-(1-piperazinyl) propyl, (4-methyl-1-piperazinyl)methyl, 2-(4-ethyl-1-piperazinyl)ethyl, 1-(4-propyl-1-piperazinyl)ethyl, 3-(4-butyl-1-piperazinyl)propyl, 4-(4-pentyl-1-piperazinyl)butyl, 5-(4-hexyl-1-piperazinyl)pentyl, 6-(3,4-dimethyl-1-piperazinyl)hexyl, 1,1-dimethyl-(3,4,5-trimethyl-1-piperazinyl)ethyl and the like.

As to the lower alkoxycarbonyl-substituted lower alkoxy group, there can be mentioned $C_{1-6}$ straight-chain or branched-chain alkoxycarbonylalkoxy groups each having a $C_{1-6}$ straight-chain or branched-chain alkoxy moiety, such as methoxycarbonylmethoxy, 3-methoxycarbonylpropoxy, ethoxycarbonylmethoxy, 4-ethoxycarbonylbutoxy, 6-propoxycarbonylhexyloxy, 5-isopropoxycarbonylpentyloxy, 1,1-dimethyl-2-butoxycarbonylethoxy, 2-methyl-3-tert-butoxycarbonylpropoxy, 2-pentyoxycarbonylethoxy, hexyloxycarbonylmethoxy and the like.

As to the carboxy-substituted lower alkoxy group, there can be mentioned carboxyalkoxy groups each having a $C_{1-6}$ straight-chain or branched-chain alkoxy moiety, such as carboxymethoxy, 2-carboxyethoxy, 1-carboxyethoxyl; 3-carboxypropyl, 4-carboxybutoxy, 5-carboxypentyloxy, 6-carboxyhexyloxy, 1,1-dimethyl-2-carboxyethoxy, 2-methyl-3-carboxypropoxy and the like.

As to the lower alkoxy-substituted alkoxy group, there can be mentioned alkoxyalkoxy groups each having a $C_{1-6}$ straight-chain or branched-chain alkoxy moiety, such as methoxymethoxy, 3-methoxypropoxy, ethoxymethoxy, 4-ethoxybutoxy, 6-propoxyhexyloxy, 5-isopropoxypentyloxy, 1,1-dimethyl-2-butoxyethoxy, 2-methyl-3-tert-butoxypropoxy, 2-pentyloxyethoxy, hexyloxymethoxy and the like.

The lower alkyl group having hydroxyl groups can be exemplified by $C_{1-6}$ straight-chain or branched-chain alkyl groups each having one to three hydroxyl groups, such as hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethy, 5,5,4-trihydroxypentyl, 5-hydroxypentyl, 6-hydroxyhexyl, 1-hydroxyisopropyl, 2-methyl-3-hydroxypropyl and the like.

The lower alkenyl group can be exemplified by $C_{1-6}$ straight-chain or branched-chain alkenyl groups such as vinyl, allyl, 2-butenyl, 3-butenyl, 1-methylallyl, 2-pentenyl, 2-hexenyl and the like.

The aminothiocarbonyloxy group which may have lower alkyl groups as substituents, can be exemplified by thiocarbonyloxy groups each having an amino group which may have one to two $C_{1-6}$ straight-chain or branched-chain alkyl groups as substituent(s), such as thiocarbamoyloxy, methylaminothiocarbonyloxy, ethylaminothiocarbonyloxy, propylaminothiocarbonyloxy, isopropylaminothiocarbonyloxy, butylaminothiocarbonyloxy, pentylaminothiocarbonyloxy, hexylaminothiocarbonyloxy, dimethylaminothiocarbonyloxy, (N-ethyl-N-propylamino) thiocarbonyloxy, (N-methyl-N-hexylamino)-thiocarbonyloxy and the like.

The aminocarbonylthio group which may have lower alkyl groups as substituents, can be exemplified by carbonylthio groups having an amino group which may have one to two $C_{1-6}$ straight-chain or branched-chain alkyl groups as substituent(s), such as aminocarbonylthio, methylaminocarbonylthio, ethylaminocarbonylthio, propylaminocarbonylthio, 3-isopropylaminocarbonylthio, butylaminocarbonylthio, pentylaminocarbonylthio, hexylaminocarbonylthio, dimethylaminocarbonylthio, (N-ethyl-N-propylamino)carbonylthio, (N-methyl-N-hexylamino)carbonylthio and the like.

As to the lower alkanoyl-substituted lower alkyl group, there can be mentioned $C_{1-6}$ straight-chain or branched-chain alkyl groups each having one to three $C_{1-6}$ straight-chain or branched-chain alkanoyl groups, such as formylmethyl, acetylmethyl, 2-propionylethyl, 1-butyrylethyl, 3-acetylpropyl, 2,3-diacetylpropyl, 4-isobutyrylbutyl, 5-pentanoylpentyl, 6-tert-butylcarbonylhexyl, 1,1-dimethyl-2-hexanoylethyl, 5,5,4-triacetylpentyl, 2-methyl-3-acetylpropyl and the like.

The phenyl group which may have one to three lower alkoxy groups as substituents on the phenyl ring, can be exemplified by phenyl rings which may each have one to three $C_{1-6}$ straight-chain or branched-chain alkoxy groups as substituents on the phenyl ring, such as phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3-propoxy-4-methoxyphenyl, 3,5-dimethoxyphenyl, 3,4-dipentyloxyphenyl, 3,4,5-trimethoxyphenyl, 3-methoxy-4-ethoxyphenyl and the like.

The pyridyl group which may have an oxo group, can be exemplified by pyridyl groups which may each have an oxo group, such as 2-pyridyl, 3-pyridyl, 4-pyridyl, 2-oxo-3-pyridyl, 4-oxo-2-pyridyl, 1-oxo-3-pyridyl, 3-oxo-2-pyridyl and the like.

The quinolyl group which may have an oxo group, can be exemplified by quinolyl groups which may each have an oxo group, such as 2-quinolyl, 3-quinolyl, 4-quinolyl, 5-quinolyl, 6-quinolyl, 7-quinolyl, 8-quinolyl, 2-oxo-4-quinolyl, 2-oxo-7-quinolyl, 2-oxo-5-quinolyl, 2-oxo-8-quinolyl, 4-oxo-6-quinolyl and the like.

The phenyl group having, as substituents on the phenyl ring, one to three groups selected from the group consisting of a lower alkanoyloxy group, a hydroxysulfonyloxy group, a cyano group, an amidino group, a nitro group, a lower alkylsulfonyl group and a tetrahydropyranyloxy group which may have, as substituents, one to four groups selected from the group consisting of a hydroxyl group, a lower alkoxycarbonyl group, a phenyl-lower alkoxy group, a lower alkanoyloxy-substituted lower alkyl group and a lower alkanoyloxy group, can be exemplified by phenyl groups each having, as substituent(s) on the phenyl ring, one to three groups selected from the group consisting of a $C_{1-6}$straight-chain or branched-chain alkanoyloxy group, a hydroxysulfonyloxy group, a cyano group, an amidino group, a nitro group, a $C_{1-6}$ straight-chain or branched-chain alkylsulfonyl group and a tetrahydropyranyloxy group which may have, as substituents, one to four groups selected from the group consisting of a hydroxyl group, a $C_{1-6}$ straight-chain or branched-chain alkoxycarbonyl group, a phenylalkoxy group having a $C_{1-6}$ straight-chain or branched-chain alkoxy moiety, a $C_{1-6}$ straight-chain or branched-chain alkyl group having one to three $C_{2-6}$ straight-chain or branched-chain alkanoyloxy groups, and a $C_{2-6}$ straight-chain or branched-chain alkanoyloxy group, such as 2-acetyloxyphenyl, 3-acetyloxyphenyl, 4-acetyloxyphenyl, 2-formyloxyphenyl, 3-propionyloxyphenyl, 4-isobutyryloxyphenyl, 2-pentanoyloxyphenyl, 3-hexanoyloxyphenyl, 3,4-diacetyloxyphenyl, 2,5-diacetyloxyphenyl, 3,5-diacetyloxyphenyl, 2,5-diacetyloxyphenyl, 3,4,5-triaceyloxyphenyl, 4-hydroxysulfonyloxyphenyl, 3-hydroxysulfonyloxyphenyl, 2-hydroxysulfonyloxyphenyl, 4-cyanophenyl, 3-cyanophenyl, 2-cyanophenyl, 4-amidinophenyl, 3-amidinophenyl, 2-amidinophenyl, 2-nitrophenyl, 3-nitrophenyl, 4-nitrophenyl, 3,4-dinitrophenyl, 2,5-dinitrophenyl, 2,6-dinitrophenyl, 3,4,5-trinitrophenyl, 3,5-dinitro-4-acetyloxyphenyl, 4-methylsulfonylphenyl, 2-methylsulfonylphenyl, 3-methylsulfonylphenyl, 2-ethylsulfonylphenyl, 4-isopropylsulfonylphenyl, 4-pentylsulfonylphenyl, 4-hexylsulfonylphenyl, 3,4-dimethylsulfonylphenyl, 3,4-diethylsulfonylphenyl, 2,5-dimethylsulfonylphenyl, 2,6-dimethylsulfonylphenyl, 3,4,5-trimethylsulfonylphenyl, 4-(2,3,4,6-tetra-o-acetyl-β-D-glucopyranosyloxy)phenyl, 4-(β-D-glucopyranosyloxy) phenyl, 4-(2,3,4,6-tetra-o-benzyl-β-D-glucopyranosyloxy) phenyl and the like.

The amino group which may have a lower alkanoyl group, can be exemplified by amino groups which may each have a $C_{1-6}$ straight-chain or branched-chain alkanoyl group, such as amino, formylamino, acetylamino, propionylamino, butyrylamino, isobutyrylamino, pentanoylamino, tertbutylcarbonylamino, pentanoylamino, hexanoylamino and the like.

The phenyl group which may have groups selected from the group consisting of a thiazolyl group having, as a substituent on the thiazolyl ring, a phenyl group which may have lower alkoxy groups on the phenyl ring, a carboxyl group and a hydroxyl group, can be exemplified by phenyl groups which may each have one to three groups selected from the group consisting of a thiazolyl group having, as a substituent on the thiazolyl ring, a phenyl group which may have one to three $C_{1-6}$ straight-chain or branched-chain alkoxy groups on the phenyl ring, a carboxyl group and a hydroxyl group, such as phenyl, 2-(3,4-diethoxyphenyl)-4-thiazolylphenyl, [2-(4-methoxyphenyl)-4-thiazolyl]phenyl, [4-(3,4,5-trimethoxyphenyl)-2-thiazolyl]phenyl, [5-(3-propoxyphenyl)-2-thiazolyl]-phenyl, [2-(2-butoxyphenyl)-4-thiazolyl]phenyl, 2-hydroxy-3-carboxyphenyl, 2-hydroxyphenyl, 3-hydroxyphenyl, 4-hydroxyphenyl, 3,4-dihydroxyphenyl, 3,5-dihydroxyphenyl, 2,5-dihydroxyphenyl, 2,4-dihydroxyphenyl, 2,6-dihydroxyphenyl, 3,4,5-trihydroxyphenyl, 2-carboxyphenyl, 3-carboxyphenyl, 4-carboxyphenyl, 3,4-dicarboxyphenyl, 2,5-dicarboxyphenyl, 2,6-dicarboxyphenyl, 3,4,5-tricarboxyphenyl, 3-carboxy-4-hydroxyphenyl, 3-carboxy-6-hydroxyphenyl and the like.

As the piperidinyl-lower alkyl group, there can be mentioned piperidinylalkyl groups each having a $C_{1-6}$ straight-chain or branched-chain alkyl moiety, such as (1-piperidinyl)methyl, 2-(1-piperidinyl)ethyl, 1-(1-piperidinyl)ethyl, 3-(1-piperidinyl)propyl, 4-(1-piperidinyl) butyl, 5-(2-piperidinyl)pentyl, 6-(3-piperidinyl)hexyl, 1,1-dimethyl-2-(4-piperidinyl)ethyl, 2-methyl-3-(1-piperidinyl) propyl and the like.

The alkoxycarbonyl group can be exemplified by, in addition to the above-mentioned lower alkoxycarbonyl groups, $C_{1-18}$ straight-chain or branched-chain alkoxycarbonyl groups, such as heptyloxycarbonyl, octyloxycarbonyl, nonyloxycarbonyl, decyloxycarbonyl, undecyloxycarbonyl, dodecyloxycarbonyl, tridecyloxycarbonyl, tetradecyloxycarbonyl, pentadecyloxycarbonyl, hexadecyloxycarbonyl, heptadecyloxycarbonyl, octadecyloxycarbonyl and the like.

The amino-lower alkoxycarbonyl group which may have a lower alkyl group as a substituent, can be exemplified by $C_{1-6}$ straight-chain or branched-chain alkoxycarbonyl groups each having an amino group which may have one to two $C_{1-6}$ straight-chain or branched-chain alkyl groups as substituents, such as aminomethoxycarbonyl, 2-aminoethoxycarbonyl, 1-aminoethoxycarbonyl, 3-aminopropoxycarbonyl, 4-aminobutoxycarbonyl, 5-aminopentyloxycarbonyl, 6-aminohexyloxycarbonyl, 1,1-dimethyl-2-aminoethoxycarbonyl, 2-methyl-3-aminopropoxycarbonyl, methylaminomethoxycarbonyl, 1-ethylaminoethoxycarbonyl, 2-propylaminoethoxycarbonyl, 3-isopropylaminopropoxycarbonyl, 4-butylaminobutoxycarbonyl, 5-pentylaminopentyloxycarbonyl, 6-hexylaminohexyloxycarbonyl, dimethylaminomethoxycarbonyl, 2-dimethylaminoethoxycarbonyl, 3-dimethylaminopropoxycarbonyl, (N-ethyl-N-propylamino)-methoxycarbonyl, 2-(N-methyl-N-hexylamino)ethoxycarbonyl and the like.

The phenyl-lower alkoxycarbonyl group-can be exemplified by phenylalkoxycarbonyl groups each having a $C_{1-6}$ straight-chain or branched-chain alkoxy moiety, such as benzyloxycarbonyl, 2-phenylethoxycarbonyl, 1-phenylethoxycarbonyl, 3-phenylpropoxycarbonyl, 4-phenylbutoxycarbonyl, 1,1-dimethyl-2-phenylethoxycarbonyl, 5-phenylpentyloxycarbonyl, 6-phenylhexyloxycarbonyl, 2-methyl-3-phenylpropoxycarbonyl and the like.

The lower alkynyl group there can be mentioned alkynyl groups each having $C_{2-6}$ straight-chain or branched-chain alkynyl moiety, such as ethynyl, 2-propynyl, 2-butynyl, 3-butynyl, 1-methyl-2-propynyl, 2-pentynyl, 2-hexynyl and the like.

As to the carboxy-substituted lower alkyl group, there can be mentioned carboxyalkyl groups each having a $C_{1-6}$ straight-chain or branched-chain alkyl moiety, such as carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, 2-methyl-3-carboxypropyl and the like.

As to the lower alkoxycarbonyl-lower alkenyl group, there can be mentioned alkoxycarbonylalkenyl groups each having a $C_{1-6}$ straight-chain or branched-chain alkoxy moiety and a $C_{2-6}$ straight-chain or branched-chain alkenyl moiety, such as 2-methoxycarbonylvinyl, 3-methoxycarbonylallyl, 2-ethoxycarbonylvinyl, 4-ethoxycarbonyl-2-butenyl, 6-propoxycarbonyl-3-hexenyl, 5-isopropoxycarbonyl-1-pentenyl, 1,1-dimethyl-2-butoxycarbonyl-2-propenyl, 2-methyl-3-tertbutoxycarbonyl-1-propenyl, 2-pentyloxycarbonylvinyl, 4-hexyloxycarbonyl-1-butenyl and the like.

As to the carboxy-substituted lower alkenyl group, there can be mentioned carboxyalkenyl groups each having a $C_{2-6}$ straight-chain or branched-chain alkenyl moiety, such as 2-carboxyvinyl, 3-carboxyallyl, 4-carboxy-2-butenyl, 6-carboxy-3-hexenyl, 5-carboxy-1-pentenyl, 1,1-dimethyl-2-carboxy-2-propenyl, 2-methyl-3-carboxy-1-propenyl, 5-carboxy-4-pentenyl, 4-carboxy-1-butenyl and the like.

The five- or six-membered saturated heterocyclic ring which $R^{23}$ and $R^{24}$ as well as the adjacent nitrogen atom being bonded thereto may form together with or without other nitrogen atom or oxygen atom, can be exemplified by piperazinyl, pyrrolidinyl, morpholinyl and piperidinyl.

The above heterocyclic ring substituted with a lower alkyl group can be exemplified by above heterocyclic rings each substituted with a $C_{1-6}$ straight-chain or branched-chain alkyl group, Such as 4-methylpiperazinyl, 4-ethylpiperazinyl, 3-ethylpyrrolidinyl, 2-propylpyrrolidinyl, 4-butylpiperidinyl, 3-pentylmorpholino, 2-hexylpiperazinyl and the like.

The lower alkylsulfonyloxy group which may have halogen atoms, can be exemplified by $C_{1-6}$ straight-chain or branched-chain alkylsulfonyloxy groups which may each have one to three halogen atoms, such as methylsulfonyloxy, ethylsulfonyloxy, propylsulfonyloxy, isopropylsulfonyloxy, butylsulfonyloxy, tert-butylsulfonyloxy, pentylsulfonyloxy, hexylsulfonyloxy, chloromethylsulfonyloxy, bromomethylsulfonyloxy, iodomethylsulfonyloxy, trifluoromethylsulfonyloxy, 2-fluoroethylsulfonyloxy, 2,2-difluoroethylsulfonyloxy, 2,2,2-trifluoroethylsulfonyloxy, 3-chloropropylsulfonyloxy, 4-chlorobutylsulfonyloxy, 3,4-dichlorobutylsulfonyloxy, 3-fluoropentylsulfonyloxy, 2,3,4-trifluoropentylsulfonyloxy, 2,3-dichlorohexylsulfonyloxy, 6,6-dibromohexylsulfonyloxy and the like.

As the lower alkoxy-substituted lower alkoxycarbonyl group, there can be mentioned $C_{1-6}$ straight-chain or branched-chain alkoxyalkoxycarbonyl groups each having a $C_{1-6}$ straight-chain or branched-chain alkoxy moiety, such as methoxymethoxycarbonyl, 3-methoxypropoxycarbonyl, ethoxymethoxycarbonyl, 4-ethoxybutoxycarbonyl, 6-propoxyhexyloxycarbonyl, 5-isopropoxypentyloxycarbonyl, 1,1-dimethyl-2-butoxyethoxycarbonyl, 2-methyl-3-tert-butoxypropoxycarbonyl, 2-pentyloxyethoxycarbonyl, hexyloxymethoxycarbonyl and the like.

The phenyl group which may have one to three lower alkoxy groups as substituents on the phenyl ring, can be exemplified by phenyl groups which may each have one to three $C_{1-6}$ straight-chain or branched-chain alkoxy groups as substituents on the phenyl ring, such as phenyl, 2-methoxyphenyl, 3-methoxyphenyl, 4-ethoxyphenyl, 2-ethoxyphenyl, 3-ethoxyphenyl, 4-methoxyphenyl, 4-isopropoxyphenyl, 3-butoxyphenyl, 4-pentyloxyphenyl, 4-hexyloxyphenyl, 3,4-dimethoxyphenyl, 3-ethoxy-4-methoxyphenyl, 2,3-dimethoxyphenyl, 3,4-diethoxyphenyl, 3,5-dimethoxyphenyl, 2,5-dimethoxyphenyl, 2,6-dimethoxyphenyl, 3,4,5-trimethoxyphenyl, 3,4-dipentyloxyphenyl and the like.

The pyridyl group which may have an oxo group, can be exemplified by pyridyl groups which may each have an oxo group, such as pyridyl, 2-oxopyridyl, 3-oxopyridyl, 4-oxopyridyl and the like.

The quinolyl group which may have an oxo group, can be exemplified by 2-oxoquinolyl and 4-oxoquinolyl.

The phenyl group having, as substituent(s) on the phenyl ring, one to three groups selected from the group consisting of a lower alkanoyloxy group, a hydroxysulfonyloxy group, a cyano group, an amidino group, a nitro group, a lower alkylsulfonyl group, a tetrahydropranyloxy group which may have, as substituent(s), one to four groups selected from the group consisting of a hydroxyl group, a lower alkoxy-carbonyl group, a phenyl-lower alkoxy group, a hydroxyl group- or lower alkanoyloxy group-substituted lower alkyl group and a lower alkanoyloxy group, a phenyl group which may have groups selected from the group consisting of a thiazolyl group having, as a substituent on the thiazolyl ring, a phenyl group which may have lower alkoxy groups on the phenyl ring, a carboxyl group and a hydroxyl group, a lower alkyl group having hydroxyl groups, and a group

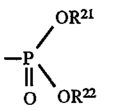

(wherein $R^{21}$ and $R^{22}$ are the same as defined above), can be exemplified by phenyl groups each having, as substituent(s) on the phenyl ring, one to three groups selected from the group consisting of a $C_{1-6}$ straight-chain or branched-chain alkanoyloxy group, a hydroxysulfonyloxy group, a cyano group, an amidino group, a nitro group, a $C_{1-6}$ straight-chain or branched-chain alkylthio group, a $C_{1-6}$ straight-chain or branched-chain alkylsulfonyl group, a tetrahydropranyloxy group which may have, as substituents, one to four groups selected from the group consisting of a hydroxyl group, a $C_{1-6}$straight-chain or branched-chain alkoxycarbonyl group, a phenylalkoxy group having a $C_{1-6}$ straight-chain or branched-chain alkoxy moiety, a $C_{1-6}$ straight-chain or branched-chain alkyl group having one to three hydroxyl groups or one to three $C_{2-6}$ straight-chain or branched-chain alkanoyloxy groups and a $C_{2-6}$ straight-chain or branched-chain alkanoyloxy group, a phenyl group which may have one to three groups selected from the group consisting of a thiazolyl group having, as a substituent on the thiazolyl ring, a phenyl group which may have one to three $C_{1-6}$ straight-chain or branched-chain alkoxy groups on the phenyl ring, .a carboxyl group and a hydroxyl group, a $C_{1-6}$ straight-chain or branched-chain alkyl group having one to three hydroxyl groups, and a group

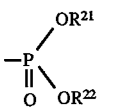

(wherein $R^{21}$ and $R^{22}$, which may be the same or different, each represent a hydrogen atom or a $C_{1-6}$ straight-chain or branched-chain alkyl group), such as 2-methylthiophenyl, 3-methylthiophenyl, 4-methylthiophenyl, 2-ethylthiophenyl, 3-ethylthiophenyl, 4-ethylthiophenyl, 4-isopropylthiophenyl, 4-pentylthiophenyl, 4-hexylthiophenyl, 3,4-dimethylthiophenyl, 3,4-diethylthiophenyl, 2-acetyloxyphenyl, 3-acetyloxyphenyl, 4-acetyloxyphenyl, 2-formyloxyphenyl, 3-propionyloxyphenyl, 4-isobutyryloxyphenyl, 2-pentanoyloxyphenyl, 3-hexanoyloxyphenyl, 3,4-diacetyloxyphenyl, 3,5-diacetyloxyphenyl, 2,5-diacetyloxyphenyl, 3,4,5-triacetyloxyphenyl-dimethylthiophenyl, 2,6-dimethylthiophenyl, 3,4,5-trimethylthiophenyl, 3-phenylphenyl, 4-phenylphenyl, 2-methylsulfonylphenyl, 3-methylsulfonylphenyl, 4-methylsulfonylphenyl, 2-ethylsulfonylphenyl, 4-isopropylsulfonylphenyl, 4-pentylsulfonylphenyl, 4-hexylsulfonylphenyl, 3,4-dimethylsulfonylphenyl, 2,5-dimethylsulfonylphenyl, 2,6-dimethylsulfonylphenyl, 3,4,5-trimethylsulfonylphenyl, 2-amidinophenyl, 4-amidinophenyl, 3-amidinophenyl, 3-nitrophenyl, 4-hydroxysulfonyloxyphenyl, 3-hydroxysulfonyloxyphenyl, 2-hydroxysulfonyloxyphenyl, 4-(2,3,4,6-tetra-O-acetyl-β-D-glucopyranosyloxy)phenyl, 4-(β-D-glucopyranosyloxy) phenyl, 4-(2,3,4,6-tetra-O-benzyl-β-D-glucopyranosyloxy) phenyl, 3,5-bis(dimethylamino)phenyl, 2-nitrophenyl, 4-nitrophenyl, 3,4-dinitrophenyl, 3,4,5-trinitrophenyl, 3,5-dinitrophenyl, 2-cyanophenyl, 4-cyanophenyl, 3-cyanophenyl, 3-(2,3-dihydroxypropyl)phenyl, 3-(2-hydroxyethyl)phenyl, 4-(2-hydroxy-3-carboxyphenyl) phenyl, 4-[2-(3,4-diethoxyphenyl-4-thiazolyl]phenyl, 3-hydroxymethylphenyl,

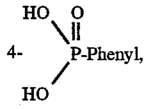

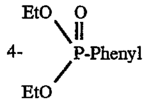

and the like.

As to the lower alkoxy-substituted lower alkyl group, there can be mentioned alkoxyalkyl groups each having a $C_{1-6}$ straight-chain or branched-chain alkoxy moiety and a 1–6 straight-chain or branched-chain alkyl moiety, such as methoxymethyl, 3-methoxypropyl, ethoxymethyl, 4-ethoxybutyl, 6-propoxyhexyl, 5-isopropoxypentyl, 1,1-dimethyl-2-butoxyethyl, 2-methyl-3-tert-butoxypropyl, 2-pentyloxyethyl, hexyloxymethyl and the like.

The lower alkenyl group having halogen atoms can be exemplified by $C_{2-6}$ straight-chain or branched-chain alkenyl groups each having one to three halogen atoms, such as 2,2-dibromovinyl, 2-chlorovinyl, 1-fluorovinyl, 3-iodoallyl, 4,4-dichloro-2-butenyl, 4,4,3-tribromo-3-butenyl, 3-chloro-1-methylallyl, 5-bromo-2-pentenyl, 5,6-difluoro-2-hexenyl and the like.

As the phenyl-lower alkyl group, there can be mentioned phenylalkyl groups each having a $C_{1-6}$ straight-chain or branched-chain alkyl moiety, such as benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl and the like.

The compound of general formula (I) according to the present invention can be produced by, for example, the processes shown below.

[Reaction scheme-1]

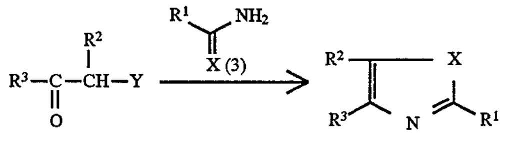

(2) (1)

(wherein X, $R^1$, $R^2$ and $R^3$ are the same as defined above; Y represents a halogen atom).

The reaction between the compound (2) and the compound (3) can be conducted by heating in an appropriate solvent. The solvent can be exemplified by alcohols such as methanol, ethanol, propanol, butanol, 3-methoxy-1-butanol, ethyl cellosolve, methyl cellosolve and the like; aromatic hydrocarbons such as benzene, toluene, xylene, o-dichlorobenzene and the like; ethers such as diethyl ether, tetrahydrofuran, dioxane, diglyme, monoglyme and the like; halogenated hydrocarbons such as dichloromethane, chloroform, carbon tetrachloride and the like; polar solvents such as dimethylformamide, dimethyl sulfoxide, hexamethylphosphoric triamide, acetonitrile and the like; and mixed solvents thereof. The reaction is conducted ordinarily at room temperature to 150° C., preferably at about room temperature to 100° C. and is completed in about 1–15 hours.

The proper amount of the compound (3) used is at least 1 mole, preferably about 1 to 1.5 moles per 1 mole of the compound (2).

[Reaction scheme-2]

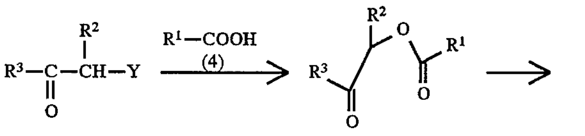

(2) (5)

(1a)

(wherein $R^1$, $R^2$, $R^3$ and Y are the same as defined above).

The reaction between the compound (2) and the compound (4) can be conducted in an appropriate solvent in the presence of a basic compound. The solvent can be exemplified by lower alcohols such as methanol, ethanol, propanol and the like; ethers such as diethyl ether, tetrahydrofuran, dioxane, ethylene glycol monomethyl ether and the like; halogenated hydrocarbons such as dichloromethane, chloroform, carbon tetrachloride and the like; aromatic hydrocarbons such as benzene, toluene, xylene and the like; esters such as methyl acetate, ethyl acetate and the like; ketones such as acetone, methyl ethyl ketone and the like; polar solvents such as acetonitrile, dimethylformamide, dimethyl sulfoxide, hexamethylphosphoric triamide and the like; and mixed solvents thereof. The basic compound can be exemplified by inorganic bases such as sodium hydroxide, potassium hydroxide, sodium carbonate, potassium carbonate, sodium hydrogencarbonate, potassium hydrogencarbonate, sodium hydride and the like; alkali metals such as metallic sodium, metallic potassium and the like; alkali metal alcoholates such as sodium methylate, sodium ethylate and the like; and organic bases such as triethylamine, pyridine, N,N-dimethylaniline, N-methylmorpholine, 4-methylaminopyridine, bicyclo[4,3,0]nonene-5 (DBN), 1,8-diazabicyclo[5,4,0]-undecene-7 (DBU), 1-4-diazabicyclo[2,2,2]octane (DABCO) and the like.

The proper amount of the compound (4) used is at least 1 mole, preferably about 1 to 1.5 moles per 1 mole of the compound (2).

The reaction is conducted ordinarily at room temperature to 200° C., preferably at room temperature to about 150° C. and is completed in about 1–5 hours.

The reaction for converting the compound (5) into the compound (1a) can be conducted in an appropriate solvent in the presence of an ammonia water or an ammonium salt such as ammonium acetate, ammonium chloride, ammonium sulfate or the like. The solvent can be any of the solvents usable in the reaction between the compound (2) and the compound (4); besides them, there can also be mentioned alkanoic acids (e.g. acetic acid), etc. The proper amount of the ammonia water or ammonium salt used is at least 1 mole, preferably 1 to 5 moles per 1 mole of the compound (5). The reaction is conducted ordinarily at room temperature to 200° C., preferably at about room temperature to 150° C. and is completed in about 1–5 hours.

[Reaction scheme-3]

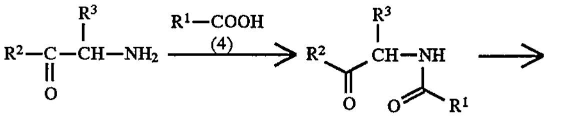

(6) (7)

(1b)

(wherein $R^1$, $R^2$ and $R^3$ are the same as defined above).

The reaction between the compound (6) and the compound (4) can be achieved by subjecting them to an ordinary amide bonding formation reaction.

In this case, as to the carboxylic acid (4), an activated compound thereof may be used. The conditions used in the amide bonding formation reaction can be those used in ordinary amide bonding formation reactions. For example, there can be used (a) a mixed acid anhydride method, i.e. a method which comprises reacting a carboxylic acid (4) with an alkylhalocarboxylic acid to obtain a mixed acid anhydride and reacting the anhydride with a compound (6); (b) an active ester or active amide method, i.e. a method which comprises converting a carboxylic acid (4) into an active ester such as p-nitrophenyl ester, N-hydroxysuccinimide ester, 1-hydroxybenzotriazole ester or the like, or into an active amide with benzoxazolin-2-thion and then reacting the active ester or active amide with a compound (6); (c) a carbodiimide method, i.e. a method which comprises subjecting a carboxylic acid (4) and a compound (6) to dehydration in the presence of a dehydrating agent such as dicyclohexylcarbodiimide, carbonyldiimidazole or the like; (d) a carboxylic acid halide method, i.e. a method which comprises converting a carboxylic acid (4) into a halide and reacting the halide with a compound (6); and (e) other methods such as a method which comprises reacting a carboxylic acid (4) with a dehydrating agent such as acetic anhydride or the like to convert into a carboxylic acid anhydride and reacting the anhydride with a compound (4) or a method which comprises converting a carboxylic acid (4) into an ester and reacting the ester with a compound (6) at a high temperature at a high pressure. There can also be used a method which comprises activating a carboxylic acid (4) with a phosphorus compound such as triphenylphosphine, diethyl chlorophosphate or the like and reacting the reaction product with a compound (6).

As to the alkylhalocarboxylic acid used in the mixed acid anhydride method, there can be mentioned, for example, methyl chloroformate, methyl bromoformate, ethyl chloroformate, ethylbromoformate and isobutyl chloroformate. The mixed acid anhydride can be obtained by an ordinary Schotten-Baumann reaction and ordinarily, without being subjected to an isolation procedure, is reacted with a compound (6), whereby a compound (7) can be produced. The Schotten-Baumann reaction is ordinarily conducted in the presence of a basic compound. The basic compound is those conventionally used in the Schotten-Baumann reaction; and there can be mentioned organic bases such as triethylamine, trimethylamine, pyridine, dimethylaniline, N-methyl-morpholine, 4-dimethylaminopyridine, DBN, DBU, DABCO and the like, and inorganic bases such as potassium carbonate, sodium carbonate, potassium hydrogen-carbonate, sodium hydrogencarbonate and the like. The reaction is conducted at about −20° C. to 100° C., preferably 0°–50° C. The reaction time is about 5 minutes to 10 hours, preferably 5 minutes to 2 hours. The reaction between the thus obtained mixed acid anhydride and the compound (6) is conducted at about −20° C. to 150° C., preferably 10°–50° C. for about 5 minutes to 10 hours, preferably about 5 minutes to 5 hours. The mixed acid anhydride method needs no solvent, but is generally conducted in a solvent. The solvent can be any of those conventionally used in the mixed acid anhydride method, and there can be specifically mentioned, for example, halogenated hydrocarbons such as methylene chloride, chloroform, dichloroethane and the like, aromatic hydrocarbons such as benzene, toluene, xylene and the like, ethers such as diethyl ether, diisopropyl ether, tetrahydrofuran, dimethoxyethane and the like, esters such as methyl acetate, ethyl acetate and the like, and aprotic polar solvents such as dimethylformamide, dimethyl sulfoxide, hexamethylphosphoric triamide and the like. In the above method, the amounts of the carboxylic acid (4), the alkylhalocarboxylic acid and the compound (6) used are ordinarily at least equimolar, but preferably the alkylhalocarboxylic acid and the compound (6) are used each in an amount of 1–2 moles per 1 mole of the carboxylic acid (4).

The active ester or active amide method (b), when a case of using, for example, benzoxazolin-2-thionamide is mentioned, is conducted by carrying out a reaction at 0°–150° C., preferably 10°–100° C. for 0.5–75 hours in an appropriate solvent not affecting the reaction, for example, the same solvent as used in the above mixed acid anhydride method, or 1-methyl-2-pyrrolidone. The amounts of the compound (6) and benzoxazolin-2-thionamide used are such that the latter is used in an amount of at least 1 mole, preferably 1–2 moles per 1 mole of the former. In a case using an N-hydroxysuccinimide ester, the reaction proceeds advantageously by using an appropriate base, for example, the same base as used in the carboxylic acid halide method to be described later.

The carboxylic acid halide method (c) is conducted by reacting a carboxylic acid (4) with a halogenating agent to convert into a carboxylic acid halide and, after or without isolating and purifying the halide, reacting the halide with a compound (6). The reaction between the carboxylic acid halide and the compound (6) is conducted in an appropriate solvent in the presence or absence of a dehydrohalogenating agent. As to the dehydrohalogenating agent, there is ordinarily used a basic compound, and there can be mentioned the basic compounds used in the above Schotten-Baumann reaction, sodium hydroxide, potassium hydroxide, sodium hydride, potassium hydride, alkali metal alcholates (e.g. sodium methylate, sodium ethylate), etc. Incidentally, it is possible to use the compound (6) in an excessive amount to utilize the compound (6) also as a dehydrohalogenating agent. As the solvent, there can be mentioned, for example, water, alcohols (e.g. methanol, ethanol, propanol, butanol, 3-methoxy-1-butanol, ethyl cellosolve, methyl cellosolve), pyridine, acetone, acetonitrile and mixed solvents thereof, in addition to the same solvents as used in the above Schotten-Baumann reaction. The proportions of the compound (6) and the carboxylic acid halide used are not particularly restricted and can be selected from a wide range, but the latter is used in an amount of ordinarily at least 1 mole, preferably 1–5 moles per 1 mole of the former. The reaction is conducted ordinarily at about −30° C. to 180° C., preferably at about 0°–150° C. and is complete generally in 5 minutes to 30 hours. The carboxylic acid halide used is produced by reacting a carboxylic acid (4) with a halogenating agent in the presence or absence of a solvent. The solvent, can be any as long as it gives no influence on the reaction, and includes aromatic hydrocarbons such as benzene, toluene, xylene and the like, halogenated hydrocarbons such as chloroform, methylene chloride, carbon tetrachloride and the like, ethers such as dioxane, tetra-hydrofuran, diethyl ether and the like, dimethylformamide, dimethyl sulfoxide, etc. As the halogenating agent, there can be used ordinary halogenating agents capable of converting the hydroxyl group of carboxylic group into a halogen, and there can be mentioned, for example, thionyl chloride, oxalyl chloride, phosphorus oxychloride, phosphorus oxybromide, phosphorus pentachloride and phosphorus pentabromide. The proportions of the carboxylic acid (4) and the halogenating agent used are not particularly restricted and can be selected appropriately; however, when the reaction is conducted in a solventless state, the latter is used ordinarily in a large excess relative to the former and, when the reaction is conducted in a solvent, the latter is used in an amount of ordinarily at least about 1 mole, preferably 2–4 moles per 1 mole of the former. The reaction temperature and time are not particularly restricted, either, but the reaction is conducted ordinarily at about room temperature to 100° C., preferably at 50°–80° C. for about 30 minutes to 6 hours.

The method which comprises activating a carboxylic acid (4) with a phosphorus compound such as triphenylphosphine, diethyl chlorophosphate, diethyl cyanophosphate or the like and then reacting the resulting product with a compound (6), is conducted in an appropriate solvent. The solvent can be any as long as it gives no influence on the reaction, and specifically includes halogenated hydrocarbons such as dichloromethane, chloroform, dichloroethane and the like, aromatic hydrocarbons such as benzene, toluene, xylene and the like, ethers such as diethyl ether, tetrahydrofuran, dimethoxyethane and the like, esters such as methyl acetate, ethyl acetate and the like, aprotic polar solvents such as dimethylformamide, dimethyl sulfoxide, hexamethylphosphoric triamide and the like, and so forth. In the reaction, the compound (6) per se acts as a basic compound, and accordingly the reaction proceeds advantageously by using it in an amount larger than the stoichiometric amount; however, there may be used, as necessary, other basic compound, for example, an organic base (e.g. triethylamine, trimethylamine, pyridine, dimethylaminopyridine, DBN, DBU, DABCO) or an inorganic base (e.g. potassium carbonate, sodium carbonate, potassium hydrogencarbonate, sodium hydrogencarbonate). The reaction is conducted at about 0°–150° C., preferably at about 0°–100° C. and is complete in about 1–30 hours. The proportions of the phosphorus compound and carboxylic acid (4) used relative to the compound (6) are each ordinarily at least about 1 mole, preferably 1–3 moles per I mole of the compound (6).

The reaction for converting the compound (7) into the compound (1b) can be conducted in a solventless state or in an appropriate solvent in the presence of a sulfurizing agent such as 2,4-bis(4-methoxyphenyl)-1,3-dithia-2,4-diphosphetan-2,4-disulfide (Lawesson's Reagent), phosphorus pentasulfide or the like. The solvent can be any of those used in the reaction between the compound (2) and the compound (4) in the above Reaction scheme-2.

The proper amount of the sulfurizing agent used is ordinarily 0.5–2 moles, preferably 0.5–1.5 moles per 1 mole of the compound (7).

The reaction is conducted ordinarily at 50°–300° C., preferably at about 50° C. to 250° C. and is completed in about 1–7 hours.

The compound (2) as a starting material can be produced by, for example, the method of the following Reaction scheme-4 or -5.

[Reaction scheme-4]

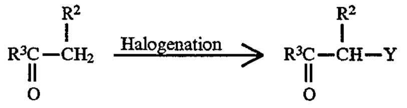

(8) (2)

(wherein $R^2$, $R^3$ and Y are the same as defined above).

The halogenation reaction for the compound (8) can be conducted in an appropriate solvent in the presence of a halogenating .agent. The halogenating agent can be exemplified by halogen molecules (e.g. bromine molecules, chlorine molecules), iodine chloride, sulfuryl chloride, copper compounds (e.g. cuprous bromide) and N-halogenated succinimides (e.g. N-bromo-succinimide, N-chlorosuccinimide). The solvent can be exemplified by halogenated hydrocarbons (e.g. dichloromethane, dichloroethane, chloroform, carbon tetrachloride), fatty acids (e.g. acetic acid, propionic acid) and carbon disulfide.

The proper amount of the halogenating agent used is ordinarily 1–10 moles, preferably 1–5 moles per 1 mole of the compound (8).

The reaction is conducted ordinarily at 0° C. to the boiling point of the solvent used, preferably at about 0° C. to 100° C. and is completed ordinarily in about 5 minutes to 20 hours.

[Reaction scheme-5]

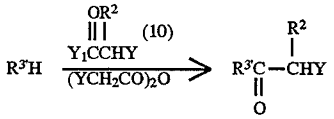

(9) (11) (2a)

(wherein $R^2$ and Y are the same as defined above; $Y_1$ represents a halogen atom; $R^3$ represents the above-mentioned $R^3$ other than a hydrogen atom, a lower alkyl group, a lower alkoxycarbonyl-lower alkyl group, a lower alkoxycarbonyl group, a carbamoyl-lower alkyl group, a phenyl-lower alkyl group which may have a lower alkoxy group as a substituent on the phenyl ring and hydroxyl groups as substituents on the lower alkyl group, a benzoyl group which may have a lower alkoxy group as a substituent on the phenyl ring, a phenyl-lower alkenyl group which may have a lower alkoxy group as a substituent on the phenyl ring, and an adamantyl group).

The reaction between the compound (9) and the compound (10) or the compound (11) is generally called as Friedel-Crafts reaction and can be conducted in an appropriate solvent in the presence of a Lewis acid. The Lewis acid can be any one of Lewis acids generally used in said reaction, and can be exemplified by aluminum chloride, zinc chloride, iron chloride, tin chloride, boron tribromide, boron trifuloride and concentrated sulfuric acid. The solvent can be exemplified by carbon disulfide, aromatic hydrocarbons (e.g. nitrobenzene, chlorobenzene) and halogenated hydrocarbons (e.g. dichloromethane, dichloroethane, carbon tetrachloride, tetrachloroethane). The proper amount of the compound (10) or the compound (11) used is at least 1 mole, preferably 1–5 moles per 1 mole of the compound (9). The proper amount of the Lewis acid used is ordinarily 2–6 moles per 1 mole of the compound (9).

The reaction is conducted ordinarily at 0°–120° C., preferably at about 0°–70° C. and is completed in about 0.5–24 hours.

The compound (3) as a starting material can be produced by, for example, the method of the following Reaction scheme-6 or -7.

[Reaction scheme-6]

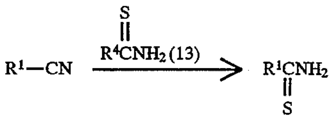

(12) (3a)

($R^1$ is the same as defined above; $R^4$ represents a lower alkyl group).

The reaction between the compound (12) and the compound (13) can be conducted in an appropriate solvent in the presence of an acid.

The solvent can be any of those used in the reaction between the compound (2) and the compound (4) in the reaction scheme 2.

The acid can be exemplified by mineral acids such as hydrochloric acid, hydrobromic acid, sulfuric acid and the like.

The amount of the compound (13) used is ordinarily 1–5 moles, preferably 1–3 moles per 1 mole of the compound (12).

The reaction is conducted ordinarily at room temperature to 200° C., preferably at about room temperature to 150° C. and is complete in about 1–15 hours.

[Reaction scheme-7]

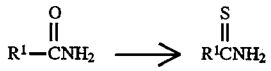

(14) (3b)

(wherein $R^1$ is the same as defined above).

The reaction for converting the compound (14) into the compound (3b) can be conducted in an appropriate solvent in the presence of a° sulfurizing agent.

The solvent can be any of those used in the reaction between the compound (2) and the compound (4) in the reaction scheme 2.

The sulfurizing agent can be exemplified by phosphorus pentasulfide and Lawesson's Reagent.

The proper amount of the sulfurizing agent used is ordinarily 1–10 moles, preferably 1–2 moles per 1 mole of the compound (14).

The reaction is conducted ordinarily at room temperature to 150° C., preferably at about room temperature to 100° C. and is complete in about 10 minutes to 5 hours.

When in general formula (1), $R^1$ or $R^3$ is a 5- to 15-membered monocyclic, bicyclic or tricyclic heterocyclic residual group having at least one tertiary nitrogen atom, the compound (1) can be converted, by oxidation, into a corresponding compound where the at least one nitrogen atom of said heterocyclic residual group is converted into an oxide form (N→0). Also, when in general formula (1), $R^1$ or $R^3$ is a phenyl group having at least one lower alkylthio group, the phenyl group can be converted, by the oxidation under the same conditions, into a phenyl group having at least one lower alkylsulfinyl group or at least one lower alkylsulfonyl group.

When the compound (1) has both of the above two groups (the 5- to 15-membered monocyclic, bicyclic or tricyclic heterocyclic residual group having at least one tertiary nitrogen atom and the phenyl group having at least one lower alkylthio group), then it is possible that the two groups be oxidized simultaneously under the above oxidation conditions. The oxidation product can be easily separated.

These oxidation reactions can be conducted in an appropriate solvent in the presence of an oxidizing agent. The solvent can be exemplified by water, organic acids (e.g. formic acid, acetic acid, trifluoroacetic acid), alcohols (e.g. methanol, ethanol), halogenated hydrocarbons e.g. chloroform, dichloromethane) and mixed solvents thereof. As to the oxidizing agent, there can be mentioned, for example, peracids (e.g. performic acid, peracetic acid, pertrifluoroacetic acid, perbenzoic acid, m-chloroperbenzoic acid, o-carbonylperbenzoic acid), hydrogen peroxide, sodium metaperiodate, bichromic acid, bichromates (e.g. sodium bichromate, potassium bichromate), permanganic acid and permanganates (e.g. potassium permanganate, sodium permanganate).

The proper amount of the oxidizing agent used is ordinarily at least 1 mole, preferably 1–2 moles per 1 mole of the starting material. The reaction is conducted ordinarily at 0°–40° C. preferably at about 0° C. to room temperature and is completed in about 1–15 hours.

When in general formula (1), $R^1$ or $R^3$ is a 5- to 15-membered monocyclic, bicyclic or tricyclic heterocyclic residual group having at least one N-oxide group, the heterocyclic residual group can be converted into a 5- to 15-membered monocyclic, bicyclic or tricyclic heterocyclic residual group having at least one oxo group, by a reaction in a high-boiling solvent (e.g. tetralin, diphenyl ether, diethylene glycol dimethyl ether or acetic anhydride), ordinarily at 100°–250° C., preferably at about 100°–200° C. for about 1–10 hours.

When in general formula (1), $R^1$ or $R^3$ is a 5- to 15-membered monocyclic, bicyclic or tricyclic heterocyclic residual group having at least one oxo group adjacent to the nitrogen atom of the heterocyclic ring, the compound (1) can be converted, by reduction, into a corresponding compound where said at least one oxo group is converted into a methylene group.

The reduction can be conducted by, for example, catalytic hydrogenation in an appropriate solvent in the presence of a catalyst. As to the solvent, there can be mentioned, for example, water, acetic acid, alcohols (e.g. methanol, ethanol, isopropanol), hydrocarbons (e.g. hexane, cyclohexane), ethers (e.g. diethylene glycol dimethyl ether, dioxane, tetrahydrofuran, diethyl ether), esters (e.g. ethyl acetate, methyl acetate), aprotic polar solvents (e.g. dimethylformamide) and mixed solvents thereof. As to the catalyst, there can be used, for example, palladium, palladium black, palladium-carbon, platinum, platinum oxide, copper chromite and Raney nickel. The proper amount of the catalyst used is generally about 0.02–1 time the weight of the starting material. Desirably, the reaction temperature is ordinarily about −20° C. to 100° C., preferably about 0°–70° C. and the hydrogen pressure is ordinarily 1–10 atm. The reaction is complete generally in about 0.5–20 hours. The reduction may be conducted by catalytic hydrogenation, but can be conducted preferably by a method using a hydride reducing agent. As the hydride reducing agent, there can be mentioned, for example, lithium aluminum hydride, sodium boron hydride and diborane. The amount of the hydride reducing agent used is ordinarily at least 1 mole, preferably 1–15 moles per 1 mole of the starting compound. The reduction reaction is conducted ordinarily at about −60° C. to 150° C. preferably at −30° C. to 100° C. for about 10 minutes to 10 hours, ordinarily using an appropriate solvent, for example, water, a lower alcohol (e.g. methanol, ethanol, isopropanol), an ether (e.g. tetrahydrofuran, diethyl ether, diisopropyl ether, diglyme) or a mixture thereof. The use of an anhydrous solvent such as diethyl ether, diisopropyl ether, tetrahydrofuran, diglyme or the like is preferred when the reducing agent used is lithium aluminum hydride or diborane.

When in the compound (1), $R^1$ or $R^3$ is a phenyl group having at least one lower alkoxy group or at least one lower alkoxy-substituted lower alkoxy group, the phenyl group can be converted into a phenyl group having at least one hydroxyl group, by a dealkylation reaction or a dealkoxyalkylation reaction.

The dealkylation reaction is conducted by treating the compound (1) in the presence of a catalytic reduction catalyst (e.g. palladium-carbon, palladium black) at about 0°–100° C. at a hydrogen pressure of 1–10 atm. for about 0.5–3 hours in an appropriate solvent, for example, water, a lower alcohol (e.g. methanol, ethanol, isopropanol), an ether (e.g. dioxane, tetrahydrofuran), acetic acid or a mixed solvent thereof, or by heat-treating the compound (1) at 30°–150° C., preferably 50°–120° C. in a mixture of an acid (e.g. hydrobromic acid, hydrochloric acid) with a solvent (e.g. water, methanol, ethanol, isopropanol), whereby a compound (1) having a hydroxyl group as $R^1$ or $R^3$ can be derived. A compound (1) having a hydroxyl group as $R^1$ or $R^3$ can also be obtained by hydrolysis. This hydrolysis is conducted in an appropriate solvent in the presence of an acid or a basic compound. As to the solvent, there can be mentioned, for example, water, lower alcohols (e.g. methanol, ethanol, isopropanol), ethers (e.g. dioxane, tetrahydrofuran), halogenated hydrocarbons (e.g. dichloromethane, chloroform, carbon tetrachloride), polar solvents (e.g. acetonitrile), fatty acids (e.g. acetic acid) and mixed solvents thereof. As to the acid, there can be mentioned, for example, mineral acids (e.g. hydrochloric acid, hydrobromic acid), organic acids (e.g. trifluoroacetic acid), Lewis acids (e.g. boron trifluoride, boron tribromide, aluminum chloride), iodides (e.g. sodium iodide, potassium iodide) and mixtures between said Lewis acid and said iodide. As to the basic compound, there can be mentioned, for example, metal hydroxides such as sodium hydroxide, potassium hydroxide, calcium hydroxide and the like. The reaction proceeds favorably ordinarily at room temperature to 200° C., preferably at room temperature to 150° C. and is completed generally in about 0.5–50 hours.

When in the compound (1), $R^1$ or $R^3$ is a phenyl group having at least one hydroxyl group, the phenyl group can be converted into a phenyl group having at least one lower alkoxy group or at least one lower alkoxy-substituted lower alkoxy group, by an alkylation reaction. The alkylation reaction can be conducted, for example, by reacting the compound (1) with an alkylating agent such as a dialkyl sulfate (e.g. dimethyl sulfate), diazomethane or a compound represented by the general formula, $R^5Y$ (15)

(wherein $R^5$ is a lower alkyl group or a lower alkoxy-substituted lower alkyl group and Y represents a halogen atom) in an appropriate solvent in the presence of a basic compound. The solvent can be exemplified by alcohols such as methanol, ethanol, propanol and the like; ethers such as diethyl ether, tetrahydrofuran, dioxane, ethylene glycol monomethyl ether and the like; aromatic hydrocarbons such as benzene, toluene, xylene and the like; esters such as methyl acetate, ethyl acetate and the like; ketones such as acetone, methyl ethyl ketone and the like; polar solvents such as acetonitrile, dimethylformamide, dimethyl sulfoxide, hexamethylphosphoric triamide and the like; and mixed solvents thereof. The basic compound can be exemplified by inorganic bases such as sodium hydroxide, potassium hydroxide, sodium carbonate, potassium carbonate, sodium hydrogencarbonate, potassium hydrogencarbonate, sodium hydride and the like; alkali metals such as metallic sodium, metallic potassium and the like; alkali metal alcoholates such as sodium ethylate, sodium ethylate and the like; and organic bases such as triethylamine, pyridine, N,N-dimethylaniline, N-methylmorpholine, 4-methylaminopyridine, DBN, DBU, DABCO and the like.

The proper amount of the alkylating agent used is at least 1 mole, preferably 1–5 moles per 1 mole of the starting compound.

The reaction is conducted ordinarily at 0°–150° C., preferably at about room temperature to 100° C. and is completed in about 0.5–20 hours.

When in the compound (1), $R^1$ or $R^3$ is a phenyl group having at least one group selected from an alkoxycarbonyl group, a lower alkoxy-substituted lower alkoxycarbonyl group, a lower alkoxycarbonyl-substituted alkenyl group and a lower alkoxycarbonyl-lower alkyl group, or is a 5- to 15-membered monocyclic, bicyclic or tricyclic heterocyclic residual group having 1–2 nitrogen, oxygen or sulfur atoms, having at least one lower alkoxycarbonyl group, the $R^1$ or $R^3$ can be converted, by hydrolysis, into a phenyl group having at least one group selected from a carboxy group, a carboxy-substituted lower alkenyl group and a carboxy-substituted lower alkyl group, or into a 5- to, 15-membered monocyclic, bicyclic or tricyclic heterocyclic residual group having 1–2 nitrogen, oxygen or sulfur atoms, having at least one carboxy group.

The hydrolysis reaction can be conducted under any conditions ordinarily employed in hydrolysis. It is specifically conducted in the presence of a basic compound (e.g. sodium carbonate, potassium carbonate, sodium hydroxide, potassium hydroxide or barium hydroxide), a mineral acid (e.g. sulfuric acid, hydrochloric acid or nitric acid), an organic acid (e.g. acetic acid or aromatic sulfonic acid) or the like in a solvent such as water, alcohol (e.g. methanol, ethanol or isopropanol), ketone (e.g. acetone or methyl ethyl ketone), ether (e.g. dioxane or ethylene glycol dimethyl ether), acetic acid or the like, or in a mixed solvent thereof. The reaction proceeds ordinarily at room temperature to 200° C., preferably at about from room temperature to 180° C. and is completed generally in about 10 minutes to 30 hours.

When in the compound (1), $R^1$ or $R^3$ is a phenyl group having at least one amino group which may have a lower alkyl group or a lower alkanoyl group, a phenyl group having, as a substituent on the phenyl ring, a group of the formula

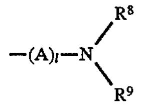

wherein $R^8$ and $R^9$, together with the nitrogen atom being bonded thereto, form a 5- to 6-membered saturated heterocyclic ring having a secondary nitrogen atom, or a 5- to 15-membered monocyclic, bicyclic or tricyclic heterocyclic residual group having at least one secondary nitrogen atom, then the $R^1$ or $R^3$ can be converted, by an alkylation reaction, into a phenyl group which has at least one amino group having 1–2 lower alkyl groups or having a lower alkyl group and a lower alkanoyl group, a phenyl group having, as a substituent on the phenyl ring, a group of the formula

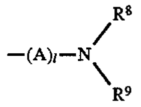

wherein $R^8$ and $R^9$, together with the nitrogen atom being bonded thereto, form a 5- to 6-membered saturated heterocyclic ring having a nitrogen atom to which a lower alkyl group is bonded, or a 5- to 15-membered monocyclic, bicyclic or tricyclic heterocyclic residual group having at least one nitrogen atom having a lower alkyl group as a substituent thereon. When the compound (1) has both of the above two groups (the phenyl group having at least one amino group, the 5- to 15-membered monocyclic, bicyclic or tricyclic heterocyclic residual group having at least one secondary nitrogen atom, or the amino-lower alkyl group), it is possible that the two groups be alkylated simultaneously, and the alkylation product can be separated easily.

The alkylation reaction is conducted by reacting the compound (1) with a compound represented by the general formula $R^5Y$ (15)

(wherein $R^5$ and Y are the same as defined above) in an appropriate inert solvent in the presence of a dehydrohalogenating agent.

The inert solvent can be exemplified by halogenated hydrocarbons such as dichloromethane, chloroform and the like; ethers such as tetrahydrofuran, diethyl ether and the like; aromatic hydrocarbons such as benzene, toluene, xylene and the like; esters such as methyl acetate, ethyl acetate and the like; and polar solvents such as dimethylformamide, dimethyl sulfoxide, hexamethylphosphoric triamide, acetonitrile, acetone, acetic acid, pyridine, water and the like. As the dehydrohalogenating agent, there can be mentioned, for example, organic bases such as triethylamine, trimethylamine, pyridine, dimethylaniline, N-methyl-morpholine, 4-dimethylaminopyridine, 4-(1-pyrrolidinyl)-pyridine, 1,5-diazabicyclo[4,3,0]nonene-5 (DBN), 1,8-diazabicyclo[5,4,0]undecene-7 (DBU), 1,4-diazabicyclo-[2,2,2]octane (DABCO), sodium acetate and the like, as well as inorganic bases such as sodium hydride, potassium carbonate, sodium carbonate, potassium hydrogencarbonate, sodium hydrogencarbonate, potassium hydroxide, sodium hydroxide and the like. The proper amount of the compound (15) used is ordinarily at least 1 mole, preferably 1–3 moles per 1 mole of the starting material. The reaction is conducted ordinarily at about –20° C. to 150° C., preferably at 0°–100° C. and is completed in about 5 minutes to 15 hours.

When in the compound (1), $R^1$ or $R^3$ is a phenyl group having at least one amino group which may have a lower alkyl group, a phenyl group having at least one hydroxyl group, a 5- to 15-membered monocyclic, bicyclic or tricyclic heterocyclic residual group having at least one secondary nitrogen atom, a phenyl group having, as a substituent on the phenyl ring, a group of the formula

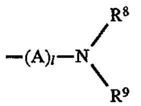

wherein $R^8$ and $R^9$, together with the nitrogen atom being bonded thereto, form a 5- to 6-membered saturated heterocyclic ring having a secondary nitrogen atom, or a phenyl group having at least one tetrahydropyranyloxy group having, as a substituent, at least one group selected from a hydroxyl group and a hydroxyl group-substituted lower alkyl group, the $R^1$ or $R^3$ can be converted, by a lower alkanoylation reaction, into a phenyl group having at least one amino group which has a lower alkanoyl group or has a lower alkanoyl group and a lower alkyl group, a phenyl group having at least one alkanoyloxy group, a 5- to 15-membered monocyclic, bicyclic or tricyclic heterocyclic residual group having at least one nitrogen atom having a lower alkanoyl group as a substituent thereon, a phenyl group having, as a substituent on the phenyl ring, a group of the formula

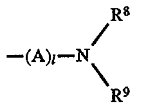

wherein $R^8$ and $R^9$ together with the nitrogen atom being bonded thereto, form a 5- to 6-membered saturated heterocyclic ring having a nitrogen atom to which a lower alkanoyl group is bonded, or a phenyl group having at least one tetrahydropyranyloxy group having, as a substituent, at least one group selected from a lower alkanoyloxy group and a lower alkanoyloxy group-substituted lower alkyl group. In the above reaction, when the compound (1) has the above three groups (the phenyl group having at least one amino group which may have a lower alkyl group, the phenyl group having at least one hydroxyl group and the 5- to 15-membered monocyclic, bicyclic or tricyclic heterocyclic residual group having at least one secondary nitrogen atom), it is possible that all of the three groups be alkanoylated simultaneously, and the alkanoylation product can be separated easily.

The alkanoylation reaction is conducted by reacting the compound (1) with an alkanoylating agent, for example, a compound represented by the general formula, $$R^6Y \quad (16)$$

or $$(R^6)_2O \quad (17)$$

(wherein $R^6$ represents a lower alkanoyl group and Y is the same as above) in a solventless state or in an appropriate solvent in the presence or absence, preferably the presence of a basic compound. As to the appropriate solvent, there can be used, for example, the above-mentioned aromatic hydrocarbons, lower alcohols (e.g. methanol, ethanol, propanol), DMF, DMSO, halogenated hydrocarbons (e.g. chloroform, methylene chloride), acetone and pyridine. The basic compound can be exemplified by tertiary amines (e.g. triethylamine, pyridine), sodium hydroxide, potassium hydroxide and sodium hydride. The proper amount of the lower alkanoylation agent used is at least 1 mole, preferably 1–10 moles per 1 mole of the starting material. The reaction is conducted ordinarily at room temperature to 200° C., preferably at room temperature to 150° C. and is completed in about 0.5–15 hours.

When in the compound (1), $R^1$ or $R^3$ is a 5- to 15-membered monocyclic, bicyclic or tricyclic heterocyclic residual group having at least one secondary nitrogen atom, the $R^1$ or $R^3$ can be converted into a 5- to 15-membered monocyclic, bicyclic or tricyclic heterocyclic residual group having at least one nitrogen atom having a benzoyl group as a substituent thereon, by reacting the compound (1) with a compound represented by the general formula, $$R^7Y \quad (18)$$

(wherein $R^7$ represents a benzoyl group and Y represents a halogen atom).

The reaction can be conducted under the same conditions as employed in the above alkylation reaction.

When in the compound (1), $R^1$ or $R^3$ is a phenyl group having at least one carboxy group or a 5- to 15-membered monocyclic, bicyclic or tricyclic heterocyclic residual group having 1–2 hetero atoms selected from a nitrogen atom, an oxygen atom and a sulfur atom, having at least one carboxy group, the $R^1$ or $R^3$ can be converted, by an esterification reaction, into a phenyl group having at least one alkoxycarbonyl group or at least one phenyl-lower alkoxycarbonyl group, or a 5- to 15-membered monocyclic, bicyclic or tricyclic heterocyclic residual group having 1–2 hetero atoms selected from a nitrogen atom, an oxygen atom and a sulfur atom, having at least one lower alkoxycarbonyl group.

The esterification reaction can be conducted by reacting the compound (1) with an alcohol such as methyl alcohol, ethyl alcohol, isopropyl alcohol, benzyl alcohol or the like, in the presence of a mineral acid (e.g. hydrochloric acid, sulfuric acid) and a halogenating agent (e.g. thionyl chloride, phosphorus oxychloride, phosphorus pentachloride, phosphorus trichloride) ordinarily at 0°–150° C., preferably at 50°–100° C. for about 1–10 hours.

When in the compound (1), $R^1$ or $R^3$ is a phenyl group having a hydroxyl group and an amino group, the hydroxyl group and the amino group being adjacent to each other, the compound (1) can be converted into a compound (1) where $R^1$ or $R^3$ is benzoxazol-2-one, by reacting the former compound (i) with phosgene in an appropriate solvent in the presence of a basic compound. The basic compound and the solvent can each be any of those used in the reaction between the compound (2) and the compound (4) in the Reaction scheme-2.

The reaction is conducted ordinarily at 0°–100° C., preferably at about 0°–70° C. and is complete in about 1–5 hours.

A compound (1) where $R^1$ or $R^3$ is a phenyl group having at least one amide group which may have a lower alkyl group as a substituent, can be obtained by reacting a compound (1) where $R^1$ or $R^3$ is a phenyl group which may have at least one carboxy group, with an amine which may have a lower alkyl group as a substituent, under the same conditions as employed in the amide bonding formation reaction in the reaction scheme 3.

A compound (1) where $R^1$ or $R^3$ is a benzoyl group which may have a lower alkoxy group as a substituent on the phenyl ring, when reduced by the same reduction using a hydride reducing agent as employed for the compound where $R^1$ or $R^3$ is a 5- to 15-membered monocyclic, bicyclic or tricyclic heterocyclic residual group having at least one oxo group adjacent to the nitrogen atom of the heterocyclic ring, can be converted into a compound (1) where $R^1$ or $R^3$ is a phenyl-lower alkyl group which may have a lower alkoxy group as a substituent on the phenyl ring and which has a hydroxyl group as a substituent on the lower alkyl group.

A compound (1) where $R^1$ or $R^3$ is a benzyl group which may have a lower alkoxy group as a substituent on the phenyl ring, when oxidized under the same conditions as employed for the compound where $R^1$ or $R^3$ is a 5- to 15-membered monocyclic, bicyclic or tricyclic heterocyclic residual group having at least one tertiary nitrogen atom, except that the reaction temperature is changed to ordinarily room temperature to 200° C., preferably room temperature to 150° C., can be converted into a compound (1) where $R^1$ or $R^3$ is a benzoyl group which may have a lower alkoxy group as a substituent on the phenyl ring.

[Reaction scheme-8]

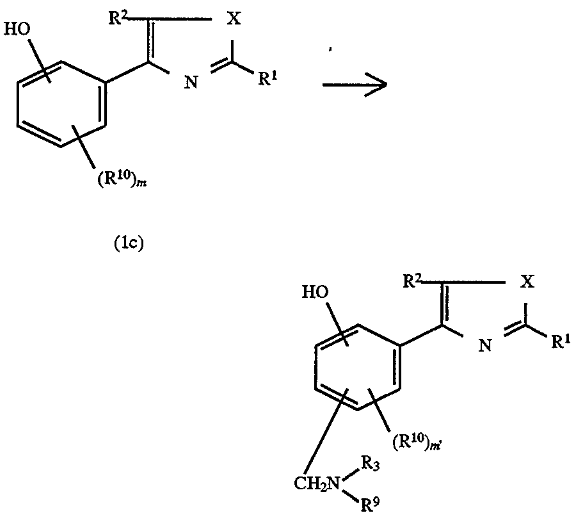

(1c)

(1d)

[wherein $R^1$, $R^2$, $R^8$, $R^9$ and X are the same as defined above; $R^{10}$ represents an alkoxy group, a tri-lower alkyl group-substituted silyloxy group, a lower alkyl group, a hydroxyl group, a lower alkenyloxy group, a lower alkylthio group, a phenyl group which may have a group selected from the group consisting of a thiazolyl group which may have, as a substituent on the thiazolyl group, a phenyl group which may have a lower alkoxy group on the phenyl ring, a carboxy group and a hydroxyl group, a lower alkylsulfinyl group, a lower alkylsulfonyl group, a halogen atom, a nitro group, a group of the formula,

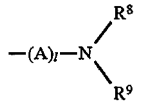

(wherein A, l, $R^8$ and $R^9$ are the same as above), a lower alkanoyl group, a lower alkanoyloxy group, an alkoxycarbonyl group, a cyano group, a tetrahydropyranyloxy group which may have 1–4 substituents selected from the group consisting of a hydroxyl group, a lower alkoxycarbonyl group, a phenyl-lower alkoxy group, a hydroxyl group- or lower alkanoyloxy group-substituted lower alkyl group and a lower alkanoyloxy group, an amidino group, a hydroxysulfonyloxy group, a lower alkoxycarbonyl-substituted lower alkoxy group, a carboxy-substituted lower alkoxy group, a mercapto group, a lower alkoxy-substituted lower alkoxy group, a lower alkyl group having hydroxyl groups, a lower alkenyl group, an aminothiocarbonyloxy group which may have a lower alkyl group as a substituent, an aminocarbonylthio group which may have a lower alkyl group as a substituent, a lower alkanoyl-substituted lower alkyl group, a carboxy group, an amino-lower alkoxycarbonyl group which may have a lower alkyl group as a substituent, a group of the formula,

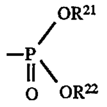

($R^{21}$ and $R^{22}$, which may be the same or different, each represent a hydrogen atom or a lower alkyl group), a phenyl-lower alkoxycarbonyl group, a cycloalkyl group, a lower alkynyl group, a lower alkoxycarbonyl-substituted lower alkyl group, a carboxy-substituted alkyl group, a lower alkoxycarbonyl-substituted lower alkenyl group, a carboxy-substituted lower alkenyl group, an amino-lower alkoxy group which may have a lower alkyl group as a substituent, an amino-lower alkoxy-substituted lower alkyl group which may have a lower alkyl group as a substituent, an amino-lower alkoxycarbonyl-substituted lower alkyl group which may have a lower alkyl group as a substituent, a lower alkylsulfonyloxy group which may have a halogen atom, or a lower alkoxy-substituted lower alkoxycarbonyl group) m and m' are each represent 0 or an integer of 1–3.]

The reaction between the compound (1c) and the compound (19) can be conducted by, for example, ① a method (Mannich reaction) wherein ,the compound (1c) is reacted with

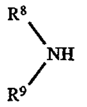

(19)

($R^8$ and $R^9$ are the same as defined above) and formaldehyde, or

② a method wherein the compound (1c) is reacted with a compound (20),

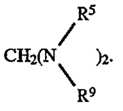

(20)

The method (1) is conducted by reacting the compound (1c), the compound (19) and formaldehyde in an appropriate solvent in the presence or absence of an acid. The solvent can be any of those ordinarily used in the Mannich reaction, and can be exemplified by water, alcohols (e.g. methanol, ethanol, isopropanol), alkanoic acids (e.g. acetic acid, propionic acid), acid anhydrides (e.g. acetic anhydride), plar solvents (e.g. acetone, dimethylformamide) and mixed solvents thereof. The acid can be exemplified by mineral acids (e.g. hydrochloric acid, hydrobromic acid) and organic acids (e.g. acetic acid). As the formaldehyde, there are ordinarily used an aqueous solution containing 20–40% by weight of formaldehyde, a formaldehyde trimer, a formaldehyde polymer (paraformaldehyde), etc. The proper amount of the compound (19) used is ordinarily at least 1 mole, preferably 1–5 moles per 1 mole of the compound (1c). The proper amount of formaldehyde used is at least 1 mole per 1 mole of the compound (1c) and ordinarily a large excess relative to the compound (1c). The reaction proceeds ordinarily at 0°–200° C., preferably at about room temperature to 150° C. and is completed in about 0.5–10 hours.

The method (2) is conducted by carrying out the reaction in the presence of an acid in an appropriate solvent or without solvent. The acid can be exemplifed by mineral acids (e.g. hydrochloric acid, hydrobromic acid, sulfuric acid) and organic acids (e.g. acetic acid, acetic anhydride), preferably acetic anhydride. The solvent can be any of those used in the method (1). The proper amount of the compound (20) used is ordinarily at least 1 mole, preferably 1–5 moles per 1 mole of the compound (1c). The reaction is conducted ordinarily at 0°–150° C., preferably at about room temperature to 100° C. and is completed in about 0.5–5 hours.

In said reaction, when $R^1$ represents a group of the formula,

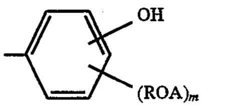

there may also be formed, in some cases, a reaction product between the group of R' in compound (1c) with compound (19) or the compound (20), and such product, can easily be separated from the reaction mixture.

[Reaction scheme-9]

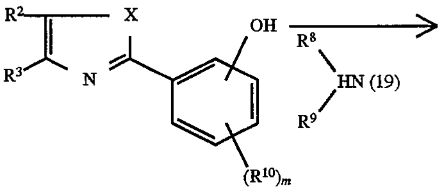

(1c')

-continued

[Reaction scheme-9]

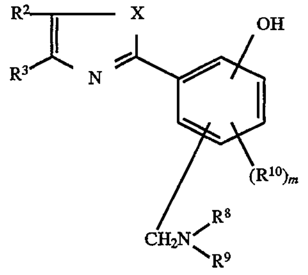

(1d')

(wherein $R^2$, $R^3$, $R^8$, $R^9$, $R^{10}$, m, m' and X are the same as defined above).

The reaction for converting the compound (1c') into a compound (1d') can be conducted under the same conditions as employed in the reaction for convering the compound (1c) into a compound (1d) in the Reaction scheme-8.

In said reaction, when $R^3$ represents a group of the formula,

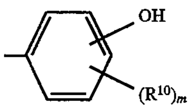

there may also be formed, in some cases, a reaction product of the group of $R^3$ in compound (1c') with compound (19) or the compound (20), and such product, can easily be separated from the reaction mixture.

[Reaction scheme-10]

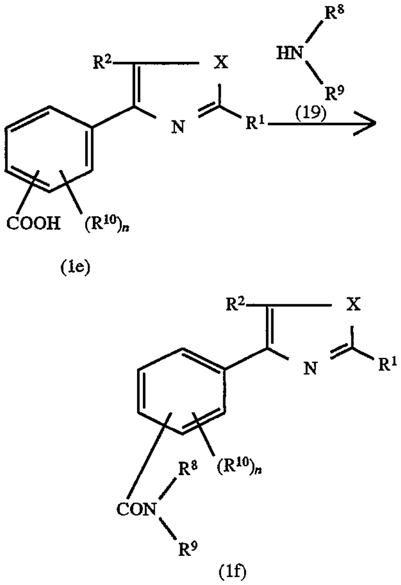

(1e)

(1f)

-continued

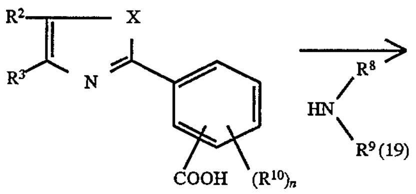

(1e')

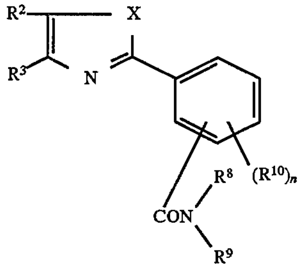

(1f')

(wherein $R^1$, $R^2$, $R^3$, $R^9$, $R^{10}$, and X are the same as defined above; n represents 0 or an integer of 1–4).

The reaction between the compound (1e) and the compound (19) and the reaction between the compound (1e') and the compound (19) can be conducted under the same conditions as employed in the reaction between the compound (6) and the compound (4) in the Reaction scheme-3.

[Reaction scheme-11]

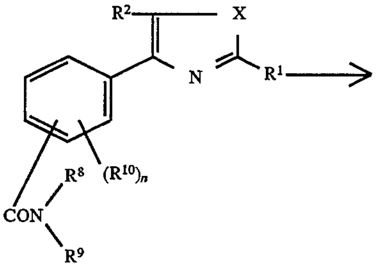

(1f)

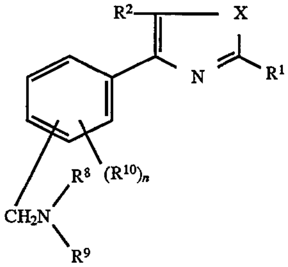

(1g)

-continued

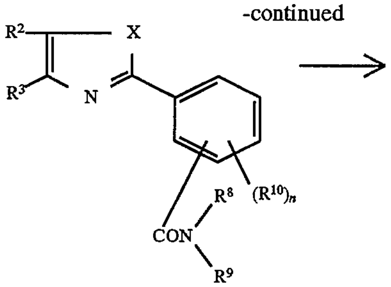

(1f')

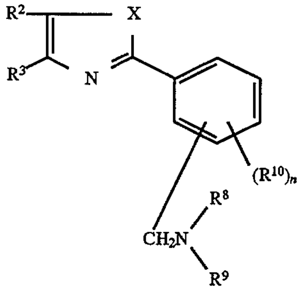

(1g')

(wherein $R^1$, $R^2$, $R^3$, $R^8$, $R^9$, $R^{10}$, n and X are the same as defined above).

The reaction for converting the compound (1f) into a compound (1g) and the reaction for converting the compound (1f') into a compound (1g') can be conducted under the same conditions as employed in the above-mentioned reduction reaction for the compound (1) where $R^1$ or $R^3$ is a 5- to 15- membered monocyclic, bicyclic or tricyclic heterocyclic residual group having at least one oxo group adjacent to the nitrogen atom of the heterocyclic ring.

[Reaction scheme-12]

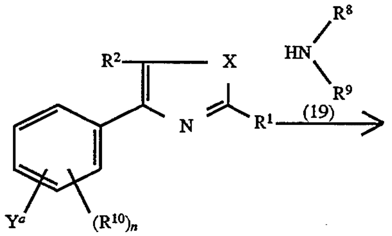

(1h)

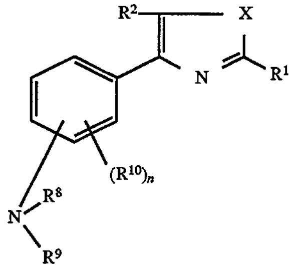

(1i)

-continued

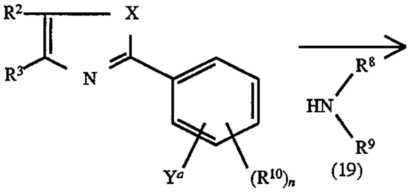

(1h')

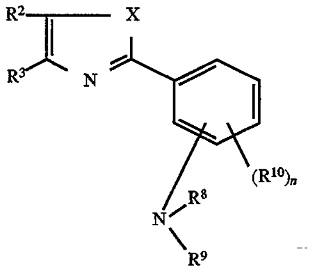

(1i')

(wherein $R^1$, $R^2$, $R^8$, $R^9$, $R^{10}$, X and n are the same as defined above; $Y^a$ represents a halogen atom or a lower alkylsulfonyloxy group which may have a halogen atom).

The reaction between the compound (1h) and the compound (19) and the reaction between the compound (1h') and the compound (19) are conducted in an appropriate inert solvent in the presence or absence of a basic compound. The inert solvent can be exemplified by halogenated hydrocarbons such as dichloromethane, chloroform and the like; ethers such as tetrahydrofuran, diethyl ether and the like; aromatic hydrocarbons such as benzene, toluene, xylene and the like; esters such as methyl acetate, ethyl acetate and the like; and polar solvents such as dimethylformamide, dimethyl sulfoxide, hexamethylphosphoric triamide, acetonitrile, acetone, acetic acid, pyridine, water and the like. As to the basic compound, there can be mentioned, for example, organic bases such as triethylamine, trimethylamine, pyridine, dimethylaniline, N-methylmorpholine, 4-dimethylaminopyridine, 4-(1-pyrrolidinyl)pyridine, 1,5-diazabicyclo[4,3,0]nonene-5 (DBN), 1,8-diazabicyclo-[5,4,0]undecene-7 (DBU), 1,4-diazabicyclo[2,2,2]octane (DABCO), sodium acetate and the like; and inorganic bases such as sodium hydride, potassium carbonate, sodium carbonate, potassium hydrogencarbonate, sodium hydrogencarbonate, potassium hydroxide, sodium hydroxide and the like. The proper amount of the compound (19) used is ordinarily at least 1 mole, preferably 1–3 moles per 1 mole of the compound (1b) or the compound (1h'). The reaction is conducted ordinarily at about −20° C. to 180° C., preferably at 0°–150° C. and is completed in about 5 minutes to 15 hours. The reaction proceeds favorably when a catalyst such as copper powder or the like is added.

[Reaction scheme-13]

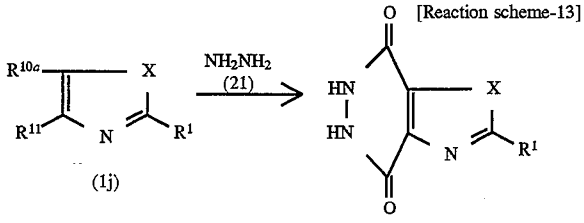

(1k)

(wherein $R^1$ and X are the same as defined above; $R^{10a}$ and $R^{11}$ each represent a lower alkoxycarbonyl group).

The reaction between the compound (ij) and the compound (21) is conducted in an appropriate solvent in a sealed tube. The solvent can be any of those used in the reaction between the compound (2) and the compound (3) in the Reaction scheme-1. The proper amount of the compound (21) used is at least 1 mole per 1 mole of the compound (1j) and is ordinarily a large excess relative to the compound (1j). The reaction is conducted ordinarily at 50°–200° C., preferably at about 50°–150° C. and is completed in about 10–50 hours.

[Reaction scheme-14]

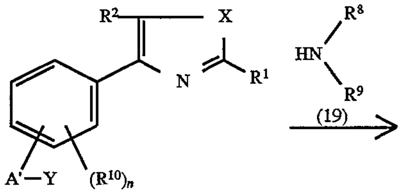

(1l)

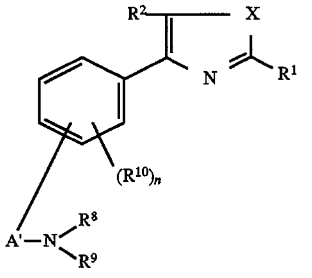

(1m)

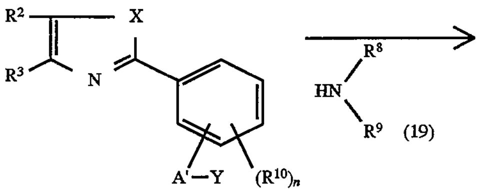

(1l')

-continued

[Reaction scheme-14]

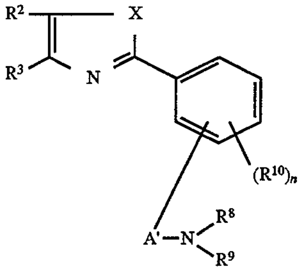

(1m')

(wherein $R^1$, $R^2$, $R^3$, $R^8$, $R^9$, $R^{10}$, X, n and Y are the same as defined above; A' represents a lower alkylene group).

The reaction between the compound (1l) and the compound (19) and the reaction between the compound (1l') and the compound (19) are conducted in an appropriate inert solvent in the presence of a dehydro-halogenating agent. The inert solvent can be exemplified by halogenated hydrocarbons such as dichloromethane, chloroform and the like; ethers such as tetrahydrofuran, diethyl ether and the like; aromatic hydrocarbons such as benzene, toluene, xylene and the like; esters such as methyl acetate, ethyl acetate and the like; polar solvents such as dimethylformamide, dimethyl sulfoxide, hexamethylphosphoric triamide, acetonitrile, acetone, acetic acid, pyridine, water and the like; and mixed solvents thereof. As to the dehydrohalogenating agent, there can be mentioned, for example, organic bases such as triethylamine, trimethylamine, pyridine, dimethylaniline, N-methylmorpholine, 4-dimethylaminopyridine, 4-(1-pyrrolidinyl)-pyridine, 1,5-diazabicyclo[4,3,0]nonene-5 (DBN), 1,8-diazabicyclo[5,4,0]undecene-7 (DBU), 1,4-diazabicyclo-[2,2,2]octane (DABCO), sodium acetate and the like; and inorganic bases such as sodium hydride, potassium carbonate, sodium carbonate, potassium hydrogencarbonate, sodium hydrogencarbonate, potassium hydroxide, sodium hydroxide and the like. The proper amount of the compound (19) used is ordinarily at least 1 mole, preferably 1–3 moles per 1 mole of the compound (1l) or the compound (1l'). The reaction is conducted ordinarily at about –20° C. to 150° C., preferably at 0°–100° C. and is completed in about 5 minutes to 20 hours.

[Reaction scheme-15]

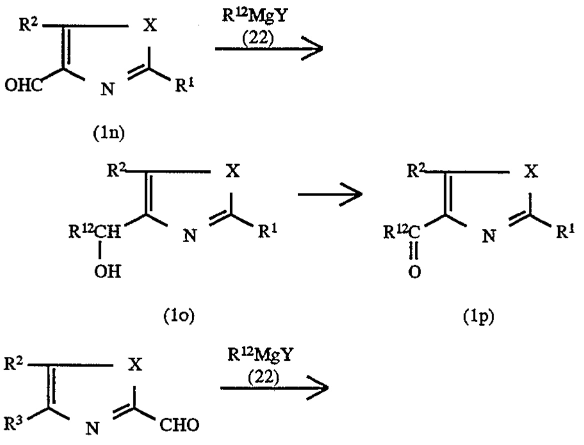

(1n) (1o) (1p) (1n')

-continued

[Reaction scheme-15]

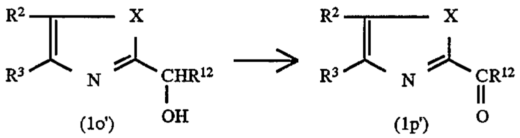

(1o') (1p')

(wherein $R^1$, $R^2$, X and Y are the same as defined above; $R^{12}$ represents a phenyl group which may have a lower alkoxy group as a substituent on the phenyl ring).

The reaction between the compound (1n) and the compound (22) and the reaction between the compound (1n') and the compound (22) can be conducted in an appropriate solvent generally at –70° C. to room temperature, preferably at about –30° C. to room temperature for 1–6 hours. The solvent can be exemplified by ethers such as diethyl ether, dioxane, tetrahydrofuran and the like; aromatic hydrocarbons such as benzene, toluene and the like; and saturated hydrocarbons such as hexane, heptane, pentane, cyclohexane and the like. The proper amount of the compound (22) used is at least 1 mole, preferably 1–2 moles per 1 mole of the compound (1n) or the compound (1n'). The reaction for converting the compound (1o) into a compound (1p) and the reaction for converting the compound (1o') into a compound (1p') are conducted in an appropriate solvent in the presence of an oxidizing agent. The oxidizing agent can be exemplified by DDQ, pyridinium chromates (e.g. pyridinium chlorochromate, pyridinium dichlorochromate), dimethyl sulfoxide-oxalyl chloride, bichromic acid, bichromates (e.g. sodium bichromate, potassium bichromate), permanganic acid, and permanganates (e.g. potassium permanganate, sodium permanganate). The solvent can be exemplified by water; organic acids such as formic acid, acetic acid, trifluoroacetic acid and the like; alcohols such as methanol, ethanol and the like; halogenated hydrocarbons such as chloroform, dichloromethane and the like; ethers such as tetrahydrofuran, diethyl ether, dioxane and the like; dimethyl sulfoxide; dimethylformamide; and mixed solvents thereof. Desirably, the oxidizing agent is ordinarily used in a large excess relative to the starting material. The reaction is conducted ordinarily at about 0°–150°, preferably at about 0°–100° C. and is completed in about 1–7 hours.

[Reaction scheme-16]

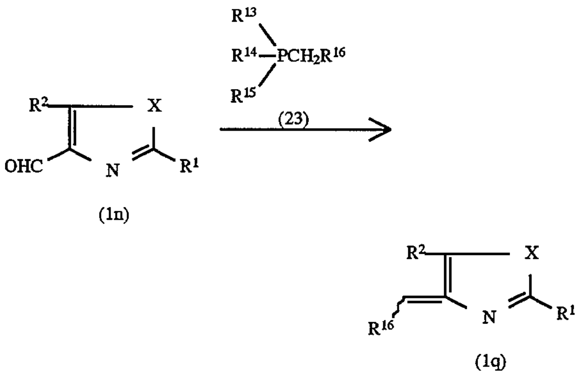

(1n) (1q)

-continued

[Reaction scheme-16]

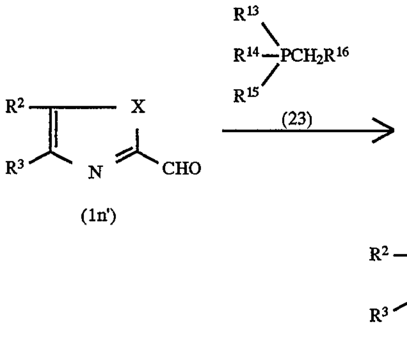

(1n')

(1q')

(wherein $R^1$, $R^2$, $R^3$ and X are the same as defined above; $R^{13}$, $R^{14}$ and $R^{15}$ are each represents a phenyl group or a lower alkyl group; $R^{16}$ represents a phenyl-lower alkyl group which may have a lower alkyl group as a substituent on the phenyl ring).

The reaction between the compound (1n) and the compound (23) and the reaction between the compound (1n') and the compound (23) are each a so-called Witting reaction. The reaction is conducted in a solvent in the presence of a basic compound. The basic compound can be exemplified by inorganic bases such as metallic sodium, metallic potassium, sodium hydride, sodium amide, sodium hydroxide, potassium hydroxide, sodium carbonate, potassium carbonate, sodium hydrogencarbonate and the like; metal alcoholates such as potassium ter-butoxide, sodium methylate, sodium ethylate and the like; lithium salts such as methyllithium, n-butyllithium, phenyllithium and the like; and organic bases such as pyridine, piperidine, quinoline, triethylamine, N,N-dimethylaniline and the like. The solvent can be any as long as it gives no adverse effect to the reaction, and there can be mentioned, for example, ethers (e.g. diethyl ether, dioxane, tetrahydrofuran, monoglyme, diglyme), armatic hydrocarbons (e.g. benzene, toluene, xylene), aliphatic hydrocarbons (e.g. n-hexane, pentane, heptane, cyclohexane), amines (e.g. pyridine, N,N-dimethylaniline) and aprotic polar solvents (e.g. dimethylformamide, dimethyl sulfoxide, hexamethylphosphoric triamide). The proper amount of the compound (23) used is ordinarily at least about 1 mole, preferably about 1–5 moles per 1 mole of the compound (1n) or the compound (1n'). The proper reaction temperature is ordinarily about −70° C. to 150° C., preferably about −50° C. to 120° C. The reaction is complete generally in about 0.5–15 hours.

[Reaction scheme-17]

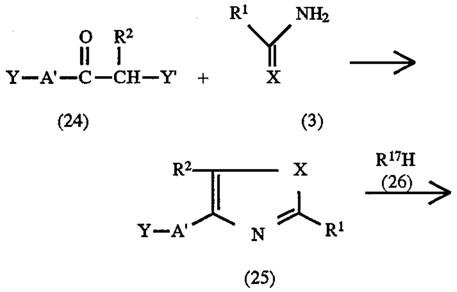

(24) (3)

(25)

-continued

[Reaction scheme-17]

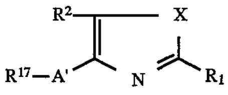

(1r)

(wherein A', Y, $R^1$, $R^2$ and X are the same as defined above; Y' represents a halogen atom; $R^{17}$ represents a piperazinyl group which may have a lower alkyl group as a substituent on the piperazine ring).

The reaction between the compound (24) and the compound (3) can be conducted under the same conditions as employed for the reaction between the compound (2) and the compound (3) in the above Reaction scheme-1. The reaction between the compound (25) and the compound (26) can be conducted under the same conditions as employed for the reaction between the compound (1#') and the compound (19) in the above Reaction scheme-14.

[Reaction scheme-18]

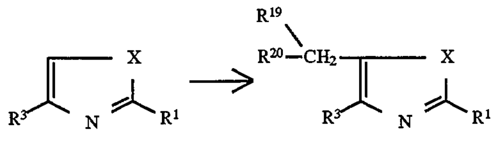

(1s) (1t)

(wherein $R^1$, $R^3$ and X are the same as defined above; $R^{19}$ and $R^{20}$ are each the same or different, and are each represents a hydrogen atom or a lower alkyl group).

The reaction between the compound (1s) and the compound (30) can be conducted by, for example, ① a method wherein the compound (1s) is reacted with

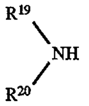

(30)

($R^{19}$ and $R^{20}$ are the same as defined above) and formaldehyde (i.e., Mannich reaction), or ② a method wherein the compound (1s) is reacted with

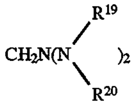

(31)

($R^{19}$ are $R^{2°}$ are the same as defined above).

The method (1) is conducted by reacting the compound (1s), the compound (30) and formaldehyde in an appropriate solvent in the presence or absence of an acid. The solvent can be any of those ordinarily used in the Mannich reaction, and can be exemplified by water, alcohols (e.g. methanol, ethanol, isopropanol), alkanoic acids (e.g. acetic acid, propionic acid), acid anhydrides (e.g. acetic anhydride), polar solvents (e.g. acetone, dimethylformamide) and mixed solvents thereof. The acid can be examplified by mineral acids (e.g. hydrochloric acid, hydrobromic acid) and organic acids (e.g. acetic acid). As the formaldehyde, there are ordinarily used an aqueous solution containing 20–40% by weight of formaldehyde, a formaldehyde trimer, a formaldehyde polymer (paraformaldehyde), etc., The proper amount of the compound (30) used is ordinarily at least 1 mole, preferably 1–5 moles per 1 mole of the compound (1s). The proper amount of formaldehyde used is at least 1 mole per 1 mole of the compound (1s) and ordinarily a large excess amount relative to the compound (1s). The reaction proceeds ordinarily at 0°–200° C., preferably at about room temperature to 150° C. and is complete in about 0.5–10 hours.

The method ② is conducted by carrying out the reaction in the presence of an acid in an appropriate solvent or without solvent. The acid can be exemplified by mineral acids (e.g. hydrochloric acid, hydrobromic acid, sulfuric acid) and organic acids (e.g. acetic acid, acetic anhydride). Acetic anhydride is preferred. The solvent can be any of those used in the method ①. The proper amount of the compound (31) used is ordinarily at least 1 mole, preferably 1–5 moles per 1 mole of the compound (1s). The reaction is conducted ordinarily at 0°–150° C., preferably at about room temperature to 100° C. and is complete in about 0.5–5 hours.

When in general formula (1), $R^1$ or $R^3$ is a phenyl group having at least one nitro group as a substituent on the phenyl ring, then $R^1$ or $R^3$ can be converted, by reduction, into a phenyl group having at least one amino group as a substituent on the phenyl ring. The reduction reaction can be conducted under the same conditions as employed in the above-mentioned catalytic reduction reaction for the oxo group adjacent to the nitrogen atom of the heterocyclic ring. The reduction reaction can also be conducted by using a reducing agent such as mentioned below. As to the reducing agent, there can be mentioned, for example, a mixture of iron, zinc, tin or stannous chloride with an acid (e.g. acetic acid, hydrochloric acid, sulfuric acid), or a mixture of iron, ferrous sulfate, zinc or tin with an alkali metal hydroxide (e.g. sodium hydroxide), a sulfide (ammonium sulfide), ammonia water, or an ammonium salt (e.g. ammonium chloride). The inert solvent can be exemplified by water, acetic acid, methanol, ethanol and dioxane. The conditions of the reduction reaction can be suitably selected depending upon the type of the reducing agent used. For example, when the reducing agent is a mixture of stannous chloride with hydrochloric acid, the reaction can be advantageously conducted at about 0° C. to room temperature for about 0.5–10 hours. The amount of the reducing agent used is at least 1 mole, ordinarily 1–10 moles per 1 mole of the starting material.

When in the compound (1), $R^1$ or $R^3$ is a phenyl group having at least one hydroxyl group as a substituent on the phenyl ring, then $R^1$ or $R^3$ can be converted, by reaction with a tetrahydrofuran derivative (27), having at least one hydroxyl group as substituent(s), into a phenyl group having at least one substituted- or unsubstituted-tetrahydropyranyloxy group as the substituent on the phenyl ring. The reaction can be conducted in an appropriate solvent (e.g. tetrahydrofuran, diethyl ether, dioxane) in the presence of a phosphorus compound (e.g. triphenylphosphine) and an azo compound (e.g. diethyl azocarboxylate) ordinarily at 0°–100° C., preferably at about 0°–70° C. for about 1–20 hours. The compound (27) is desirably used in an amount of at least 1 mole, preferably 1–2 moles per 1 mole of the strating material.

When in the compound (1), $R^1$ or $R^3$ is a phenyl group having, as substituent(s) on the phenyl ring, at least one tetrahydropyranyloxy group having at least one lower alkanoyloxy group, then $R^1$ or $R^3$ can be converted, by hydrolysis, into a phenyl group having, as substituent(s) on the phenyl ring, at least one tetrahydropyranyloxy group having at least one hydroxyl group. The hydrolysis reaction can be conducted in an appropriate solvent in the presence of a basic compound. The basic compound can be exemplified by sodium carbonate, potassium carbonate, sodium hydroxide, potassium hydroxide, barium hydroxide and alkali metal alcoholates (e.g. sodium methylate, sodium ethylate). The solvent can be exemplified by water; alcohols such as methanol, ethanol, isopropanol and the like; ethers such as tetrahydrofuran, dioxane, dimethoxyethane and the like; halogenated hydrocarbons such as chloroform, dichloromethane, carbon tetrachloride and the like; dimethylformamide, dimethyl sulfoxide, hexamethylphosphoric triamide and mixed solvents thereof. The above reaction proceeds ordinarily at about 0°–200° C., preferably at about room temperature to 150° C. and is complete generally in about 0.5–15 hours.

When in the compound (1), $R^1$ or $R^3$ is a phenyl group having at least one hydroxyl group as a substituent on the phenyl ring, then $R^1$ or $R^3$ can be converted, by reaction with a compound of the formula (28), $$YSO_3H \quad (28)$$

(Y is the same as defined above), into a phenyl group having at least one hydroxysulfonyloxy group as a substituent on the phenyl ring. The reaction can be conducted under the same conditions as employed in the reaction between the compound (11) and the compound (19) in the Reaction scheme-14. Preferably, the amount of the compound (28) used is ordinarily in a large excess amount relative to the starting material.

When in the compound (1), $R^1$ or $R^3$ is a phenyl group having at least one hydroxyl as a substituent on the phenyl ring, then $R^1$ or $R^3$, can be converted, by reaction with a compound of the formula (29), $$R^{18}Y \quad (29)$$

($R^{18}$ represents a lower alkoxycarbonyl-substituted lower alkyl group, a lower alkenyl group or a thiocarbamoyl group which may have a lower alkyl group as a substituent; and Y is the same as defined above) or with a compound of the formula (30), $$(R^{25}SO_2)_2O \quad (30)$$

($R^{25}$ represents a lower alkyl group which may have halogen atoms), into a phenyl group having, on the phenyl ring, at least one substituent selected from a group of the formula, $—OR^{18}$ ($R^{18}$ is the same as defined above) and a group of the formula, $R^{25}SO_2—$ ($R^{25}$ is the same as defined above). The reaction can be conducted under the same conditions as employed in the reaction of the compound (11) with the compound (19) in the Reaction scheme-14.

When in the compound (1), $R^1$ or $R^3$ is a phenyl group having at least one lower alkenyloxy group as a substituent on the phenyl ring, then $R^1$ or $R^3$ can be converted, by the Claisen rearrangement, into a phenyl group having, on the phenyl ring, at least two substituents selected from a hydroxyl group and a lower alkenyl group. The reaction can be conducted by heating in an appropriate solvent. The solvent can be exemplified by one having high-boiling point such as dimethylformamide, tetrahydronaphthalene, o-dichlorobenzene, N,N-dimethylaniline, N,N-diethylaniline and diphenyl ether. The reaction is conducted ordinarily at 100°–250° C., preferably at 150–250° C. and is completed in about 1–30 hours.

When in the compound (1), $R^1$ or $R^3$ is a phenyl group having, as substituent(s) on the phenyl ring, a thiocarbamoyloxy group which may have a lower alkyl group, then $R^1$ or $R^3$ can be converted, by heating, into a phenyl group having, as substituent(s on the phenyl ring, at least one aminocarbonylthio group which may have a lower alkyl group as a substituent. The reaction is conducted in the absence of a solvent ordinarily at 100°–250° C., preferably at 150°–250° C. and is completed in about 1–10 hours.

When in the compound (1), $R^1$ or $R^3$ is a phenyl group having, as substituent(s) on the phenyl ring, at least one aminocarbonylthio group which may have a lower alkyl group, then $R^1$ or $R^3$ can be converted into a phenyl group having at least one mercapto group as a substituent on the phenyl ring, by hydrolysis under the same conditions as employed in the hydrolysis reaction for the compound (1) where $R^1$ or $R^3$ is a phenyl group having at least one lower alkoxycarbonyl group.

When in the compound (1), $R^1$ or $R^3$ is a phenyl group having at least one nitro group, as substituent(s) on the phenyl ring, then $R^1$ or $R^3$ can be converted, by reduction, into a phenyl group having at least one amino group, as substituent(s) on the phenyl ring.

The reduction reaction is conducted by, for example, ① reduction in an appropriate solvent using a catalytic reduction catalyst or ② reduction, in an appropriate inert solvent using, as a reducing agent, for example, a mixture between a metal or a metal salt and an acid, or between a metal or a metal salt and an alkali metal hydroxide, ammonium sulfide or the like.

In the case ① using a reduction catalyst, the solvent includes, for example, water; acetic acid; alcohols such as methanol, ethanol, isopropanol and the like; halogenated hydrocarbons such as dichloromethane, chloroform, dichloroethane and the like; hydrocarbons such as hexane, cyclohexane and the like; ethers such as dioxane, tetrahydrofuran, diethyl ether, diethylene glycol dimethyl ether and the like; esters such as ethyl acetate, methyl acetate and the like; aprotic polar solvents such as N,N-dimethylformamide and the like; and mixed solvents thereof. The catalytic reduction catalyst includes, for example, palladium, palladium black, palladium-carbon, platinum, platinum oxide, copper chromite and Raney nickel. The proper amount of the catalyst used is generally about 0.02–1 time the weight of the starting material. Desirably, the reaction temperature is ordinarily about −20° C. to 150° C., preferably about 0°–100° C. and the reaction pressure is ordinarily 1–10 atom. The reaction is completed generally in about 0.5–10 hours. An acid such as hydrochloric acid or the like may be added in the reaction.

In the case ②, there is used, as a reducing agent, a mixture of iron, zinc, tin or stannous chloride with a mineral acid such as hydrochloric acid, sulfuric acid or the like, or a mixture of iron, ferrous sulfate, zinc or tin with an alkali metal hydroxide (e.g. sodium hydride), a sulfide (e.g. ammonium sulfide), ammonia water or an ammonium salt (e.g. ammonium chloride). The inert solvent can be exemplified by water, acetic acid, methanol, ethanol and dioxane. The conditions for the reduction reaction can be suitably selected depending upon the type of the reducing agent used. For example, when the reducing agent is a mixture of stannous chloride with hydrochloric acid, the reaction can be conducted advantageously at about 0° C. to room temperature for about 0.5–70 hours. The amount of the reducing agent is at least 1 mole, ordinarily 1–5 moles per 1 mole of the starting material.

When in the compound 91), $R^1$ or $R^3$ is a phenyl group having at least one lower alkenyl group as a substituent on the phenyl ring, then $R^1$ or $R^3$ can be converted, by oxidation, into a phenyl group having, as substituent(s) on the phenyl ring, at least one lower alkyl group having two hydroxyl groups.

The reaction can be conducted by reacting the compound (1) with an oxidizing agent in the presence of a co-oxidizing agent in an appropriate solvent.

As to the solvent used in the reaction with an oxidizing agent, there can be mentioned, for example, ethers such as dioxane, tetrahydrofuran, diethyl ether and the like; aromatic hydrocarbons such as benzene, toluene, xylene and the like; halogenated hydrocarbons such as dichloromethane, dichloroethane, chloroform, carbon tetrachloride and the like; esters such as ethyl acetate and the like; water; alcohols such as methanol, ethanol, isopropanol, tert-butanol and the like; and mixed solvents thereof. The co-oxidizing agent can be exemplified by organic amine N-oxides such as pyridine N-oxide, N-ethyldiisopropylamine N-oxide, 4-methylmorpholine N-oxide, trimethylamine N-oxide, triethylamine N-oxide and the like. The oxidizing agent can be exemplified by osmium tertoxide. The proper amount of the oxidizing agent used is ordinarily 1 mole, preferably 1–5 moles per 1 mole of the starting compound. The reaction is conducted at −20° C. to 150° C., preferably at room temperature to 100° C. and is complete generally in about 1–15 hours.

When in the compound (1), $R^1$ or $R^3$ is a phenyl group having at least one lower alkenyl group as substituent(s) on the phenyl ring, then $R^1$ or $R^3$ can be converted, by oxidation, into a phenyl group having, as substituent(s) on the phenyl ring, at least one lower alkanoyl group-substituted lower alkyl group or at least one lower alkanoyl group. The reaction can be conducted in an appropriate solvent in the presence of an oxidizing agent. As to the solvent, there can be mentioned, for example, ethers such as dioxane, tetrahydrofuran, diethyl ether and the like; aromatic hydrocarbons such as benzene, toluene, xylene end the like; halogenated hydrocarbons such as dichloromethane, dichloroethane, chloroform, carbon tetrachloride and the like; esters such as ethyl acetate and the like; water; alcohols such as methanol, ethanol, isopropanol, tert-butanol and the like; and mixed solvents thereof. The oxidizing agent can be exemplified by ozone and osmium tetroxide-sodium metaperiodate. The reaction is conducted at 20°–150° C., preferably at about 00°–100° C. and is complete generally in about 1–20 hours.

When in the compound (1), $R^1$ or $R^3$ is a phenyl group having at least one formyl group-substituted lower alkyl group as substituent(s) on the phenyl, then $R^1$ or $R^3$ can be converted, by reduction, into a phenyl group having at least one lower alkyl group having hydroxyl groups, as substituent(s) on the phenyl ring. The reduction can be conducted under the same conditions as employed in the reduction reaction using a hydride reducing agent, for the compound (1) where $R^1$ or $R^3$ is a 5- to 15-membered monocyclic, bicyclic or tricyclic heterocyclic residual group having at least one oxo group adjacent to the nitrogen atom of the heterocyclic ring.

When in the compound (1), $R^1$ or $R^3$ is a phenyl group having at least one nitrile group or at least one carbamoyl group as substituent(s) on the phenyl ring, or a 5- to 15-membered monocyclic, bicyclic or tricyclic heterocyclic residual group having 1–2 hetero atoms selected from a nitrogen atom, an oxygen atom and a sulfur atom, having at least one nitrile group or at least one carbamoyl group as substituent(s), then $R^1$ or $R^3$ can be converted, by hydrolysis, into a phenyl group having at least one carboxy group as substituent(s) on the phenyl ring, or a 5- to 15-membered monocyclic, bicyclic or tricyclic heterocyclic residual group having 1–2 hetero atoms selected from a nitrogen atom, an oxygen atom and a sulfur atom, having at least one carboxyl group as substituent(s). The hydrolysis reaction can be conducted under the same conditions as employed in the hydrolysis reaction for the compound 91)

where $R^1$ or $R^3$ is a phenyl group having at least one alkoxycarbonyl group.

When in the compound (1), $R^1$ or $R^3$ is a phenyl group having, as substituent(s) on the phenyl ring, at least one group of the formula,

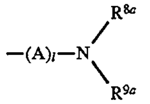

(A and l are the same as above; $R^{8a}$ represents a lower alkanoyl group; $R^{9a}$ represents a hydrogen atom, a lower alkyl group, a lower alkanoyl group, an amino-lower alkyl group which may have a lower alkyl group as a substituent, or a piperidinyl-lower alkyl group), then $R^1$ or $R^3$ can be converted, by hydrolysis, into a phenyl group having, as substituent(s) on the phenyl ring, at least one group of the formula, $$-(A)_l-NH-R^{9a}$$

(A, l and $R^{9a}$ are the same as defined above). The hydrolysis reaction can be conducted under the same conditions as employed in the hydrolysis reaction for the compound (1) where $R^1$ or $R^3$ is a phenyl group having at least one lower alkoxycarbonyl group.

When in the compound (1), $R^1$ or $R^3$ is a phenyl group having at least one lower alkenyl group as substituent(s) on the phenyl ring, then $R^1$ or $R^3$ can be converted, by reduction, into a phenyl group having at least one lower alkyl group as substituent(s) on the phenyl ring.

The reduction can be conducted under the same conditions as employed in the reduction reaction by catalytic hydrogenation for the compound (1) where $R^1$ or $R^3$ is a 5- to 15-membered monocyclic, bicyclic or tricyclic heterocyclic residual group having at least one oxy group adjacent to the nitrogen atom of mthe heterocyclic ring.

When in the compound 91), $R^1$ or $R^3$ is a phenyl group having at least one hydroxyl group as substituent(s) on the phenyl ring, then $R^1$ or $R^3$ can be converted, by carboxylation, into a phenyl group having at least one hydroxyl group and at least one carboxyl group on the phenyl ring.

The carboxylation reaction can be conducted by reacting the compound (1) with carbon dioxide in the presence of an alkali metal carbonate such as potassium hydrogencarbonate, potassium carbonate or the like in an appropriate solvent or in the absence of a solvent. The solvent can be exemplified by ehters such as dioxane, tetrahydrofuran, diethyl ether and the like; ketones such as methyl ethyl ketone, acetone and the like; water; pyridine; and glycerine. The reaction is conducted ordinarily under 1 to 10 atmospheric pressure at 100°–250° C., preferably at about 100°–200° C. and is complete in about 1–20 hours.

When in the compound (1), $R^1$ or $R^3$ is a substituted or unsubstituted phenyl group, then $R^1$ or $R^3$ can be converted, by nitration, into a phenyl group having at least one nitro group on the phenyl ring. The nitration reaction is conducted under the same conditions as ordinarily employed in the nitration for aromatic compounds, for example, by using a nitrating agent in the absence of or presence of an appropriate inert solvent. The inert solvent can be exemplified by acetic acid, acetic anhydride and concentrated sulfuric acid. The nitrating agent can be exemplified by fuming nitric acid, concentrated nitric acid, mixed acid (a mixture of sulfuric acid, fuming sulfuric acid, phosphoric acid or acetic anhydride with nitric acid) and a mixture of sulfuric acid-alkali metal nitrate (e.g. potassium nitrate, sodium nitrate). The proper amount of the nitrating agent used is at least 1 mole per 1 mole of the starting compound and is ordinarily a large excess relative to the starting compound. The reaction is advantageously conducted at about 0° C. to room temperature for 1–4 hours.

When in the compound (1), $R^1$ or $R^3$ is a phenyl group having at least one carboxyl group as substituent(s) on the phenyl ring, then $R^1$ or $R^3$ can be converted, by reaction with a compound of the general formula (32), $$R^{32}Y \quad (32)$$

($R^{32}$ represents an alkyl group, a phenyl-lower alkyl group or a lower alkoxy-substituted lower alkyl group), into a phenyl group having at least one group $-COOR^{32}$ ($R^{32}$ is the same as defined above) as substituent(s) on the phenyl ring. The reaction can be conducted under the same conditions as employed in the reaction between the compound (1l) and the compound (19) in the Reaction scheme-14.

When in the compound (1), $R^1$ or $R^3$ is a phenyl group having at least one lower alkenyl group having halogen atoms, as substituent(s) on the phenyl ring, then $R^1$ or $R^3$ can be converted into a phenyl group having at least one lower alkynyl group as substituent(s) on the phenyl ring, by a reaction in an appropriate solvent in the presence of a basic compound.

The solvent can be exemplified by ethers such as diethyl ether, dioxane, tetrahydrofuran, monoglyme, diglyme and the like; aromatic hydrocarbons such as benzene, toluene, xylene and the like; and aliphatic hydrocarbons such as n-hexane, heptane, cyclohexane and the like. The basic compound can be exemplified by alkyl- or aryl-lithium and lithium amides such as methyllithium, n-butyllithium, phenyllithium lithium diisopropylamide and the like.

The reaction temperature is −80° C. to 100° C., preferably at about −80° C. to 70° C. The reaction is completed in about 0.5–15 hours.

When in the compound (1), $R^1$ or $R^3$ is a phenyl group having at least one formyl group as substituent(s) on the phenyl ring, then $R^1$ or $R^3$ can be converted into a phenyl group having at least one cyano group as substituent(s) on the phenyl ring, by a reaction with hydroxylamino-O-sulfonic acid in an appropriate solvent. The solvent can be the same as used in the reaction between the compound (1l) and the compound (19) in the Reaction scheme-14. The reaction is conducted ordinarily at 0°–100° C. preferably at about 0°–70° C. and is complete in about 1–10 hours. The proper amount of hydroxylamine-O-sulfonic acid used is at least 1 mole, preferably about 1–2 moles per 1 mole of the starting material.

When in the compound (1), $R^1$ or $R^3$ is a phenyl group having at least one halogen atom as substituent(s) on the phenyl ring, then $R^1$ or $R^3$ can be converted, by halogenation, into a phenyl group having at least one hydroxyl group as substituent(s) on the phenyl ring.

The reaction can be conducted by a reaction with a lower alkylsiloxane such as hexamethyldisolxane or the like in an appropriate solvent in the presence of a basic compound.

The solvent can be exemplified by ethers such as diethyl ether, dioxane, tetrahydrofuran, monoglyme, diglyme and the like; aromatic hydrocarbons such as benzene, toluene, xylene and the like; and aliphatic hydrocarbons such as n-hexane, heptane, cyclohexane and the like. The basic compound can be exemplified by alkyl- or aryl-lithium and lithium amides such as methyllithium, n-butyllithium, phenyllithium, lithium diisopropylamide and the like. The reaction temperature is −80° C. to 100° C., preferably about −80° C. to 70° C., and the reaction is complete in about 0.5–15 hours. The proper amount of the lower alkylsiloxane used is at least 1 mole, preferably about 1–2 moles per 1 mole of the starting material.

When in the compound (1), $R^1$ or $R^3$ is a phenyl group having at least one formyl group as substituent(s) on the phenyl ring, then $R^1$ or $R^3$ can be converted, by oxidation, into a phenyl group having at least one carboxy group on the phenyl ring.

The reaction can be conducted in an appropriate solvent in the presence of an oxidizing agent. The solvent can be exemplified by water; alcohols such as methanol, ethanol, isopropanol and the like; ketones such as acetone, methyl ethyl ketone and the like; carboxylic acids such as acetic acid, propionic acid and the like; esters such as ethyl acetate and the like; aromatic hydrocarbons such as benzene, chlorobenzene, toluene, xylene and the like; hexamethylphosphoric triamide; dimethylformamide; dimethyl sulfoxide; pyridine; and mixed solvents thereof. As the oxidizing agent, there can be mentioned, for example, per acids (e.g. performic acid, peracetic acid, pertrifluoroacetic acid, perbenzoic acid, m-chloroperbenzoic acid, o-carbonylperbenzoic acid), hydrogen peroxide, sodium metaperiodate, bichromic acid, bichromates (e.g. sodium bichromate, potassium bichromate), permanganic acid, permanganates (e.g. potassium permanganate, sodium permanganate), lead salts (e.g. lead tetraacetate) and silver oxide. The proper amount of the oxidizing agent used is ordinarily at least 1 mole, preferably 1–2 moles per 1 mole of the starting material.

The reaction is conducted ordinarily at −10° C. to 100° C., preferably at about 0°–50° C. and is complete in about 30 minutes to 24 hours.

When in the compound (1), $R^1$ or $R^3$ is a phenyl group having at least one hydroxyl group as substituent(s) on the phenyl ring, the $R^1$ or $R^3$ can be converted into a phenyl group having at least one tri-lower alkyl group-substituted silyloxy group as substituent(s) on the phenyl ring, by a reaction with a tri-lower alkyl-halogensilane.

The reaction can be conducted in an appropriate solvent in the presence of a basic compound. The solvent can be any of those used in the reaction between the compound (11) and the compound (19) in the Reaction scheme 14.

The basic compound can be exemplified by organic bases such as imidazole and the like. The reaction is conducted ordinarily at −20° C. to 150° C., preferably at 0°–100° C. and is complete in about 5 minutes to 10 hours.

The proper amount of the tri-lower alkyl-halogenosilane used is at least 1 mole, preferably 1–3 moles per 1 mole of the starting material.

[Reaction scheme-19]

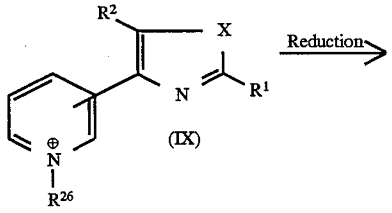

(IX)

(1u)

-continued

[Reaction scheme-19]

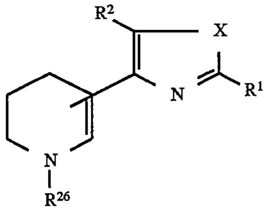

(1v)

(wherein $R^1$, $R^2$ and X are the same as above. $R^{26}$ represents a lower alkyl group.)

The reduction of the compound (1u) is preferably conducted by a reduction using a hydride reducing agent. As the hydride reducing agent, there can be mentioned, for example, lithium aluminum hydride, sodium boron hydride and diborane. The amount of the reducing agent used is ordinarily at least 1 mole, preferably 1–15 moles per 1 mole of the starting compound. The reduction reaction is conducted ordinarily at about −60° C. to 150° C., preferably at −30° C. to 100° C. for about 1–20 hours ordinarily in an appropriate solvent such as water, lower alcohol (e.g. methanol, ethanol, isopropanol), ether (e.g. tetrahydrofuran, diethyl ether, diisopropyl ether, diglyme), or mixed solvent thereof. When lithium aluminum hydride or diborane is used as the reducing agent, there is preferably used an anhydrous solvent such as diethyl ether, diisopropyl ether, tetrahydrofuran, diglyme or the like.

[Reaction scheme-20]

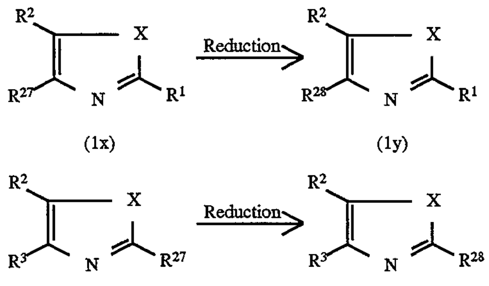

(1x) (1y)

(1x) (1A)

{wherein $R^1$, $R^2$, $R^3$ and X are the same as defined above. $R^{27}$ represents a group of the formula,

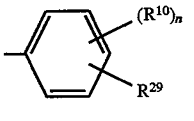

($R^{10}$ and n are the same as defined above; $R^{29}$ represents a formyl group or an alkoxycarbonyl group.) or a group of the formula,

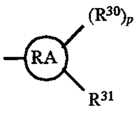

[the group of 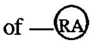 represents a 5- to 15-membered monocyclic bicyclic or tricyclic heterocyclic residual group having 1–2 hetero atoms selected from a nitrogen atom, an oxygen atom and a sulfur atom; $R^{20}$ may have 1–3 substituents selected from the group consisting of an oxo group, an alkyl group, a benzoyl group, a lower alkanoyl group, a hydroxyl group, a carboxy group, a lower alkoxycarbonyl group, a lower alkylthio group, a group of the formula,

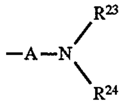

(A is the same as above. $R^{23}$ and $R^{24}$, which may be the same or different, each represent a hydrogen atom or a lower alkyl group; $R^{23}$ and $R^{24}$ as well as the nitrogen atom being bonded thereto, together with or without other nitrogen atom or oxygen atom, may form a 5- to 6-membered saturated heterocyclic ring. The heterocyclic ring may have a lower alkyl group as a substituent.); a cyano group, a lower alkyl group having hydroxyl groups, a phenylaminothiocarbonyl group and an amino-lower alkoxycarbonyl group which may have a lower alkyl group as a substituent. $R^{31}$ represents a formyl group or a lower alkoxycarbonyl group. p represents 0 or an integer of 1 or 2.] $R^{28}$ represents a group of the formula,

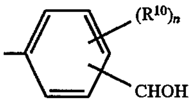

($R^{10}$ and n are the same as defined above) or a group of the formula,

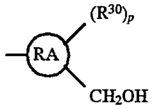

(the group of , $R^{30}$ and p are the same as defined above).}

The reduction of the compound (1x) or the compound (1z) can be conducted under the same conditions as employed in the reduction conducted using a hydride reducing agent for the compound (1) where $R^1$ or $R^3$ is a 5- to 15-membered monocyclic, bicyclic or tricyclic heterocyclic residual group having at least one oxo group adjacent to the nitrogen atom of the heterocyclic ring.

[Reaction scheme-21]

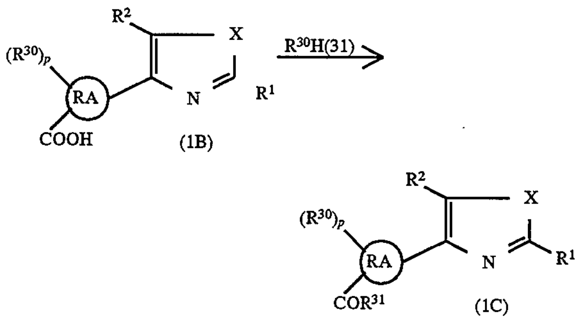

(1B)

(1C)

-continued

[Reaction scheme-21]

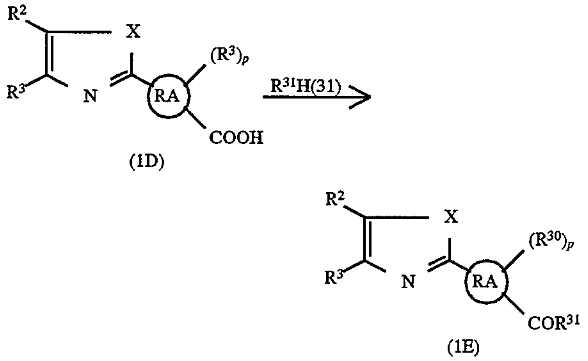

(1D)

(1E)

[wherein $R^1$, $R^2$, $R^3$, X, $R^{30}$, p and  are the same as defined above; $R^{31}$ represents a group of the formula,

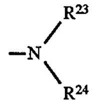

($R^{23}$ and $R^{24}$ are the same as defined above) or an amino-lower alkoxy group which may have a lower alkyl group as a substituent.]

The reaction between the compound (1D) and the compound (31) can be conducted under the same conditions as employed in the reaction between the compound (6) and the compound (4) in the Reaction scheme 3.

[Reaction scheme-22]

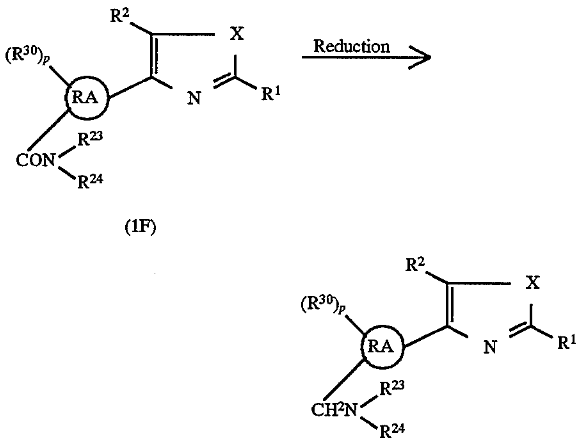

(1F)

(1G)

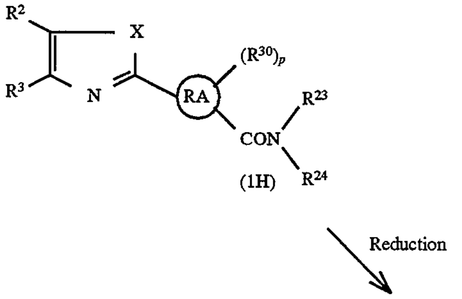

(1H)

-continued

[Reaction scheme-22]

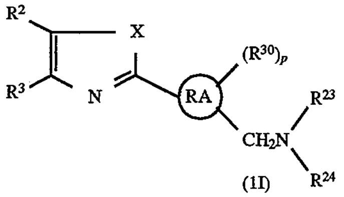

(1I)

(wherein $R^1$, $R^2$, X, $R^{30}$, p, $R^{23}$, $R^{24}$ and (RA) are the same as defined above.)

The reduction of the compound (1F) or (1H) can be conducted under the same conditions as employed in the reduction reaction for the compound (1) where $R^1$ or $R^3$ is a 5- to 15-membered monocyclic, bicyclic or tricyclic heterocyclic residual group having at least one oxo group adjacent to the nitrogen atom of the heterocyclic ring.

[Reaction scheme-23]

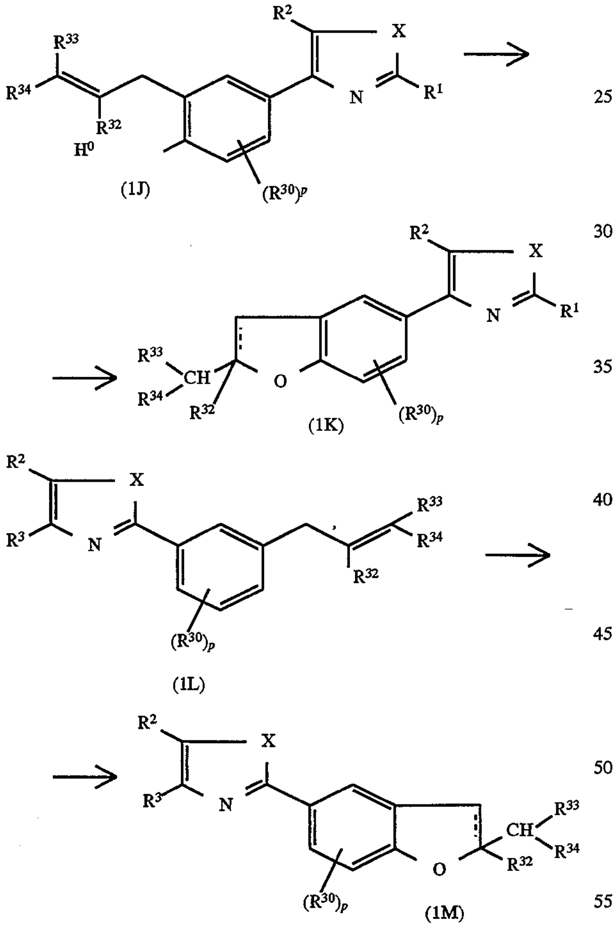

(1J) (1K) (1L) (1M)

[wherein $R^1$, $R^2$, X, p and $R^{30}$ are the same as above. $R^{32}$, $R^{33}$ and $R^{34}$ each represent a hydrogen atom or a lower alkyl group. The bond between the 2- and 3-positions in the compound (1K) or (1M) represents a single bond or a double bond.]

The reaction for converting the compound (1J) or (1L) into a compound (1K) or (1M), respectively, can be conducted in an appropriate solvent in the presence of a catalyst. The solvent can be any of those used in the reaction between the compound (2) and the compound (3) in the reaction scheme 1. The catalyst can be exemplified by metal compounds such as $Pd(OAc)_2+Cu(OAc)_2 \cdot H_2O$ and the like, and halides such as $KI+I_2$ and the like. The proper amount of the catalyst used is ordinarily 0.1–1 mole per 1 mole of the compound (1J) or (1L). When a halide is used, it is used ordinarily in an amount of 0.005–3 moles per 1 mole of the compound (1J) or (1L). The reaction is conducted ordinarily at room temperature to 250° C., preferably at room temperature to 200° C. and is complete ordinarily in about 5–40 hours. When a metal compound is used as the catalyst, the reaction is preferably conducted in an oxygen atmosphere. When $R^{32}$ represents a lower alkyl group, the bond between the 2- and 3-positions of the compound (1K) represents a single bond.

[Reaction scheme-24]

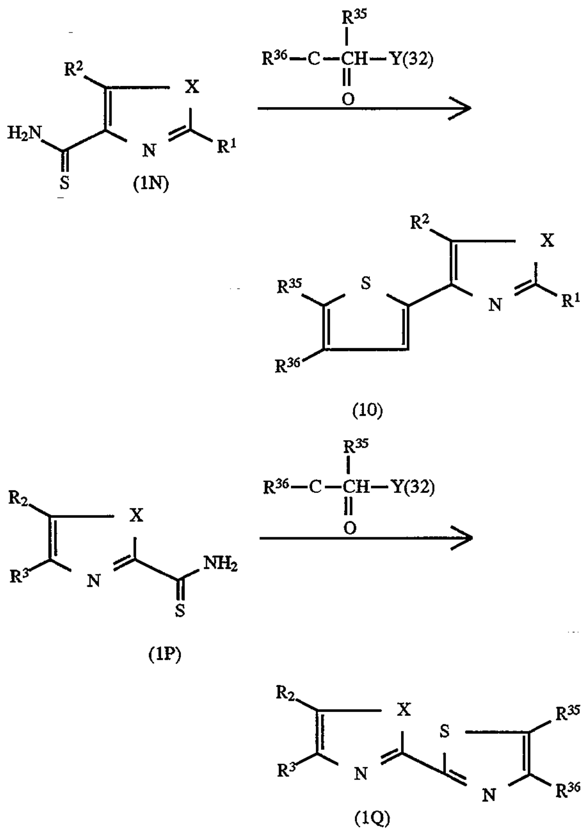

(1N) (10) (1P) (1Q)

(wherein $R^1$, $R^2$, $R^3$, X and Y are the same as above; $R^{35}$ and $R^{36}$ each represent the above-mentioned $R^{30}$).

The reaction between the compound (1W) and the compound (32) and the reaction between the compound (1P) and the compound (32) can be conducted under the same conditions as employed in the reaction between the compound (2) and the compound (3) in the Reaction scheme 1.

[Reaction scheme-25]

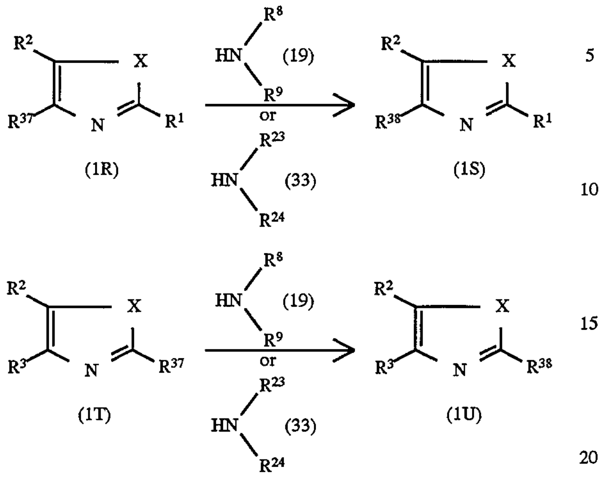

[wherein $R^1$, $R^2$, $R^3$, X, $R^8$ and $R^9$ are the same as defined above; $R^{37}$ represents a group of the formula,

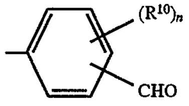

($R^{10}$ and n are the same as defined above) or a group of the formula,

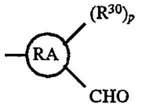

(RA, $R^{30}$ and p are the same as defined above); $R^{38}$ represents a group of the formula,

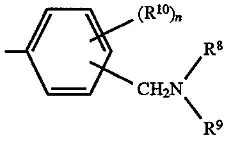

($R^{10}$, $R^8$, $R^9$ and n are the same as defined above) or a group of the formula,

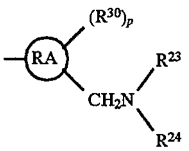

($R^{30}$, $R^{23}$, $R^{24}$, RA and p are the same as defined above)].

In the above reaction, when the $R^{37}$ of the compound (1R) or (1T) represents a group of the formula,

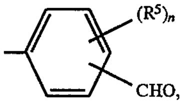

the compound (1R) or (1T) reacts with the compound (19); when the $R^{37}$ represents a group of the formula,

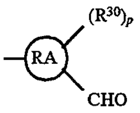

the compound (1R) or (1T) reacts with the compound (33).

The reaction between the compound (1R) or (1T) and the compound (19) or (33) is conducted in the absence of a solvent or in an appropriate solvent in the presence of a reducing agent. The solvent can be exemplified by water; alcohols such as methanol, ethanol, isopropanol and the like; acetic acid; ethers such as dioxane, tetrahydrofuran, diethyl ether, diglyme and the like; and aromatic hydrocarbons such as benzene, toluene, xylene and the like. The reduction method can be exemplified by a method using formic acid or a hydride reducing agent such as sodium boron hydride, sodium cyanoborohydride, lithium aluminum hydride or the like, and a catalytic reduction method using a catalytic reduction catalyst such as palladium black, palladium-carbon, platinum oxide, platinum black, Raney nickel or the like. When formic acid is used as the reducing agent, the appropriate reaction temperature is ordinarily room temperature to 200° C., preferably about 50°–150° C., and the reaction is complete in about 1–10 hours. The proper amount of formic acid used is a large excess relative to the compound (1R) or (1T). When a hydride reducing agent is used, the appropriate reaction temperature is ordinarily –30° C. to 100° C., preferably about 0°–70° C., and the reaction is complete in about 30 minutes to 20 hours. The proper amount of the reducing agent is ordinarily 1–20 moles, preferably 1–15 moles per 1 mole of the compound (1R) or (1T). In particular, when lithium aluminum hydride is used as the reducing agent, it is preferable to use, as a solvent, an ether such as dioxane, tetrahydrofuran, diethyl ether, diglyme or the like, or an aromatic hydrocarbon such as benzene, toluene, xylene or the like. When a catalytic reduction catalyst is used, the reaction is conducted in a hydrogen atmosphere of ordinarily normal pressure to 20 atm., preferably normal pressure to 10 atm. ordinarily at –30° C. to 100° C. preferably at 0°–60° C. The proper amount of the catalyst used is ordinarily 0.1–40% by weight, preferably 1–20% by weight based on the compound (1R) or (1T). The proper amount of the compound (19) or (33) used is ordinarily 1 mole per 1 mole of the compound (1R) or (1T), preferably equimolar to a large excess relative to the compound (1R) or (1T).

[Reaction scheme-26]

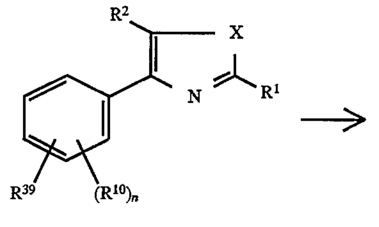

(1V)

-continued

[Reaction scheme-26]

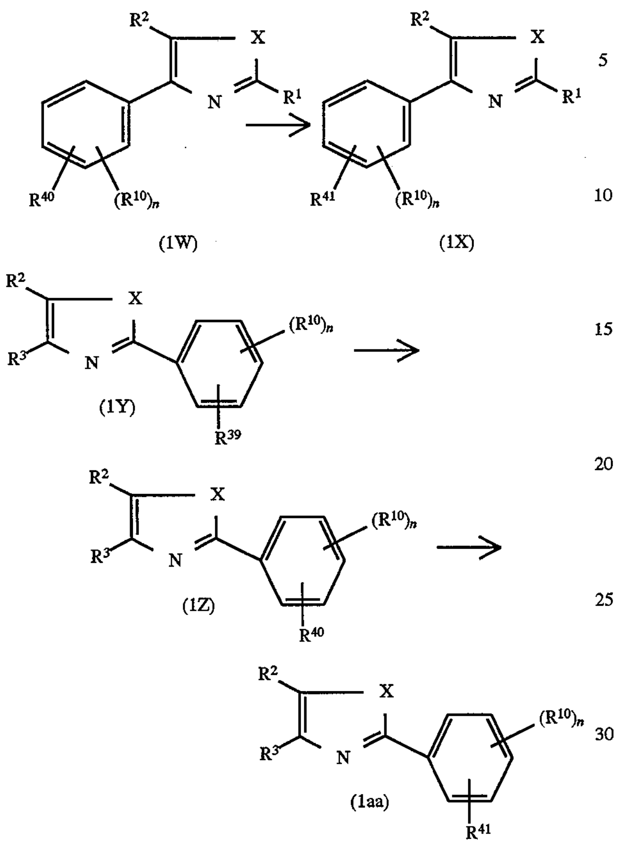

(1W) (1X) (1Y) (1Z) (1aa)

(wherein $R^1$, $R^2$, $R^3$, $R^{10}$, n and X are the same as above; $R^{39}$ represents a lower alkanoyl group; $R^{40}$ represents a lower alkenyl group, a lower alkoxycarbonyl-substituted lower alkenyl group, a carboxy-substituted lower alkenyl group or a lower alkenyl group having halogen atoms; $R^{41}$ represents a lower alkyl group, a lower alkoxycarbonyl-substituted lower alkyl group or a carboxy-substituted lower alkyl group).

The reaction for converting the compound (1V) or (1Y) into a compound (1W) or (1Z), respectively, is conducted in an appropriate solvent in the presence of a Witting reagent and a basic compound.

As the Witting reagent, there can be mentioned, for example, phosphorus compounds represented by the general formula (A), $$(R^{42})_3P—CH—R^{43}Y^- \quad (A)$$

(wherein $R^{42}$ represents a phenyl group, and $R^{35}$ represents a lower alkyl group which may have a lower alkoxycarbonyl group, a carboxyl group or a halogen atom as a substituent; Y is the same as above), and phosphorus compounds represented by general formula (B),

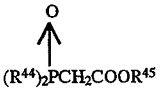

(B)

(wherein $R^{44}$ represents a lower alkoxy group; and $R^{45}$ represents a lower alkyl group). The basic compound can be exemplified by inorganic bases such as metallic sodium, metallic potassium, sodium hydride, sodium amide, sodium hydroxide, potassium hydroxide, sodium carbonate, potassium carbonate, sodium hydrogencarbonate and the like; metal alcoholates such as sodium methylate, sodium ethylate, potassium tert-butoxide and the like; alkyl- or aryllithiums and lithium amides such as methyllithium, n-butyllithium, phenyllithium, lithium diisopropylamide and the like; and organic bases such as pyridine, piperidine, quinoline, triethylamine, N,N-dimethylaniline and the like. The solvent can be any as long as it gives no adverse effect on the reaction, and there can be mentioned, for example, ethers such as diethyl ether, dioxane, tetrahydrofuran, monoglyme, digyme and the like; aromatic hydrocarbons such as benzene, toluene, xylene and the like; aliphatic hydrocarbons such as n-hexane, heptane, cyclohexane and the like; aprotic polar solvents such as pyridine, N,N-dimethylformamide, dimethyl sulfoxide, hexamethylphosphoric triamide and the like; and alcohols such as methanol, ethanol, isopropanol and the like. The appropriate reaction temperature is ordinarily −80° C. to 150° C., preferably about −80° C. to 120° C., and the reaction is complete generally in about 0.5–15 hours.

When the $R^{40}$ of the compound (1W) or (1Z) is a group other than a lower alkenyl group which have a halogen atom, the reaction for converting the compound (1W) or (1Z) into a compound (1X) or (1aa), respectively, can be conducted under the same conditions as employed in the reduction reaction by catalytic hydrogenation for the compound (1) where $R^1$ or $R^3$ is a 5- to 15-membered monocyclic, bicyclic or tricyclic heterocyclic residual group having at least one oxo group adjacent to the nitrogen atom of the heterocyclic ring.

[Reaction scheme-27]

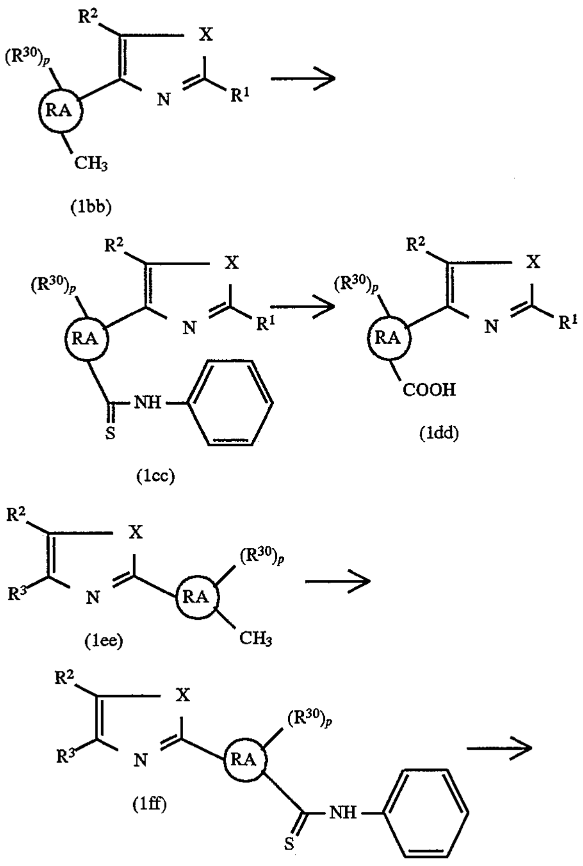

(1bb) (1cc) (1dd) (1ee) (1ff)

-continued
[Reaction scheme-27]

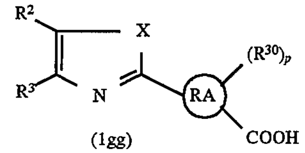

(1gg)

(wherein $R^1$, $R^2$, $R^3$, X, (RA), $R^{30}$ and p are the same as above.)

The reaction for converting the compound (1bb) and (1cc) into a compound (1cc) and (1ff), respectively, can be conducted by heating with aniline and sulfur in the absence of a solvent state.

The reaction is conducted ordinarily at 100°–250° C., preferably at about 100°–200° C., and is complete in about 1–20 hours.

The amounts of aniline and sulfur used are each ordinarily 1–10 moles, preferably 1–2 moles per 1 mole of the compound (1bb) or (1ee).

The reaction for converting the compound (1cc) and (1ff) into a compound (1dd) and (1gg), respectively, can be conducted under the same conditions as employed in the above-mentioned hydrolysis reaction for the compound (1) where $R^1$ or $R^3$ is a phenyl group having at least one alkoxycarbonyl group.

The products thus obtained in each step can be separated and purified by ordinary means. The separation means can be exemplified by solvent extraction, dilution, recrystallization, column chromatography and preparative thin-layer chromatography.

Needless to say, the compounds of the present invention include stereoisomers and optical isomers.

The oxazole derivatives represented by general formula (1) of the present invention can be easily converted into acid addition salts by allowing a pharmaceutically acceptable acid to act on said derivatives. The acid addition salts are also included in the present invention. As the acid, there can be mentioned, for example, inorganic acids such as hydrochloric acid, sulfuric acid, phosphoric acid, hydrobromic acid and the like, as well as organic acids such as acetic acid, oxalic acid, succinic acid, maleic acid, fumaric acid, malic acid, tartaric acid, citric acid, malonic acid, methanesulfonic acid, benzoic acid and the like.

Of the thiazole or oxazole derivatives represented by general formula (1) of the present invention, those compounds having acidic groups can be easily converted into respective salts by allowing a pharmceutically acceptable basic compound to act on the compounds. As the basic compound, there can be mentioned, for example, sodium hydroxide, potassium hydroxide, calcium hydroxide, sodium carbonate and potassium hydrogencarbonate.

The compounds of the present invention are generally used in the form of ordinary pharmaceutical preparations. The pharmaceutical preparations are prepared using diluents or excipients ordinarily used, such as filler, bulking agent, binder, humectant, disintegrator, surfactant, lubricant and the like. The pharmaceutical preparations can be used in various forms depending upon the purpose of remedy, and typical forms include tablets, pills, powders, solutions, suspensions, emulsions, granules, capsules, suppositories, injections (solutions, suspensions, etc.), ointments, etc. In preparing tablets, various carriers conventionally known in the art can be used. The carriers can be exemplified by excipients such as lactose, white sugar, sodium chloride, grape sugar, urea, starch, calcium carbonate, kaolin, crystalline cellulose, silicic acid and the like; binders such as water, ethanol, propanol, simple syrup, grape sugar solution, starch solution, gelation solution, carboxymethyl cellulose, shellac, methyl cellulose, potassium phosphate, polyvinylpyrrolidone and the like; disintegrators such as dry starch, sodium alginate, powdered agar, powdered laminaran, sodium hydrogencarbonate, calcium carbonate, polyoxyethylene sorbitan-fatty acid esters, sodium lauryl sulfate, stearic acid monoglyceride, starch, lactose and the like; disintegration inhibitors such as white sugar, stearin, cacao butter, hydrogenated oil and the like; absorption promoters such as quaternary ammonium salts, sodium lauryl sulfate and the like; humectants such as glycerine, starch and the like; adsorbents such as starch, lactose, kaolin, bentonite, colloidal silicic acid and the like; and lubricants such as refined talc, stearic acid salts, boric acid powder, polyethylene glycol and the like. The tablets can be prepared, as necessary, in the form of ordinary coated tablets, such as sugar-coated tablets, enteric coated tablets or film-coated tablets, or in the form of double-layered tablets or multi-layered tablets. In preparing pills, various carriers conventionally known in the art can be used. The carriers can be exemplified by excipients such as grape sugar, lactose, starch, cacao butter, hardened vegetable oils, kaolin, talc and the like; binders such as powdered acacia, powdered tragacanth, gelatin, ethanol and the like; and disintegrators such as laminaran, agar and the like. In preparing suppositories, various carriers conventionally known in the art can be used. The carriers can be exemplified by a polyethylene glycol, cacao butter, a higher alcohol, a higher alcohol ester, gelatin and a semi-synthetic glyceride. In preparing injections (solutions, emulsions, suspensions), they are sterilized and preferably isotonic to blood. In preparing these solutions, emulsions and suspensions, there can be used all of the diluents conventionally used in the art, such as water, aqueous lactic acid solution, ethyl alcohol, propylene glycol, ethoxylated isostearyl alcohol, polyoxyisostearyl alcohol and polyoxyethylene sorbitan-fatty acid ester. In this case, the injections may contain sodium chloride, grape sugar or glycerine in an amount sufficient to make the injections isotonic, and may further contain a solubilizing agent, a buffer solution, a soothing agent, etc. all ordinarily used. The pharmaceutical preparations may furthermore contain, as necessary, a coloring agent, a preservative, a perfume, a flavoring agent, a sweetening agent and other drugs. In preparing pastes, creams and gels, there can be used various diluents conventionally known in the art, such as white petrolatum, paraffin, glycerine, cellulose derivative, polyethylene glycol, silicon, bentonite and the like.

The amount of the present compound of general formula (1) or a salt thereof to be contained in a pharmaceutical preparation is not particularly restricted and can be appropriately selected in a wide range, but preferably is ordinarily 1–70% by weight in the pharmaceutical preparation.

The method for administering the pharmaceutical preparation is not particularly restricted. The pharmaceutical preparation can be administered in various methods depending upon the form of preparation, the age, sex and other conditions of patient, the degree of disease condition of patient, etc. For example, tablets, pills, a solution, a suspension, an emulsion, granules or capsules are administered orally. An injection is intravenously administered singly or in admixture with an ordinary auxiliary solution of grape sugar, amino acid or the like, or, as necessary, is singly administered intramuscularly, intradermally, subcutaneously or intraperitoneally. Suppositories are administered intrarectally.

The dose of the pharmaceutical preparation of the present invention is appropriately selected depending upon the administration method, the age, sex and other conditions of patient, the degree of disease condition of patient, etc., but preferably is ordinarily about 0.2–200 mg per kg of body weight per day in terms of the amount of the active ingredient, i.e. the present compound (1).

Examples

The present invention is hereinafter described with reference to Reference Examples, Examples, Preparation Examples and Pharmacological Tests.

Reference Example 1

25 g of 3,4-dimethoxybenzonitrile and 23 g of thioacetamide were dissolved in 120 ml of 10% hydrochloric acid-DMF. The solution was heated at 90° C. for 3 hours. The solution was further heated at 130° C. for 5 hours to conduct a reaction. The solvent was removed by distillation. The residue was washed twice with 100 ml of diethyl ether. Similar washing was conducted with 100 ml of water. The resulting crystals were collected by filtration and dried. Recrystallization from methanol was conducted to obtain 18.7 g of 3,4-dimethoxythiobenzamide as light brown columnar crystals.

M.p.: 170°–175° C. (decomposed) NMR (CDC"3) δ: 3.94 (3H, s) 3.95 (3H, s) 6.83 (1H, d, J=8.4 Hz), 7.15 (1H, brs), 7.38 (1H, dd, J=2.2 Hz, 8.4 Hz), 7.52 (1H, brs), 7.63 (1H, d, J=2.2 Hz).

Reference Example 2

500 mg of 3,4,5-trimethoxybenzamide was suspended in 15 ml of benzene. Thereto was added 526 mg of phosphorus pentasulfide. The mixture was refluxed for 30 minutes with heating. The solvent was removed by distillation. To the residue were added 5 ml of 10% sodium hydroxide and 5 ml of water. The mixture was stirred for 30 minutes. The reaction mixture was filtered, and the resulting solid was washed with small amounts of water and ethanol and dried to obtain 330 mg of 3,4,5-trimethoxythiobenzamide as a yellow powder.

M.p.: 182.5°–184° C.

Reference Example 3

4 g of 3',5'-diacetyloxyacetophenone was suspended in 75 ml of carbon disulfide. Thereto was dropwise added a solution of 0.90 ml of bromine dissolved in 25 ml of carbon disulfide, at room temperature in about 1 hour. The system was heated to about 50° C. ocassionally in the course of dropwise addition and, each time when a reaction started, the system was returned to room temperature and stirred. After the completion of the dropwise addition, stirring was conducted at room temperature for 1 hour. After the completion of the reaction, the solvent was removed by distillation to obtain 5.53 g of 3',5'-diacetyloxy-2-bromoacetophenone as brown crystals.

M.p.: 61°–62° C.

Reference Example 4

5.47 g of chloroacetyl chloride was dissolved in 20 ml of dichloromethane. Thereto was added 6.46 g of finely ground aluminum chloride with ice-cooling. Stirring was conducted for 30 minutes. Thereto was added 2 g of 3,4-dihydro-2H-1,4-benzothiazin-3(4H)-one. The mixture was stirred for 4 hours with ice-cooling and then overnight at room temperature. The reaction mixture was poured into ice water. The resulting crystals were collected by filtration, water-washed and dried to obtain 3.03 g of 6-α-chloroacetyl-3,4-dihydro-2H-1,4-benzothiazin-3-one.

NMR (DNSO-d6) δ: 3.55 (2H, s), 5.10 (2H, s), 7.65-7.45 (3H, m), 10.76 (1H, s).

Reference Example 5

2 g of 3,4-dimethoxybenzoic acid was dissolved in 80 ml of methanol. Thereto was added 600 mg of sodium methoxide. The mixture was stirred for 30 minutes. The solvent was removed by distillation. The residue was dissolved in 50 ml of DMF. Thereto was added 2.56 g of 6-α-chloroacetyl-3,4-dihydrocarbostyril. The mixture was stirred at 140° C. for 2 hours. The solvent was removed by distillation. Water was added to the residue. The resulting crystals were collected by filtration and dried to obtain 4.8 g of 6-[2-(3,4-dimethoxybenzoyloxy)acetyl]-3,4-dihydrocarbostyril as a white powder.

M.p.: 215°–216° C.

Reference Example 6

3 g of 6-α-aminoacetyl-3,4-dihydrocarbostyril monohydrochloride was suspended in 60 ml of tetrahydrofuran. Thereto were added 7 ml of triethylamine and 2.8 mg of 3,4-dimethoxybenzoyl chloride. The mixture was stirred at room temperature. After 3 hours, the resulting crystals were collected by filtration, methanol-washed and dried to obtain 2.6 g of 6-[2-(3,4-dimethoxybenzoylamino)acetyl]-3,4-dihydrocarbostyril as white acicular crystals.

M.p.: 246°–247° C.

Reference Examples 7–38

Compounds shown in Table 1 were obtained by using respective starting materials, in the same procedure as in Reference Example 1 or 2.

TABLE 1

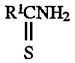

| Reference Example | $R^1$ | Properties |
|---|---|---|
| 7 | 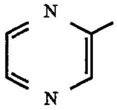 | NMR (DMSO-$d_6$) δ:<br>8.62–8.67 (1H, m)<br>8.83 (1H, d, J-2.6Hz),<br>9.55 (1H, d, J=1.4Hz),<br>10.02 (1H, brs),<br>10.32 (1H, brs) |
| 8 | 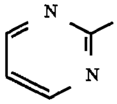 | NMR (DMSO-$d_6$) δ:<br>7.60 (1H, t, J=4.8Hz),<br>8.89 (2H, d, J=4.8Hz),<br>9.89 (1H, brs),<br>10.30 (1H, brs) |
| 9 | 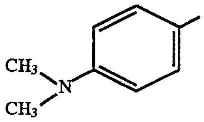 | Crystal form: Light brown acicular<br>(recrystallized from ethanol)<br>Mp: 86–87° C. (HCl salt) |
| 10 | 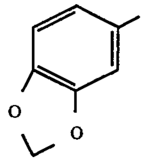 | NMR (DMSO-$d_6$) δ:<br>6.12 (2H, s),<br>6.96 (1H, d, J=8.2Hz),<br>7.51 (1H, d, J=1.8Hz),<br>7.59 (1H, dd, J=1.8Hz, 8.2Hz),<br>9.37 (1H, brs),<br>9.73 (1H, brs) |
| 11 | 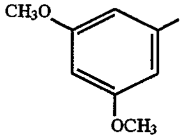 | Crystal form: Yellow columnar<br>(recrystallized from<br>ethyl acetate-n-hexane)<br>Mp: 116–117° C. |
| 12 | 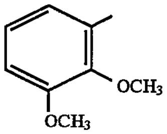 | Crystal form: Yellow columnar<br>(recrystallized from<br>ethyl acetate)<br>Mp: 130–131° C. |
| 13 | 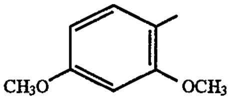 | NMR (DMSO-$d_6$) δ:<br>3.80 (3H, s),<br>3.84 (3H, s),<br>6.50–6.63 (2H, m),<br>8.00–8.10 (1H, m),<br>9.14 (1H, brs),<br>9.79 (1H, brs) |
| 14 | 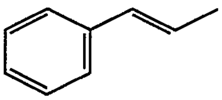 | Crystal form: Brown plate<br>(recrystallized from<br>methanol)<br>Mp: 144–145° C. |
| 15 | 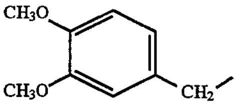 | Crystal form: Light brown powder<br>(recrystallized from<br>ethanol)<br>Mp: 133–134° C. |
| 16 | 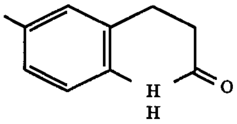 | Crystal form: Brown powder<br>(recrystallized from<br>dimethylformamide-<br>ethanol)<br>Mp: 243–246° C. |

TABLE 1-continued

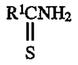

| Reference Example | $R^1$ | Properties |
|---|---|---|
| 17 | 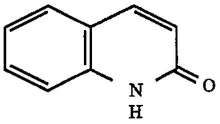 | Crystal form: Yellow scaly (recrystallized from dimethylformamide-water) |
| 18 | 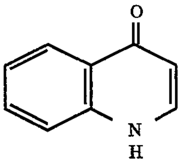 | NMR (DMSO-$d_6$) δ:<br>12.90 (1H, brs),<br>11.66 (1H, brs),<br>9.81 (1H, brs),<br>9.39 (1H, d, J=7Hz),<br>8.27 (1H, d, J=8Hz),<br>7.9–7.6 (2H, m),<br>7.6–7.4 (1H, m) |
| 19 | 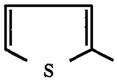 | NMR ($CDCl_3$) δ:<br>7.57 (1H, dd, J=5.1Hz, 1.1Hz),<br>7.50 (1H, dd, J=3.9Hz, 1.1Hz),<br>7.09 (1H, dd, J=5.0Hz, 3.9Hz),<br>7.6–6.9 (2H, br) |
| 20 | 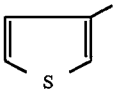 | NMR ($CDCl_3$) δ:<br>8.00 (1H, dd, J=3.0Hz, 1.4Hz),<br>7.51 (1H, dd, J=5.1Hz, 1.4=Hz),<br>7.33 (1H, dd, J=5.1Hz, 3.0Hz),<br>7.9–7.0 (2H, br) |
| 21 | 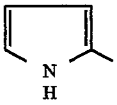 | NMR ($CDCl_3$) δ:<br>10.0–9.3 (1H, br),<br>7.05 (1H, brs),<br>7.1–6.7 (2H, br),<br>6.65 (1H, brs),<br>6.35–6.25 (1H, m) |
| 22 | 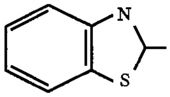 | NMR (DMSO-$d_6$) δ:<br>10.38 (1H, brs),<br>10.15 (1H, brs),<br>8.25–8.0 (2H, m),<br>7.7–7.45 (2H, m) |
| 23 | 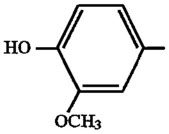 | NMR ($CDCl_3$) δ:<br>7.71 (1H, d, J=2.1Hz),<br>7.6 (1H, brs),<br>7.3 (1H, brs),<br>7.32 (1H, dd, J=8.3Hz, 2.1Hz),<br>7.27 (1H, s),<br>6.89 (1H, d, J=8.3Hz),<br>6.22 (1H, s),<br>3.97 (3H, s) |
| 24 | 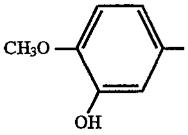 | NMR ($CDCl_3$) δ:<br>7.55 (1H, dd, J=8.5Hz, 2.3Hz),<br>7.5 (1H, brs),<br>7.45 (1H, d, J=2.3Hz),<br>7.15 (1H, brs),<br>6.86 (1H, d, J=8.5Hz),<br>5.73 (1H, s),<br>3.95 (3H, s) |
| 25 | 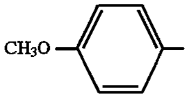 | NMR ($CDCl_3$) δ:<br>8.0–7.85 (2H, m),<br>7.55 (1H, brs),<br>7.1 (1H, brs),<br>7.0–6.85 (2H, m),<br>3.86 (3H, s) |
| 26 | 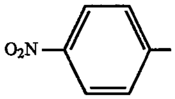 | NMR (DMSO-$d_6$) δ:<br>10.22 (1H, brs),<br>9.81 (1H, brs),<br>8.24 (2H, d, J=8.6Hz),<br>8.01 (2H, d, J=8.8Hz) |

TABLE 1-continued

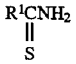

| Reference Example | $R^1$ | Properties |
|---|---|---|
| 27 | 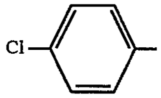 | NMR (DMSO-$d_6$) δ: 9.95 (1H, brs), 9.55 (1H, brs), 7.95–7.85 (2H, m), 7.55–7.45 (2H, m) |
| 28 | 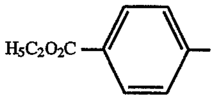 | NMR (DMSO-$d_6$) δ: 10.06 (1H, brs), 9.67 (1H, brs), 8.15–7.85 (4H, m), 4.33 (2H, dg, J=7.2Hz, 4.0Hz), 1.31 (3H, t, J=7.2Hz) |
| 29 | 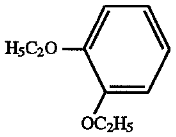 | NMR (DMSO-$d_6$) δ: 9.62 (1H, brs), 9.30 (1H, brs), 7.65–7.5 (2H, m), 6.95 (1H, d, J=9.1Hz), 4.07 (2H, q, J=7Hz), 4.04 (2H, q, J=7Hz), 1.33 (6H, t, J=7Hz) |
| 30 | 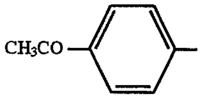 | NMR (DMSO-$d_6$) δ: 10.05 (1H, brs), 9.65 (1H, brs), 8.02–7.85 (4H, m), 2.60 (3H, s) |
| 31 | 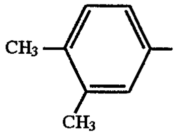 | NMR (DMSO-$d_6$) δ: 9.68 (1H, brs), 9.33 (1H, brs), 7.71 (1H, d, J=1.7Hz), 7.63 (1H, dd, J=7.8Hz, 1.9Hz), 7.15 (1H, d, J=7.9Hz), 2.24 (6H, s) |
| 32 | 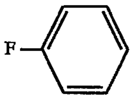 | NMR (DMSO-$d_6$) δ: 9.88 (1H, brs), 9.50 (1H, brs), 8.05–7.9 (2H, m), 7.3–7.15 (2H, m) |
| 33 | 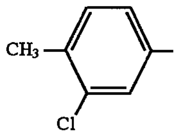 | NMR (DMSO-$d_6$) δ: 9.93 (1H, brs), 9.54 (1H, brs), 7.93 (1H, d, J=1.8Hz), 7.77 (1H, dd, J=8.0Hz, 1.9Hz) 7.39 (1H, d, J=8.0Hz), 2.34 (3H, s) |
| 34 | 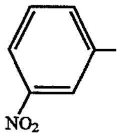 | NMR (DMSO-$d_6$) δ: 10.21 (1H, brs), 9.85 (1H, brs), 8.69 (1H, t, J=2Hz), 8.4–8.2 (2H, m), 7.71 (1H, t, J=8Hz) |
| 35 | 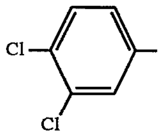 | NMR (DMSO-$d_6$) δ: 10.09 (1H, brs), 9.66 (1H, brs), 8.08 (1H, d, J=2.2Hz), 7.86 (1H, dd, J=8.6Hz, 2.2Hz), 7.69 (1H, d, J=8.6Hz) |

TABLE 1-continued

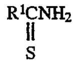

| Reference Example | $R^1$ | Properties |
|---|---|---|
| 36 | 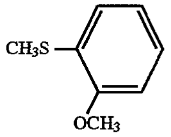 | NMR (DMSO-$d_6$) δ: 9.76 (1H, brs), 9.43 (1H, brs), 7.59 (1H, dd, J=6.6Hz, 1.4Hz), 7.49 (1H, d, J=1.3Hz), 7.14 (1H, d, J=6.6Hz), 3.85 (3H, s), 2.41 (3H, s) |
| 37 | 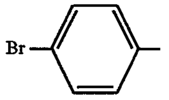 | NMR (DMSO-$d_6$) δ: 9.95 (1H, brs), 9.56 (1H, brs), 7.9–7.7 (2H, m), 7.7–7.5 (2H, m) |
| 38 | 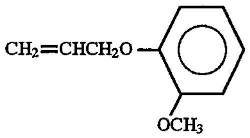 | NMR (DMSO-$d_6$) δ: 9.65 (1H, brs), 9.32 (1H, brs), 7.65–7.5 (2H, m), 7.45–7.3 (1H, m), 7.15–6.9 (1H, m), 6.15–5.9 (1H, m), 5.5–5.2 (2H, m), 4.8–4.55 (2H, m), 3.80 (3H, s) |

Reference Examples 39–60

Compounds shown in Table 3 were obtained by using respective starting materials, in the same procedure as in Reference Example 3 or 4.

TABLE 2

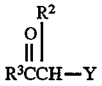

| Reference Example | $R^2$ | $R^3$ | Y | Properties |
|---|---|---|---|---|
| 39 | H | 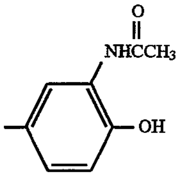 | Cl | Crystal form: White powder (recrystallized from acetone) Mp: 210–212° C. (decomposed) |
| 40 | H | 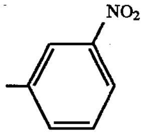 | Br | Crystal form: White powder (recrystallized from ethyl acetate-n-hexane) Mp: 85–86° C. |
| 41 | H | 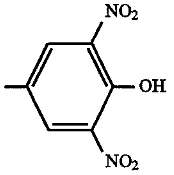 | Br | NMR ($CDCl_3$) δ: 4.42 (2H, s), 8.93 (2H, s) |

TABLE 2-continued
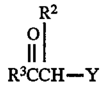
| Reference Example | $R^2$ | $R^3$ | Y | Properties |
|---|---|---|---|---|
| 42 | H | 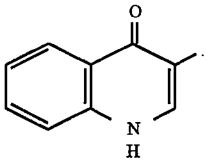 | Br | NMR (DMSO-$d_6$) δ: 12.75 (1H, brs), 8.64 (1H, d, J=6.8Hz), 8.23 (1H, d, J=8.1Hz), 7.8–7.6 (2H, m), 7.55–7.4 (1H, m), 4.93 (2H, s) |
| 43 | H | 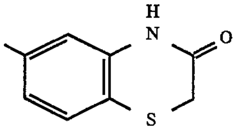 | Cl | NMR (DMSO-$d_6$) δ: 10.76 (1H, s), 7.65–7.45 (3H, m), 5.10 (2H, s), 3.55 (2H, s) |
| 44 | H | 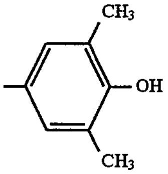 | Cl | NMR ($CDCl_3$) δ: 2.30 (6H, s), 4.65 (2H, s), 7.64 (2H, s) |
| 45 | H | 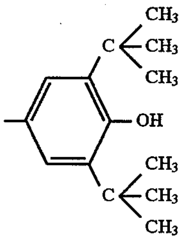 | Cl | NMR ($CDCl_3$) δ: 1.32 (9H, s), 1.42 (9H, s), 4.75 (2H, s), 7.50 (1H, d, J=2.4Hz), 7.60 (1H, d, J-2.4Hz) |
| 46 | H | 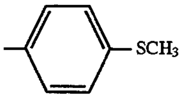 | Cl | NMR ($CDCl_3$) δ: 2.53 (3H, s), 4.66 (2H, s), 7.29 (1H, d, J=8.8Hz), 7.87 (1H, d, J=8.8Hz), |
| 47 | H | 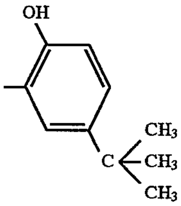 | Cl | NMR ($CDCl_3$) δ: 1.33 (9H, s), 4.30 (1H, s), 4.76 (1H, s), 6.91–7.18 (1H, m), 7.34–7.48 (1H, m), 7.58–7.72 (1H, m) |
| 48 | H | 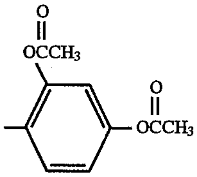 | Br | NMR ($CDCl_3$) δ: 7.89 (1H, d, J=8.6Hz), 7.14 (1H, dd, J=8.6Hz, 2.3Hz), 7.05 (1H, d, J=2.2Hz), 4.40 (2H, s), 2.37 (3H, s), 2.32 (3H, s) |
| 49 | H | 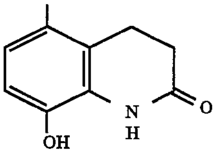 | Cl | Crystal form: White powder Mp: 189–191° C. |

TABLE 2-continued

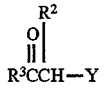

| Reference Example | $R^2$ | $R^3$ | Y | Properties |
|---|---|---|---|---|
| 50 | | 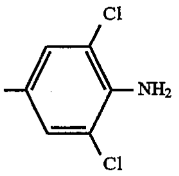 | Br | Crystal form: Light green acicular (recrystallized from methanol)<br>Mp: 151–153° C. |
| 51 | H | 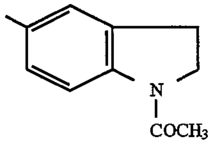 | Cl | Crystal form: Colorless acicular<br>Mp: 238–240° C. |
| 52 | H | 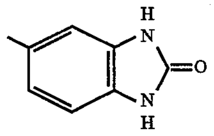 | Cl | NMR (DMSO-$d_6$) δ:<br>5.14 (2H, s),<br>7.06 (1H, d, J=8.2Hz),<br>7.52 (1H, s),<br>7.70 (1H, dd, J=1.6Hz, 8.2Hz),<br>10.97 (1H, s),<br>11.12 (1H, s) |
| 53 | H | 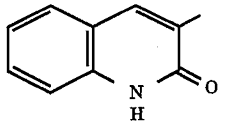 | Br | Crystal form: White powder<br>Mp: 201–210° C. (decomposed) |
| 54 | H | 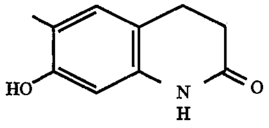 | Cl | Crystal form: Colorless plate<br>Mp: 210–215° C. |
| 55 | H | 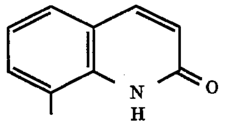 | Cl | Crystal form: Light yellow acicular<br>Mp: 179–180° C. |
| 56 | H | 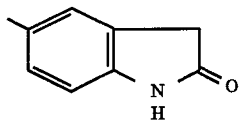 | Cl | Crystal form: White powder (recrystallized from methanol-chloroform)<br>Mp: 246.5–247° C. |
| 57 | H | 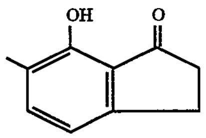 | Cl | Crystal form: White powder<br>Mp: 146–148° C. |
| 58 | H | 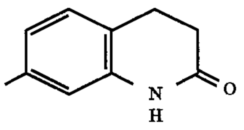 | Cl | NMR (DMSO-$d_6$) δ:<br>2.43–2.56 (2H, m),<br>2.93–3.03 (2H, m),<br>5.13 (2H, s),<br>7.35 (1H, d, J=6.4Hz),<br>7.43 (1H, d, J=1.4Hz),<br>7.58 (1H, dd, J=1.4Hz, 6.4Hz),<br>10.28 (1H, s) |

TABLE 2-continued

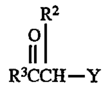

| Reference Example | $R^2$ | $R^3$ | Y | Properties |
|---|---|---|---|---|
| 59 | H | 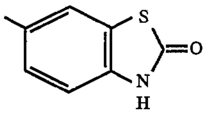 | Br | Crystal form: White powder<br>NMR (DMSO-$d_6$) δ:<br>4.82 (2H, s),<br>7.18 (1H, d, J=8.4Hz),<br>7.90 (1H, dd, J=1.8Hz, 8.4Hz),<br>8.25 (1H, d, J=1.8Hz) |
| 60 | H | 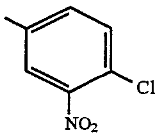 | Br | Crystal form: Yellow acicular<br>(recrystallized from<br>ethyl acetate-n-<br>hexane)<br>Mp: 83–84° C. |

Reference Example 61

1.5 g of 1,3-dichloroacetone and 2.3 g of 3,4-dimethoxythiobenzamide were suspended in 100 ml of ethanol. The suspension was heated for 3 hours to complete the reaction. The solvent was removed by distillation. The residue was purified by silica gel column chromatography to obtain 1.86 g of 2-(3,4-dimethoxyphenyl)-4-chloromethylthiazole as a colorless viscous oil.

NMR ($CDCl_3$) δ: 3.94 (3H, s), 3.99 (3H, s), 4.74 (2H, s), 6.90 (1H, d, J=8.3 Hz), 7.24 (1H, s), 7.46 (1H, dd, J=2.1 Hz, 8.3 Hz), 7.53 (1H, d, J=2.1 Hz).

Reference Examples 62–70

Compounds shown in Table 3 where obtained by using respective starting materials, in the same procedure in Reference Example 1 or 2.

TABLE 3

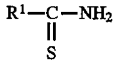

| Reference Example | $R^1$ | Properties |
|---|---|---|
| 62 | 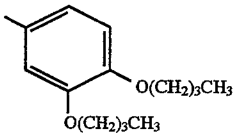 | NMR (DMSO-$d_6$) δ:<br>0.86 (6H, brs), 1.10–1.53 (28H, m),<br>1.60–1.8 (4H, m), 3.85–4.15 (4H, m),<br>6.94 (1H, d, J=9.2Hz), 7.53–7.65 (2H,<br>m), 9.29 (1H, brs), 9.61 (1H, brs) |
| 63 | 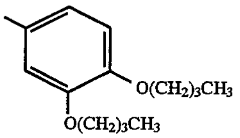 | NMR (DMSO-$d_6$) δ:<br>0.92 (6H, t, J=7.2Hz), 1.30–1.55 (4H,<br>m), 1.55–1.81 (4H, m), 3.99 (4H, q,<br>J=6.2Hz), 6.96 (1H, d, J=9.1Hz), 7.50–<br>7.65 (1H, m), 9.30 (1H, brs), 9.62 (1H,<br>brs) |
| 64 | 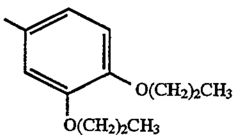 | NMR (DMSO-$d_6$) δ:<br>0.97 (6H, t, J=7.4Hz), 1.58–1.85 (4H, m)<br>3.95 (4H, q, J=6.4Hz), 6.96 (1H, d,<br>J=9.1Hz), 7.50–7.62 (2H, m), 9.30 (1H,<br>brs), 9.62 (1H, brs) |
| 65 | 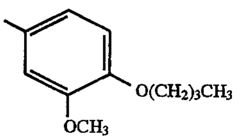 | NMR (DMSO-$d_6$) δ:<br>0.96 (3H, t, J=7.3Hz), 1.61–1.86 (2H,<br>m), 3.97 (3H, s), 3.96 (2H, t, J=6.6Hz),<br>6.96 (1H, d, J=9.2Hz), 7.50–7.62 (2H,<br>m), 9.32 (1H, brs), 9.63 (1H, brs) |

TABLE 3-continued

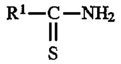

| Reference Example | $R^1$ | Properties |
|---|---|---|
| 66 | 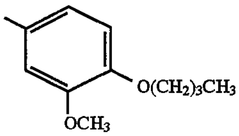 | NMR (DMSO-$d_6$) δ: 0.92 (3H, t, J=7.2Hz), 1.30–1.55 (2H, m), 1.55–1.80 (2H, m), 3.78 (3H, s), 4.00 (2H, t, J=6.5Hz), 6.96 (1H, d), J=9.1Hz), 7.52–7.66 (2H, m), 9.31 (1H, brs), 9.63 (1H, brs) |
| 67 | 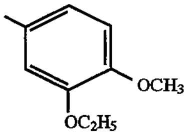 | NMR (DMSO-$d_6$) δ: 1.33 (3H, t, J=6.9Hz), 3.80 (3H, s), 4.04 (2H, q, J=6.9Hz), 6.96 (1H, d, J=8.2Hz), 7.50–7.66 (2H, m), 9.31 (1H, brs), 9.63 (1H, brs) |
| 68 | 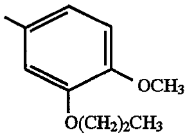 | NMR (DMSO-$d_6$) δ: 0.97 (3H, t, J=7.4Hz), 1.63–1.88 (2H, m), 3.80 (3H, s), 3.94 (2H, t, J=6.6Hz), 6.96 (1H, d, J=8.3Hz), 7.53–7.67 (2H, m), 9.31 (1H, brs), 9.63 (1H, brs) |
| 69 | 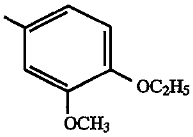 | NMR (DMSO-$d_6$) δ: 1.33 (3H, t, J=7.0Hz), 3.78 (3H, s), 4.05 (2H, q, J=7.0Hz), 6.95 (1H, d, J=9.1Hz), 7.51–7.66 (2H, m), 9.31 (1H, brs), 9.64 (1H, brs) |
| 70 | 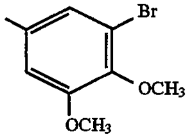 | NMR (DMSO-$d_6$) δ: 3.77 (3H, s), 3.87 (3H, s), 7.58 (1H, d, J=2.1Hz), 7.75 (1H, d, J=2.1Hz), 9.52 (1H, brs), 9.95 (1H, brs) |

Reference Examples 71–74

Compounds shown in Table 4 were obtained by using respective starting materials, in the same procedure as in Reference Example 3 or 4.

TABLE 4

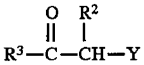

| Reference Example | $R^2$ | $R^3$ | Y | Properties |
|---|---|---|---|---|
| 71 | | 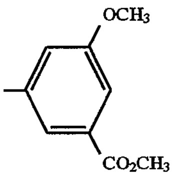 | Br | NMR ($CDCl_3$) δ: 3.91 (3H, s), 3.96 (3H, s), 4.49 (2H, s), 7.66–7.75 (1H, m), 7.75–7.86 (1H, m), 8.19 (1H, t, J=1.4Hz) |
| 72 | | 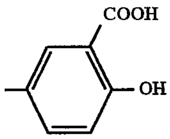 | Br | NMR (DMSO-$d_6$) δ: 4.90 (2H, s), 7.10 (1H, t, J=6.5Hz), 8.04–8.20 (1H, m), 8.45 (1H, d, J=1.7Hz) |

TABLE 4-continued

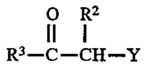

| Reference Example | $R^2$ | $R^3$ | Y | Properties |
|---|---|---|---|---|
| 73 | H | 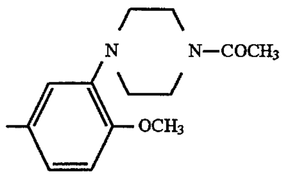 | Cl | Light pink powder NMR (DMSO-$d_6$) δ: 2.05 (3H, s), 2.84–3.a0 (4H, m), 3.52–3.67 (4H, m), 3.92 (3H, s), 5.13 (2H, s), 7.12 (1H, d, J=8.6Hz), 7.45 (1H, d, J=2.0Hz), 7.73 (1H, dd, J=2.0Hz, 8.6Hz) |
| 74 | H | 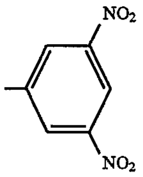 | Br | NMR ($CDCl_3$) δ: 4.50 (2H, s), 9.07–9.49 (3H, m) |

Reference Examples 75–77

Compounds shown in Table 5 were obtained by using respective starting materials, in the same procedure as in Reference Examples 1 or 2.

TABLE 5

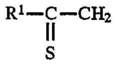

| Reference Example | $R^1$ | Properties |
|---|---|---|
| 75 | 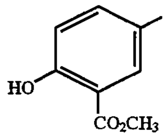 | NMR ($CDCl_3$) δ: 4.00 (3H, s), 7.25 (1H, d, J=8.8Hz), 7.15 (1H, brs), 7.52 (1H, brs), 8.08 (1H, dd, J=2.5Hz, 8.8Hz), 8.46 (1H, d, J=2.5Hz), 11.17 (1H, s) |
| 76 | 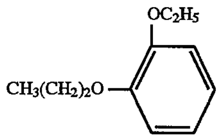 | NMR ($CDCl_3$) δ: 1.05 (3H, t, J=7.5Hz), 1.46 (3H, t, J=7.0Hz), 1.79–1.93 (2H, m), 4.02 (2H, t, J=6.8Hz), 4.13 (2H, q, J=7.0Hz), 6.85 (1H, d, J=8.4Hz), 7.16 (1H, brs), 7.37 (1H, dd, J=2.3Hz, 8.4Hz), 7.54 (1H, brs), 7.60 (1H, d, J=2.3Hz) |
| 77 | 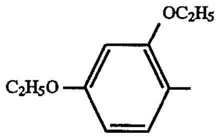 | NMR ($CDCl^3$) δ: 1.43 (3H, t, J=7.0Hz), 1.50 (3H, t, J=7.0Hz), 4.01–4.23 (4H, m) 6.43 (1H, d, J=2.3Hz), 6.53 (1H, dd, J=9.0Hz, 2.3Hz), 7.98 (1H, brs), 8.69 (1H, d, J=9.0Hz), 9.23 (1H, brs) |

Reference Examples 78–97

Compounds shown in Table 6 were obtained by using respective starting materials, in the same procedure as in Reference Example 3 or 4.

TABLE 6
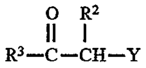
| Reference Example | $R^2$ | $R^3$ | Y | Crystal form (recrystallization solvent) | Melting point (°C.) (salt form) |
|---|---|---|---|---|---|
| 78 | H | 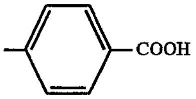 | Br | | NMR[1) (—) |
| 79 | " | 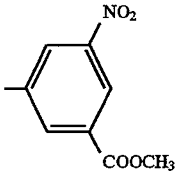 | " | | NMR[2) (1) |
| 80 | " | 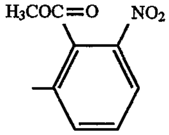 | " | | NMR[3) (1) |
| 81 | H | 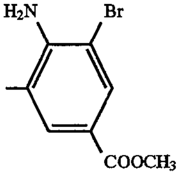 | " | | NMR[4) (—) |
| 82 | " | 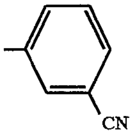 | " | | NMR[5) (—) |
| 83 | " | 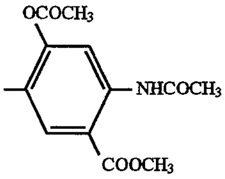 | " | | NMR[6) (—) |
| 84 | H | 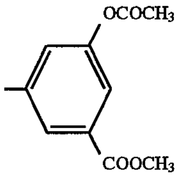 | " | | NMR[7) (—) |
| 85 | " | 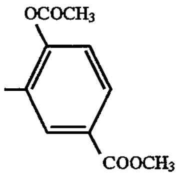 | " | | NMR[8) (—) |

TABLE 6-continued

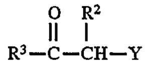

| Reference Example | $R^2$ | $R^3$ | Y | Crystal form (recrystallization solvent) | Melting point (°C.) (salt form) |
|---|---|---|---|---|---|
| 86 | " | 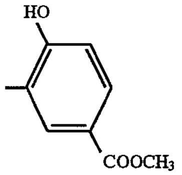 | " | | NMR[9) ] (—) |
| 87 | H | 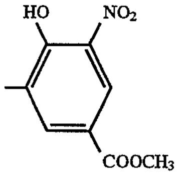 | Br | | NMR[10)] (—) |
| 88 | " | 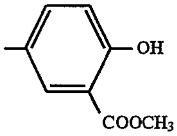 | Cl | White powdery crystals (ethyl acetate-n-hexane) | 105–107 (—) |
| 89 | " | 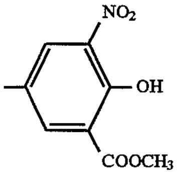 | " | White powdery crystals (ethyl acetate-n-hexane) | 99–100 (—) |
| 90 | " | 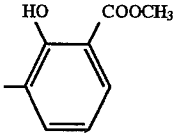 | " | White powdery crystals (ethyl acetate) | 109–110 (—) |
| 91 | H | 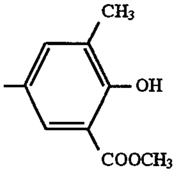 | Cl | Colorless prismatic crystals (ethyl acetate-n-hexane) | 126–127 (—) |
| 92 | " | 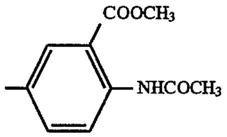 | Br | Light brown acicular crystals (dichloro-methane-ethanol) | 130–131 (—) |
| 93 | " | 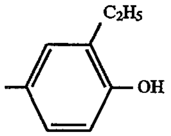 | Cl | | NMR[11)] (—) |
| 94 | $CH_3$ | 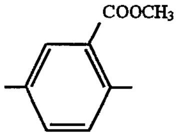 | Br | White acicular crystals (n-hexane-dichloro-methane) | 102–103 (—) |

TABLE 6-continued

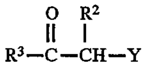

| Reference Example | $R^2$ | $R^3$ | Y | Crystal form (recrystallization solvent) | Melting point (°C.) (salt form) |
|---|---|---|---|---|---|
| 95 | H | 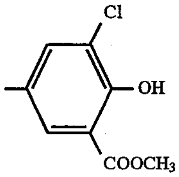 | Cl | White acicular crystals (ethyl acetate-n-hexane) | 121–122 (—) |
| 96 | " | 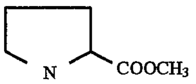 | " | | NMR[12] (—) |
| 97 | " | 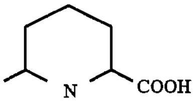 | Br | | NMR[13] (—) |

NMR[1]) Compound of Reference Example 78

NMR ($CDCl_3$) δppm: 2.65 (3H, s) 4.65 (2H, s) 7.98–8.16 (5H, m)

NMR[2]) Compound of Reference Example 79

NMR ($CDCl_3$) δppm: 4.06 (3H, s) 4.57 (2H, s) 8.91 (1H, t, J=1.9 Hz) 8.98 (1H, t, J=1.9 Hz) 9.05 (1H, t, J=1.9 Hz)

NMR[3]) Compound of Reference Example 80

NMR ($CDCl_3$) δppm: 4.00 (3H, s) 4.42 (2H, s) 7.76 (1H, t, J=8.0 Hz) 8.11 (1H, dd, J=1.1 Hz, J=8.0 Hz) 8.32 (1H, dd, J=1.1 Hz, J=8.0 Hz)

NMR[4]) Compound of Reference Example 81

NMR ($CDCl_3$) δppm: 3.88 (3H, s) 4.52 (2H, s) 5.62 (2H, brs) 8.40 (1H, d, J=1.8 Hz) 8.42 (1H, d, J=1.8 Hz)

NMR[5]) Compound of Reference Example 82

NMR ($CDCl_3$) δppm: 4.45 (2H, s) 7.65 (1H, m) 7.67 (1H, m) 8.21 (1H, m) 8.28 (1H, m)

NMR[6]) Compound of Reference Example 83

NMR ($CDCl_3$) δppm: 2.27 (3H, s) 2.62 (3H, s) 3.94 (3H, s) 4.43 (2H, s) 8.30 (1H, s) 8.48 (1H, s)

NMR[7]) Compound of Reference Example 84

NMR ($CDCl_3$) δppm: 2.34 (3H, s) 3.94 (3H, s) 4.52 (2H, s) 7.89 (1H, m) 7.97 (1H, m) 8.43 (1H, m)

NMR[8]) Compound of Reference Example 85

NMR ($CDCl_3$) δppm: 2.39 (3H, s) 3.96 (3H, s) 4.46 (2H, s) 7.21 (1H, d, J=8.6 Hz) 8.29 (1H, dd, J=2.0 Hz, J=8.6 Hz) 8.58 (1H, d, J=2.0 Hz)

NMR[9]) Compound of Reference Example 86

NMR ($CDCl_3$) δppm: 3.94 (3H, s) 4.54 (2H, s) 7.09 (1H, d, J=8.7 Hz) 8.15 (1H, dd, J=2.0 Hz, J=8.7 Hz) 8.49 (1H, d, J=2.0 Hz) 12.11 (1H, s)

NMR[10]) Compound of Reference Example 87

NMR ($CDCl_3$) δppm: 4.00 (3H, s) 4.64 (2H, s) 8.76 (2H, d, J=2.2 Hz) 8.85 (1H, d, J=2.2 Hz) 12.50 (1H, brs)

NMR[11]) Compound of Reference Example 93

NMR ($CDCl_3$) δppm: 1.27 (3H, t, J=7.5 Hz) 2.68 (2H, t, J=7.5 Hz) 4.67 (3H, s) 5.73 (1H, s) 6.85 (1H, d, J=8.4 Hz) 7.75 (1H, dd, J=2.3 Hz, 8.4 Hz) 7.82 (1H, d, J=2.3 Hz)

NMR[12]) Compound of Reference Example 96

NMR ($CDCl_3$) δppm: 3.91 (3H, s) 4.48 (2H, s) 7.35 (1H, m) 7.71 (1H, m) 10.48 (1H, brs)

NMR[13]) Compound of Reference Example 97

NMR ($DMSO-d_6$) δppm: 5.04 (2H, s) 7.56 (1H, brs) 8.10–8.39 (3H, m)

Reference Examples 98–116

Compounds shown in Table 7 were obtained using respective starting materials, in the same procedure as in Reference Example 3 or 4.

TABLE 7

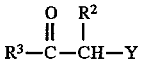

| Reference Example | $R^2$ | $R^3$ | Y | Crystal form (recrystallization solvent) | Melting point (°C.) (salt form) |
|---|---|---|---|---|---|
| 98 | H | 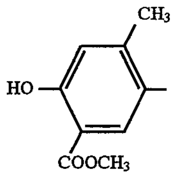 | Cl | | NMR[14] (—) |

TABLE 7-continued
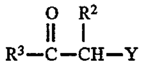
| Reference Example | $R^2$ | $R^3$ | Y | Crystal form (recrystallization solvent) | Melting point (°C.) (salt form) |
|---|---|---|---|---|---|
| 99 | " | 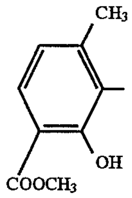 | " | | NMR[15] (—) |
| 100 | H | 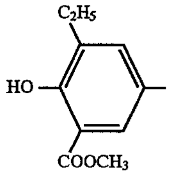 | Cl | Brown solid | NMR[16] (—) |
| 101 | " | 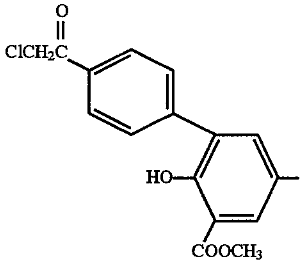 | " | | NMR[17] (—) |
| 102 | " | 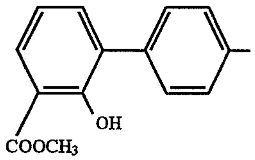 | " | White acicular crystals | NMR[18] (—) |
| 103 | H | 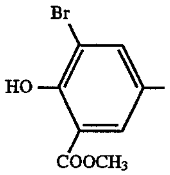 | Cl | White acicular crystals (ethanol) | 107–108 (—) |
| 104 | " | 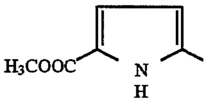 | Br | | NMR[19] (—) |
| 105 | " | 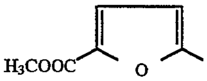 | " | | NMR[20] (—) |
| 106 | " | 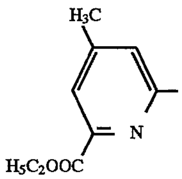 | " | | NMR[21] (—) |
| 107 | H | 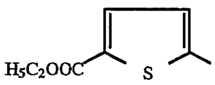 | Br | | NMR[22] (—) |

TABLE 7-continued

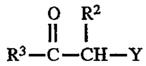

| Reference Example | $R^2$ | $R^3$ | Y | Crystal form (recrystallization solvent) | Melting point (°C.) (salt form) |
|---|---|---|---|---|---|
| 108 | " | 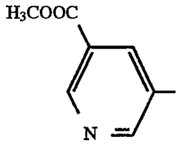 | " | | NMR[23)] (HBr) |
| 109 | " | 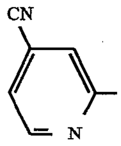 | " | | NMR[24)] (HBr) |
| 110 | " | 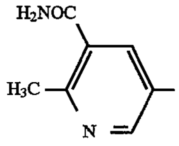 | " | | NMR[25)] (HBr) |
| 111 | H | 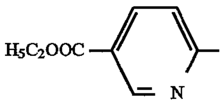 | Br | | NMR[26)] (—) |
| 112 | " | 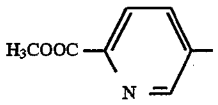 | " | | NMR[27)] (HBr) |
| 113 | " | 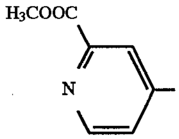 | " | | NMR[28)] (—) |
| 114 | " | 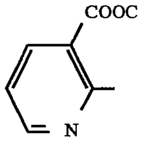 | " | | NMR[29)] (HBr) |
| 115 | H | 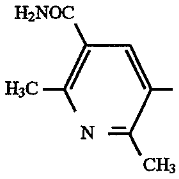 | Br | | NMR[30)] (HBr) |

NMR data of the compounds of Reference Examples 98–102, 105–113 and 115–116

NMR[14)]: Compound of Reference Example 98

$^1$H-NMR($CDCl_3$) δ: 2.59 (3H, s), 4.00 (3H, s), 4.64 (2H, s), 6.90 (1H, s), 8.25 (1H, s), 11.12 (1H, s)

NMR[15)]: Compound of Reference Example 99

$^1$H-NMR($CDCl_3$) δ: 2.33 (3H, s), 3.96 (3H, s), 4.62 (2H, s), 6.79 (1H, d, J=8.1 Hz), 7.80 (1H, d, J=8.1 Hz), 11.40 (1H, s)

NMR[16)]: Compound of Reference Example 100

$^1$H-NMR($CDCl_3$) δ: 1.25 (3H, t, J=7.5 Hz), 2.73 (2H, q, J=7.5 Hz), 4.00 (3H, s), 4.67 (2H, s), 7.98 (1H, d, J=1.7 Hz), 8.35 (1H, d, J=1.7 Hz), 11.66 (1H, s)

NMR[17)]: Compound of Reference Example 101

$^1$H-NMR($CDCl_3$) δ: 4.06 (3H, s), 4.68 (2H, s), 4.75 (2H, s), 7.74 (1H, dd, J=2.0 Hz, 6.7 Hz), 8.06 (1H, dd, J=2.0 Hz, 6.7 Hz), 8.19 (1H, d, J=2.3 Hz), 8.55 (1H, d, J=2.3 Hz), 12.04 (1H, s)

NMR[18)]: Compound of Reference Example 102

$^1$H-NMR($CDCl_3$) δ: 3.99 (3H, s), 4.75 (2H, s) 7.00 (1H, t, J=7.8 Hz), 7.56 (1H, d, J=7.8 Hz), 7.99 (1H, dd, J=1.8 Hz, 7.8 Hz), 8.03 (2H, d, J=8.5 Hz), 11.43 (1H, s), 7.74 (2H, d, J=8.5 Hz)

NMR[19)]: Compound of Reference Example 104

$^1$H-NMR($CDCl_3$) δ: 3.92 (3H, s), 4.28 (2H, s), 6.90 (1H, dd, J=2.1 Hz, 3.3 Hz), 6.95 (1H, dd, J=2.1 Hz, 3.3 Hz), 9.90 (1H, brs)

NMR[20)]: Compound of Reference Example 105

$^1$H-NMR($CDCl_3$) δ: 3.95 (3H, s), 4.42 (2H, s), 7.26 (1H, d, J=3.7 Hz), 7.34 (1H, d, J=3.7 Hz)

NMR[21)]: Compound of Reference Example 106

$^1$H-NMR($CDCl_3$) δ: 1.47 (3H, t, J=7.1 Hz), 2.61 (3H, s), 4.46 (2H, q, J=7.1 Hz), 5.00 (2H, s), 8.21 (2H, m)

NMR[22)]: Compound of Reference Example 107

$^1$H-NMR($CDCl_3$) δ: 1.40 (3H, t, J=7.1 Hz), 4.36 (2H, s), 4.38 (2H, q, J=7.1 Hz), 7.74 (1H, d, J=4.0 Hz), 7.78 (1H, d, J=4.0 Hz)

NMR[23)]: Compound of Reference Example 108

$^1$H-NMR($CDCl_3$) δ: 4.10 (3H, s), 4.92 (2H, s), 9.41–10.01 (3H, m)

NMR[24)]: Compound of Reference Example 109

$^1$H-NMR(DMSO-$d_6$) δ: 5.05 (2H, s), 8.20 (1H, dd, J=1.6 Hz, 5.0 Hz), 8.42 (1H, dd, J=0.9 Hz, 1.6 Hz), 9.01 (1H, dd, J=0.9 Hz, 5.0 Hz)

NMR[25)]: Compound of Reference Example 110

$^1$H-NMR(DMSO-$d_6$) δ: 2.73 (3H, s), 5.03 (2H, s), 8.17 (1H, brs), 8.26 (1H, brs), 8.44 (1H, d, J=2.1 Hz), 8.54 (1H, d, J=2.1 Hz)

NMR[26)]: Compound of Reference Example 111

$^1$H-NMR($CDCl_3$) δ: 4.01 (3H, s), 4.88 (2H, s), 8.15 (1H, dd, J=0.7 Hz, 8.1 Hz), 8.45 (1H, dd, J=2.1 Hz, 8.1 Hz), 9.13 (1H, m)

NMR[27)]: Compound of Reference Example 112

$^1$H-NMR($CDCl_3$) δ: 1.45 (3H, t, J=7.1 Hz), 4.52 (2H, q, J=7.1 Hz), 4.78 (2H, s), 8.49 (1H, d, J=8.1 Hz) 8.96 (1H, dd, J=1.9 Hz, 8.1 Hz), 9.55 (1H, d, J=1.9 Hz)

NMR[28)]: Compound of Reference Example 113

$^1$H-NMR(DMSO-$d_6$) δ: 2.77 (3H, s), 5.08 (2H, s), 8.11 (1H, d, J=5.7 Hz), 8.25 (1H, s), 8.96 (1H, d, J=5.7 Hz)

NMR[29)]: Compound of Reference Example 114

$^1$H-NMR($CDCl_3$) δ: 4.11 (3H, s), 4.76 (2H, s), 7.60 (1H, dd, J=4.8 Hz, 7.9 Hz), 8.12 (1H, dd, J=1.5 Hz, 7.9 Hz), 8.96 (1H, dd, J=1.5 Hz, 4.8 Hz)

NMR[30)]: Compound of Reference Example 115

$^1$H-NMR(DMSO-$d_6$) δ: 2.82 (3H, s), 2.87 (3H, s), 5.20 (2H, s), 8.09 (1H, brs), 8.42 (1H, brs), 9.01 (1H, s)

Example 1

In 20 ml of ethanol were suspended 367 mg of 3',4'-dihydroxy-2-chloroacetophenone and 430 mg of 3,4-dimethoxythiobenzamide. The suspension was refluxed for 3 hours with heating. After cooling, the resulting crystals were collected by filtration, ethanol-washed and dried. The dried material was recrystallized from ethanol to obtain 160 mg of 2-(3,4-dimethoxyphenyl)-4-(3,4-dihydroxyphenyl) thiazole hydrochloride as yellow acicular crystals.

M.p.: 146°–148° C.

Examples 2–136

Compounds shown in Tables 8 and 9 were obtained by using respective starting materials, in the same procedure as in Example 1.

TABLE 8

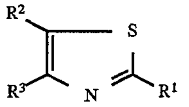

Compound of Example 2

R1= 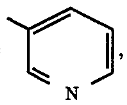 , R2=H,

R3= 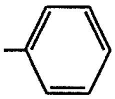

Crystal form: yellow prismatic (recrystallized from methanol)

Mp: 182–183° C. (decomposed, ¼$FeCl_2$ salt)

Compound of Example 3

R1= 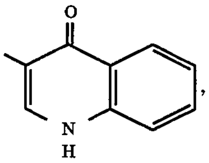 , R2=H,

R3= 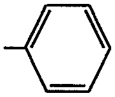

Crystal form: light brown powdery (recrystallized from dimethylformamide)

Mp: 300° C. or above

Compound of Example 4

R1= 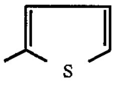 , R2=H,

R3= 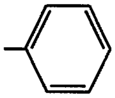

Crystal form: colorless acicular (recrystallized from diethyl ether-n-hexane)

Mp: 59–60° C.

TABLE 8-continued

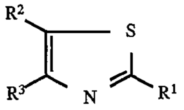

Compound of Example 5

$R^1$= 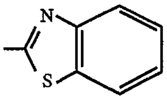 , $R^2$=H, $R^3$= 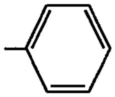

Crystal form: light yellow prismatic (recrystallized from ethanol)
Mp: 172–173° C.

Compound of Example 6

$R^1$= 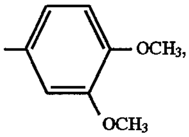 , $R^2$=H, $R^3$= 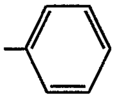

Crystal form: light brown acicular (recrystallized from ethanol)
Mp: 88–89° C. (HCl salt)

Compound of Example 7

$R^1$= 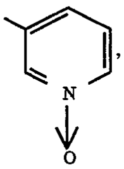 , $R^2$=H, $R^3$= 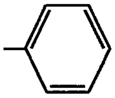

Crystal form: brown powdery (recrystallized from ethanol acetate)
Mp: 140–141° C.

Compound of Example 8

$R^1$= 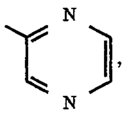 , $R^2$=H, $R^3$= 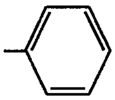

Crystal form: light brown plate (recrystallized from ethanol)
Mp: 129–130° C.

TABLE 8-continued

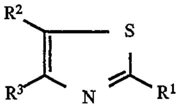

Compound of Example 9

$R^1$= 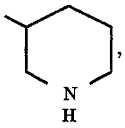 , $R^2$=H, $R^3$= 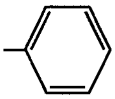

Crystal form: colorless acicular (recrystallized from methanol-ethyl acetate)
Mp: 188–189° C.

Compound of Example 10

$R^1$= 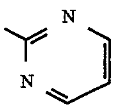 , $R^2$=H, $R^3$= 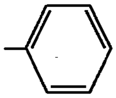

Crystal form: light brown acicular (recrystallized from ethyl acetate)
Mp: 129–130° C.

Compound of Example 11

$R^1$= 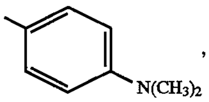 , $R^2$=H, $R^3$= 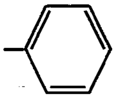

Crystal form: light green columnar (recrystallized from methanol)
Mp: 135–136° C.

Compound of Example 12

$R^1$= 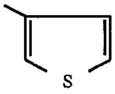 , $R^2$=H, $R^3$= 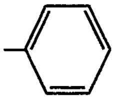

Crystal form: colorless acicular (recrystallized from diethyl ether-n-hexane)
Mp: 57.5–58.5° C.

TABLE 8-continued

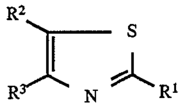

Compound of Example 13

$R^1$ = 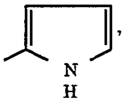 , $R^2$ = H, $R^3$ = 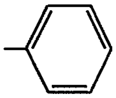

Crystal form: white acicular (recrystallized from diethyl ether-n-hexane)
Mp: 91.5–92° C.

Compound of Example 14

$R^1$ = 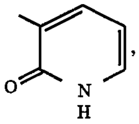 , $R^2$ = H, $R^3$ = 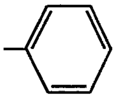

Crystal form: light brown plate (recrystallized from methanol)
Mp: 206–207° C. (decomposed)

Compound of Example 15

$R^1$ = 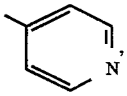 , $R^2$ = H, $R^3$ = 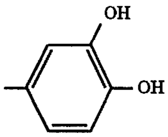

Crystal form: orange powdery (recrystallized from ethanol-water)
Mp: 209–210° C. (decomposed, HCl salt)

Compound of Example 16

$R^1$ = 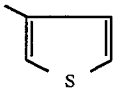 , $R^2$ = H, $R^3$ = 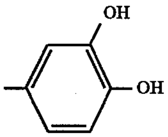

Crystal form: colorless acicular (recrystallized from diethyl ether-n-hexane)
Mp: 83–84° C.

TABLE 8-continued

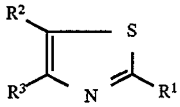

Compound of Example 17

$R^1$ = 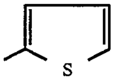 , $R^2$ = H, $R^3$ = 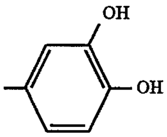

Crystal form: colorless acicular (recrystallized from diethyl ether-n-hexane)
Mp: 76–78° C.

Compound of Example 18

$R^1$ = 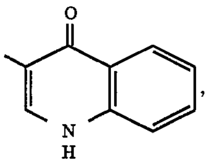 , $R^2$ = H, $R^3$ = 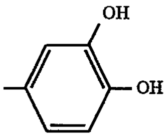

Crystal form: brown powdery (recrystallized from dimethylformamide-water)
Mp: 300° C. or above Compound of Example 19

$R^1$ = 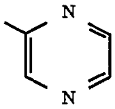 , $R^2$ = H, $R^3$ = 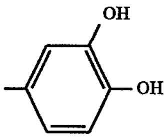

Crystal form: yellow powdery (recrystallized from dioxane-water)
Mp: 280–281° C.

Compound of Example 20

$R^1$ = 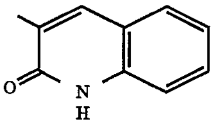 , $R^2$ = H, $R^3$ = 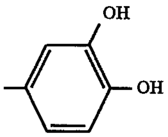

TABLE 8-continued

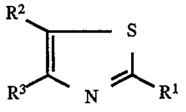

Crystal form: yellow powdery (recrystallized from dimethylformamide-water)
Mp: 262–263° C.

Compound of Example 21

$R^1=$ 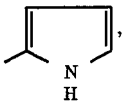 , $R^2$ = H, $R^3=$ 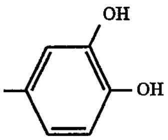

Crystal form: light yellow powdery (recrystallized from ethyl acetate)
Mp: 180–181° C. (decomposed)

Compound of Example 22

$R^1=$ 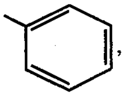 , $R^2$ = H, $R^3=$ 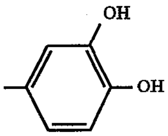

Crystal form: yellow prismatic (recrystallized from ethanol)
Mp: 124–126° C. (HCl salt)

Compound of Example 23

$R^1=$ 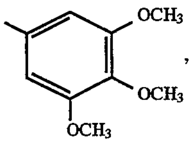 , $R^2$ = H, $R^3=$ 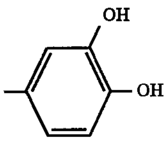

Crystal form: yellow acicular (recrystallized from ethyl acetate-diethyl ether)
Mp: 128–129° C. (HCl—½$H_2O$ salt)

Compound of Example 24

$R^1=$ 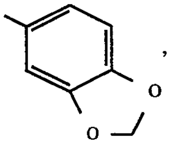 , $R^2$ = H,

TABLE 8-continued

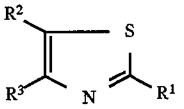

$R^3=$ 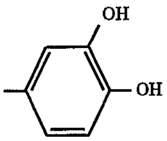

Crystal form: light brown powdery (recrystallized from dimethylformamide-water)
Mp: 187–188° C.

Compound of Example 25

$R^1=$ 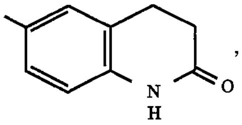 , $R^2$ = H, $R^3=$ 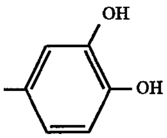

Crystal form: yellow powdery (recrystallized from ethanol)
Mp: 248–249° C. (HCl salt)

Compound of Example 26

$R^1=$ 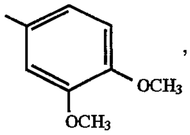 , $R^2$ = H, $R^3=$ 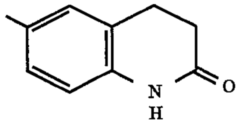

Crystal form: white acicular (recrystallized from ethanol)
Mp: 205–206° C.

Compound of Example 27

$R^1=$ 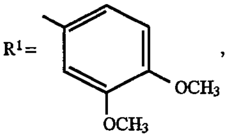 , $R^2$ = H, $R^3=$ 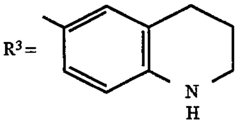

Crystal form: light brown powdery (recrystallized from ethanol)
Mp: 156–158° C. (HCl salt)

TABLE 8-continued

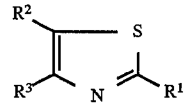

Compound of Example 28

$R^1$ = 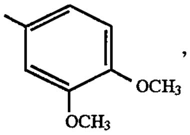 , $R^2$ = H, $R^3$ = 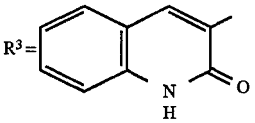

Crystal form: light brown acicular (recrystallized from dimethylformamide)
Mp: 282–284° C. (decomposed)

Compound of Example 29

$R^1$ = 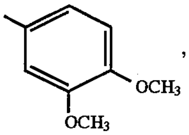 , $R^2$ = H, $R^3$ = 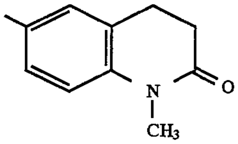

Crystal form: colorless acicular (recrystallized from dimethylformamide)
Mp: 199–200° C.

Compound of Example 30

$R^1$ = 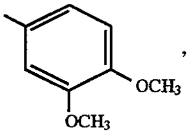 , $R^2$ = H, $R^3$ = 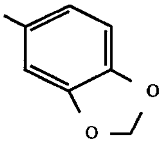

Crystal form: colorless prismatic (recrystallized from ethyl acetate)
Mp: 163–163.5° C.

Compound of Example 31

$R^1$ = 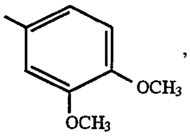 , $R^2$ = H,

TABLE 8-continued

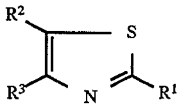

$R^3$ = 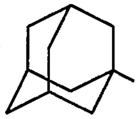

Crystal form: light yellow plate (recrystallized from n-hexane)
Mp: 98–99° C.

Compound of Example 32

$R^1$ = 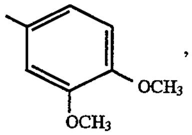 , $R^2$ = H, $R^3$ = 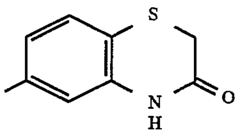

Crystal form: light yellow powdery (recrystallized from dimethylformamide)
Mp: 249–250° C.

Compound of Example 33

$R^1$ = 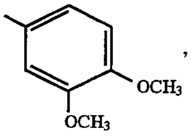 , $R^2$ = H, $R^3$ = 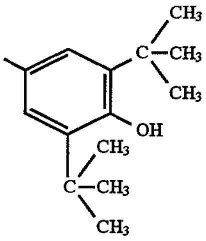

Crystal form: white acicular (recrystallized from ethanol)
Mp: 149–150° C.

Compound of Example 34

$R^1$ = 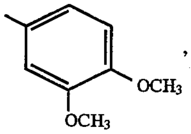 , $R^2$ = H, $R^3$ = 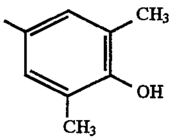

Crystal form: white acicular (recrystallized from methanol)
Mp: 160–161° C.

TABLE 8-continued

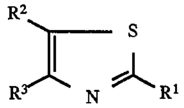

Compound of Example 35

$R^1$ = 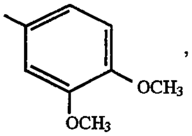 , $R^2$ = H, $R^3$ = 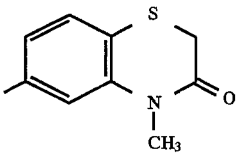

Crystal form: light yellow powdery (recrystallized from dimethylformamide-water)
Mp: 143.5–144° C.

Compound of Example 36

$R^1$ = 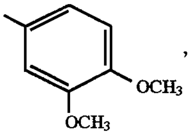 , $R^2$ = H, $R^3$ = 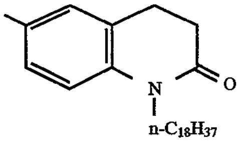

Crystal form: white powdery (recrystallized from ethanol)
Mp: 94–95° C.

Compound of Example 37

$R^1$ = 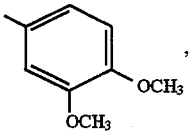 , $R^2$ = H, $R^3$ = 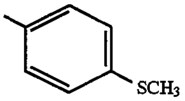

Crystal form: light brown acicular (recrystallized from ethanol)
Mp: 151–152° C.

Compound of Example 38

$R^1$ = 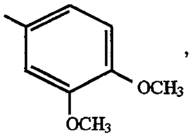 , $R^2$ = H, $R^3$ = 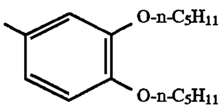

TABLE 8-continued

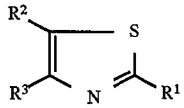

Crystal form: white acicular (recrystallized from petroleum ether)
Mp: 67–68° C.

Compound of Example 39

$R^1$ = 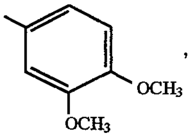 , $R^2$ = H, $R^3$ = 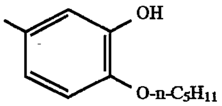

Crystal form: white acicular (recrystallized from methanol)
Mp: 122–123° C.

Compound of Example 40

$R^1$ = 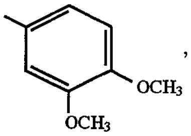 , $R^2$ = H, $R^3$ = 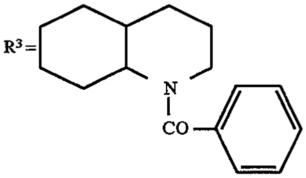

Crystal form: light yellow powdery (recrystallized from ethanol)
Mp: 152.5–153.5° C.

Compound of Example 41

$R^1$ = 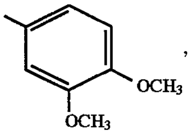 , $R^2$ = H, $R^3$ = 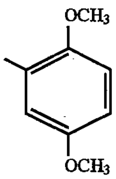

Crystal form: light yellow prismatic (recrystallized from ethanol-water)
Mp: 83–84° C.

Compound of Example 42

$R^1$ = 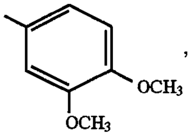 , $R^2$ = H,

TABLE 8-continued

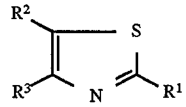

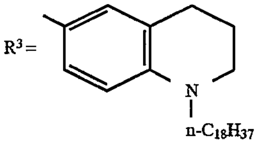

Crystal form: yellow powdery (recrystallized from ethanol)
Mp: 69–70° C.

Compound of Example 43

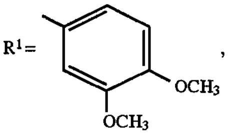

, $R^2$ = H,

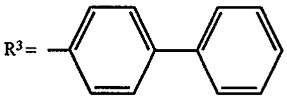

Crystal form: colorless acicular (recrystallized from ethyl acetate)
Mp: 174.5–175.5° C.

Compound of Example 44

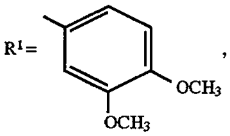

, $R^2$ = H,

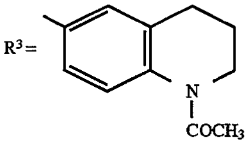

Crystal form: colorless acicular (recrystallized from ethanol)
Mp: 147.5–148.5° C.

Compound of Example 45

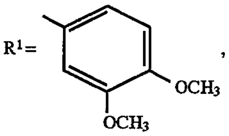

, $R^2$ = H,

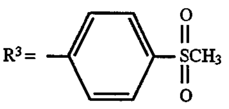

Crystal form: light yellow acicular (recrystallized from methanol)
Mp: 151–152° C.

Compound of Example 46

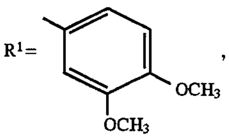

, $R^2$ = H,

TABLE 8-continued

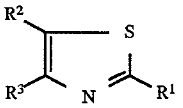

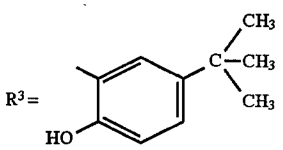

Crystal form: colorless plate (recrystallized from diethyl ether-petroleum ether)
Mp: 150–152° C.

Compound of Example 47

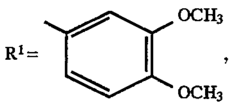

, $R^2$ = H,

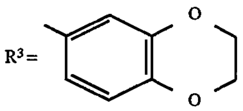

Crystal form: white powdery (recrystallized from ethyl acetate-n-hexane)
Mp: 126–127° C.

Compound of Example 48

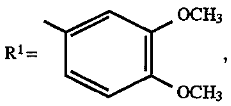

, $R^2$ = H,

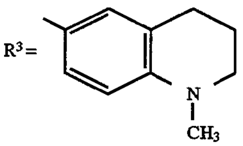

Crystal form: yellow powdery (recrystallized from ethanol-diethyl ether)
Mp: 124–126° C. (HCl salt)

Compound of Example 49

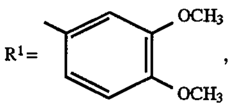

, $R^2$ = H,

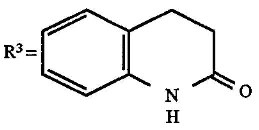

Crystal form: white powdery (recrystallized from dimethylformamide)
Mp: 263–265° C.

Compound of Example 50

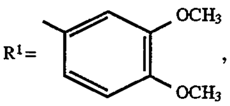

, $R^2$ = H,

TABLE 8-continued

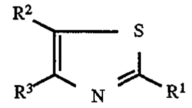

$R^3$ = 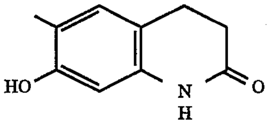

Crystal form: colorless prismatic (recrystallized from dimethylformamide-water)
Mp: 249–250° C. (decomposed)
Compound of Example 51

$R^1$ = 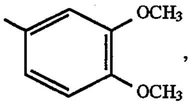 , $R^2$ = H, $R^3$ = 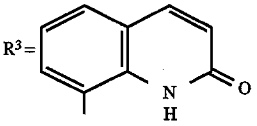

Crystal form: light brown prismatic (recrystallized from dimethylformamide)
Mp: 225–226° C.
Compound of Example 52

$R^1$ = 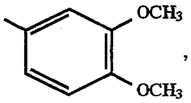 , $R^2$ = H, $R^3$ = 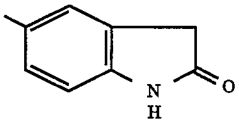

Crystal form: light brown acicular (recrystallized from dimethylformamide)
Mp: 250–251° C.
Compound of Example 53

$R^1$ = 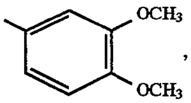 , $R^2$ = H, $R^3$ = 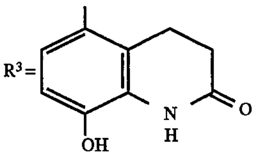

Crystal form: white powdery (recrystallized from dimethylformamide)
Mp: 145–146° C.
Compound of Example 54

$R^1$ = 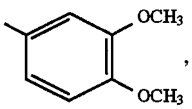 , $R^2$ = H,

TABLE 8-continued

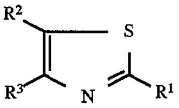

$R^3$ = 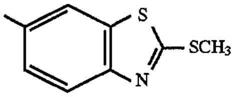

Crystal form: light brown acicular (recrystallized from dimethylformamide-methanol)
Mp: 182–183° C.
Compound of Example 55

$R^1$ = 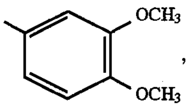 , $R^2$ = H, $R^3$ = 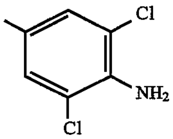

Crystal form: light brown prismatic (recrystallized from dimethylformamide-methanol)
Mp: 184–185° C.
Compound of Example 56

$R^1$ = 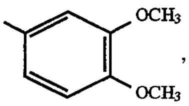 , $R^2$ = H, $R^3$ = 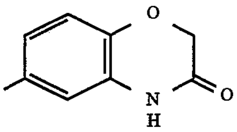

Crystal form: white prismatic (recrystallized from dioxane)
Mp: 223–234° C.
Compound of Example 57

$R^1$ = 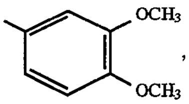 , $R^2$ = H, $R^3$ = 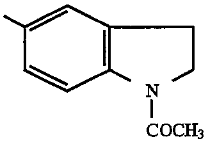

Crystal form: light brown granular (recrystallized ethanol)
Mp: 178–179°
Compound of Example 58

$R^1$ = 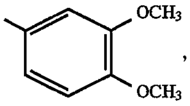 , $R^2$ = H,

TABLE 8-continued

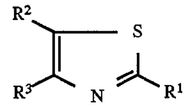

$R^3$ = 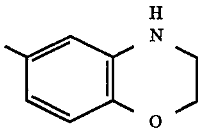

Crystal form: light brown powdery (recrystallized from ethanol-water)
Mp: 159–161° C. (HCl salt)
Compound of Example 59

$R^1$ = 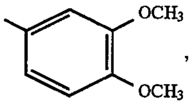 , $R^2$ = H, $R^3$ = 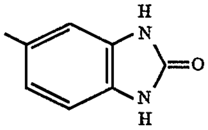

Crystal form: white powdery (recrystallized from dimethylformamide)
Mp: 300° or above
Compound of Example 60

$R^1$ = 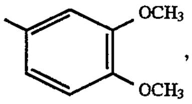 , $R^2$ = H, $R^3$ = 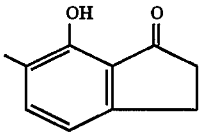

Crystal form: light brown powdery (recrystallized from dimethylformamide)
Mp: 215–216° C.
Compound of Example 61

$R^1$ = 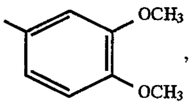 , $R^2$ = H, $R^3$ = 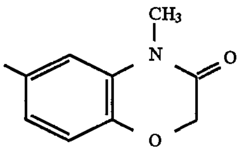

Crystal form: colorless acicular (recrystallized from acetonitrile)
Mp: 156–157° C.
Compound of Example 62

$R^1$ = 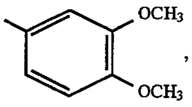 , $R^2$ = H,

TABLE 8-continued

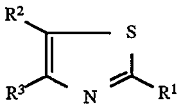

$R^3$ = 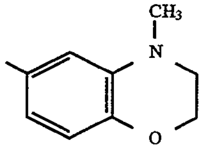

Crystal form: light yellow powdery (recrystallized from ethanol)
Mp: 128–130° C. (HCl salt)
Compound of Example 63

$R^1$ = 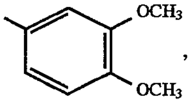 , $R^2$ = H, $R^3$ = 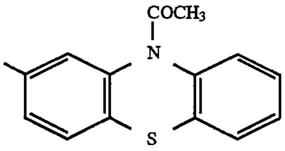

Crystal form: colorless acicular (recrystallized from ethyl acetate)
Mp: 155–156° C.
Compound of Example 64

$R^1$ = 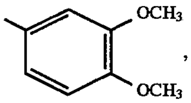 , $R^2$ = H, $R^3$ = 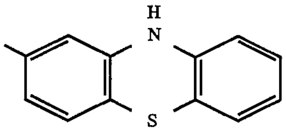

Crystal form: light yellow acicular (recrystallized from dimethylformamide-water)
Mp: 206–208° C.
Compound of Example 65

$R^1$ = 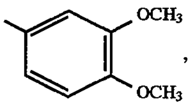 , $R^2$ = H, $R^3$ = 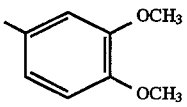

Crystal form: light brown acicular (recrystallized from dimethylformamide)
Mp: 168–169° C.
Compound of Example 66

$R^1$ = 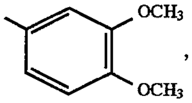 , $R^2$ = H,

TABLE 8-continued

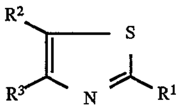

$R^3$ = 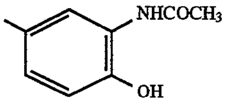

Crystal form: white powdery (recrystallized from ethanol)
Mp: 191–192° C.
Compound of Example 67

$R^1$ = 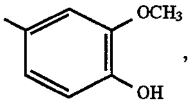 , $R^2$ = H, $R^3$ = 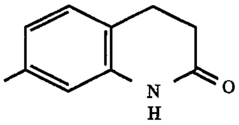

Crystal form: white powdery (recrystallized from dimethylformamide-methanol)
Mp: 226–227° C.
Compound of Example 68

$R^1$ = 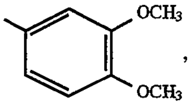 , $R^2$ = H, $R^3$ = 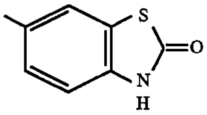

Crystal form: light brown acicular (recrystallized from dimethylformamide-water)
Mp: 227–228° C.
Compound of Example 69

$R^1$ = 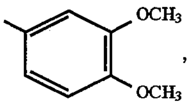 , $R^2$ = H, $R^3$ = 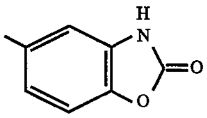

Crystal form: white powdery (recrystallized from methanol)
Mp: 271–272° C.
Compound of Example 70

$R^1$ = 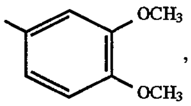 , $R^2$ = H, $R^3$ = 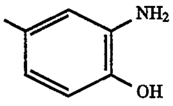

TABLE 8-continued

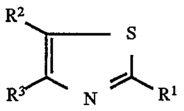

Crystal form: yellow powdery (recrystallized from methanol)
Mp: 165–167° C. (decomposed, 2HCl salt)
Compound of Example 71

$R^1$ = 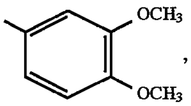 , $R^2$ = H, $R^3$ = 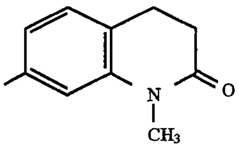

Crystal form: white powdery (recrystallized from diethyl ether-petroleum ether)
Mp: 114–115° C.
Compound of Example 72

$R^1$ = 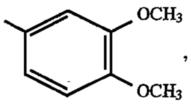 , $R^2$ = H, $R^3$ = 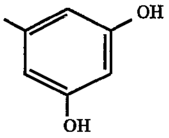

Crystal form: white powdery (recrystallized from ethanol-n-hexane)
Mp: 229–230° C.
Compound of Example 73

$R^1$ = 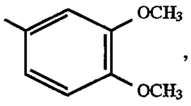 , $R^2$ = H, $R^3$ = 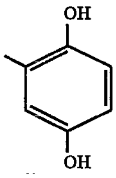

Crystal form: Orange plate (recrystallized from ethanol)
Mp: 192–192.5° C.
Compound of Example 74

$R^1$ = 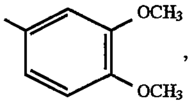 , $R^2$ = H, $R^3$ = 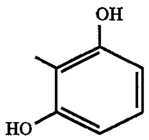

TABLE 8-continued

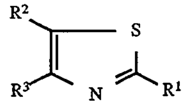

Crystal form: light yellow prismatic (recrystallized from ethanol-n-hexane)
Mp: 196–197° C.

Compound of Example 75

$R^1$ = 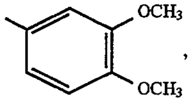 , $R^2$ = H, $R^3$ = 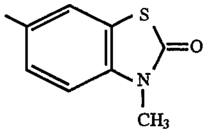

Crystal form: light brown powdery (recrystallized from dimethylformamide)
Mp: 203–204° C.

Compound of Example 76

$R^1$ = 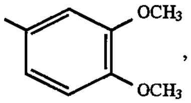 , $R^2$ = H, $R^3$ = 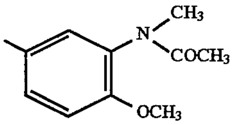

Crystal form: white powdery (recrystallized from diethyl ether)
Mp: 111–112° C.

Compound of Example 77

$R^1$ = 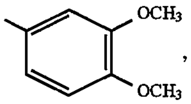 , $R^2$ = H, $R^3$ = 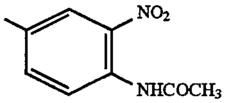

Crystal form: yellow acicular (recrystallized from acetonitrile)
Mp: 219–220.5° C.

Compound of Example 78

$R^1$ = 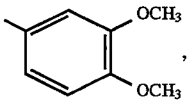 , $R^2$ = H, $R^3$ = 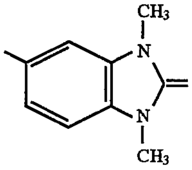

Crystal form: light brown powdery (recrystallized from

TABLE 8-continued

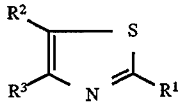

acetonitrile)
Mp: 172.5–173.5° C.

Compound of Example 79

$R^1$ = 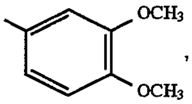 , $R^2$ = H, $R^3$ = 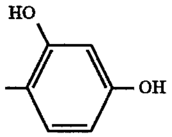

Crystal form: light yellow powdery (recrystallized from ethanol-n-hexane)
Mp: 203–204° C.

Compound of Example 80

$R^1$ = 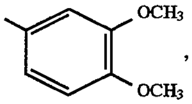 , $R^2$ = H, $R^3$ = 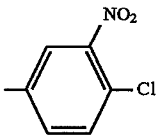

Crystal form: yellow acicular (recrystallized from ethanol)
Mp: 177–178° C.

Compound of Example 81

$R^1$ = 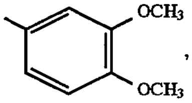 , $R^2$ = H, $R^3$ = 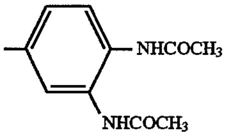

Crystal form: light yellow powdery (recrystallized from acetonitrile)
Mp: 224–225° C.

Compound of Example 82

$R^1$ = 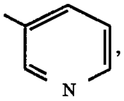 , $R^2$ = H, $R^3$ = 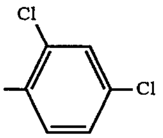

TABLE 8-continued

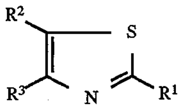

Crystal form: white acicular (recrystallized from ethanol-water)
Mp: 125–126° C.

Compound of Example 83

$R^1$ = 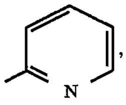, $R^2$ = H, $R^3$ = 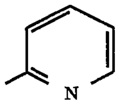

Crystal form: yellow prismatic (recrystallized from ethyl acetate-n-hexane)
Mp: 147–148° C.

Compound of Example 84

$R^1$ = 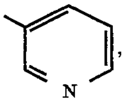, $R^2$ = 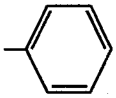, $R^3$ = 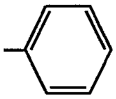

Crystal form: light yellow powdery (recrystallized from isopropanol)
Mp: 202–204° C. (HBr salt)

Compound of Example 85

$R^1$ = 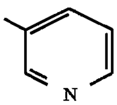, $R^2$ = H, $R^3$ = 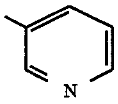

Crystal form: brown plate (recrystallized from ethyl acetate)
Mp: 131–132° C.

Compound of Example 86

$R^1$ = 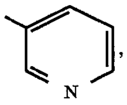, $R^2$ = Br, $R^3$ = 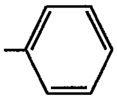

Crystal form: colorless acicular (recrystallized from ethanol)
Mp: 147–149°

TABLE 8-continued

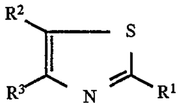

Compound of Example 87

$R^1$ = 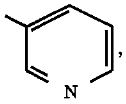, $R^2$ = $-CO_2C_2H_5$, $R^3$ = $-CH_3$

Crystal form: white powdery (recrystallized from ethanol-water)
Mp: 147–148° C. (HCl salt)

Compound of Example 88

$R^1$ = 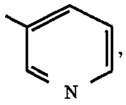, $R^2$ = H, $R^3$ = $-CH_2CO_2C_2H_5$

Crystal form: white prismatic (recrystallized from ethanol)
Mp: 119–120° C. (HCl salt)

Compound of Example 89

$R^1$ = 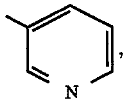, $R^2$ = H, $R^3$ = $-CH_2CONH_2$

Crystal form: white prismatic (recrystallized from ethanol)
Mp: 198–200° C. (decomposed, HCl salt)

Compound of Example 90

$R^1$ = 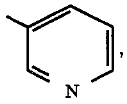, $R^2$ = H, $R^3$ = 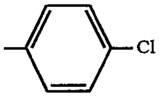

Crystal form: white powdery (recrystallized from ethanol-water)
Mp: 118–119° C.

Compound of Example 91

$R^1$ = 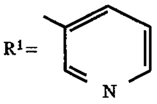, $R^2$ = H, $R^3$ = 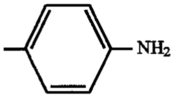

Crystal form: yellow columnar (recrystallized from ethanol)
Mp: 176–177° C.

TABLE 8-continued

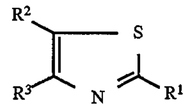

Compound of Example 92

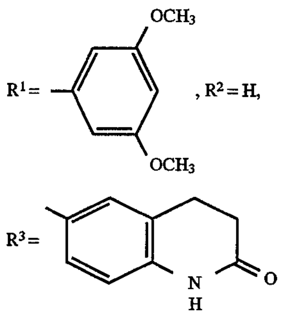

Crystal form: light brown acicular (recrystallized from ethanol)
Mp: 184–185° C.

Compound of Example 93

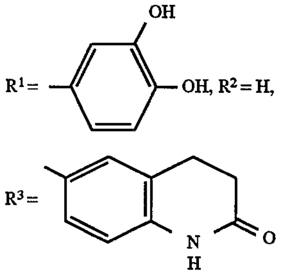

Crystal form: yellow powdery (recrystallized from ethanol)
Mp: 255–258° C. (decomposed, HBr salt)

Compound of Example 94

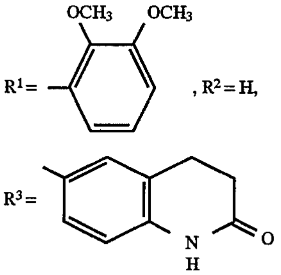

Crystal form: light brown acicular (recrystallized from DMF)
Mp: 235–236° C.

Compound of Example 95

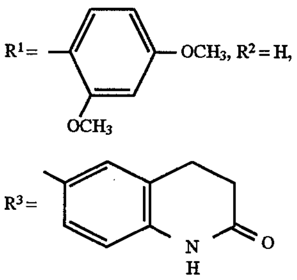

TABLE 8-continued

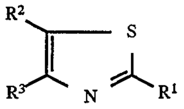

Crystal form: light brown powdery (recrystallized from dimethylformamide)
Mp: 236–237° C.

Compound of Example 96

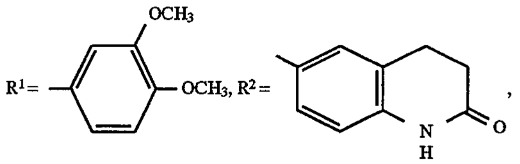

$R^3$ = H
Crystal form: white powdery (recrystallized from methanol)
Mp: 235–236° C.

Compound of Example 97

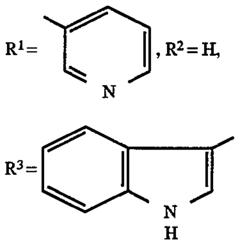

Crystal form: colorless prismatic (recrystallized from ethyl acetate)
Mp: 198–199° C.

Compound of Example 98

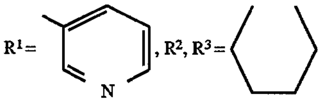

Crystal form: light brown prismatic (recrystallized from ethanol-diethyl ether)
Mp: 148–149° C. (HCl salt)

Compound of Example 99

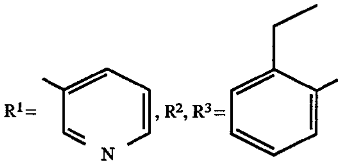

Crystal form: yellow acicular (recrystallized from ethanol)
Mp: 226–228° C. (HBr salt)

Compound of Example 100

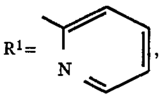

TABLE 8-continued

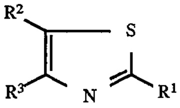

$R^2$, $R^3$ = 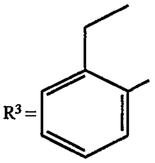

Crystal form: dark green acicular (recrystallized from ethanol)
Mp: 154–155° C. (HBr salt)

Compound of Example 101

$R^1$ = 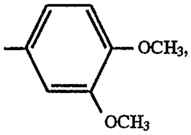, $R^2$ = H, $R^3$ = 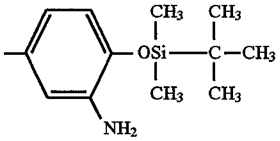

Crystal form: light brown acicular (recrystallized from ethanol)
Mp: 128–129° C.

Compound of Example 102

$R^1$ = 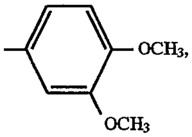, $R^2$ = H, $R^3$ = 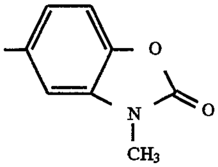

Crystal form: white acicular (recrystallized from ethanol)
Mp: 170–171° C.

Compound of Example 103

$R^1$ = 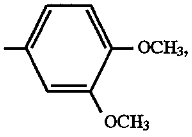, $R^2$ = H, $R^3$ = 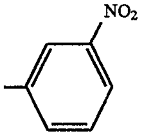

Crystal form: yellow acicular (recrystallized from chloroform-ethanol)
Mp: 149–150° C.

TABLE 8-continued

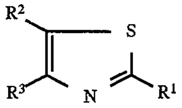

Compound of Example 104

$R^1$ = 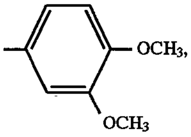, $R^2$ = H, $R^3$ = 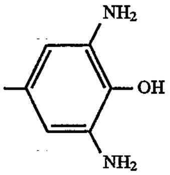

Crystal form: light violet plate (recrystallized from ethanol)
Mp: 167–169° C. (decomposed)

Compound of Example 105

$R^1$ = 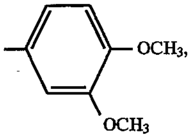, $R^2$ = H, $R^3$ = 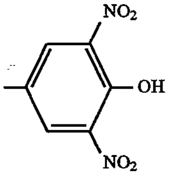

Crystal form: red powdery (recrystallized from ethanol)
Mp: 184–186° C. (decomposed)

Compound of Example 106

$R^1$ = 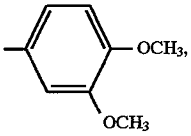, $R^2$ = H, $R^3$ = 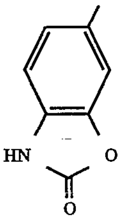

Crystal form: brown acicular (recrystallized from ethanol)
Mp: 221–224° C.

TABLE 8-continued

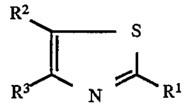

Compound of Example 107

$R^1$ = 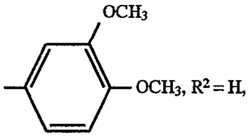 $R^2$ = H, $R^3$ = 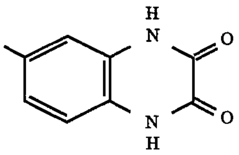

NMR (DMSO-$D_6$) δ:
10.5(2H, brs), 8.18(1H, d, J=1.7Hz), 8.09(1H, s), 7.96(1H, dd, J=8.5Hz, 1.7Hz), 7.71(1H, d, J=8.5Hz), 7.5–7.65(2H, m), 7.09(1H, d, J=8.4Hz), 3.86(3H, s), 3.83(3H, s)

Compound of Example 108

$R^1$ = 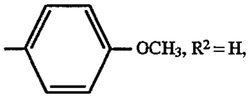 $R^2$ = H, $R^3$ = 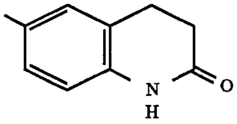

Crystal form: colorless prismatic (recrystallized from ethanol)
Mp: 216–217° C.

Compound of Example 109

$R^1$ = 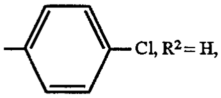 $R^2$ = H, $R^3$ = 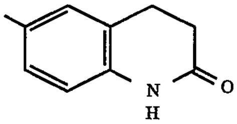

Crystal form: light yellow prismatic (recrystallized from dimethylformamide)
Mp: 263–264° C.

Compound of Example 110

$R^1$ = 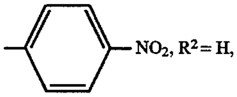 $R^2$ = H, $R^3$ = 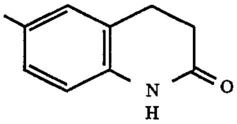

Crystal form: orange acicular (recrystallized from dimethylformamide)

TABLE 8-continued

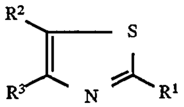

Mp: 300° C. or above

Compound of Example 111

$R^1$ = 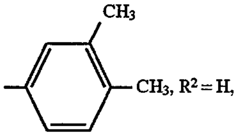 $R^2$ = H, $R^3$ = 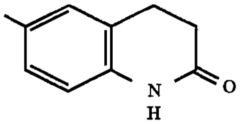

Crystal form: light yellow plate (recrystallized from dimethylformamide)
Mp: 231–232° C.

Compound of Example 112

$R^1$ = 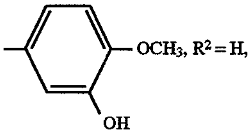 $R^2$ = H, $R^3$ = 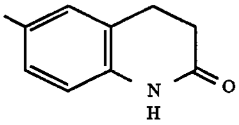

Crystal form: light brown powdery (recrystallized from dioxane)
Mp: 272.5–273.5° C.

Compound of Example 113

$R^1$ = 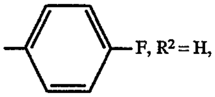 $R^2$ = H, $R^3$ = 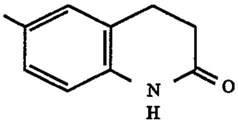

Crystal form: light yellow prismatic (recrystallized from dioxane)
Mp: 242–243° C.

Compound of Example 114

$R^1$ = 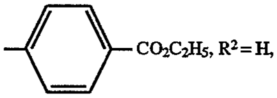 $R^2$ = H, $R^3$ = 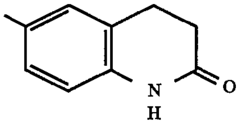

Crystal form: light yellow acicular (recrystallized from dioxane)
Mp: 236–237° C.

TABLE 8-continued

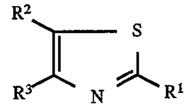

Compound of Example 115

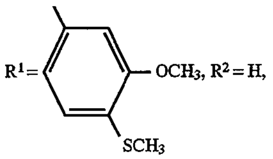

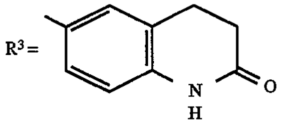

Crystal form: light brown prismatic (recrystallized from dimethylformamide)
Mp: 255–256° C.

Compound of Example 116

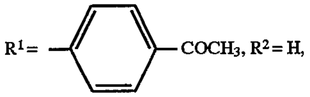

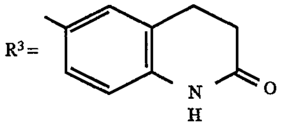

Crystal form: light yellow columnar (recrystallized from diethylformamide)
Mp: 264–265° C.

Compound of Example 117

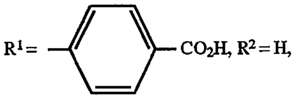

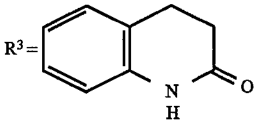

Crystal form: light yellow powdery (recrystallized from dimethylformamide)
Mp: 300° C. or above Compound of Example 118

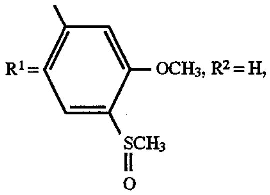

TABLE 8-continued

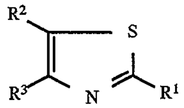

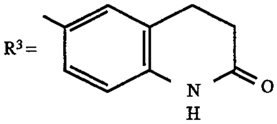

Crystal form: light yellow acicular (recrystallized from dimethylformamide)
Mp: 264–265° C.

Compound of Example 119

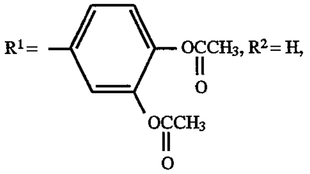

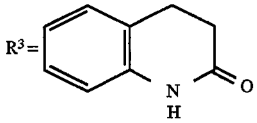

Crystal form: colorless acicular (recrystallized from acetonitrile)
Mp: 209–210° C.

Compound of Example 120

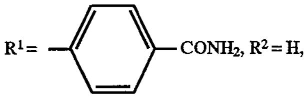

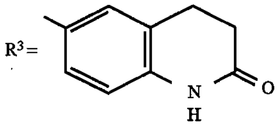

Crystal form: light yellow powdery (recrystallized from dimethylformamide)
Mp: 300° C. or above Compound of Example 121

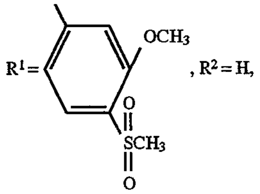

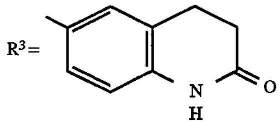

Crystal form: white powdery (recrystallized from dimethylformamide-water)
Mp: 284–286° C.

TABLE 8-continued

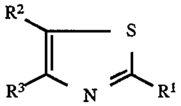

Compound of Example 122

$R^1$ = 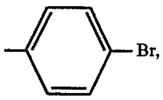, $R^2$ = H, $R^3$ = 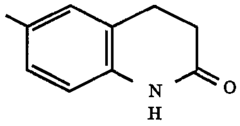

Crystal form: colorless acicular (recrystallized from dioxane-water)
Mp: 252–253° C.

Compound of Example 123

$R^1$ = 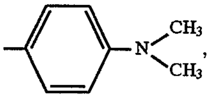, $R^2$ = H, $R^3$ = 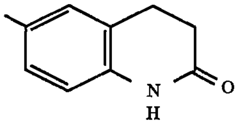

Crystal form: light green powdery (recrystallized from ethanol-water)
Mp: 256–258° C. (HCl salt)

Compound of Example 124

$R^1$ = 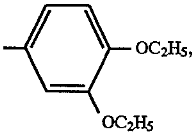, $R^2$ = H, $R^3$ = 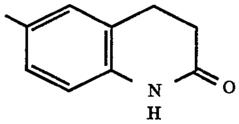

Crystal form: colorless acicular (recrystallized from dioxane)
Mp: 191–192° C.

Compound of Example 125

$R^1$ = 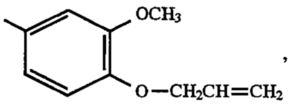, $R^2$ = H, $R^3$ = 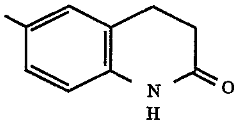

Crystal form: colorless prismatic (recrystallized from dioxane-water)
Mp: 178–179° C.

TABLE 8-continued

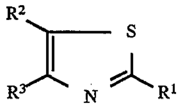

Compound of Example 126

$R^1$ = 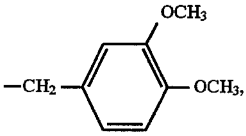, $R^2$ = H, $R^3$ = 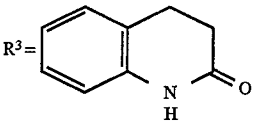

Crystal form: white powdery (recrystallized from dimethylformamide)
Mp: 185–186° C. (HCl salt)

Compound of Example 127

$R^1$ = 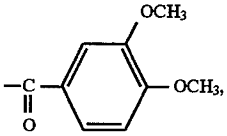, $R^2$ = H, $R^3$ = 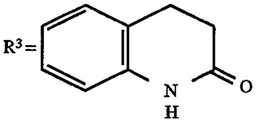

Crystal form: light brown acicular (recrystallized from chloroform-ethanol)
Mp: 249–251° C.

Compound of Example 128

$R^1$ = 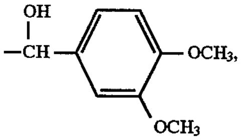, $R^2$ = H, $R^3$ = 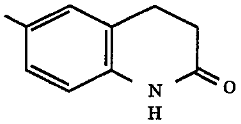

Crystal form: Light brown prisms (recrystallized from ethyl acetate)
Mp. 188–189° C.

Compound of Example 129

$R^1$ = 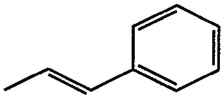, $R^2$ = H, $R^3$ = 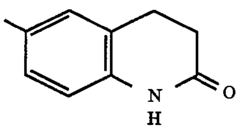

TABLE 8-continued

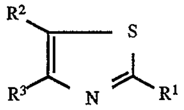

Crystal form: Brown granules (recrystallized from ethanol)
Mp. 231–231° C.

Compound of Example 130

$R^1$ = 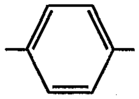 , $R^2$ = H, $R^3$ = 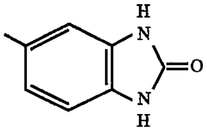

Crystal form: white powdery (recrystallized from dimethylformamide)
Mp: 300° C. or above Compound of Example 131

$R^1$ = 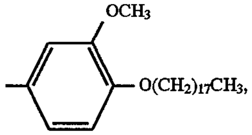 , $R^2$ = H, $R^3$ = 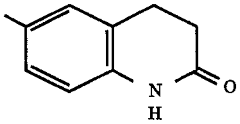

Crystal form: white powdery (recrystallized from ethanol)
Mp: 127–128° C.

Compound of Example 132

$R^1$ = 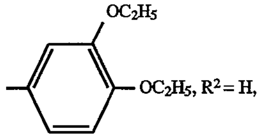 , $R^2$ = H, $R^3$ = 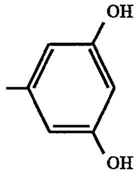

Crystal form: colorless columnar (recrystallized from petroleum ether-diethyl ether)
Mp: 141–142° C.

Compound of Example 133

$R^1$ = 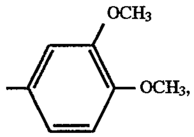 , $R^2$ = H,

TABLE 8-continued

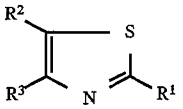

$R^3$ = 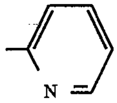

Crystal form: light yellow powdery (recrystallized from ethanol)
Mp: 157–167° C. (decomposed, HCl salt)
NMR ($CDCl_3$) δ:
3.80(3H, s), 3.87(3H, s), 7.06(1H, d, J=8.5Hz), 7.56(1H, dd, J=2.1Hz, 8.5Hz), 7.65–7.82(2H, m), 8.31(1H, t, J=6.7Hz), 8.46(1H, d, J=7.9Hz), 8.65–8.82(2H, m)

Compound of Example 134

$R^1$ = 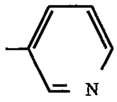 , $R^2$ = H, $R^3$ = 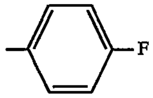

Crystal form: light yellow powdery (recrystallized from methanol)
Mp: 270–271° C. (decomposed, ½$FeCl_2$ salt)

Compound of Example 135

$R^1$ = 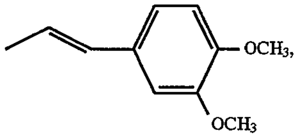 , $R^2$ = H, $R^3$ = 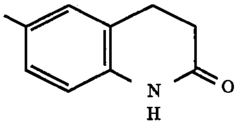

Crystal form: yellow powdery (recrystallized from dimethylformamide-water)
Mp: 182–183° C.

TABLE 9

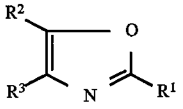

Compound of Example 136

$R^1$ = 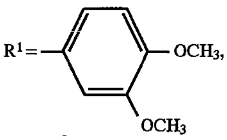 , $R^2$ = H,

TABLE 9-continued

| 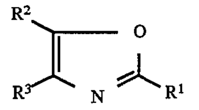 |
|---|
| $R^3$ = 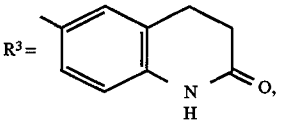 Crystal form: light brown powdery (recrystallized from ethanol) Mp: 191–192° C. |

EXAMPLE 137

In 25 ml of acetic acid was dissolved 2 g of 6-[2-(3,4-dimethoxybenzoyloxy)acetyl]-3,4-dihydro-carbostyril. Thereto was added 2 g of ammonium acetate. The mixture was stirred at 130° C. for 3 hours with heating. The solvent was removed by distillation. The residue was dissolved in ethanol. The solution was treated with active carbon, and then recrystallization was conducted to obtain 120 mg of 2-(3,4-dimethoxyphenyl)-4-(3,4-dihydrocarbostyril-6-yl) oxazole as light brown acicular crystals.

M.p.: 191°–192° C.

EXAMPLE 138

There were mixed, each in a powdery state, 500 mg of 6-[2-(3,4-dimethoxybenzoylamino)acetyl]-3,4-dihydrocarbostyril and 2,4-bis(4-methoxyphenyl)-1,3-dithia-2,4-diphosphetane-2,4-disulfide (Lawesson's reagent). The mixture was stirred at 200° C. with heating. After 3 hours, the reaction was completed. The residue was subjected to silica gel column chromatography (dichloromethane:methanol=49:1 by v/v). A solid obtained from the eluate was recrystallized from ethanol to obtain 98 mg of 2-(3,4-dimethoxyphenyl)-5-(3,4-dihydrocarbostyril-6-yl) thiazole as a white powder.

M.p. 235°–236° C.

The compounds of Examples 1–95 and 97–135 were obtained by using respective starting materials, in the same procedure as in Example 138.

EXAMPLE 139

In 50 ml of dichloromethane was dissolved 1 g of 2-(pyridin-3-yl)-4-phenylthiazole. Thereto was added 900 mg of m-chloroperbenzoic acid at room temperature. The mixture was stirred at the same temperature for 2 hours. The reaction mixture was washed with an aqueous sodium hydrogencarbonate solution and dried. The solvent was removed by distillation. The residue was recrystallized from ethyl acetate to obtain 306 mg of 3-(4-phenylthiazol-2-yl) pyridine-N-oxide as a brown powder.

M.p.: 140°–141° C.

EXAMPLE 140

In 25 ml of acetic anhydride was dissolved 2.8 g of 3-(4-phenylthiazol-2-yl)pyridine-N-oxide. The solution was refluxed for 6 hours with heating. The solvent was removed by distillation. The residue was treated with ammonia water and extracted with dichloromethane. The extract was water-washed, dried and subjected to solvent removal by distillation. The residue was mixed with a small amount of dichloromethane. The resulting crystals were collected by filtration and recrystallized from methanol to obtain 60 mg of 2-(2-oxopyridin-3-yl)4-phenylthiazole as light brown plate crystals.

M.p.: 206°–207° C. (decomposed)

EXAMPLE 141

In 50 ml of tetrahydrofuran was suspended 103 mg of lithium aluminum hydride. Thereto was added, in small portions, 1 g of 2-(3,4-dimethoxyphenyl)-4-(3,4-dihydrocarbostyril-6-yl)thiazole. The mixture was stirred at 90° C. for 3 hours with heating. 0.3 ml of water was added under ice-cooling, and the mixture was stirred and then filtered. The residue was extracted with dichloromethane. The extract was water-washed, dried and subjected to solvent removal by distillation. The residue was treated with active carbon and then converted into a hydrochloride with methanolhydrochloric acid. The hydrochloride was recrystallized from ethanol to obtain 465 mg of 2-(3,4-dimethoxyphenyl)-4-(1,2,3,4-tetrahydroquinolin-6-yl) thiazole hydrochloride as a light brown powder.

M.p.: 156°–158° C.

EXAMPLE 142

In 4 ml of acetic acid and 2 ml of hydrobromic acid was suspended 500 mg of 2-(3,4-dimethoxyphenyl)-4-(3,4-dihydrocarbostyril-6-yl)thiazole. The suspension was refluxed for 6 hours with heating. After cooling, the resulting crystals were collected by filtration, dried and recrystallized from ethanol to obtain 67 mg of 2-(3,4-dihydroxyphenyl)-4-(3,4-dihydrocarbostyreil-6-yl)thiazole as a yellow powder.

M.p.: 255°–258° C. (decomposed)

EXAMPLE 143

In 20 ml of DMF was dissolved 0.57 g of 2-(3,4-dimethoxyphenl)-4-(3,4-dihydro-2H-1,4-benzothiazin-3 (4H)-one-6-yl)thiazole. 0.065 g of 60% sodium hydride was added under ice-cooling. The mixture was stirred for 30 minutes. 0.18 ml of methyl iodide was added, and the mixture was stirred at 0° C. to room temperature overnight. The solution was concentrated and mixed with water. The resulting crystals were collected by filtration, water-washed and dried. The crystals were recrystallized from DMF-water to obtain 0.32 g of 2-(3,4-dimethoxyphenyl)-4-(4-methyl-2H-1,4-benzothiazin-3(4H)-one-6-yl)thiazole as a light yellow powder.

M.p.: 143.5°–144° C.

The compounds of Examples 11, 29, 36, 42, 48, 61, 62, 71, 75, 78, 102 and 123 were obtained by using respective starting materials, in the same procedure as in Example 143.

EXAMPLE 144

In 10 ml of pyridine was dissolved 1 g of 2-(3,4-dimethoxyphenyl)-4-(1,2,3,4-tetrahydroquinolin-6-yl) thiazole. Thereto was added 0.44 g of benzoyl chloride at 0° C., and the mixture was stirred for 5 hours. The solution was concentrated and mixed with ethanol and water in this order. The resulting crystals were collected by filtration and recrystallized from ethanol to obtain 0.7 g of 2-(3,4-dimethoxyphenyl)-4-(1-benzoyl-1,2,3,4-tetrahydroquinolin-6-yl)thiazole as a light yellow powder.

M.p.: 152.5°–153.5° C.

EXAMPLE 145

In 20 ml of tetrahydrofuran was dissolved 300 mg of 2-(3,4-dimethoxyphenyl)-4-(3-amino-4-hydroxyphenyl) thiazole. Thereto was added 0.46 ml of, triethylamine at room temperature. The mixture was stirred at the same temperature for 30 minutes. 100 mg of phosgene was blown thereinto, and the resulting mixture was stirred for 2 hours. The solvent was distilled off. The residue was washed with diethyl ether, followed by filtration to collect crystals. The crystals were recrystallized from methanol to obtain 50 mg of 2-(3,4-dimethoxyphenyl)-4-(benzoxazol-2-on-5-yl) thiazole as a white powder.

M.p.: 271°–272° C.

EXAMPLE 146

In 10 ml of aceticanhydride and 10 ml of pyridine was dissolved 1 g of 2-(3,4-dimethoxyphenyl)-4-(1,2,3,4-tetrahydroquinolin-6-yl)thiazole. The solution was stirred at room temperature overnight. The reaction mixture was concentrated. The concentrate was mixed with water. The resulting crystals were collected by filtration, water-washed and dried. Recrystallization from ethanol was conducted to obtain 0.31 g of 2-(3,4-dimethoxyphenyl)-4-(1-acetyl-1,2,3,4-tetrahydroquinolin-6-yl)thiazole as colorless acicular crystals.

M.p.: 147.5°–148.5° C.

The compounds of Examples 57, 63, 66, 76, 77 and 81 were obtained by using respective starting materials, in the same procedure as in Example 146.

EXAMPLE 147

2.05 g of 2-(4-ethoxycarbonylphenyl)-4-(3,4-dihydrocarbostyril-6-yl)thiazole was suspended in 20 ml of a 10% aqueous potassium hydroxide solution and 50 ml of ethanol. The suspension was refluxed for 5 hours. Ethanol was removed by distillation. After cooling, the residue was mixed with hydrochloric acid to make it acidic (pH 1). The resulting crystals were collected by filtration and recrystallized from dimethylformamide to obtain 0.70 g of 2-(4-carboxyphenyl)-4-(3,4-dihydrocarbostyril-6-yl)thiazole as a light yellow powder.

M.p.: 300° C. or above

EXAMPLE 148

In 20 ml of oxalyl chloride was suspended 0.62 g of 2-(4-carboxyphenyl)-4-(3,4-dihydrocarbostyril-6-yl) thiazole. The suspension was refluxed for 1 hour with heating. Oxalyl chloride was distilled off. The residue was suspended in acetone under ice-cooling. Thereto was added ammonia water. The mixture was returned to room temperature and stirred overnight. The mixture was mixed with water. The resulting crystals were collected by filtration, water-washed, dried and recrystallized from dimethylformamide to obtain 0.29 g of 2-(4-carbamoylphenyl)-4-(3,4-dihydrocarbostyril-6-yl)thiazole as a light yellow powder.

M.p.: 300° C. or above.

EXAMPLE 149

In 150 ml of chloroform-ethanol was suspended 3.40 g of 2-(3-methoxy-4-methylthiophenyl)-4-(3,4-dihydrocarbostyril-6-yl)thiazole. Thereto was added, in small portions, 1.97 g of methachloroperbenzoic acid (80%) under ice-cooling. The mixture was stirred for 1 hour. Then, the mixture was returned to room temperature and stirred overnight. Thereto was added an aqueous sodium carbonate solution. The mixture was extracted with chloroform three times. The combined extract was washed with a saturated aqueous sodium chloride solution and dried over magnesium sulfate. The solvent was distilled off and the resulting crystals were recrystallized from dimethylformamide to obtain 0.50 g of 2-(3-methoxy-4-methylsulfinylphenyl)-4-(3,4-dihydrocarbostyril-6-yl)thiazole as light yellow acicular crystals.

M.p.: 264°–265° C.

The compound of Example 45 was obtained by using the starting material, in the same procedure as in Example 149.

EXAMPLE 150

In 100 ml of chloroform-ethanol was suspended 2.9 g of 2-(3-methoxy-4-methylsulfinylphenyl)-4-(3,4-dihydrocarbostyril-6-yl)thiazole. Under ice-cooling, 1.72 g of m-chloroperbenzoic acid (80%) was added in small portions and the mixture was stirred for 1 hour. Then, the mixture was returned to room temperature and stirred overnight. The resulting crystals were collected by filtration, washed with ethanol and diethyl ether, and dried. Recrystallization from dimethylformamide-water to obtain 0.50 g of 2-(3-methoxy-4-methylsuflonylphenyl)-4-(3,4-dihydrocarbostyril-6-yl)thiazole as a white powder.

M.p.: 284°–286° C.

EXAMPLE 151

In 6 ml of chloroform was dissolved 100 mg of 2-(3,4-dimethoxybenzoyl)-4-(3,4-dihydroxycarbostyril-6-yl) thiazole. Thereto was added sodium boron hydride at room temperature, and the mixture was stirred for 1 hour at the same temperature. The solvent was distilled off. The residue was extracted with chloroform. The extract was water-washed, dried and then subjected to solvent removal by distilation. The residue was purified by silica gel column chromatography (eluent: chloroform/methanol=99/1) and then recrystallized from ethyl acetate to obtain 52 mg of 2-[1-(3,4-dimethoxyphenyl)-1-hydroxymethyl]-4-(3,4-dihydroxycarbostyril-6-yl)thiazole as light brown prismatic crystals.

M.p.: 188°–189° C.

EXAMPLE 152

In 50 ml of acetic acid was suspended 2 g of 2-(3,4-dimebthoxybenzyl)-3,4-dihydroxycarbostyril-6-yl)thiazole. Thereto was added 1.2 g of $CrO_3$. The mixture was stirred at 70°–80° C. for 3 hours. Then, 2 g of activated magnesium silicate [Florisil (trade name) manufactured by Wako Pure Chemical Industry, Ltd.] was added, and the mixture was stirred at room temperature for 1 hour. After the completion of a reaction, the solvent was removed by distillation, and the residue was suspended in a chloroform-methanol (4:1) mixture. The suspension was filtered. The filtrate was subjected to solvent removal by distillation. The residue was purified by silica gel column chromatography (eluent: chloroform/methanol=199/1) and then recrystallized from chloroform-ethanol to obtain 300 mg of 2-(3,4-dimethoxybenzoyl)-4-(3,4-dihydroxycarbostyril-6-yl) thiazole as light brown acicular crystals.

M.p.: 249°–251° C.

EXAMPLES 154–234

Compounds shown in the following Table 10 were obtained by using respective starting materials, in the same procedures as in Examples 1 and 138.

TABLE 10

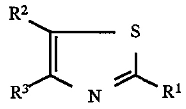

Compound of Example 154

$R^1$ = 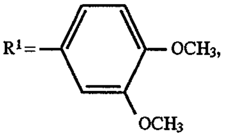

$R^2$ = H, $R^3$ = 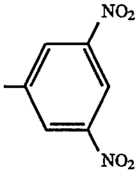

Crystal form: yellow powdery (recrystallized from dioxane)

Mp: 196.5–197° C. Form: free

Compound of Example 155

$R^1$ = 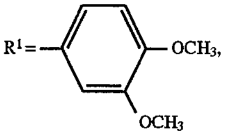

$R^2$ = H, $R^3$ = 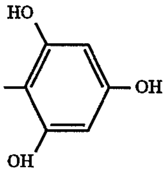

Crystal form: light brown acicular (recrystallized from methanol)

Mp: 133–135° C. Form: free

Compound of Example 156

$R^1$ = 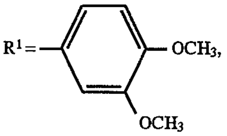

$R^2$ = H, $R^3$ = 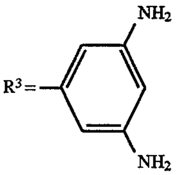

Crystal form: light yellow powdery (recrystallized from ethanol-water)

Mp: 198–200° C. Form: 2 HCl salt

TABLE 10-continued

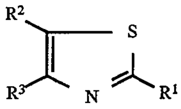

Compound of Example 157

$R^1$ = 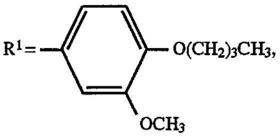

$R^2$ = H, $R^3$ = 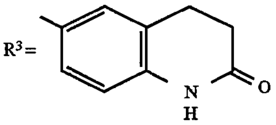

Crystal form: colorless acicular (recrystallized from dioxane)

Mp: 185–186° C. Form: free

Compound of Example 158

$R^1$ = 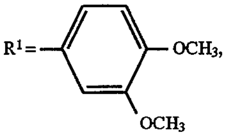

$R^2 = -\overset{O}{\overset{\|}{C}}OCH_2CH_3$, $R^3$ = 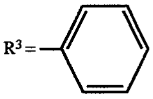

Crystal form: white powdery (recrystallized from ethanol)

Mp: 121–123° C. Form: free

Compound of Example 159

$R^1$ = 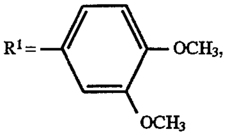

$R^2$ = H, $R^3$ = 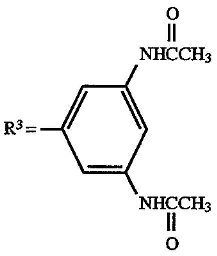

Crystal form: white powdery (recrystallized from dioxane-water)

Mp: 255–256° C. Form: free

Compound of Example 160

$R^1$ = 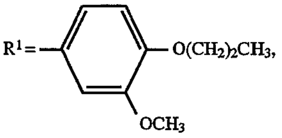

TABLE 10-continued

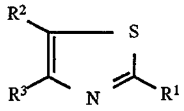

$R^2$ = H, $R^3$ = 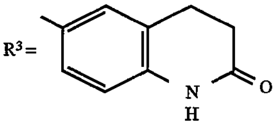

Crystal form: white powdery (recrystallized from dioxane)
Mp: 164–165° C. Form: free
Compound of Example 161

$R^1$ = 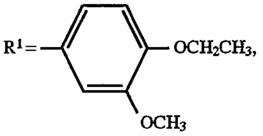

$R^2$ = H, $R^3$ = 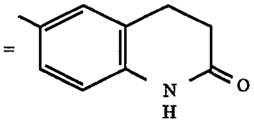

Crystal form: colorless acicular (recrystallized from dioxane)
Mp: 203–204° C. Form: free
Compound of Example 162

$R^1$ = 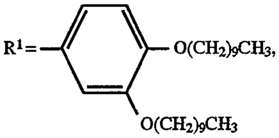

$R^2$ = H, $R^3$ = 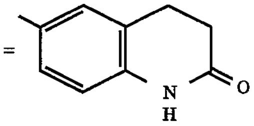

Crystal form: colorless acicular (recrystallized from ethanol)
Mp: 125.5–126.5° C. Form: free
Compound of Example 163

$R^1$ = 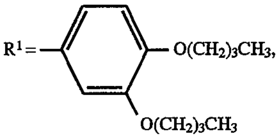

$R^2$ = H, $R^3$ = 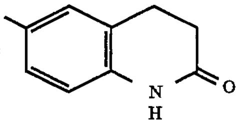

Crystal form: colorless acicular (recrystallized from ethanol)
Mp: 170–171° C. Form: free TABLE 10-continued

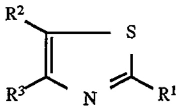

Compound of Example 164

$R^1$ = 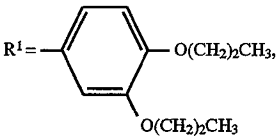

$R^2$ = H, $R^3$ = 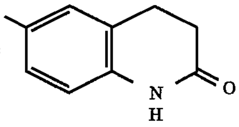

Crystal form: white powdery (recrystallized from dioxane)
Mp: 203–204° C. Form: free
Compound of Example 165

$R^1$ = 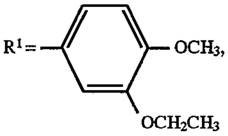

$R^2$ = H, $R^3$ = 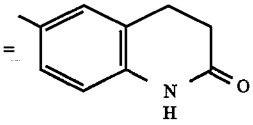

Crystal form: colorless acicular (recrystallized from dioxane)
Mp: 179–181° C. Form: free
Compound of Example 166

$R^1$ = 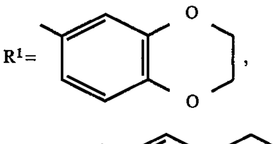

$R^2$ = H, $R^3$ = 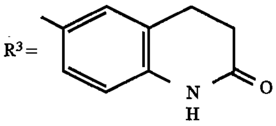

Crystal form: light yellow prismatic (recrystallized from dioxane)
Mp: 250–251° C. Form: free
Compound of Example 167

$R^1$ = 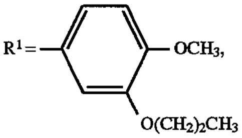

$R^2$ = H, $R^3$ = 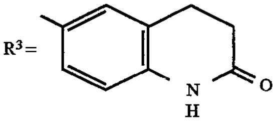

TABLE 10-continued

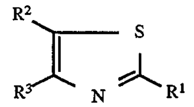

Crystal form: white acicular (recrystallized from dioxane-water)
Mp: 188–189° C. Form: free
Compound of Example 168

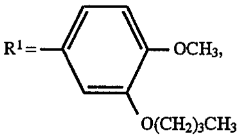

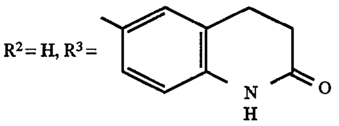

Crystal form: light yellow acicular (recrystallized from dioxane-water)
Mp: 189–190° C. Form: free
Compound of Example 169

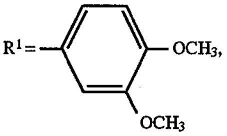

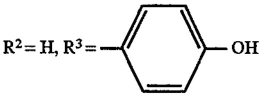

Crystal form: light brown prismatic (recrystallized from ethyl acetate)
Mp: 171–172° C. Form: free
Compound of Example 170

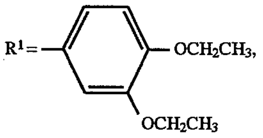

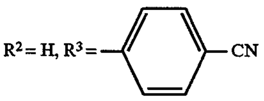

Crystal form: colorless acicular (recrystallized from ethanol)
Mp: 125–126° C. Form: free
Compound of Example 171

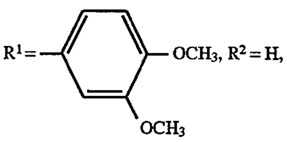

TABLE 10-continued

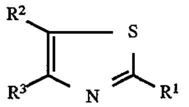

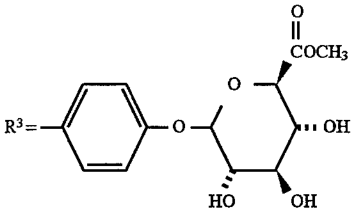

Crystal form: colorless acicular (recrystallized from ethanol)
Mp: 195–197° C. Form: free
Compound of Example 172

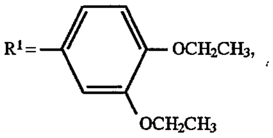

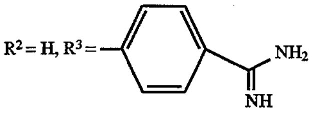

Crystal form: light yellow powdery (recrystallized from ethanol-water)
Mp: 96–97° C. Form: HCl salt
Compound of Example 173

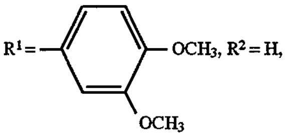

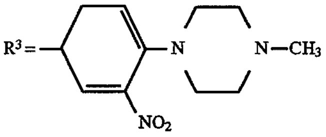

Crystal form: light brown powdery (recrystallized from ethanol)
Mp: 138–139° C. Form: dihydrochloride
Compound of Example 174

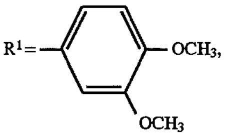

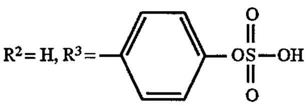

Crystal form: light yellow powdery
Mp: 248–249° C. Form: free

TABLE 10-continued

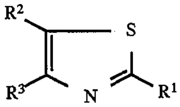

Compound of Example 175

$R^1$ = 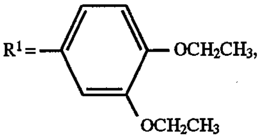

$R^2$ = H, $R^3$ = 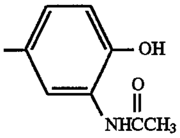

Crystal form: light yellow plate (recrystallized from ethanol)
Mp: 195–196° C. Form: free Compound of Example 176

$R^1$ = 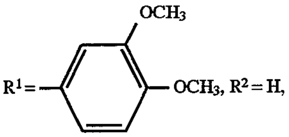

$R^3$ = 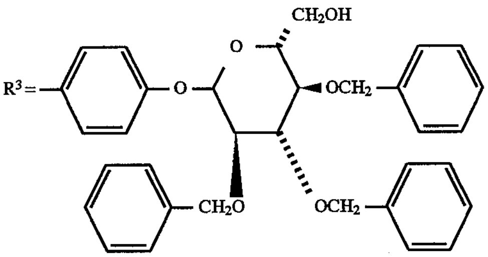

Crystal form: white powdery (recrystallized from ethyl acetate)
Mp: 180–181° C. Form: free Compound of Example 177

$R^1$ = 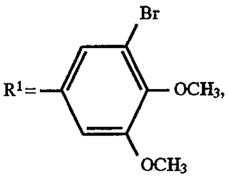

$R^2$ = H, $R^3$ = 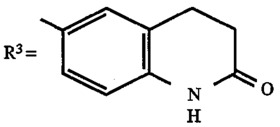

Crystal form: light yellow prismatic (recrystallized from dioxane)
Mp: 254–255° C. Form: free TABLE 10-continued

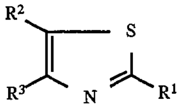

Compound of Example 178

$R^1$ = 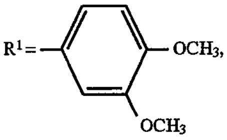

$R^2$ = H, $R^3$ = 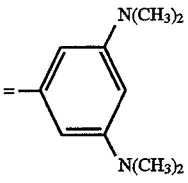

Crystal form: brown powdery (recrystallized from ethanol-diethyl ether)
Mp: 164–165° C. Form: dihydrochloride Compound of Example 179

$R^1$ = 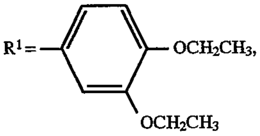

$R^2$ = H, $R^3$ = 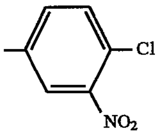

Crystal form: light yellow acicular (recrystallized from ethanol)
Mp: 138–139° C. Form: free Compound of Example 180

$R^1$ = 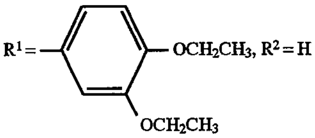

$R^3$ = 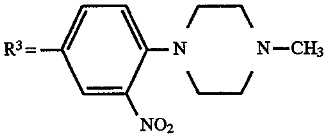

Crystal form: yellow acicular (recrystallized from ethanol)
Mp: 117–118° C. Form: dihydrochloride Compound of Example 181

$R^1$ = 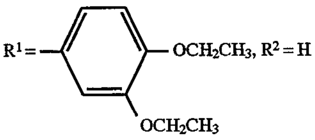

TABLE 10-continued

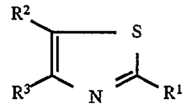

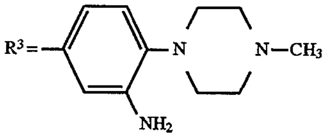

Crystal form: colorless acicular (recrystallized from ethanol)
Mp: 168–170° C. Form: trihydrochloride Compound of Example 182

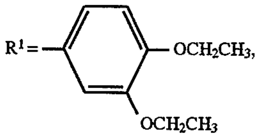

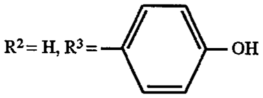

Crystal form: white prismatic (recrystallized from toluene)
Mp: 175–176° C. Form: free Compound of Example 183

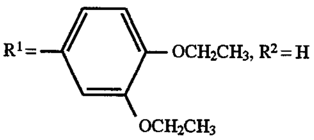

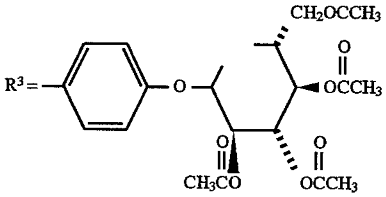

Crystal form: white powdery (recrystallized from ethyl acetate-n-hexane)
Mp: 180–181° C. Form: free Compound of Example 184

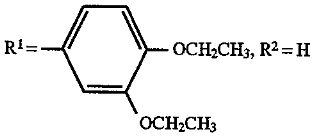

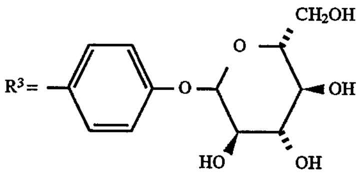

Crystal form: white acicular (recrystallized from ethanol)
Mp: 138–140° C. Form: free TABLE 10-continued

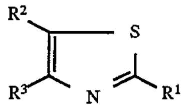

Compound of Example 185

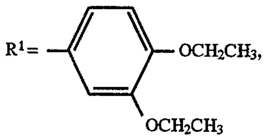

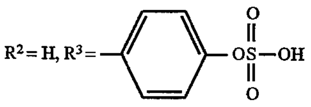

Crystal form: yellow powdery (recrystallized from ethanol-water)
Mp: 175–176° C. Form: free Compound of Example 186

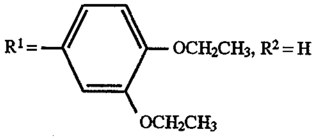

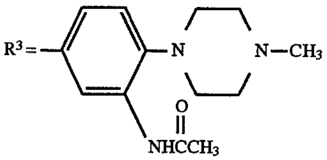

Crystal form: light yellow acicular (recrystallized from ethanol-diethyl ether)
Mp: 138–140° C. Form: hydrochloride Compound of Example 187

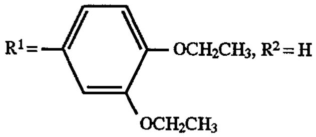

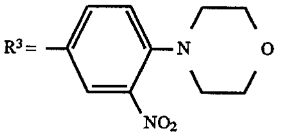

Crystal form: orange acicular (recrystallized from ethyl acetate-n-hexane)
Mp: 119–120° C. Form: free Compound of Example 188

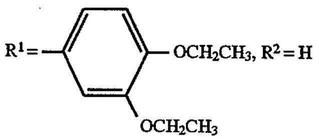

TABLE 10-continued

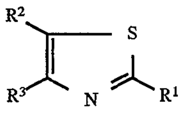

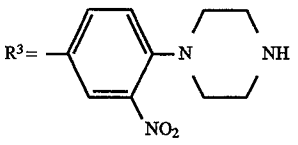

Crystal form: brown prismatic (recrystallized from ethanol)
Mp: 202–203° C. Form: hydrochloride Compound of Example 189

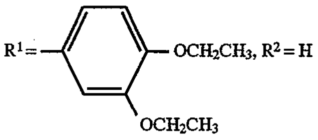

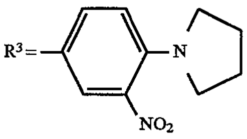

Crystal form: yellow acicular (recrystallized from dioxane-water)
Mp: 142–143° C. Form: free Compound of Example 190

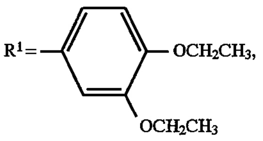

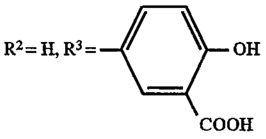

Crystal form: white acicular (recrystallized from ethanol)
Mp: 194–195° C. Form: free Compound of Example 191

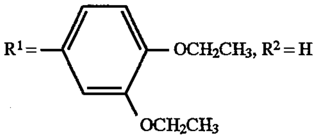

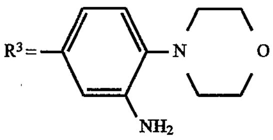

Crystal form: colorless acicular (recrystallized from ethanol-water)
Mp: 173–175° C. Form: hydrochloride TABLE 10-continued

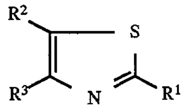

Compound of Example 192

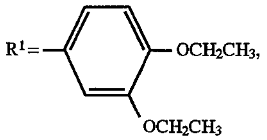

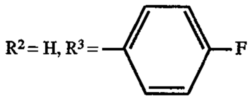

Crystal form: light yellow acicular (recrystallized from ethanol)
Mp: 98–99° C. Form: free Compound of Example 193

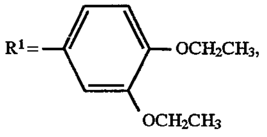

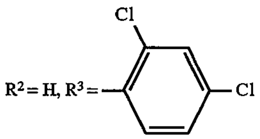

Crystal form: colorless acicular (recrystallized from ethanol)
Mp: 95–96° C. Form: free Compound of Example 194

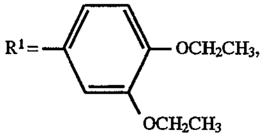

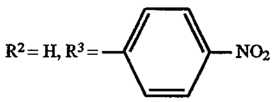

Crystal form: yellow acicular (recrystallized from dioxane-water)
Mp: 145–146.5° C. Form: free Compound of Example 195

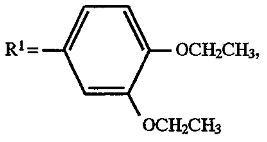

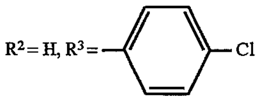

Crystal form: colorless acicular (recrystallized

TABLE 10-continued

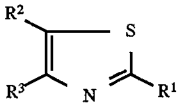

from ethanol)
Mp: 114–114.5° C. Form: free
Compound of Example 196

$R^1$ = 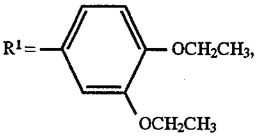

$R^2$ = H, $R^3$ = 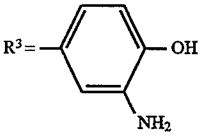

Crystal form: yellow powdery (recrystallized from ethanol)
Mp: 158–180° C. (decomposed) Form: dihydrochloride
NMR(DMSO-$d_6$)δ:
1.28–1.5(6H, m), 4.02–4.25(4H, m), 7.10(1H, d, J=8.3Hz), 7.19(1H, d, J=8.5Hz), 7.46–7.63(2H, m), 7.83–7.97(2H, m), 8.12(1H, d, J=2Hz)
Compound of Example 197

$R^1$ = 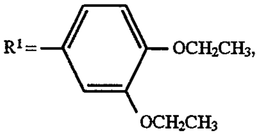

$R^2$ = H, $R^3$ = 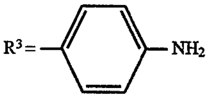

Crystal form: light green powdery (recrystallized from ethanol-water)
Mp: 230° C. (decomposed) Form:. hydrochloride
Compound of Example 198

$R^1$ = 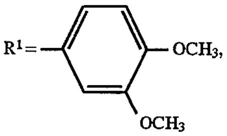

$R^2$ = H, $R^3$ = 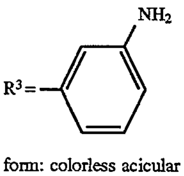

Crystal form: colorless acicular (recrystallized from ethanol)
Mp: 244° C. (decomposed) Form: hydrochloride
Compound of Example 199

$R^1$ = 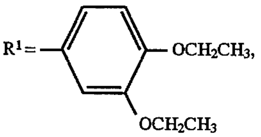

TABLE 10-continued

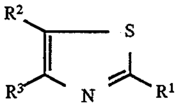

$R^2$ = H, $R^3$ = 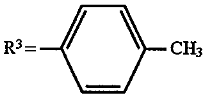

Crystal form: colorless acicular (recrystallized from ethanol)
Mp: 111–112° C. Form: free
Compound of Example 200

$R^1$ = 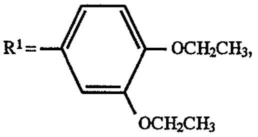

$R^2$ = H, $R^3$ = 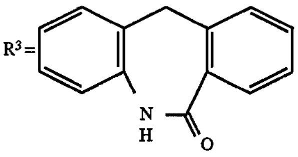

Crystal form: colorless column (recrystallized from dioxane)
Mp: 228–229° C. Form: free
Compound of Example 201

$R^1$ = 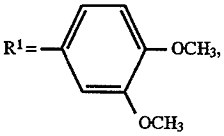 , $R^2$ = H $R^3$ = 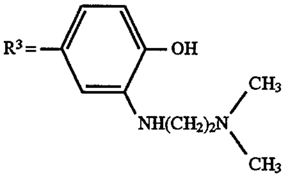

Crystal form: white powdery (recrystallized from ethanol-water)
Mp: 186–188° C. Form: dihydrochloride
Compound of Example 202

$R^1$ = 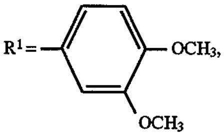 , $R^2$ = H $R^3$ = 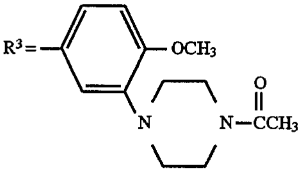

Crystal form: yellow acicular (recrystallized from methanol-ethyl acetate)

TABLE 10-continued

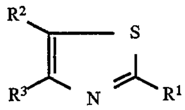

Mp: 170–171° C. Form: free

Compound of Example 203

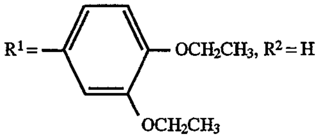

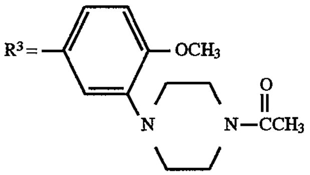

Crystal form: white powdery (recrystallized from ethyl acetate-n-hexane)
Mp: 112–113° C. Form: free Compound of Example 204

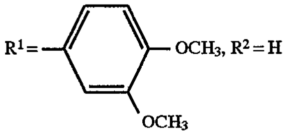

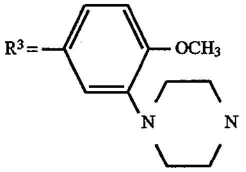

Crystal form: white powdery (recrystallized from ethanol)
Mp: 150–154° C. (decomposed) Form: dihydrochloride Compound of Example 205

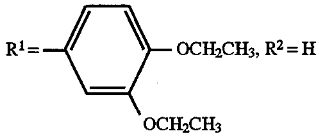

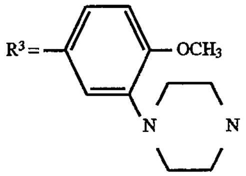

Crystal form: white powdery (recrystallized from methanol-ethyl acetate)
Mp: 206–208° C. Form: trihydrochloride TABLE 10-continued

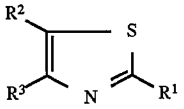

Compound of Example 206

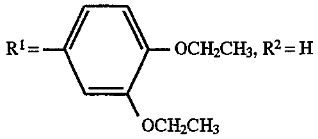

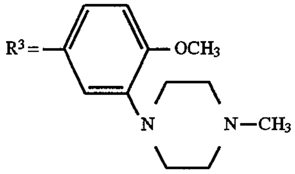

Crystal form: white powdery (recrystallized from ethanol)
Mp: 155–158° C. (decomposed) Form: trihydrochloride Compound of Example 207

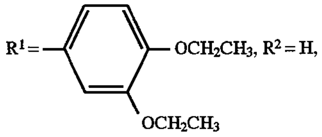

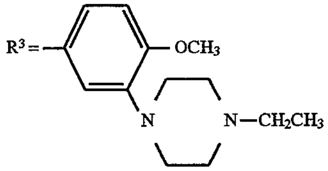

Crystal form: white powdery (recrystallized from ethanol)
Mp: 241–242° C. Form: trihydrochloride Compound of Example 208

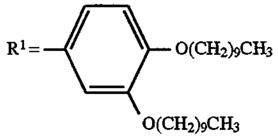

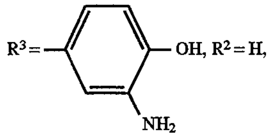

Crystal form: yellow powdery (recrystallized from ethanol)
Mp: 156–162° C. Form: dihydrochloride Compound of Example 209

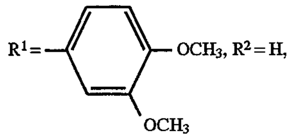

TABLE 10-continued

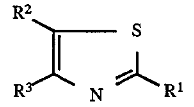

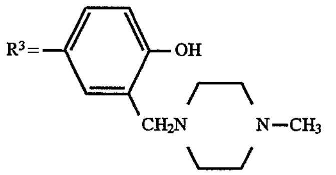

NMR(DMSO-$d_6$)δ:
2.83(3H, brs), 3.28–3.82(8H, m), 3.85(3H, s), 3.91(3H, s), 7.11(2H, d, J=8.4Hz), 7.52–7.68 (2H, m), 7.87(1H, s), 7.98(1H, dd, J=2.0Hz, 8.5Hz), 8.30(1H, d, J=2.0Hz)
Crystal form: yellow powdery (recrystallized from ethanol)
Mp: 178–190° C. Form: trihydrochloride
Compound of Example 210

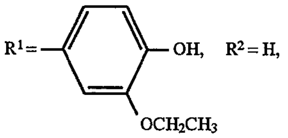

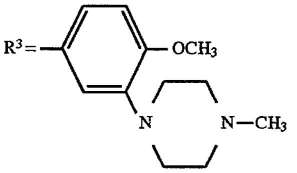

Crystal form: white powdery (recrystallized from ethanol)
Mp: 188–192° C. (decomosed) Form: dihydrochloride
Compound of Example 211

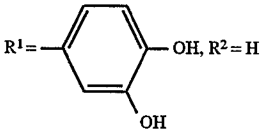

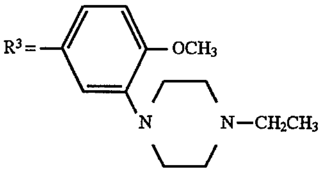

Crystal form: yellow acicular (recrystallized from ethyl acetate-ethanol)
Mp: 166–170° C. Form: trihydrochloride
Compound of Example 212

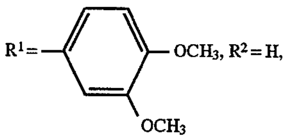

TABLE 10-continued

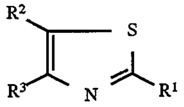

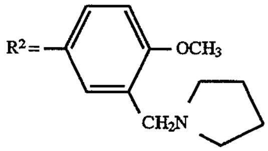

Crystal form: yellow powdery (recrystallized from ethanol)
Mp: 167–171° C. Form: dihydrochloride
Compound of Example 213

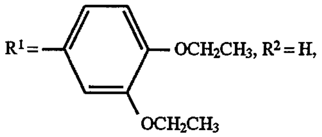

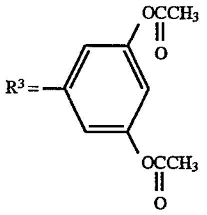

Crystal form: white acicular (recrystallized from ethanol)
Mp: 137–138° C. Form: free
Compound of Example 214

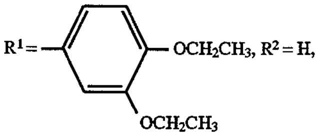

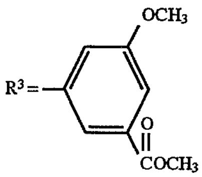

Crystal form: colorless prismatic (recrystallized from ethyl acetate)
Mp: 121–122° C. Form: free
Compound of Example 215

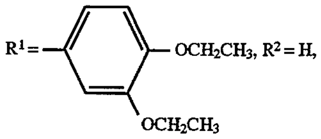

TABLE 10-continued

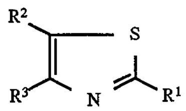

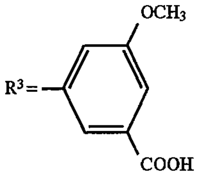

Crystal form: colorless acicular (recrystallized from ethanol)
Mp: 176–177° C. Form: free Compound of Example 216

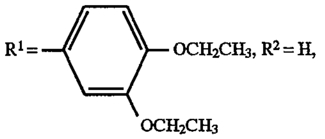

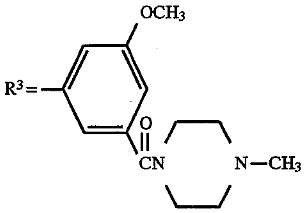

Crystal form: white powdery (recrystallized from ethyl acetate)
Mp: 185–186° C. Form: hydrochloride Compound of Example 217

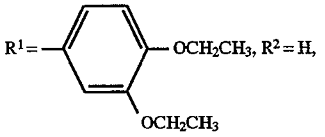

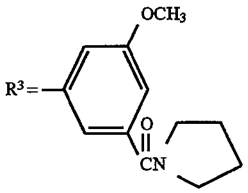

Crystal form: white granular (recrystallized from diisopropyl ether)
Mp: 113–114° C. Form: free Compound of Example 218

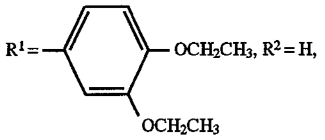

TABLE 10-continued

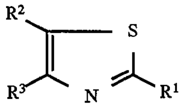

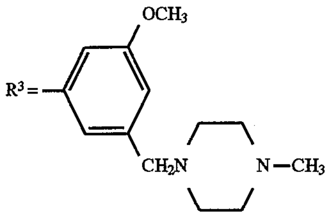

Crystal form: white powdery (recrystallized from ethyl acetate)
Mp: 212–214° C. Form: dihydrochloride Compound of Example 219

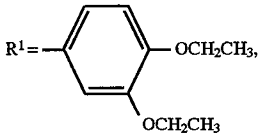

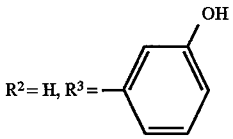

Crystal form: white plate (recrystallized from ethanol)
Mp: 126–128° C. Form: free Compound of Example 220

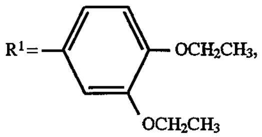

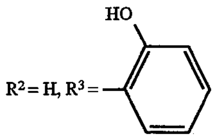

Crystal form: light yellow acicular (recrystallized from ethanol)
Mp: 97–98° C. Form: free Compound of Example 221

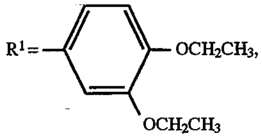

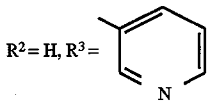

Crystal form: white acicular (recrystallized from ethanol)
Mp: 161–164° C. Form: hydrochloride TABLE 10-continued

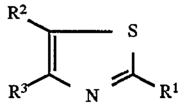

Compound of Example 222

$R^1$ = 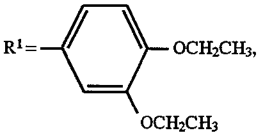

$R^2$ = $-CO_2C_2H_5$, $R^3$ = $-CO_2C_2H_5$,
Crystal form: white powdery (recrystallized from ethyl acetate)
Mp: 212–214° C. Form: dihydrochloride Compound of Example 223

$R^1$ = 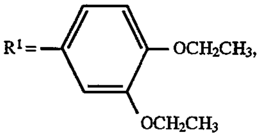

$R^2$, $R^3$ = 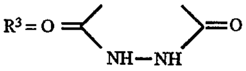

Crystal form: yellow powdery (recrystallized from dimethylformamide)
Mp: 270–279° C. (decomposed) Form: free
NMR(DMSO-$D_6$)δ:
1.39(3H, t, J=6.8Hz), 1.40(3H, t, J=6.8Hz), 4.00–4.3(4H, m), 7.13(1H, d, J=8.4Hz), 7.16(1H, d, J=2.0Hz), 7.68(1H, dd, J=2.0Hz, 8.4Hz), 11.97(2H, brs)

Compound of Example 224

$R^1$ = 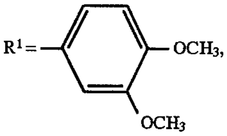 , $R^2$ = H, $R^3$ = 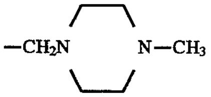

Crystal form: light brown powdery (recrystallized from ethanol)
Mp: 188–210° C. (decomposed) Form: dihydrochloride
NMR(DMSO-$d_6$)δ:
2.82(3H, s), 3.25–3.78(8H, m), 3.85(3H, s), 3.88 (3H, s), 4.49(2H, brs), 7.09(1H, d, J=8.6Hz), 7.44–7.60(2H, m), 7.92(1H, s)

Compound of Example 225

$R^1$ = 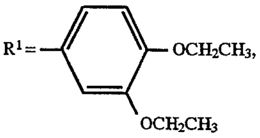

$R^2$ = H, $R^3$ = 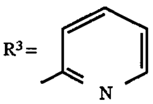

TABLE 10-continued

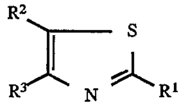

Crystal form: yellow powdery (recrystallized from acetone)
Mp: 114–115° C. Form: hydrochloride Compound of Example 226

$R^1$ = 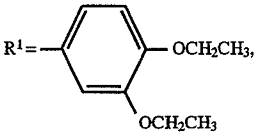 , $R^2$ = H, $R^3$ = 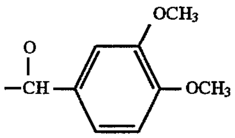

Crystal form: light brown powdery (recrystallized from diethyl ether)
Mp: 122–123° C. Form: free Compound of Example 227

$R^1$ = 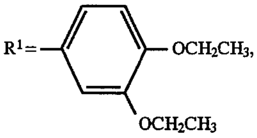 , $R^2$ = H, $R^3$ = 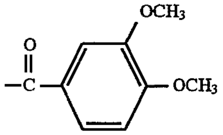

Crystal form: white powdery (recrystallized from ethyl acetate-n-hexane)
Mp: 128–129° C. Form: free Compound of Example 228

$R^1$ = 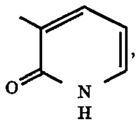 , $R^2$ = H, $R^3$ = 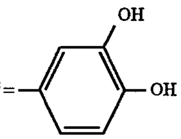

Crystal form: dark yellow powdery (recrystallized from dimethylformamide-water)
Mp: 285–290° C. (decomposed) Form: free Compound of Example 229

$R^1$ = 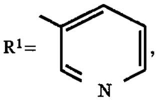 , $R^2$ = H,

TABLE 10-continued

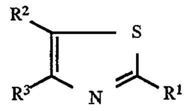

R³=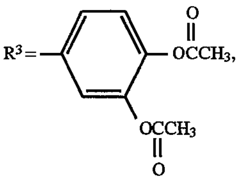

Crystal form: colorless prismatic (recrystallized from ethyl)
Mp: 130–131° C. Form: free Compound of Example 230

R¹=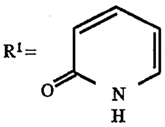, $R^2$=H, $R^3$=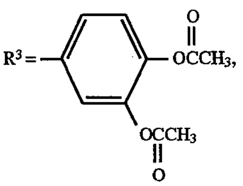

Crystal form: light brown powdery (recrystallized from dimethylformamide-ethanol)
Mp: 256–257° C. Form: free Compound of Example 231

$R^1$=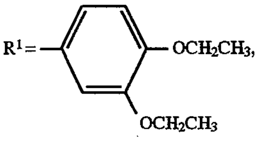, $R^2$ = H,

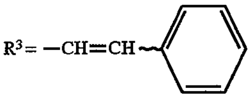

Crystal form: light yellow powdery
Mp: 94–95° C. Form: free

Compound of Example 232

$R^1$=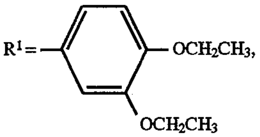

$R^2$ = H, $R^3$ =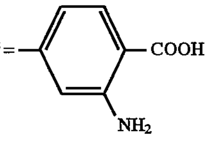

TABLE 10-continued

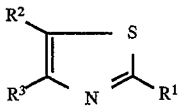

Compound of Example 233

$R^1$=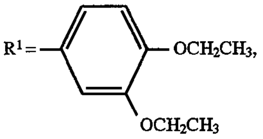

$R^2$= H, $R^3$=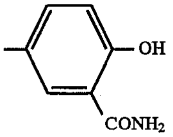

Crystal form: colorless prismatic (recrystallized from methylene chloride-ehtanol)
Mp: 195–196° C. Form: free Compound of Example 234

$R^1$=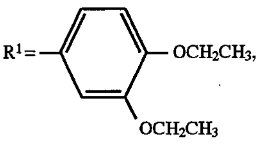

$R^2$= H, $R^3$=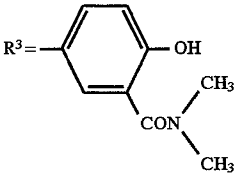

EXAMPLE 235

5.9 g of 4-(3,5-dinitrophenyl)-2-(3,4-dimethoxyphenyl) triazole and a solution of 24.4 g of stannous chloride dihydrate dissolved in 90 ml of concentrated hydrochloric acid were stirred at room temperature for 2 hours. After cooling, the resulting crystals were collected by filtration and recrystallized from ethanol-water to obtain 3.73 g of 4-(3,5-diaminophenyl)-2-(3,4-dimethoxyphenyl)thiazole dihydrochloride.

M.p.: 198°–200° C.

Light yellow powder

The compounds of Examples 55, 91, 104, 181, 191, 196, 197, 198, 208 and 232 were obtained using respective starting materials, in the same procedure as in Example 235.

EXAMPLE 236

In 45 ml of tetrahydrofuran were dissolved 1.5 g of 4-(4-hydroxyphenyl)-2-(3,4-diethoxyphenyl)thiazole, 1.4 g of 2,3,4,6-tetra-O-acetyl-β-D-glucopyranose and 1.3 g of triphenylphosphine. Thereto was added, in small portions at 0° C., a solution of 0.9 g of diethyl azodicarboxylate dissolved in 5 ml of tetrahydrofuran. The mixture was stirred at room temperature for 14 hours. The solvent was removed by distillation. The residue was purified by silica gel column chromatography (elutant: dichloromethane) and recrystallized from ethyl acetate-n-hexane to obtain 1.52 g of 4-[4-

(2,3,4,6-tetra-O-acetyl-β-D-glucopyranosyloxy)phenyl]-2-(3,4-diethoxyphenyl)-thiazole.

M.p.: 180°–181° C.

White powder

The compounds of Examples 171 and 184 were obtained using respective starting materials, in the same procedure as in Example 236.

EXAMPLE 237

In 6 ml of a methanol-dichloromethane (2:1) mixed solvent was suspended 0.15 g of 4-[4-(2,3,4,6-tetra-O-acetyl-β-D-glucopyranosyloxy)phenyl]-2-(3,4-diethoxyphenyl)thiazole. Thereto was added a catalytic amount of sodium methylate. The mixture was stirred at room temperature for 2 hours. The solvent was removed by distillation. The residue was recrystallized from methanol to obtain 71 mg of 4-[4-(β-D-glucopyranosyloxy)-phenyl]-2-(3,4-diethoxyphenyl)thiazole.

M.p.: 138°–140° C.

White acicular crystals

EXAMPLE 238

2 ml of chlorosulfonic acid was dropwise added to 40 ml of pyridine at room temperature. The mixture was stirred at 50° C. for 12 hours. Thereto was added 0.33 g of 4-(4-hydroxyphenyl-2-(3,4-dimethoxyphenyl)thiazole. The mixture was stirred at 50° C. for 6 hours and then at room temperature overnight. The reaction mixture was concentrated to dryness under reduced pressure. The residue was mixed with water and the resulting crystals were collected by filtration. The resulting 4-(4-hydroxysulfonyloxyphenyl)-2-(3,4-dimethoxyphenyl)thiazole pyridinium salt was suspended in 3 ml of methanol. Thereto was added 5 ml of a 0.1N aqueous potassium hydroxide solution. The mixture was stirred at room temperature overnight. The reaction mixture was concentrated. The residue was dissolved in water. The solution was treated with 0.5 g of an ion exchange resin (Dowex 50W×8). The filtrate was concentrated to obtain 0.04 g of 4-(4-hydroxysulfonyloxyphenyl)-2-(3,4-dimethoxyphenyl)thiazole.

M.p.: 248°–249° C.

Light yellow powder

EXAMPLE 239

In 25 ml of ethanol were suspended 0.5 g of 4-(4-hydroxyphenyl)-2-(3,4-dimethoxyphenyl)thiazole, 1 g of paraformaldehyde and 0.5 g of N-methylpiperazine. The suspension was refluxed for 8 hours with heating. The reaction mixture was subjected to distillation under reduced pressure to remove the solvent. The residue was purified by silica gel column chromatography (eluent: dichloromethane/methanol=49/1 by v/v) and dissolved in 10 ml of ethanol. Thereto was added 0.5 ml of ethanol saturated with hydrogen chloride gas, and the mixture was allowed to stand. The resulting crystals were collected by filtration, dried and recrystallized from ethanol to obtain 0.2 g of 4-[4-hydroxy-3-(4-methyl-1-piperazinylmethyl)phenyl]-2-(3,4-dimethoxyphenyl)thiazole trihydrochloride.

M.p.: 178°–190° C.

Yellow powder

NMR (DMSO-$d_6$) δ:

2.83–3.82 (3H, brs), 3.28–3.82 (8H, m), 3.85 (3H, s), 3.91 (3H, s), 7.11 (2H, d, J=8.4 Hz), 7.52–7.68 (2H, m), 7.87 (1H, s), 7.98 (1H, dd, J=2.0 Hz, 8.5 Hz), 8.30 (1H, d, J=2.0 Hz).

EXAMPLE 240

20 ml of a dimethylformamide solution containing 1.5 g of 4-(3-methoxy-5-carboxyphenyl)-2-(3,4-diethoxyphenyl) thiazole, 0.4 g of N-methylpiperazine and 0.7 g of diethyl cyanophosphonate was stirred with ice-cooling. Thereto was added 0.6 ml of triethylamine. The mixture was stirred at room temperature for 14 hours. The solvent was distilled off. The residue was mixed with 80 ml of dichloromethane and 30 ml of water. Phase separation was conducted and the dichloromethane layer was washed with 20 ml of a saturated aqueous sodium hydrogencarbonate solution was 20 ml of a saturated aqueous sodium chloride solution, and dried. The solvent was removed by distillation. The residue was purified by silica gel column chromatography (eluent: dichloromethane/methanol=200/3 by v/v) and then dissolved in ethyl acetate. To the solution was added hydrochloric acid-ethanol. The resulting crystals were collected by filtration, dried and recrystallized from ethyl acetate to obtain 1.2 g of 4-[3-methoxy-5-(4-methyl-1-piperzinylcarbonyl)phenyl-2-(3,4-diethoxyphenyl)thiazole hydrochloride.

White powder

M.p.: 185°–186° C.

The compounds of Examples 120, 217 and 233 were obtained by using respective starting materials, in the same procedure as in Example 240.

EXAMPLE 241

In 20 ml of tetrahydrofuran was dissolved 0.4 g of 4-[3-methoxy-5-(4-methyl-1-piperazinylcarbonyl)phenyl-2-(3,4-diethoxyphenyl)thiazole. Thereto was added 32 mg of lithium aluminum hydride in small portions. The mixture was stirred at 0° C. for 30 minutes and at room temperature for 2 hours. Then, there were added 0.05 ml of a 10% aqueous sodium hydroxide solution and 0.1 ml of water. The mixture was stirred at room temperature for 20 minutes. The reaction mixture was filtered. The filtrate was concentrated. The residue was purified by silica gel column chromatography (eluent: dichloromethane/methanol=99/1 by v/v) and dissolved in ethyl acetate. Thereto was added hydrochloric acid-ethanol. The resulting crystals were collected by filtration, dried and recrystallized from ethyl acetate to obtain 40 mg of 4-[3-methoxy-5-(4-methyl-1-piperazinylmethyl)-phenyl]-2-(3,4-diethoxyphenyl)thiazole dihydrochloride.

White powder

M.p.: 212°–214° C.

The compound of Example 209 was obtained by using starting materials, in the same procedure as in Example 241.

EXAMPLE 242

A solution of 1 g of 4-(4-chloro-3-nitrophenyl)-2-(3,4-diethoxyphenyl)thiazole and 636 mg of morpholine dissolved in 20 ml of dimethylformamide and 20 ml of dimethyl sulfoxide was refluxed at 150° C. for 2–3.5 hours with heating. The reaction mixture was subjected to vacuum distillation. The residue was added to ice water, and an aqueous sodium hydrogencarbonate solution was added. The solution was extracted with dichloromethane three times. The combined extract was washed with an aqueous sodium chloride solution and dried over magnesium sulfate. The solvent was removed by distillation. The residue was purified by silica gel column chromatography and recrystallized from ethyl acetate-n-hexane to obtain 1.03 g of 4-(4-morpholino-3-nitrophenyl)-2-(3,4-diethoxyphenyl) thiazole.

Orange acicular crystals

M.p.: 119°–120° C.

The compounds of Examples 173, 180, 188 and 189 were obtained by using respective starting materials, in the same procedure as in Example 242.

EXAMPLE 243

In 4 ml of ethanol was suspended 1 g of 4,5-diethoxycarbonyl-2-(3,4-diethoxyphenyl)thiazole. Thereto was added 2 ml of hydrazine hydrate. The mixture was sealed in a tube and heated at 130° C. for 48 hours. After cooling, the resulting crystals were collected by filtration, washed with ethanol, dried and recrystallized from dimethylformamide to obtain 220 mg of 2-(3,4-diethoxyphenyl)-5,6-dihydrothiazolo[4,5-d]pyridazine-4,7-dione.

M.p.: 270°–279° C. (decomposed)

Yellow powder

NMR (DMSO-$d_6$) δ:

1.39 (3H, t, J=6.8 Hz), 1.40 (3H, t, J=6.8 Hz), 4.00–4.35 (4H, m), 7.13 (1H, d, J=8.4 Hz), 7.61 (1H, d, J=2.0 Hz), 7.68 (1H, dd, J=2.0 Hz, 8.4 Hz), 11.97 (2H, brs).

EXAMPLE 244

In 10 ml of dimethylformamide were dissolved 860 mg of 2-(3,4-dimethoxyphenyl)-4-chloromethylthiazole and 320 mg of N-methylpiperazine. Thereto was added 130 mg of sodium hydride. The mixture was stirred at room temperature for 14 hours. The solvent was removed by distillation. The residue was extracted with chloroform. The extract was water-washed, dried and subjected to distillation to remove the solvent. The residue was dissolved in ethanol. To the solution was added ethanol saturated with hydrogen chloride gas, and the mixture was allowed to stand. The resulting crystals were collected by filtration, washed with a small amount of ethanol, dried and recrystallized from ethanol to obtain 820 mg of 2-(3,4-dimethoxyphenyl)-4-(4-methylpiperazinylmethyl)thiazole.

M.p.: 188°–210° C. (decomposed)

Light brown powder

The compounds of Examples 209, 212 and 218 were obtained by using respective starting materials, in the same procedure as in Example 244.

EXAMPLE 245

60 ml of a tetrahydrofuran solution of a Grignard reagent prepared from 2.4 g of 1-bromo-3,4-dimethoxybenzene was stirred with ice-cooling. Thereto was added 20 ml of a tetrahydrofuran solution of 3 g of 2-(3,4-diethoxyphenyl)-4-formylthiazole. The mixture was stirred at the same temperature for 1 hour and at room temperature for 3 hours. 10 ml of a saturated aqueous ammonium chloride solution was added. The solvent was removed by distillation. The residue was extracted with 100 ml of chloroform. The extract was washed with 20 ml of water and 20 ml of a saturated aqueous sodium chloride solution, and dried. The solvent was removed by distillation. The residue was purified by silica gel column chromatography (elutant: dichloromethane/acetone=99/1 by v/v) and recrystallized from diethyl ether to obtain 2.2 g of 2-(3,4-diethoxyphenyl)-4-[1-hydroxy-1-(3,4-dimethoxyphenyl)methyl]thiazole.

M.p.: 122°–123° C.

Light brown powder

The compound of Example 128 was obtained by using starting materials, in the same procedure as in Example 245.

EXAMPLE 246

In 20 ml of chloroform was dissolved, 150 mg of 2-(3,4-diethoxyphenyl)-4-[1-hydroxy-1-(3,4-dimethoxyphenyl)methyl]thiazole. 1 g of manganese dioxide was added. The mixture was refluxed for 2 hours with heating. The reaction mixture was filtered. The filtrate was concentrated. The residue was recrystallized from ethyl acetate-n-hexane to obtain 98 mg 2-(3,4-diethoxyphenyl)-4-(3,4-diethoxybenzoyl)thiazole.

M.p.: 128°–129° C.

White powder

The compound of Example 127 was obtained by using starting materials, in the same procedure as in Example 246.

EXAMPLE 247

4.2 ml of n-butyllithiumwas dropwise added in small portions to a suspension of 2.6 g of benzyltriphenylphosphonium chloride in 10 ml of tetrahydrofuran, with stirring at −50° C. The mixture was heated to room temperature and, after cooling again to −50° C., was mixed with 12 ml of a tetrahydrofuran solution of 2 g of 2-(3,4-diethoxyphenyl)-4-formylthiazole. The mixture was stirred at the same temperature for 30 minutes and at room temperature for 14 hours. 10 ml of water and 40 ml of ethyl acetate were added to conduct extraction and phase separation. The solvent layer was dried and subjected to distillation to remove the solvent. The residue was purified by silica gel column chromatography to obtain 2 g of 2-(3,4-diethoxyphenyl)-4-styrylthiazole as a 1:1 mixture of cis form and trans form.

M.p.: 94°–95° C.

Light yellow powder

The compounds of Examples 129 and 135 were obtained by using respective starting materials, in the same procedure as in Example 247.

EXAMPLE 248

The compounds of Examples 155, 169, 175, 182, 190, 196, 201, 208, 209, 210, 211, 219, 220, 228 and 233 were obtained by using respective starting materials, in the same procedure as in Example 142.

EXAMPLE 249

The compounds of Examples 172, 178, 180, 181, 186, 201, 206, 207, 209, 210, 211, 216 and 234 were obtained by using respective starting materials, in the same procedure as in Example 143.

EXAMPLE 250

The compound of Example 226 was obtained by using starting materials, in the same procedure as in Example 151.

EXAMPLE 251

The compound of Example 227 was obtained by using starting materials, in the same procedure as in Example 152.

EXAMPLE 252

The compounds of Examples 159, 175, 186, 202 and 203 were obtained by using respective starting materials, in the same procedure as in Example 146.

EXAMPLES 253-351

The compounds shown in the following Table 11 were obtained by using respective starting materials, in the same procedures as in Examples 1 and 138.

TABLE 11

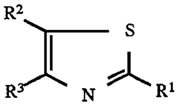

Compound of Example 253

$R^1$ = 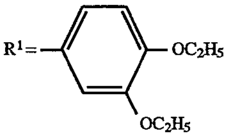

$R^2$ = H, $R^3$ = 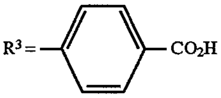

Crystal form: white powdery (recrystallized from methanol-chloroform
M.p.: 219.3–220.3° C. Form: free Compound of Example 254

$R^1$ = 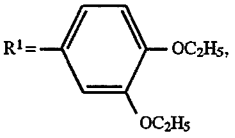

$R^2$ = H, $R^3$ = 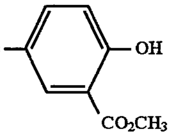

Crystal form: white acicular (recrystallized from ethanol)
M.p.: 137–138° C. Form: free Compound of Example 255

$R^1$ = 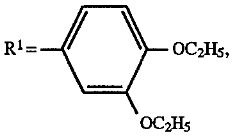

$R^2$ = H, $R^3$ = 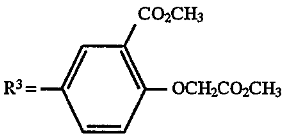

Crystal form: colorless acicular (recrystallized from diisopropyl ether)
M.p.: 96–97° C. Form: free TABLE 11-continued

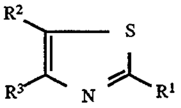

Compound of Example 256

$R^1$ = 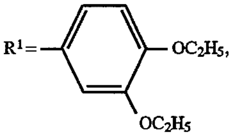

$R^2$ = H, $R^3$ = 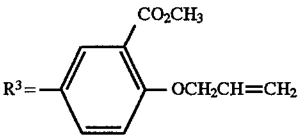

Crystal form: white powdery (recrystallized from diisopropyl ether)
M.p.: 86–87° C. Form: free Compound of Example 257

$R^1$ = 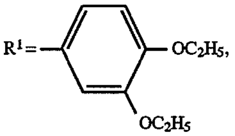

$R^2$ = H, $R^3$ = 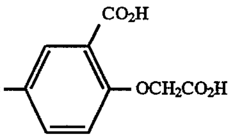

Crystal form: light brown granular (recrystallized from diisopropyl ether)
M.p.: 199–200° C. Form: free Compound of Example 258

$R^1$ = 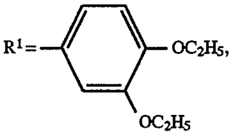

$R^2$ = H, $R^3$ = 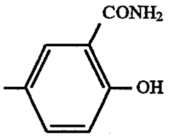

Crystal form: colorless prismatic (recrystallized from dichloromethane-ethanol)
M.p.: 195–196° C. Form: free Compound of Example 259

$R^1$ = 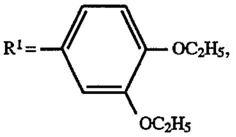

TABLE 11-continued

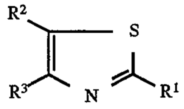

$R^2$ = H, $R^3$ = 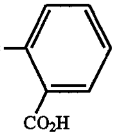

Crystal form: white powdery (recrystallized from diethyl ether-n-hexane)
M.p.: 131–131.8° C. Form: free
Compound of Example 260

$R^1$ = 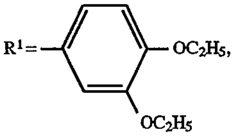

$R^2$ = H, $R^3$ = 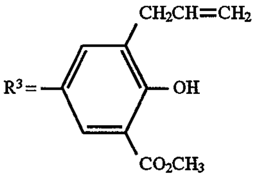

Crystal form: colorless prismatic (recrystallized from diisopropyl ether)
M.p.: 118–119° C. Form: free
Compound of Example 261

$R^1$ = 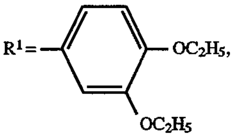

$R^2$ = H, $R^3$ = 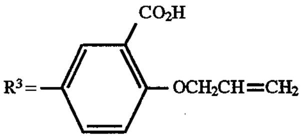

Crystal form: white acicular (recrystallized from ethyl acetate)
M.p.: 159–160° C. Form: free
Compound of Example 262

$R^1$ = 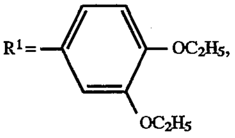

$R^2$ = H, $R^3$ = 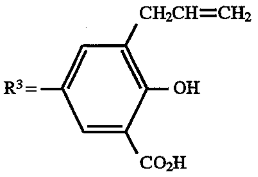

Crystal form: white acicular (recrystallized from ethanol)
M.p.: 156–157° C. Form: free
Compound of Example 263

TABLE 11-continued

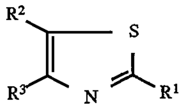

$R^1$ = 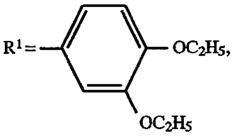

$R^2$ = H, $R^3$ = 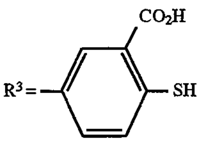

Crystal form: light brown powdery (recrystallized from dioxane-ethanol)
M.p.: 283–285° C. Form: free
Compound of Example 264

$R^1$ = 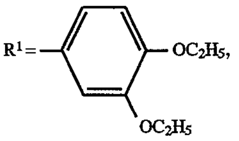

$R^2$ = H, $R^3$ = 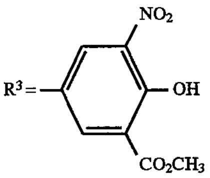

Crystal form: yellow acicular (recrystallized from dichloromethane-ethanol)
M.p.: 194–195° C. Form: free
Compound of Example 265

$R^1$ = 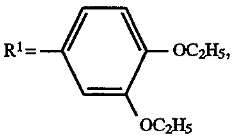

$R^2$ = H, $R^3$ = 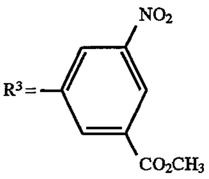

Crystal form: yellow powdery (recrystallized from ethanol-chloroform)
M.p.: 150.4–152° C. Form: free TABLE 11-continued

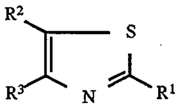

Compound of Example 266

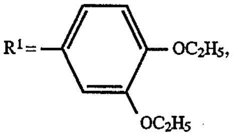

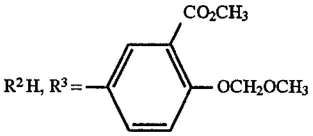

Crystal form: white acicular (recrystallized from ethanol)
M.p.: 82–83° C. Form: free Compound of Example 267

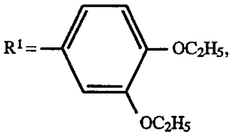

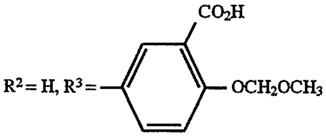

Crystal form: white acicular (recrystallized from ethyl acetate)
M.p.: 134–135° C. Form: free Compound of Example 268

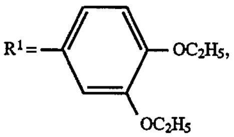

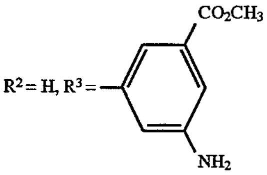

Crystal form: white acicular (recrystallized from methanol)
M.p.: 139.8–141° C. Form: free Compound of Example 269

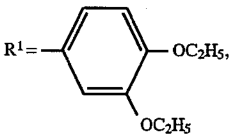

TABLE 11-continued

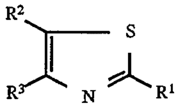

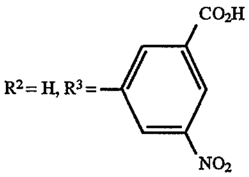

Crystal form: brown powdery (recrystallized from methanol)
M.p.: 247–248° C. Form: free Compound of Example 270

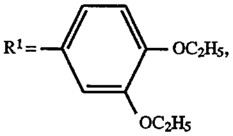

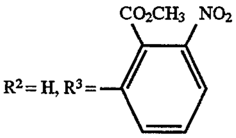

Crystal form: white powdery (recrystallized from diethyl ether-n-hexane)
M.p.: 95.8–97.4° C. Form: free Compound of Example 271

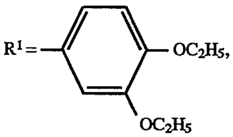

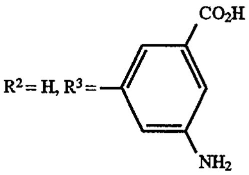

Crystal form: white powdery (recrystallized from methanol-chloroform)
M.p.: 248–258° C. Form: dihydrochloride Compound of Example 272

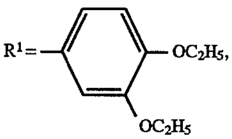

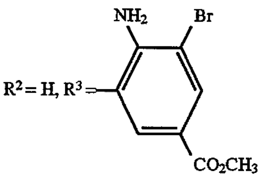

TABLE 11-continued

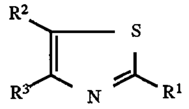

Crystal form: light yellow acicular (recrystallized from methanol)
M.p.: 116.6–118.2° C. Form: free Compound of Example 273

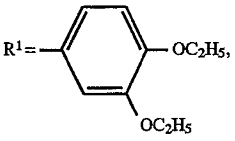

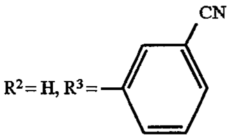

Crystal form: white acicular (recrystallized from ethanol)
M.p.: 128.6–129.2° C. Form: free Compound of Example 274

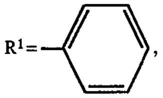

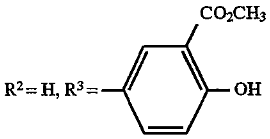

Crystal form: white prismatic (recrystallized from ethanol)
M.p.: 128.2–129° C. Form: free Compound of Example 275

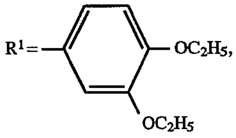

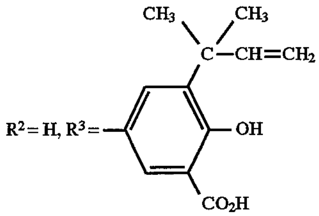

Crystal form: light brown granular (recrystallized from ethyl acetate-n-hexane)
M.p.: 164–165° C. Form: free TABLE 11-continued

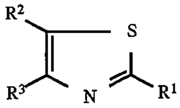

Compound of Example 276

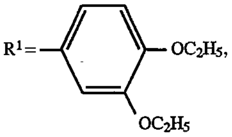

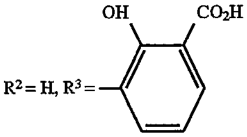

Crystal form: white acicular (recrystallized from ethyl acetate)
M.p.: 197–198° C. Form: free Compound of Example 277

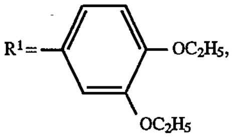

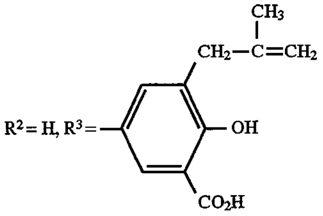

Crystal form: white acicular (recrystallized from ethyl acetate-n-hexane)
M.p.: 184–185° C. Form: free Compound of Example 278

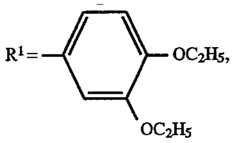

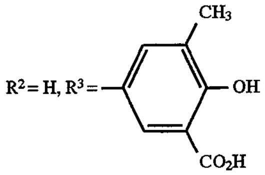

Crystal form: white acicular (recrystallized from ethyl acetate)
M.p.: 211–212° C. Form: free TABLE 11-continued

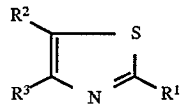

Compound of Example 279

$R^1$ = 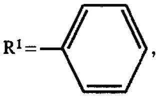 , $R^2$ = H, $R^2$ = 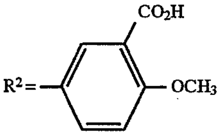

Crystal form: white prismatic (recrystallized from toluene-diethyl ether)
M.p.: 100.6–101.4° C. Form: free Compound of Example 280

$R^1$ = 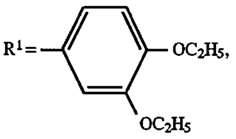

$R^2$ = H, $R^3$ = 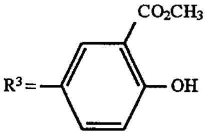

Crystal form: light brown powdery (recrystallized from ethanol-chloroform)
M.p.: 138.6–140.6° C. Form: free Compound of Example 281

$R^1$ = 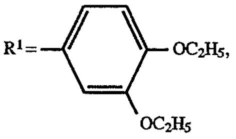

$R^2$ = H, $R^3$ = 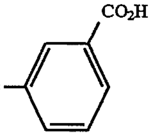

Crystal form: light pink acicular (recrystallized from ethanol)
M.p.: 192–192.8° C. Form: free Compound of Example 282

$R^1$ = 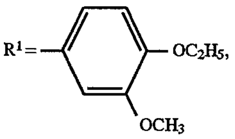

TABLE 11-continued

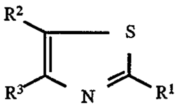

$R^2$ = H, $R^3$ = 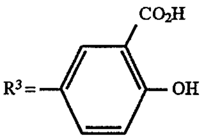

Crystal form: white powdery (recrystallized from ethanol)
M.p.: 208.6–211.6° C. Form: free Compound of Example 283

$R^1$ = 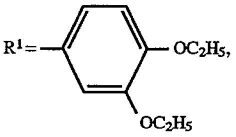

$R^2$ = H, $R^3$ = 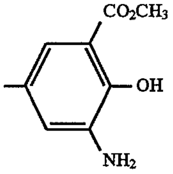

Crystal form: white acicular (recrystallized from methanol)
M.p.: 135–136° C. Form: free Compound of Example 284

$R^1$ = 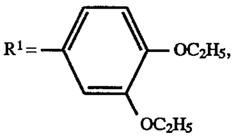

$R^2$ = H, $R^3$ = 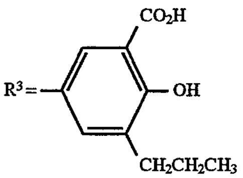

Crystal form: white powdery (recrystallized from ethanol)
M.p.: 179–180° C. Form: free Compound of Example 285

$R^1$ = 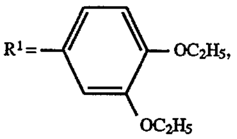

$R^2$ = H, $R^3$ = 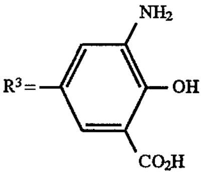

TABLE 11-continued

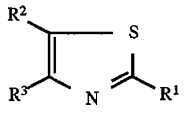

Crystal form: white powdery (recrystallized from ethanol)
M.p.: 215–216° C. Form: free Compound of Example 286

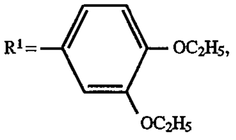

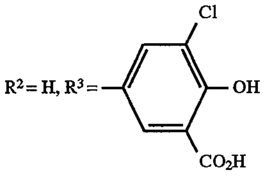

Crystal form: light green acicular (recrystallized from methanol)
M.p.: 194–196° C. Form: free Compound of Example 287

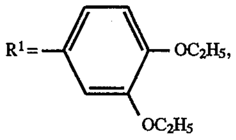

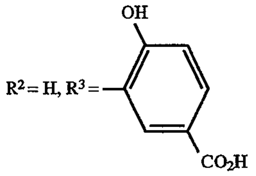

Crystal form: white powdery (recrystallized from dioxane)
M.p.: 272–273° C. Form: free Compound of Example 288

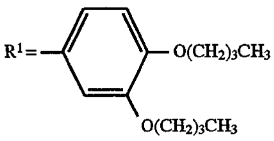

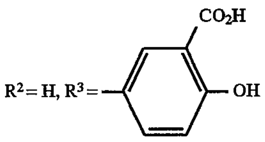

Crystal form: white powdery (recrystallized from ethanol)
M.p.: 140.2–141.6° C. Form: free TABLE 11-continued

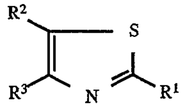

Compound of Example 289

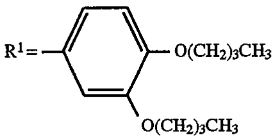

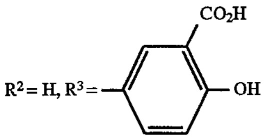

Crystal form: white powdery (recrystallized from ethanol)
M.p.: 177.6–178.8° C. Form: free Compound of Example 290

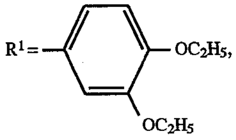

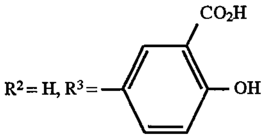

Crystal form: white acicular (recrystallized from ethanol)
M.p.: 201.5–203.4° C. Form: free Compound of Example 291

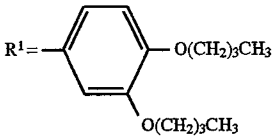

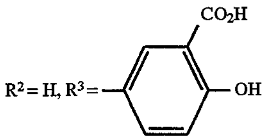

Crystal form: white powdery (recrystallized from ethanol)
M.p.: 120.2–121.6° C. Form: free Compound of Example 292

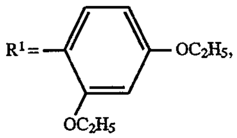

TABLE 11-continued

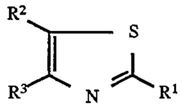

$R^2$ = H, $R^3$ = 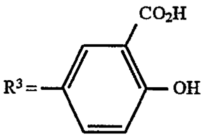

Crystal form: gray acicular (recrystallized from ethanol)
M.p.: 224.5–226.5° C. Form: free Compound of Example 293

$R^1$ = 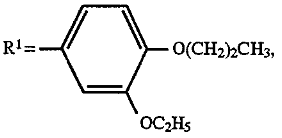

$R^2$ = H, $R^3$ = 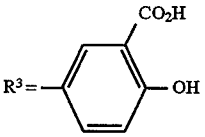

Crystal form: white powdery (recrystallized from ethanol)
176–176.6° C. Form: free Compound of Example 294

$R^1$ = 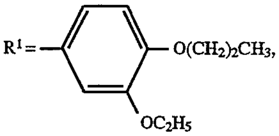

$R^2$ = H, $R^3$ = 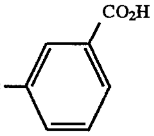

Crystal form: white powdery (recrystallized from ethanol)
M.p.: 168.4–168.6° C. Form: free Compound of Example 295

$R^1$ = 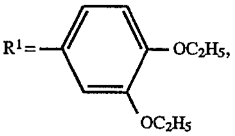

$R^2$ = H, $R^3$ = 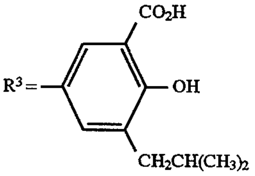

Crystal form: white acicular (recrystallized from methanol)
M.p.: 180–181° C. Form: free TABLE 11-continued

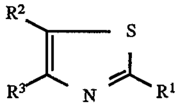

Compound of Example 296

$R^1$ = 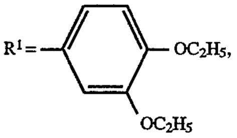

$R^2$ = H, $R^3$ = 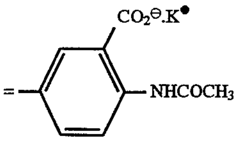

Crystal form: white powdery (recrystallized from ethyl acetate)
M.p.: 271–273° C. Form: free Compound of Example 297

$R^1$ = 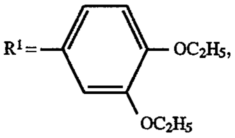

$R^2$ = H, $R^3$ = 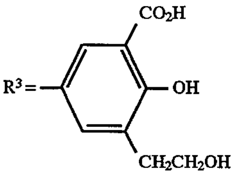

Crystal form: light yellow powdery (recrystallized from ethyl acetate)
M.p.: 170–171° C. Form: free Compound of Example 298

$R^1$ = 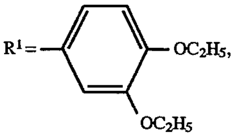

$R^2$ = H, $R^3$ = 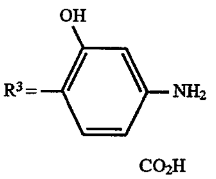

Crystal form: dark yellow powdery (recrystallized from ethanol-ethyl acetate)
M.p.: 239–243° C. (decomposed) Form: free TABLE 11-continued

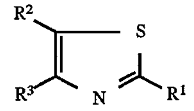

Compound of Example 299

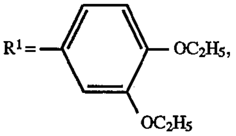

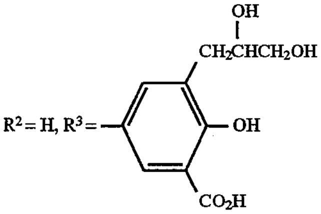

Crystal form: white acicular (recrystallized from ethyl acetate)
M.p.: 199–200° C. Form: free Compound of Example 300

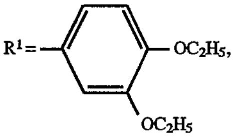

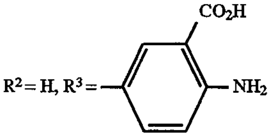

Crystal form: yellow acicular (recrystallized from ethyl acetate)
M.p.: 228–229° C. Form: free Compound of Example 301

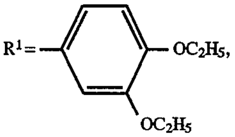

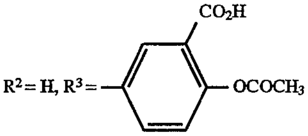

Crystal form: white acicular (recrystallized from ethyl acetate)
M.p.: 178–179° C. (decomposed) Form: free TABLE 11-continued

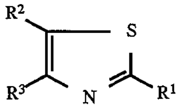

Compound of Example 302

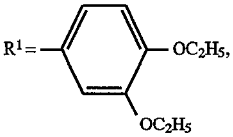

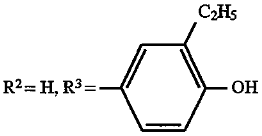

Crystal form: yellow acicular (recrystallized from ethyl acetate-n-hexane)
M.p.: 138–140° C. Form: free Compound of Example 303

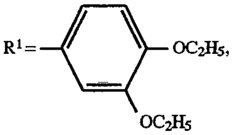

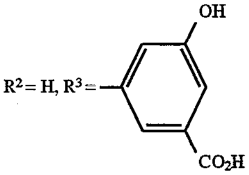

Crystal form: light yellow powdery (recrystallized from ethanol)
M.p.: 203.2–203.8° C. Form: free Compound of Example 304

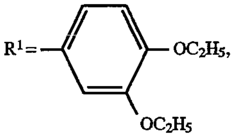

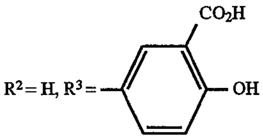

Crystal form: white acicular (recrystallized from ethyl acetate)
M.p.: 252–253° C. Form: free Compound of Example 305

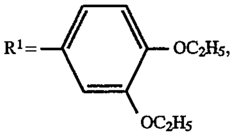

TABLE 11-continued

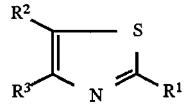

R²= H, R³=
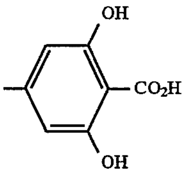

Form: free
NMR: 54)
Compound of Example 306

R¹=
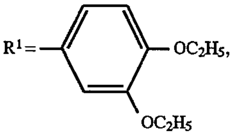

R²= H, R³=
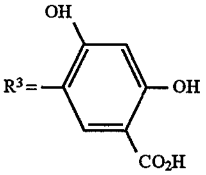

Crystal form: light brown plate (recrystallized from ethyl acetate)
M.p.: 233–234° C. Form: free
Compound of Example 307

R¹=
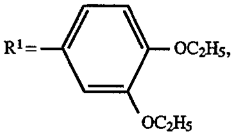

R²= H, R³=
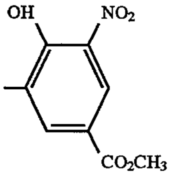

Crystal form: light brown powdery (recrystallized from ethanol)
M.p.: 185.8–187° C. Form: free
Compound of Example 308

R¹=
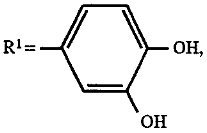

R²= H, R³=
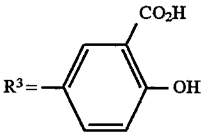

TABLE 11-continued

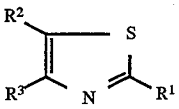

Crystal form: yellow powdery (recrystallized from ethanol-n-hexane-water)
M.p.: 239–240.4° C. Form: free
Compound of Example 309

R¹=
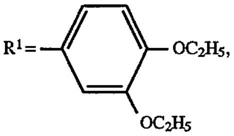

R²= H, R³=
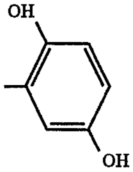

Form: free
NMR: 55)
Compound of Example 310

R¹=
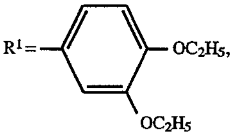

R²= H, R³=
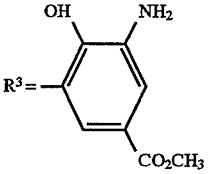

Crystal form: light yellow acicular (recrystallized from methanol)
M.p.: 132.8–134° C. Form: free
Compound of Example 311

R¹=
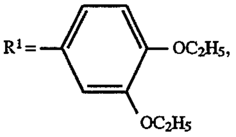

R²= H, R³=
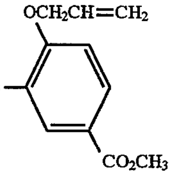

Crystal form: white acicular (recrystallized from ethyl acetate)
M.p.: 92.8–94° C. Form: free TABLE 11-continued

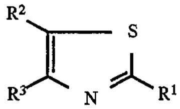

Compound of Example 312

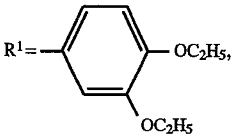

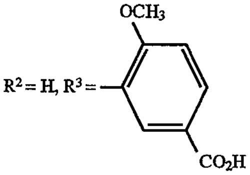

Crystal form: white powdery (recrystallized from ethyl acetate)
M.p.: 237.4–238.5° C. Form: free Compound of Example 313

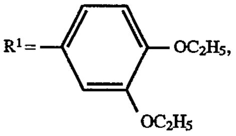

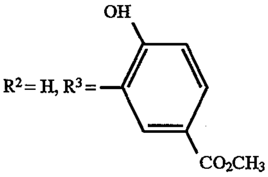

Crystal form: white acicular (recrystallized from ethanol)
M.p.: 151.8–152.5° C. Form: free Compound of Example 314

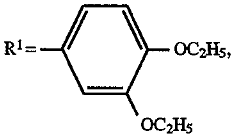

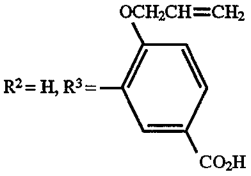

Crystal form: white powdery (recrystallized from ethanol)
M.P.: 194–195.2° C. Form: free TABLE 11-continued

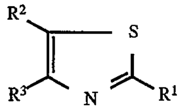

Compound of Example 315

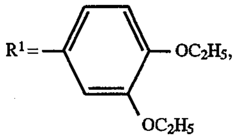

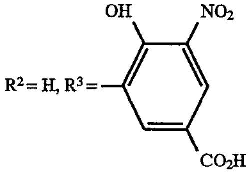

Crystal form: light brown powdery (recrystallized from acetic acid)
M.p.: 252.8–253.8° C. Form: free Compound of Example 316

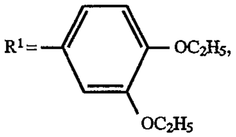

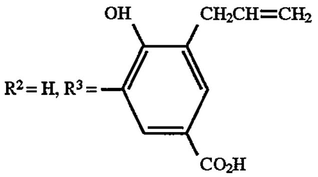

Crystal form: white powdery (recrystallized from ethanol)
M.p.: 251.6–252° C. Form: free Compound of Example 317

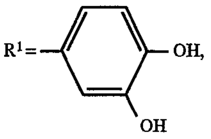

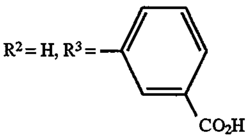

Crystal form: yellow powdery (recrystallized from ethanol)
M.p.: 230–234.5° C. Form: free TABLE 11-continued

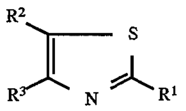

Compound of Example 318

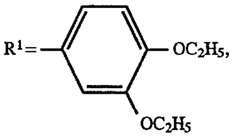

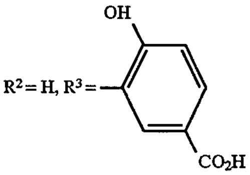

Crystal form: white powdery (recrystallized from dioxane)
M.p.: 270–271° C. Form: free Compound of Example 319

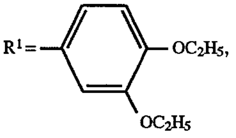

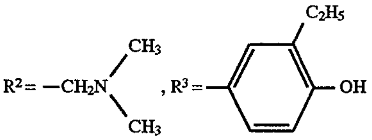

Crystal form: yellow powdery (recrystallized from acetone)
M.p.: 163–168° C. Form: dihydrochloride Compound of Example 320

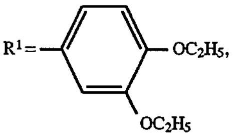

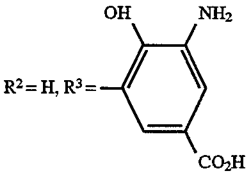

Crystal form: gray powdery (recrystallized from ethanol)
M.p.: 264–266° C. Form: hydrochloride TABLE 11-continued

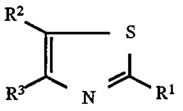

Compound of Example 321

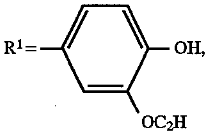

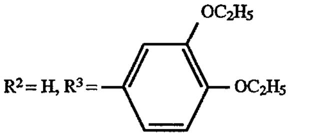

Crystal form: white powdery (recrystallized from methanol)
M.p.: 170–171° C. Form: free Compound of Example 322

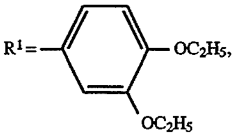

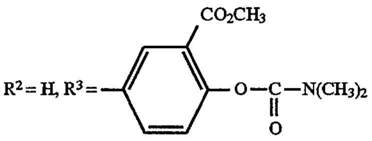

Form: free
NMR: 31)

Compound of Example 323

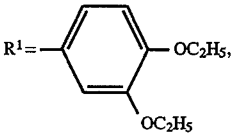

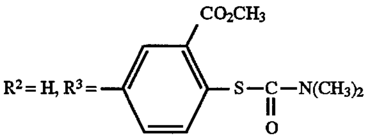

Crystal form: yellow powdery (recrystallized from ethanol)
M.p.: 108–109° C. Form: free Compound of Example 324

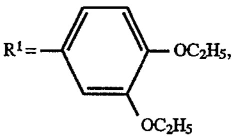

TABLE 11-continued

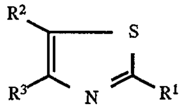

R2 = H, R3 =
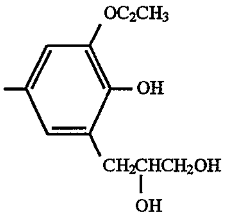

Form: free
NMR: 32)
Compound of Example 325

R1 =
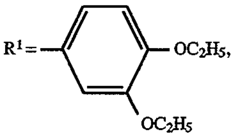

R2 = H, R3 =
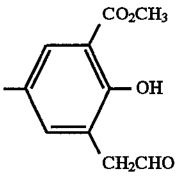

Form: free
NMR: 33)
Compound of Example 326

R1 =
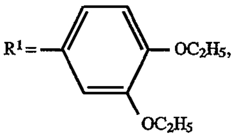

R2 = H, R3 =
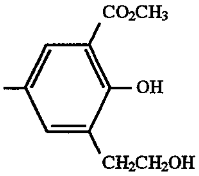

Crystal form: light brown acicular (recrystallized from diethyl ether)
M.p.: 113–114° C. Form: free
Compound of Example 327

R1 =
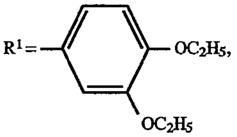

R2 = H, R3 =
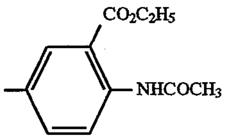

TABLE 11-continued

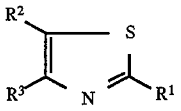

Form: free
NMR: 34)
Compound of Example 328

R1 =
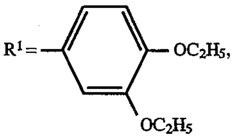

R2 = H, R3 =
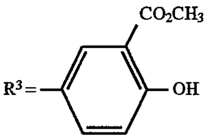

Crystal form: white acicular (recrystallized from dichloromethane-ethanol)
M.p.: 139–140° C. Form: free
Compound of Example 329

R1 =
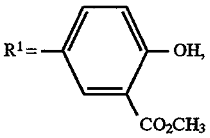

R2 = H, R3 =
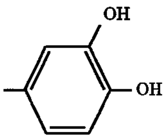

Form: hydrochloride
NMR: 35)
Compound of Example 330

R1 =
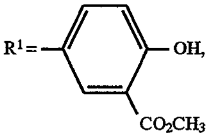

R2 = H, R3 =
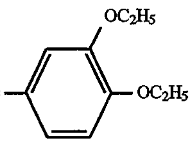

Form: free
NMR: 36)
Compound of Example 331

R1 =
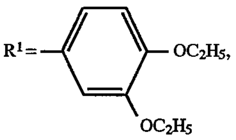

TABLE 11-continued
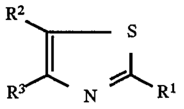
R²=H, R³=
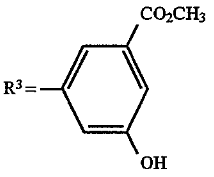
Form: free
NMR: 37)
Compound of Example 332
R¹=
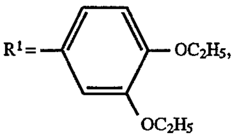
R²=H, R³=
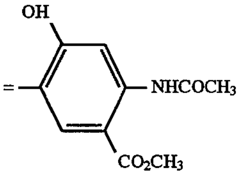
Form: free
NMR: 38)
Compound of Example 333
R¹=
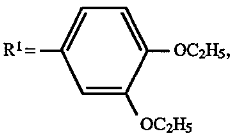
R²=H, R³=
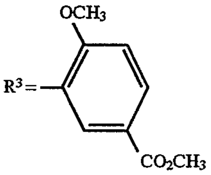
Form: free
NMR: 39)
Compound of Example 334
R¹=
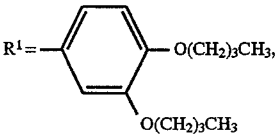
R²=H, R³=
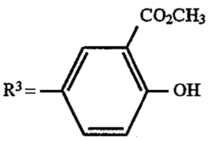
Form: free
NMR: 40)
TABLE 11-continued
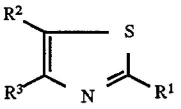
Compound of Example 335
R¹=
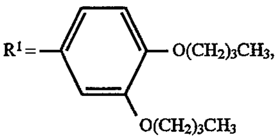
R²=H, R³=
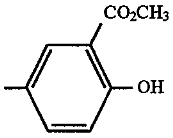
Form: free
NMR: 41)
Compound of Example 336
R¹=
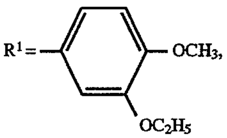
R²=H, R³=
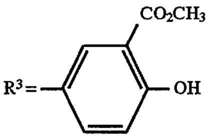
Form: free
NMR: 42)
Compound of Example 337
R¹=H, R³=
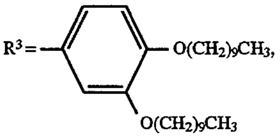
R²=H, R³=
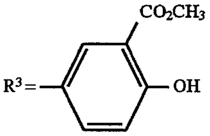
Form: free
NMR: 43)
Compound of Example 338
R¹=
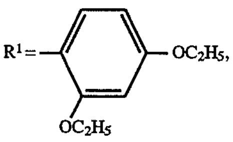

TABLE 11-continued
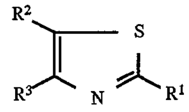
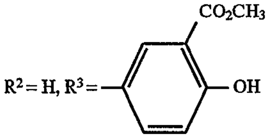
Form: free
NMR: 44)
Compound of Example 339
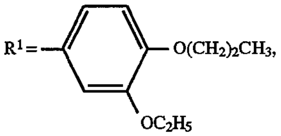
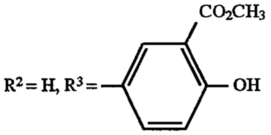
Form: free
NMR: 45)
Compound of Example 340
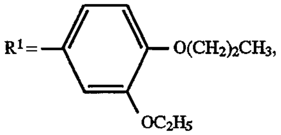
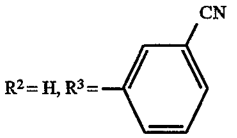
Form: free
NMR: 46)
Compound of Example 341
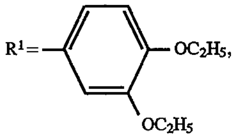
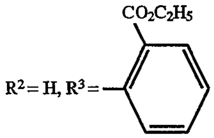
Form: free
NMR: 47)
TABLE 11-continued
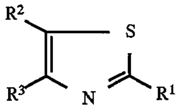
Compound of Example 342
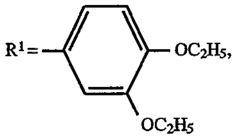
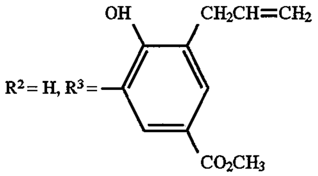
Form: free
NMR: 48)
Compound of Example 343
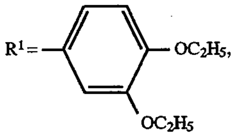
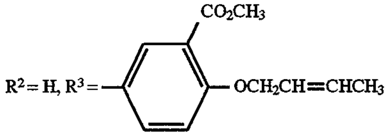
Crystal form: white acicular (recrystallized from ethanol)
M.p.: 103–104° C. Form: free
Compound of Example 344
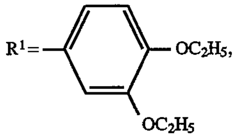
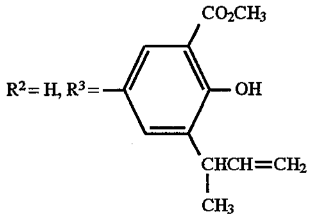
Crystal form: colorless amorphous Form: free
NMR: 50)

TABLE 11-continued

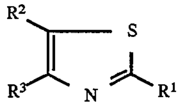

Compound of Example 345

$R^1$ = 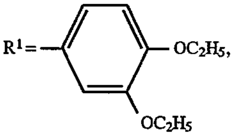

$R^2$ = H, $R^3$ = 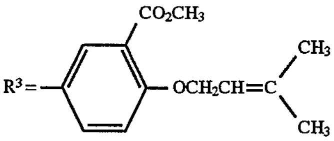

Form: free
NMR: 50)

Compound of Example 346

$R^1$ = 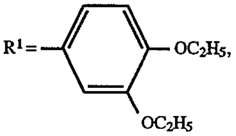

$R^2$ = H, $R^3$ = 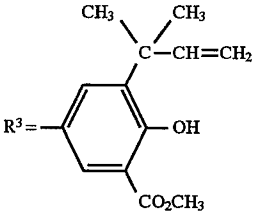

Form: free
NMR: 51)

Compound of Example 347

$R^1$ = 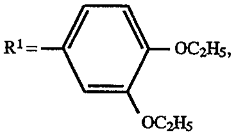

$R^2$ = H, $R^3$ = 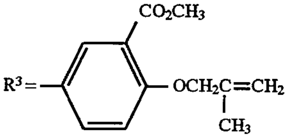

Form: free
NMR: 52)

Compound of Example 348

$R^1$ = 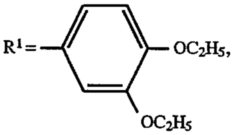

TABLE 11-continued

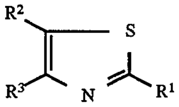

$R^2$ = H, $R^3$ = 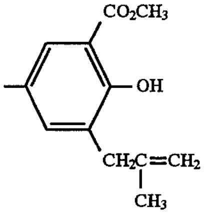

Crystal form: white powdery (recrystallized from ethanol)
M.p.: 85–86° C. Form: free Compound of Example 349

$R^1$ = 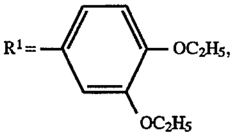

$R^2$ = H, $R^3$ = 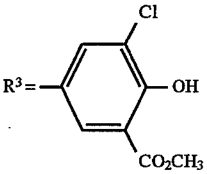

Crystal form: white powdery (recrystallized from ethanol)
M.p.: 178–179° C.

Compound of Example 350

$R^1$ = 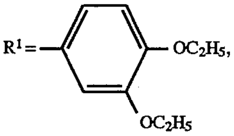

$R^2$ = H, $R^3$ = 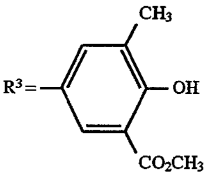

Crystal form: light brown plate (recrystallized from ethanol)
M.p.: 149–150° C. Form: free Compound of Example 351

$R^1$ = 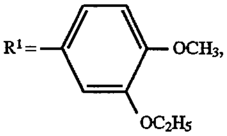

TABLE 11-continued

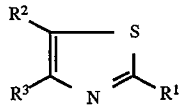

$R^2$=H, $R^3$= 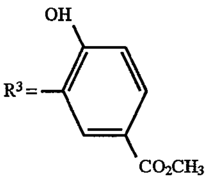

Form: free
NMR: 53)

NMR data of the compounds of Examples 305, 309, 322, 324, 325, 327, 329–342, 344–347 and 351

NMR: 31) Compound of Example 322:
NMR ($CDCl_3$) δ:
1.49 (3H, t, J=5.6 Hz), 1.52 (3H, t, J=5.6 Hz), 3.08 (3H, s), 3.43 (3H, s), 3.49 (3H, s), 3.67 (3H, s), 4.10–4.30 (4H, m), 6.92 (1H, d, J=6.7 Hz), 7.11 (1H, d, J=6.7 Hz), 7.47 (1H, s), 7.52 (1H, dd, J=1.7 Hz, 6.7 Hz), 7.61 (1H, d, J=1.7 Hz), 8.20 (1H, dd, J=1.8 Hz, 6.4 Hz), 8.56 (1H, d, J=1.8 Hz)

NMR: 32) Compound of Example 324:
NMR ($CDCl_3$) δ:
1.50 (3H, t, J=6.9 Hz), 1.52 (3H, t, J=6.9 Hz), 2.25–2.40 (1H, m), 2.59 (1H, d, J=5.3 Hz), 2.86–3.14 (2H, m), 3.45–3.80 (2H, m), 4.01 (3H, s), 4.01 (1H, brs), 4.10–4.30 (4H, m), 6.93 (1H, d, J=8.3Hz), 7.32 (1H, s), 7.54 (1H, dd, J=2.1Hz, 8.3Hz), 7.59 (1H, d, J=2.1Hz), 8.02 (1H, d, J=2.2Hz), 8.34 (1H, d, J=2.2Hz), 11.40 (1H, s)

NMR: 33) Compound of Example 325:
NMR ($CDCl_3$) δ: 1.50 (3H, t, J=7.0Hz), 1.52 (3H, t, J=7.0Hz), 3.82 (2H, d, J=1.8Hz), 4.01 (3H, s), 4.10–4.30 (4H, m), 6.92 (1H, d, J=8.4Hz), 7.33 (1H, s), 7.54 (1H, dd, J=2.1Hz, 8.4Hz), 7.59 (1H, d, J=2.1Hz), 8.02 (1H, d, J=2.2Hz), 8.39 (1H, d, J=2.2Hz), 9.81 (1H, t, J=1.8Hz), 11.20 (1H, s)

NMR: 34) Compound of Example 327:
NMR ($CDCl_3$) δ: 1.40–1.60 (9H, m), 2.26 (3H, s), 4.16 (2H, q, J=7.0Hz), 4.23 (2H, q, J=7.0Hz), 4.44 (2H, q, J=7.1Hz), 6.93 (1H, d, J=8.4Hz), 7.40 (1H, s), 7.54 (1H, dd, J=2.1Hz, 8.4Hz), 7.64 (1H, d, J=2.1Hz), 8.14 (1H, dd, J=2.2Hz, 8.8Hz), 8.66 (1H, d, J=2.2Hz), 8.80 (1H, d, J=8.8Hz), 11.20 (1H, s)

NMR: 35) Compound of Example 329:
NMR (DMSO-$d_6$) δ: 3.97 (3H, s), 6.82 (1H, d, J=8.2Hz), 7.16 (1H, d, J=8.9Hz), 7.32 (1H, dd, J=2.1Hz, 8.2Hz), 7.47 (1H, d, J=2.1Hz), 7.80 (1H, s), 8.11 (1H, dd, J=2.4Hz, 8.9Hz), 8.38 (1H, d, J=2.4Hz), 10.85 (1H, brs)

NMR: 36) Compound of Example 330:
NMR ($CDCl_3$) δ: 1.35–1.60 (6H, m), 3.94 (3H, s), 4.10–4.30 (4H, m), 5.73 (1H, s), 6.90 (1H, d, J=8.3Hz), 7.03 (1H, d, J=8.8Hz), 7.30 (1H, s), 7.48–7.65 (2H, m), 8.13 (1H, dd, J=2.3Hz, 8.8Hz), 8.41 (1H, d, J=2.3Hz)

NMR: 37) Compound of Example 331:
NMR ($CDCl_3$) δ: 1.46 (6H, t, J=7.0Hz), 3.92 (3H, s), 4.07–4.21 (4H, m), 6.90 (1H, d, J=8.4Hz), 7.15 (1H, brs), 7.27–7.49 (2H, m), 7.57 (1H, d, J=2.1Hz), 7.74 (1H, m), 8.16 (1H, s)

NMR: 38) Compound of Example 332:
NMR ($CDCl_3$) δ: 1.50 (3H, t, J=6.9Hz), 1.51 (3H, t, J=6.9Hz), 3.93 (3H, s), 4.11–4.24 (4H, m), 6.95 (1H, d, J=8.2Hz), 7.44–7.49 (3H, m), 8.34 (1H, s), 8.40 (1H, s), 11.19 (1H, s)

NMR: 39) Compound of Example 333:
NMR ($CDCl_3$) δ: 1.49 (3H, t, J=7.0Hz), 1.51 (3H, t, J=7.0Hz), 3.93 (3H, s), 4.02 (3H, s), 4.10–4.29 (4H, m), 6.95 (1H, d, J=8.3Hz), 7.05 (1H, d, J=8.7Hz), 7.55 (1H, dd, J=2.0Hz, 8.3Hz), 7.64 (1H, d, J=2.0Hz), 7.86 (1H, s), 8.00 (1H, dd, J=2.3Hz, 8.7Hz), 9.05 (1H, d, J=2.3Hz)

NMR: 40) Compound of Example 334:
NMR ($CDCl_3$) δ: 1.00 (3H, t, J=7.3Hz), 1.01 (3H, t, J=7.3Hz), 1.51–1.58 (4H, m), 1.81–1.90 (4H, m), 4.01 (3H, s), 4.03–4.17 (4H, m), 6.95 (1H, d, J=8.3Hz), 7.09 (1H, d, J=8.7Hz), 7.33 (1H, s), 7.52 (1H, dd, J=2.1Hz, 8.3Hz), 7.60 (1H, d, J=2.1Hz), 8.06 (1H, dd, J=2.3Hz, 8.7Hz), 8.44 (1H, d, J=2.3Hz )

NMR: 41) Compound of Example 335:
NMR ($CDCl_3$) δ: 1.07 (3H, t, J=7.4Hz), 1.09 (3H, t, J=7.4Hz), 1.83–1.96 (4H, m), 4.00–4.13 (4H, m), 4.01 (3H, s), 6.95 (1H, d, J=8.4Hz), 7.09 (1H, d, J=8.8Hz), 7.32 (1H, s), 7.52 (1H, dd, J=2.2Hz, 8.4Hz), 7.60 (1H, d, J=2.2Hz), 8.08 (1H, dd, J=2.2Hz, 8.8Hz), 8.45 (1H, d, J=2.2Hz), 10.86 (1H, s)

NMR: 42) Compound of Example 336:
NMR ($CDCl_3$) δ: 1.54 (3H, t, J=7.0Hz), 3.94 (3H, s), 4.01 (3H, s), 4.26 (2H, q, J=7.0Hz), 6.95 (1H, d, J=8.4Hz), 7.09 (1H, d, J=8.6Hz), 7.32 (1H, s), 7.54 (1H, dd, J=2.0Hz, 8.4Hz), 7.60 (1H, d, J=2.0Hz), 8.09 (1H, dd, J=2.2Hz, 8.6Hz), 8.45 (1H, d, J=2.2Hz), 10.86 (1H, s)

NMR: 43) Compound of Example 337:
NMR ($CDCl_3$) δ: 0.88 (6H, t, J=6.4Hz), 1.27 (28H, brs), 1.40–1.63 (4H, m), 1.78–1.91 (4H, m), 3.99 (3H, s), 4.01–4.15 (4H, m), 6.93 (1H, d, J=8.4Hz), 7.08 (1H, d, J=8.6Hz), 7.30 (1H, s), 7.51 (1H, dd, J=2.2Hz, 8.4Hz), 7.59 (1H, d, J=2.2Hz), 8.07 (1H, dd, J=2.2Hz, 8.6Hz), 8.43 (1H, d, J=2.2Hz), 10.86 (1H, s)

NMR 44) Compound of Example 338:
NMR ($CDCl_3$) δ: 1.45 (3H, t, J=7.0Hz), 1.62 (3H, t, J=7.0Hz), 4.01 (3H, s), 4.09 (2H, q, J=7.0Hz), 4.22 (2H, q, J=7.0Hz), 6.55 (1H, d, J=2.4Hz), 6.61 (1H, dd, J=2.4Hz, 8.8Hz), 7.08 (1H, d, J=8.8Hz), 7.37 (1H, s), 8.10 (1H, dd, J=2.4Hz, 8.8Hz), 8.46 (1H, d, J=8.8Hz), 8.49 (1H, d, J=2.4Hz), 10.84 (1H, s)

NMR: 45) Compound of Example 339:
NMR ($CDCl_3$) δ: 1.07 (3H, t, J=7.5Hz), 1.50 (3H, t, J=6.8Hz), 1.80–2.10 (2H, m), 4.00 (3H, s), 4.12–4.47 (4H, m), 6.95 (1H, d, J=8.4Hz), 7.09 (1H, d, J=8.6Hz), 7.31–7.49 (1H, m), 7.50–7.77 (2H, m), 8.13–8.27 (1H, m), 8.45 (1H, s), 10.86 (1H, s)

NMR: 46) Compound of Example 340:
NMR ($CDCl_3$) δ: 1.07 (3H, t, J=7.4Hz), 1.52 (3H, t, J=7.0Hz), 1.85–1.96 (2H, m), 4.04 (2H, t, J=6.7Hz), 4.25 (2H, q, J=7.0Hz), 6.95 (1H, d, J=8.3Hz), 7.49–7.63 (5H, m), 8.16–8.20 (1H, m), 8.34 (1H, s)

NMR: 47) Compound of Example 341:
NMR ($CDCl_3$) δ: 1.05 (3H, t, J=7.1Hz, 1.43 (3H, t, J=7.0Hz), 1.46 (3H, t, J=7.0Hz), 4.02–4.22 (6H, m), 6.87 (1H, d, J=8.4Hz), 7.34–7.49 (3H, m), 7.58–7.62 (2H, m), 7.63–7.74 (1H, m)

NMR 48) Compound of Example 342:
NMR ($CDCl_3$) δ: 1.50 (3H, t, J=7.0Hz), 1.52 (3H, t, J=7.0Hz), 3.54 (2H, d, J=6.6Hz), 3.92 (3H, s), 4.12–4.26 (4H, m), 5.09–5.18 (2H, m), 6.09–6.12 (1H, m), 6.96 (1H, d, J=8.3Hz), 7.45 (1H, d, J=2.0Hz), 7.49 (1H, dd, J=2.0Hz, 8.3Hz), 7.54 (1H, s), 7.84 (1H, d, J=2.2Hz), 8.28 (1H, d, J=2.2Hz), 12.84 (1H, s)

NMR: 49) Compound of Example 344:

NMR ($CDCl_3$) δ: 1.42 (3H, d, J=7.0Hz), 1.50 (3H, t, J=7.0Hz), 1.52 (3H, t, J=7.0Hz), 4.00 (3H, s), 4.10–433 (4H, m), 5.07–5.23 (2H, m), 6.03–6.25 (1H, m), 6.93 (1H, d, J=8.3Hz), 7.31 (1H, s), 7.50–7.66 (2H, m), 7.94 (1H, d, J=2.2Hz), 8.33 (1H, d, J=2.3Hz), 11.26 (1H, s)

NMR: 50) Compound of Example 345:

NMR ($CDCl_3$) δ: 1.49 (3H, t, J=7.0Hz), 1.51 (3H, t, J=7.0Hz), 1.78 (6H, d, J=6.7Hz), 3.93 (3H, s), 4.10–4.30 (4H, m), 4.68 (2H, d, J=6.3Hz), 5.42–5.62 (1H, m), 6.92 (1H, d, J=8.4Hz), 7.04 (1H, d, J=8.8Hz), 7.34 (1H, s), 7.52 (1H, dd, J=2.1Hz, 8.3Hz), 7.61 (1H, d, J=2.0Hz), 8.10 (1H, dd, J=2.4Hz, 8.7Hz), 8.36 (1H, d, J=2.3Hz)

NMR 51) Compound of Example 346:

NMR ($CDCl_3$) δ: 1.49 (3H, t, J=7.0Hz), 1.49 (3H, t, J=7.0Hz), 3.98 (3H, s), 4.05–4.30 (4H, m), 5.01 (1H, dd, J=1.2Hz, 5.8Hz), 5.08 (1H, s), 6.23–6.43 (1H, m), 6.92 (1H, d, J=8.4Hz), 7.30 (1H, s), 7.54 (1H, dd, J=2.1Hz, 8.3Hz), 7.61 (1H, d, J=2.0Hz), 8.10 (1H, d, J=2.2Hz), 8.34 (1H, d, J=2.2Hz), 11.60 (1H, s)

NMR 52) Compound of Example 347:

NMR ($CDCl_3$) δ: 1.49 (3H, t, J=6.9Hz), 1.51 (3H, t, J=6.9Hz), 1.87 (3H, s), 3.94 (3H, s), 4.10–4.30 (4H, m), 4.56 (2H, s), 5.03 (1H, brs), 5.22 (1H, brs), 6.91 (1H, d, J=8.4Hz), 7.02 (1H, d, J=8.8Hz), 7.34 (1H, s), 7.52 (1H, dd, J=2.1Hz, 8.4Hz), 7.61 (1H, d, J=2.1Hz), 8.10 (1H, dd, J=2.4Hz, 8.8Hz), 8.39 (1H, d, J=2.4Hz)

NMR: 53) Compound of Example 351:

NMR ($CDCl_3$) δ: 1.53 (3H, t, J=7.0Hz), 3.92 (3H, s), 3.95 (3H, s), 4.21 (2H, q, J=7.0Hz), 6.95 (1H, d, J=8.4Hz), 7.05 (1H, d, J=8.6Hz), 7.45 (1H, d, J=2.1Hz), 7.52 (1H, dd, J=2.1Hz, 8.4Hz), 7.64 (1H, s), 7.95 (1H, dd, J=2.1Hz, 8.6Hz), 8.39 (1H, d, J=2.1Hz), 12.66 (1H, s)

NMR: 54) Compound of Example 305:

NMR (DMSO-$d_6$) δ: 1.38 (3H, t, J=7.0Hz), 1.40 (3H, t, J=6.9Hz), 4.07–4.27 (4H, m), 6.81 (2H, s), 7.08 (1H, q, J=8.3Hz), 7.48–7.58 (2H, m), 8.04 (1H, s), 14.77 (2H, s)

NMR: 55) Compound of Example 309:

NMR ($CDCl_3$) δ: 1.50 (3H, t, J=7.0Hz), 1.51 (3H, t, J=7.0Hz), 4.10–4.33 (4H, m), 6.44 (1H, dd, J=2.5Hz, 8.5Hz), 6.52 (1H, d, J=2.5Hz), 6.93 (1H, d, J=9.0Hz), 7.29 (1H, s), 7.42–7.57 (3H, m)

Example 352

In 10 ml of dimethylformamide were suspended 1 g of 2-(3,4-diethoxyphenyl)-4-(4-hydroxy-3-methoxycarbonylphenyl)thiazole and 0.35 g of potassium carbonate. The suspension was stirred at room temperature for 30 minutes. Thereto was added 0.46 g of methyl bromoacetate. The mixture was stirred at the same temperature for 4 hours. The solvent was removed by distillation. The residue was extracted with 40 ml of dichloromethane. The extract was washed with 10 ml of water and 10 ml of a saturated aqueous sodium chloride solution, dried over magnesium sulfate, and subjected to distillation to remove the solvent. The residue was recrystallized from diisopropyl ether to obtain 1.1 g of 2-(3,4-diethoxyphenyl)-4-(4-methoxycarbonylmethoxy-3-methoxycarbonylphenyl)thiazole.

Colorless acicular crystals

M.p.: 96°–97° C.

In the same procedure as in Example 352 were obtained the compounds of Examples 1, 6, 23, 26–81, 92, 94–96, 101–108, 112, 115, 118, 121, 124, 125–128, 130–133, 135, 136, 154–165, 167–227, 229–234, 253–273, 275–307, 309–316, 318–328 and 330–351, by using respective starting materials.

Example 353

A solution of 1 g of 2-(3,4-diethoxyphenyl)-4-(4-allyloxy-3-methoxycarbonylphenyl)thiazole in 25 ml of o-dichlorobenzene was refluxed for 15 hours with heating. After the completion of a reaction, the solvent was removed by distillation. The residue was recrystallized from diisopropyl ether to obtain 1 g of 2-(3,4-diethoxyphenyl)-4-(3-methoxycarbonyl-4-hydroxy-5-allylphenyl)thiazole.

Colorless prismatic crystals

M.p.: 118°–119° C.

In the same procedure as in Example 353 were obtained the compounds of Examples 262, 275, 277, 316, 342, 344, 346 and 348, by using respective starting materials.

Example 354

4.9 g of 2-(3,4-diethoxyphenyl)-4-(4-dimethylaminothiocarbonyloxy-3-methoxycarbonylphenyl)-thiazole was stirred with heating, at 170° C. for 5 hours. The product was purified by silica gel column chromatography (eluent: dichloromethane) and recrystallized from ethanol to obtain 2.83 g of 2-(3,4-diethoxyphenyl)-4-(4-dimethylaminocarbonylthio-3-methoxycarbonylphenyl)thiazole.

Yellow powder

M.p.: 108°–109° C.

Example 355

1 ml of 10% potassium hydroxide was added to a solution of 250 mg of 2-(3,4-diethoxyphenyl-4-(4-dimethylaminocarbonylthio-3-methoxycarbonylphenyl)-thiazole in 5 ml of ethanol. The mixture was refluxed for 8 hours with heating. The solvent was removed by distillation. The residue was extracted with 40 ml of hot ethyl acetate. The extract was made acidic with 10% hydrochloric acid, washed with 5 ml of water and 10 ml of a saturated aqueous sodium chloride solution, and dried. The solvent was removed by distillation. The residue was recrystallized from dioxane-ethanol to obtain 130 mg of 2-(3,4-diethoxyphenyl)-4-(4-mercapto-2-carboxyphenyl)-thiazole.

Light brown powder

M.p.: 283°–285° C.

Example 356

To a solution of 1 g of 2-(3,4-diethoxyphenyl)-4-(3-methoxycarbonyl-4-hydroxy-4-allylphenyl)thiazole in 20 ml of methanol and 20 ml of tetrahydrofuran were added 0.5 ml of osmium tetroxide (a 4% aqueous solution) and 1.22 g of 4-methylmorpholine N-oxide. The mixture was stirred at room temperature for 4 hours. The solvent was removed by distillation. The residue was mixed with 50 ml of dichloromethane and 25 ml of water for phase separation. The organic layer was washed with 25 ml of a saturated aqueous sodium chloride solution and dried. The solvent was removed by distillation. The residue was purified by silica gel column chromatography (eluent: dichloromethane/methanol =199/1) to obtain 860 mg of 2-(3,4-diethoxyphenyl)-4-(3-methoxycarbonyl-4-hydroxy-5-(2,3-dihydroxypropyl)phenyl]thiazole.

$^1$H-NMR ($CDCl_3$) δ: 1.50 (3H, t, J=6.9Hz), 1.52 (3H, t, J=6.9Hz), 2.25–2.40 (1H, m), 2.59 (1H, d, J=5.3Hz), 2.86–3.14 (2H, m), 3.45–3.80 (2H, m), 4.01 (3H, s), 4.01 (1H, brs), 4.10–4.30 (4H, m), 6.93 (1H, d, J=8.3Hz), 7.32 (1H, s), 7.54 (1H, dd, J=2.1Hz, 8.3Hz), 7.59 (1H, d, J=2.1Hz), 8.02 (1H, d, J=2.2Hz), 8.34 (1H, d, J=2.2Hz), 11.40 (1H, s)

Example 357

To a solution of 2 g of 2-(3,4-diethoxyphenyl)-4-(3-methoxycarbonyl)-4-hydroxy-5-allylphenyl)thiazole in 100 ml of tetrahydrofuran and 15 ml of water were added 2.5 ml of osmium tetroxide (a 4% aqueous solution) and 3.9 g of sodium metaperiodate. The mixture was stirred at room temperature for 14 hours. After the completion of a reaction, the solvent was removed by distillation. The residue was mixed with 60 ml of dichloromethane and 30 ml of water for extraction and phase separation. The organic layer was dried and subjected to distillation to remove the solvent. The residue was purified by silica gel column chromatography (eluent: dichloromethane) to obtain 1.33 g of 2-(3,4-diethoxyphenyl)-4-(3-methoxycarbonyl-4-hydroxy-5-formylmethylphenyl)thiazole.

$^1$H-NMR ($CDCl_3$) δ: 1.50 (3H, t, J=7.0Hz), 1.52 (3H, t, J=7.0Hz), 3.82 (2H, d, J=1.8Hz), 4.01 (3H, s), 4.10–4.30 (4H, m), 6.92 (1H, d, J=8.4Hz), 7.33 (1H, s), 7.54 (1H, dd, J=2.1Hz, 8.4Hz), 7.59 (1H, d, J=2.1Hz), 8.02 (1H, d, J=2.2Hz), 8.39 (1H, d, J=2.2Hz), 9.81 (1H, t, J=1.8Hz), 11.20 (1H, s)

Example 358

111 mg of sodium boron hydride was added to a solution of 1.3 g of 2-(3,4-diethoxyphenyl)-4-(3-methoxycarbonyl-4-hydroxy-5-formylmethylphenyl)thiazole in 30 ml of methanol, with stirring under ice-cooling. The mixture was stirred at the same temperature for 30 minutes. After the completion of a reaction, the solvent was removed by distillation. The residue was purified by silica gel column chromatography (eluent: dichloromethane/n-hexane =4/1) and recrystallized from diethyl ether to obtain 570 mg of 2-(3,4-diethoxyphenyl)-4-[3-methoxycarbonyl-4-hydroxy-5-(2-hydroxyethyl)phenyl]-thiazole.

Light brown acicular crystals

M.p.: 113°–114° C.

Example 359

A solution of 1 g of potassium 3-[2-(3,4-diethoxyphenyl) thiazole-4-yl]-6-acetylaminobenzoate in 50 ml of water and 10 ml of 30% potassium hydroxide was refluxed for 8 hours with heating. After the completion of a reaction, the solvent was removed by distillation. The residue was made weakly acidic with 10% hydrochloric acid and extracted with 80 ml of ethyl acetate. The extract was washed with 20 ml of a saturated aqueous sodium chloride solution, dried and subjected to distillation to remove the solvent. The residue was recrystallized from ethyl acetate to obtain 168 mg of 2-(3, 4-diethoxyphenyl)- 4-(3-carboxy-4-aminophenyl)thiazole.

Yellow acicular crystals

M.p.: 228°–229° C.

The compound of Example 298 was obtained by using starting materials, in the same procedure as in Example 359.

Example 360

2 g of potassium carbonate was added to a solution of 1.5 g of 2-(3,4-diethoxyphenyl)-4-(2,4-dihydroxyphenyl) thiazole in 40 ml of acetone. Thereto was added 40 g of dry ice under cooling at –78° C. The mixture was sealed in a tube and stirred at 150° C. for 18 hours. The solvent was distilled off. The residue was made weakly acidic with 100 ml of ethyl acetate and 10% hydrochloric acid, and extraction and phase separation was conducted. The organic layer was washed with 30 ml of a saturated aqueous sodium chloride solution and dried. The solvent was distilled off. The residue was mixed with 40 ml of dichloromethane. The insoluble was collected by filtration, washed with a small amount of dichloromethane, dried and recrystallized from ethyl acetate to obtain 241 mg of 2-(3,4-diethoxyphenyl)-4-(3-carboxy-4,6-dihydroxyphenyl)thiazole.

Light brown plate crystals

M.p.: 233°–234° C.

In the same procedure as in Example 360 were obtained the compounds of Examples 190, 262, 275, 276, 277, 278, 282, 284–286, 288–293, 295, 297, 299, 304, 305 and 308, by using respective starting materials.

Example 361

A suspension of 1 g of 2-(3,4-diethoxyphenyl)-4-(3-ethyl-4-hydroxyphenyl)thiazole, 1 g of paraformaldehyde and 1.1 g of dimethylamine hydrochloride in 20 ml of ethanol was stirred at 100° C. for 4 hours with heating. The solvent was distilled off. The residue was mixed with 20 ml of water and 30 ml of ethyl acetate for extraction and phase separation. The ethyl acetate layer was extracted with 10% hydrochloric acid (20 ml×3). The combined aqueous layer was made basic with 10% sodium hydroxide and extracted with dichloromethane. The extract was washed with 20 ml of a saturated aqueous sodium chloride solution, dried and subjected to distillation to remove the solvent. The residue was purified by silica gel column chromatography (eluent: dichloromethane/methanol =49/1). The product was dissolved in acetone, mixed with hydrochloric acid-methanol and heated. The resulting crystals were collected by filtration, dried and recrystallized from acetone to obtain 117 mg of 2-(3,4-diethoxyphenyl)-4-(3-ethyl-4-hydroxyphenyl) -5-dimethylaminomethylthiazole dihydrochloride.

Yellow powder

M.p.: 163°–168° C.

Example 362

A solution of 16 g of 2-(3,4-diethoxyphenyl)-4-(3-cyanophenyl)thiazole in 120 ml of ethanol and 90 ml of a 40% aqueous sodium hydroxide solution was refluxed for 15 hours with heating. The reaction mixture was mixed with water, made acidic with concentrated hydrochloric acid and extracted with ethyl acetate (200 ml×3). The extract was washed with water (10 ml×3) and subjected to distillation to remove the solvent. The residue was recrystallized from ethanol to obtain 7 g of 2-(3,4-diethoxyphenyl)-4-(3-carboxyphenyl)thiazole.

Light pink acicular crystals

M.p.: 192°–192.8° C.

Example 363

A catalytic amount of 5% Pd-C was added to a solution of 250 mg of 2-(3,4-diethoxyphenyl)-4-(3-carboxy-4-hydroxy-5-allylphenyl)thiazole in 10 ml of methanol. The mixture was stirred in a hydrogen atmosphere at room temperature for 6 hours. After the completion of a reaction, the reaction mixture was filtered. The filtrate was concentrated. The residue was recrystallized from ethanol to obtain 193 mg of 2-(3,4-diethoxyphenyl)-4-(3-carboxy-4-hydroxy-5-propylphenyl)thiazole.

White powder

M.p.: 179°–180° C.

The compounds of Examples 295, 302 and 319 were obtained in the same procedure as in Example 363 by using respective starting materials.

Example 364

A solution of 1 g of 2-(3,4-diethoxyphenyl)-4-(3-carboxy-4-hydroxyphenyl)thiazole in 5 ml of acetic anhydride was stirred at 100° C. for 4 hours with heating. The solvent was distilled off. The residue was dissolved in 50 ml of ethyl acetate. To the solution was added 10 ml of a saturated sodium hydrogencarbonate solution, and phase separation was conducted. The ethyl acetate layer was made acidic with 10% hydrochloric acid, washed with 10 ml of a saturated aqueous sodium chloride solution, dried and subjected to distillation to remove the solvent. The residue was recrystallized from ethyl acetate to obtain 145 mg of 2-(3,4-diethoxyphenyl)-4-(3-carboxy-4-acetyloxyphenyl)thiazole.

White acicular crystals

M.p.: 178°–179° C.

Example 365

1.2 g of ethyl iodide and 1.5 g of potassium carbonate were added to a solution of 1.2 g of 2-(3-methoxycarbonyl-4-hydroxyphenyl)-4-(3,4-dihydroxyphenyl)thiazole in 20 ml of dimethylformamide. The mixture was stirred at room temperature for 14 hours. The solvent was removed by distillation. The residue was mixed with 40 ml of chloroform and 40 ml of water. The mixture was made acidic with 10% hydrochloric acid and phase separation was conducted. The organic layer was washed with 20 ml of a saturated aqueous sodium chloride solution, dried and subjected to distillation to remove the solvent. The residue was purified by silica gel column chromatography (eluent: dichloromethane/n-hexane=3/1) to obtain 400 mg of 2-(3-methoxycarbonyl-4-hydroxyphenyl)-4-(3,4-diethoxyphenyl)thiazole.

NMR ($CDCl_3$) δ:

1.35–1.60 (6H, m), 3.94 (3H, s), 4.10–4.30 (4H, m), 5.73 (1H, s), 6.90 (1H, d, J=8.3Hz), 7.03 (1H, d, J=8.8Hz), 7.30 (1H, s), 7.48–7.65 (2H, m), 8.13 (1H, dd, J=2.3Hz, 8.8Hz), 8.41 (1H, d, J=2.3Hz)

In the same procedure as in Example 365 were obtained the compounds of Examples 1, 6, 23, 26–81, 92, 94–96, 101–108, 112, 115, 118, 121, 124, 125–128, 130–133, 135, 136, 154–165, 167–227, 229–234, 253–273, 275–307, 309–316, 318–328 and 330–351, by using respective starting materials.

Example 366

In the same procedure as in Example 147 were obtained the compounds of Examples 253, 257, 259, 261–263, 267, 269, 271, 275–278, 281, 282, 284–296, 297–301, 303–306, 308, 312, 314–318 and 320, by using respective starting materials.

Example 367

The compound of Example 258 was obtained in the same procedure as in Example 148, by using starting materials.

Example 368

In the same procedure as in Example 235 were obtained the compounds of Examples 268, 271, 272, 283, 285, 298, 300, 310 and 320, by using respective starting materials.

Examples 367–374

The compounds shown in Table 12 were obtained in the same procedures as ih Example 1 and Example 138, by using respective starting materials.

TABLE 12

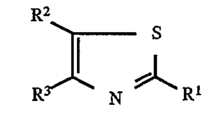

Compound of Example 367

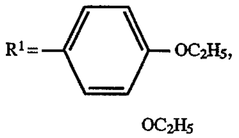

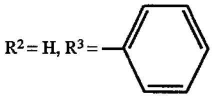

Crystal form: light brown acicular (recrystallized from ethyl acetate-n-hexane)
M.p.: 92–93° C.

Compound of Example 368

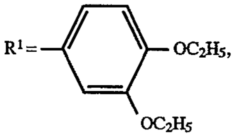

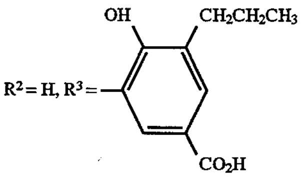

Crystal form: white acicular (recrystallized from ethanol)
M.p.: 256.8–257.0° C. Form: free Compound of Example 369

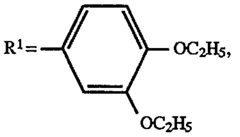

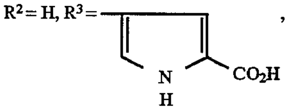

Crystal form: white powdery (recrystallized from ethyl acetate-ethanol)
M.p.: 236.6–238.0° C. Form: free Compound of Example 370

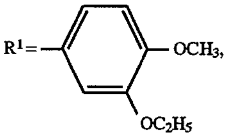

TABLE 12-continued

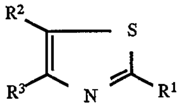

$R^2$ = H, $R^3$ = 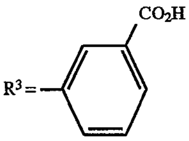

Crystal form: light yellow acicular (recrystallized from ethanol)
M.p.: 197.8–199.3° C. Form: free Compound of Example 371

$R^1$ = 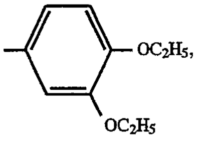

$R^2$ = H, $R^3$ = 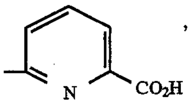

Crystal form: white powdery (recrystallized from ethanol)
M.p.: 182–184° C. Form: free Compound of Example 372

$R^1$ = 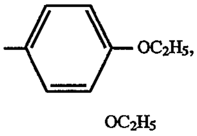

$R^2$ = H, $R^3$ = 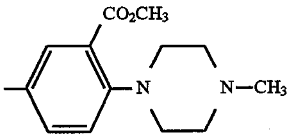

Crystal form: yellow powdery (recrystallized from acetone-diethyl ether)
M.p.: 111–114° C. Form: trihydrochloride ½ hydrate.

Compound of Example 373

$R^1$ = 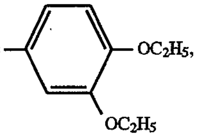

$R^2$ = H, $R^3$ = 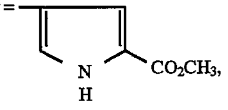

Form: free
NMR: 56)

TABLE 12-continued

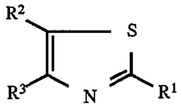

Compound of Example 374

$R^1$ = 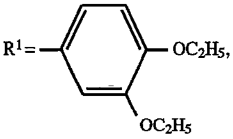

$R^2$ = H, $R^3$ = 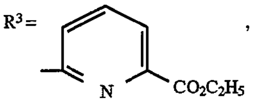

Form: free
NMR: 57)

56) NMR (DMSO-$d_6$) δ:

1.37 (3H, t, J=6.9Hz), 1.39 (3H, t, J=6.9Hz), 3.82 (3H, s), 4.13 (4H, m), 7.09 (1H, d, J=8.4Hz), 7.30 (1H, m), 7.48 (1H, dd, J=2.0Hz, 8.4Hz), 7.58 (2H, m), 7.71 (1H, s), 12.10 (1H, brs)

57) NMR ($CDCl_3$) δ:

1.41–1.54 (9H, m), 4.07–4.26 (6H, m), 6.92 (1H, d, J=8.4Hz), 7.49 (1H, dd, J=2.0Hz, 8.4Hz), 7.63 (1H, d, J=2.0Hz), 7.86–8.05 (2H, m), 8.20 (1H, s), 8.44 (1H, dd, J-1.0Hz, 7.7Hz)

Example 375

The compounds of Examples 368–371 were obtained in the same procedure as in Example 147, by using respective starting materials.

Example 376

The compound of Example 368 was obtained in the same procedure as in Example 363, by using starting materials.

Example 377

The compounds of Examples 367–374 were obtained in the same procedure as in Example 365, by using respective starting materials.

The compounds of Examples 378–452, shown in Table 13 were obtained in the same procedures as in Example 1 and Example 138, by using respective starting materials.

TABLE 13
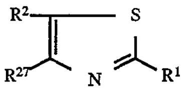
| Example No. | $R^1$ | $R^2$ | $R^3$ | Crystal form (recrystallization solvent) | M.p. (°C.) (salt form) |
|---|---|---|---|---|---|
| 378 | 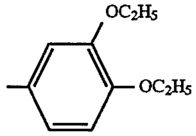 | H | 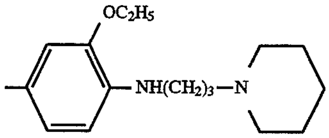 | Yellow powder (diethyl ether) | 93–94 (2 HCl) |
| 379 | " | H | 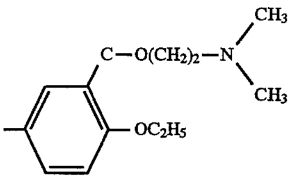 | Yellow powder (acetone) | 119–122 (3 HCl) |
| 380 | 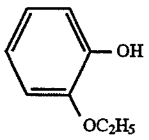 | H | 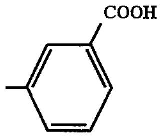 | Light yellow powder (ethanol) | 203–205.6 |
| 381 | 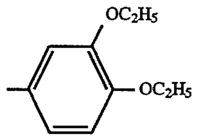 | H | 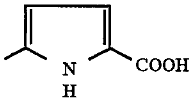 | Light yellow powder (ethyl acetate) | 188.4–190.4 (decomposed) (—) |
| 382 | " | H | 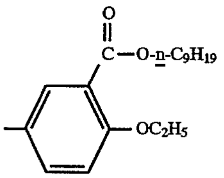 | White powder (ethanol) | 67–68 (—) |
| 383 | " | H | 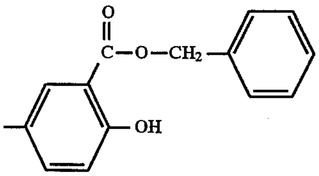 | White powder (ethanol) | 108–109 (—) |
| 384 | " | H | 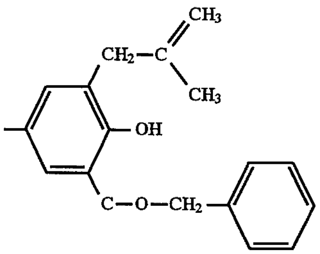 | White powder (diethyl ether) | 99–100 (—) |

TABLE 13-continued

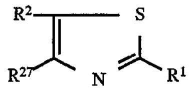

| Example No. | $R^1$ | $R^2$ | $R^3$ | Crystal form (recrystallization solvent) | M.p. (°C.) (salt form) |
|---|---|---|---|---|---|
| 385 | " | H | 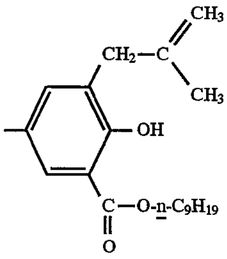 | White acicular (diethyl ether-n-hexane) | 94–95 (—) |
| 386 | " | H | 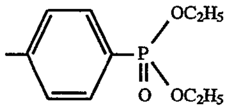 | White powder (diethyl ether) | 69—71.4 (—) |
| 387 | " | H | 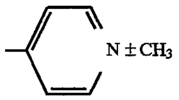 | Dark yellow acicular (acetone) | 213–214 (I) |
| 388 | " | H | 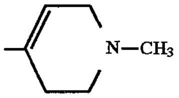 | Light brown powder (diethyl ether) | 81.2–83.6 (—) |
| 389 | " | H | 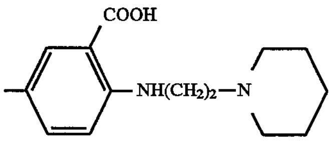 | White powder (ethanol-diethyl ether) | 212–214 (HCl) |
| 390 | " | H | 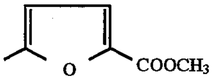 | White powder (ethanol) | 126.8–128.8 (—) |
| 391 | " | H | 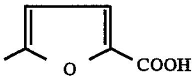 | White powder (ethyl acetate) | 206.8–208.6 (—) |
| 392 | " | H | 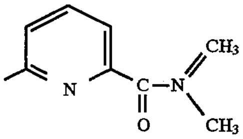 | White acicular (n-hexane-ethyl acetate-dichloromethane) | 163.2–164.1 (—) |
| 393 | " | H | 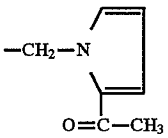 | White acicular (methanol) | 123–124 (—) |
| 394 | " | H | 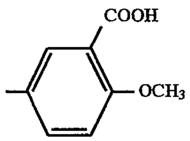 | White acicular (ethyl acetate) | 144–145 (—) |

TABLE 13-continued

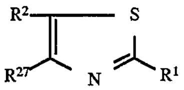

| Example No. | $R^1$ | $R^2$ | $R^3$ | Crystal form (recrystallization solvent) | M.p. (°C.) (salt form) |
|---|---|---|---|---|---|
| 395 | " | H | 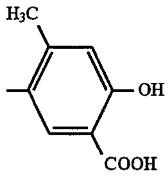 | Light brown prismatic (ethyl acetate) | 171–172 (—) |
| 396 | " | H | 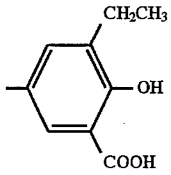 | White powder (ethyl acetate) | 216–217 (—) |
| 397 | " | H | 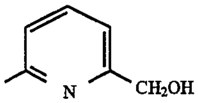 | White powder (ethyl acetate-n-hexane) | 109–113 (—) |
| 398 | " | H | 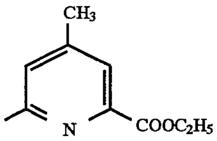 | Yellow powder (ethanol) | 181.8–182.4 (decomposed) (—) |
| 399 | " | H | 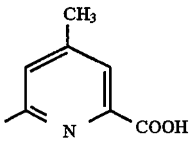 | White acicular (ethyl acetate) | 180.8–182.2 (—) |
| 400 | " | H | 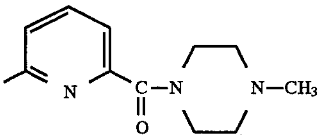 | Yellow amorphous | 242.5 (decomposed) (4 HCl) |
| 401 | " | H | 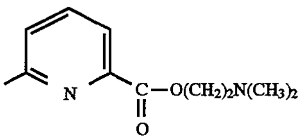 | White acicular (diethyl ether-n-hexane) | 216–217 (—) |
| 402 | " | H | 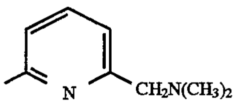 | Yellow powder (diethyl ether-ethanol) | 195 (decomposed) (2 HCl) |
| 403 | 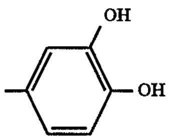 | H | 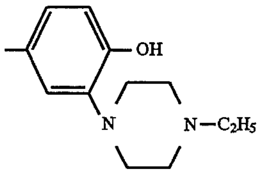 | Gray powder (acetic acid-water) | 184–186 (decomposed) (HBr) |

TABLE 13-continued

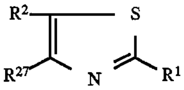

| Example No. | $R^1$ | $R^2$ | $R^3$ | Crystal form (recrystallization solvent) | M.p. (°C.) (salt form) |
|---|---|---|---|---|---|
| 404 | 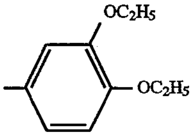 | H | 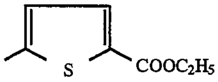 | Yellow acicular (ethanol) | 104.8–108.8 (—) |
| 405 | " | H | 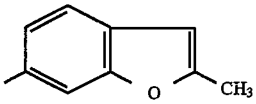 | White acicular (ethyl acetate) | 217–219 (—) |
| 406 | " | H | 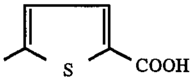 | Light yellow powder (ethanol) | 189.8—191 (—) |
| 407 | " | H | 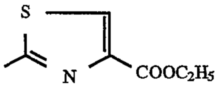 | White acicular (ethanol) | 138.2–139 (—) |
| 408 | " | H | 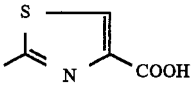 | White acicular (ethanol) | 222–223 (—) |
| 409 | " | H | 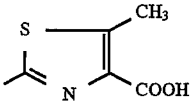 | White acicular (ethyl acetate-ethanol) | 240–242 (—) |
| 410 | " | H | 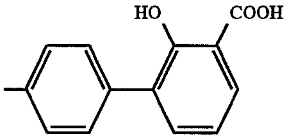 | Light yellow acicular (ethyl acetate) | 222–223 |
| 411 | " | H | 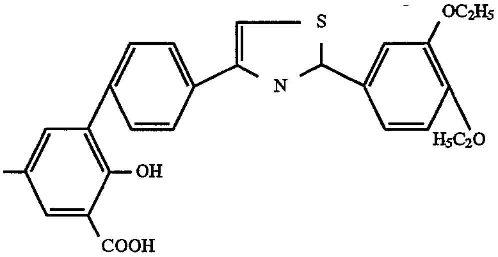 | White powder (ethyl acetate) | 215–216 (—) |
| 412 | " | H | 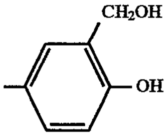 | White acicular (ethyl acetate) | 158–159 (—) |
| 413 | " | H | 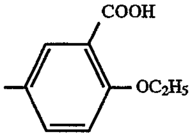 | White acicular (ethyl acetate) | 140–141 (—) |

TABLE 13-continued
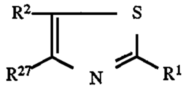
| Example No. | $R^1$ | $R^2$ | $R^3$ | Crystal form (recrystallization solvent) | M.p. (°C.) (salt form) |
|---|---|---|---|---|---|
| 414 | " | H | 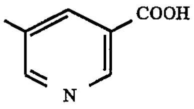 | White powder (ethanol) | 234.6–239.4 (HCl) |
| 415 | " | H | 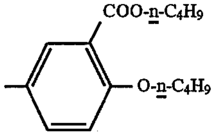 | White powder (n-hexane) | 75–76.5 |
| 416 | " | H | 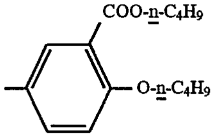 | White acicular (ethyl acetate) | 126.5–128 (—) |
| 417 | " | H | 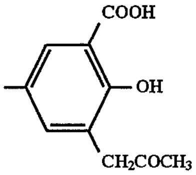 | White powder (ethyl acetate-n-hexane) | NMR[58)] (—) |
| 418 | " | H | 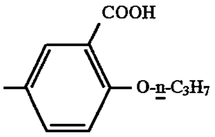 | White acicular (ethyl acetate) | 159–161 (—) |
| 419 | " | H | 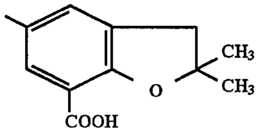 | White acicular (ethyl acetate) | 106–107 (—) |
| 420 | " | H | 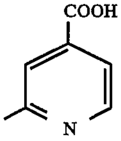 | White powder (ethyl acetate) | 236.2–237.2 (—) |
| 421 | " | H | 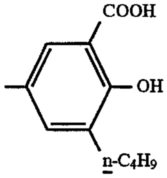 | | |
| 422 | " | H | 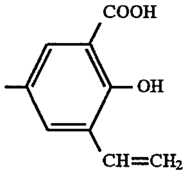 | White powder (ethyl acetate) | 212–213 (—) |

TABLE 13-continued
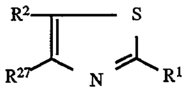
| Example No. | $R^1$ | $R^2$ | $R^3$ | Crystal form (recrystallization solvent) | M.p. (°C.) (salt form) |
|---|---|---|---|---|---|
| 423 | " | H | 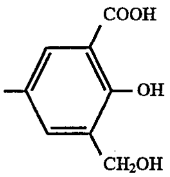 | | NMR[59] |
| 424 | " | H | 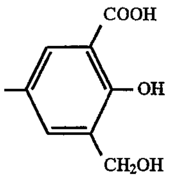 | Yellow powder (ethyl acetate) | 210–212 (—) |
| 425 | " | H | 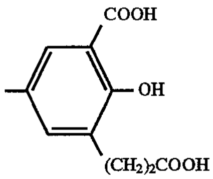 | | NMR[60] (—) |
| 426 | " | H | 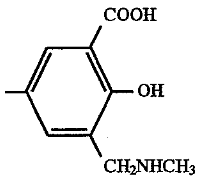 | Light brown granular (dimethylform-amide) | 271–273 (—) |
| 427 | " | H | 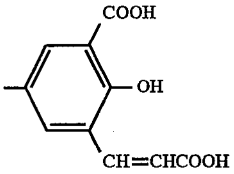 | Yellow powder (ethyl acetate) | 260–261 (—) |
| 428 | " | H | 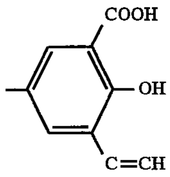 | | |
| 429 | " | H | 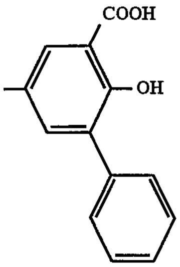 | | |

TABLE 13-continued
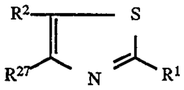
| Example No. | $R^1$ | $R^2$ | $R^3$ | Crystal form (recrystallization solvent) | M.p. (°C.) (salt form) |
| --- | --- | --- | --- | --- | --- |
| 430 | " | H | 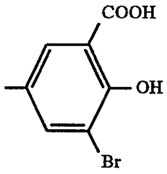 | Yellow powder (ethanol) | 202–203 |
| 431 | " | H | 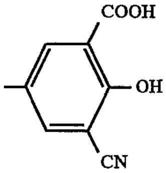 | White powder (methanol) | 254–255 (—) |
| 432 | " | H | 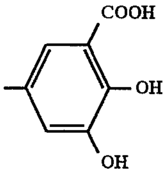 | | |
| 433 | " | H | 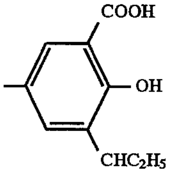 | | |
| 434 | " | H | 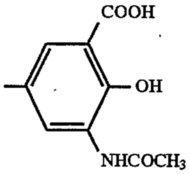 | White acicular (ethyl acetate) | 243–246 (—) |
| 435 | " | H | 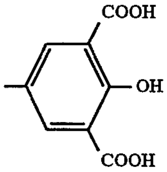 | Yellow acicular (ethanol) | 243–244 |
| 436 | " | H | 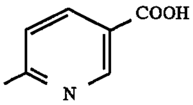 | Light orange prismatic (ethyl acetate) | 230.4–231.4 (—) |
| 437 | " | H | 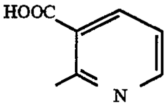 | Dark yellow prismatic (ethyl acetate-diethyl ether-n-hexane) | 11 164.6–165.5 (—) |

TABLE 13-continued

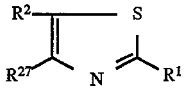

| Example No. | $R^1$ | $R^2$ | $R^3$ | Crystal form (recrystallization solvent) | M.p. (°C.) (salt form) |
|---|---|---|---|---|---|
| 438 | " | H | 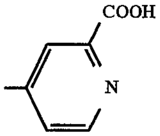 | Light brown powder (ethyl acetate) | 153.8–155.4 (—) |
| 439 | " | H | 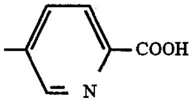 | White powder (ethyl acetate) | 178–178.6 (—) |
| 440 | " | H | 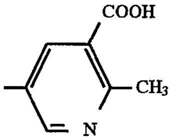 | Light yellow powder (ethanol-diethyl ether) | 220.8–223.4 |
| 441 | " | H | 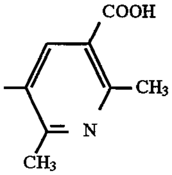 | Brown powder (ethanol) | 174.4–175.6 (—) |
| 442 | " | H | 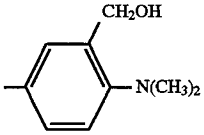 | White acicular (methanol-diethyl ether) | 102.5–103.5 (—) |
| 443 | " | H | 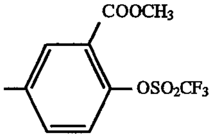 | White powder (ethanol) | 112–113 (—) |
| 444 | " | H | 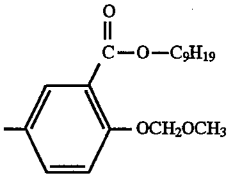 | Colorless oily | NMR[61)] |
| 445 | " | H | 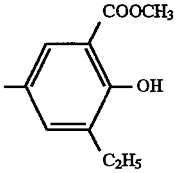 | Light brown acicular (ethanol) | 93–94 (—) |
| 446 | " | H | 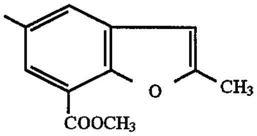 | Light brown prismatic (methanol-dichloromethane) | 144–145 NMR[62)] (—) |

TABLE 13-continued

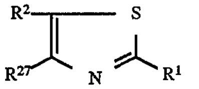

| Example No. | $R^1$ | $R^2$ | $R^3$ | Crystal form (recrystallization solvent) | M.p. (°C.) (salt form) |
|---|---|---|---|---|---|
| 447 | " | H | 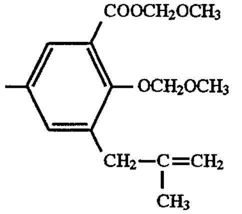 | Brown oily | NMR[63] (—) |
| 448 | " | H | 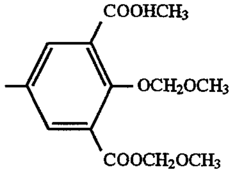 | Colorless oily | NMR[64] |
| 449 | " | H | 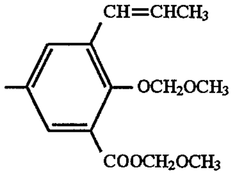 | White solid | NMR[65] |
| 450 | " | H | 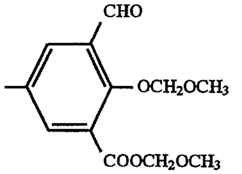 | White acicular (ethanol) | 113–114 (—) |
| 451 | " | H | 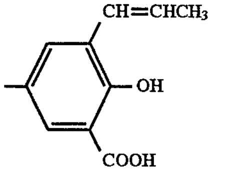 | Yellow acicular (ethyl acetate) | 202–203 (—) |
| 452 | " | H | 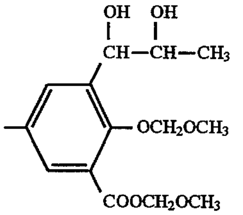 | | NMR[66] |

Example 453

94 mg of sodium boron hydride was added, at 0° C., to a solution of 540 mg of 4-[2-(3,4-diethoxyphenyl)-4-thiazole]-1-methylpyridinium iodide in 60 ml of methanol. The mixture was stirred at room temperature for 15 hours. After the completion of a reaction, the reaction mixture was concentrated. The residue was mixed with 100 ml of ethyl acetate and washed with 50 ml of water. The ethyl acetate layer was dried over sodium sulfate and concentrated. The residue was recrystallized from diethyl ether to obtain 300 mg of 2-(3,4-diethoxyphenyl)-4-(1-methyl-1,2,5,6-tetrahydropyridin-4-yl)thiazole.

Light brown powder

M.p.: 81.2°–83.6° C.

Example 454

200 mg of lithium aluminum hydride was added, at 0° C., to a solution of 1.92 g of 2-(3,4-diethoxyphenyl)-4-(2-ethoxycarbonyl-6-pyridyl)thiazole in 150 ml of tetrahydrofuran. The mixture was stirred in an argon atmosphere for 2 hours. The reaction mixture was mixed with 1 ml of a saturated sodium sulfate slution. The resulting mixture was stirred at 0° C. for 30 minutes and filtered through Celite. The filtrate was concentrated. The residue was purified by silica gel column chromatography and recrystallized from ethyl acetate-n-hexane to obtain 360 mg of 2-(3,4-diethoxyphenyl)-4-(2-hydroxymethyl-6-pyridyl)thiazole.

White acicular

M.p.: 109°–113° C.

The compounds of Examples 412, 423 and 442 were obtained in the same procedure as in Example 454, by using respective starting materials.

Example 455

1.13 ml of triethylamine was dropwise added, at room temperature, to a solution of 1 g of 2-(3,4-diethoxyphenyl)-4-(2-carboxy-6-pyridyl)thiazole, 245 mg of dimethylamine hydrochloride and 515 mg of diethyl cyanophosphate in 15 ml of dimethylformamide. The mixture was stirred at the same temperature for 3 hours. The reaction mixture was mixed with 20 ml of water. The resulting mixture was extracted with 50 ml of dichloromethane three times. The dichloromethane layer was dried over sodium sulfate and concentrated. The residue was recrystallized from n-hexane-ethyl acetate-dichloromethane to obtain 800 mg of 2-(3,4-diethoxyphenyl)-4-(2-dimethylaminocarbonyl-6-pyrdyl) thiazole.

White acicular

M.p.: 163.2°–164.1° C.

The compounds of Examples 379, 400 and 401 were obtained in the same procedure as in Example 455, using respective starting materials.

Example 456

730 Milligrams of 2-(3,4-diethoxyphenyl)-4-(2-dimethylaminocarbonyl-6-pyridyl)thiazole was dissolved in 15 ml of tetrahydrofuran at room temperature, then this solution was dropwise added to a suspension of 70 mg of lithium aluminum hydride in 10 ml of diethyl ether, in an argon atmosphere so as to refluxing the reaction mixture. After the completion of the dropwise addition, refluxing was continued for a further 1 hour and 30 minutes. The reaction mixture was mixed with 50 ml of water. The resulting mixture was extracted with three 50-ml portions of dichloromethane. The, dichloromethane layer was concentrated. The residue was purified by silica gel thin-layer chromatography. The resulting ethanol solution was mixed with concentrated hydrochloric acid to obtain a hydrochloride. The hydrochloride was recrystallized from a diethyl ether-ethanol mixed solvent to obtain 60 mg of 2-(3,4-diethoxyphenyl)-4-(2-dimethylaminomethyl-6-pyridyl)-thiazole dihydrochloride as a yellow powder.

M.p.: 195° C. (decomposed)

Example 457

8.5 g of trifluoromethanesulfonic acid anhydride was added to a solution of 10 g of 2-(3,4-diethoxyphenyl)-4-(3-methoxycarbonyl-4-hydroxyphenyl)-thiazole dissolved in 100 ml of dichloromethane. Thereto was dropwise added 6 ml of triethylamine with stirring under ice-cooling. The reaction mixture was stirred at room temperature for 2 hours. Thereto was added 40 ml of water for phase separation. The organic layer was dried and subjected to distillation to remove the solvent. The residue was recrystallized from ethanol to obtain 12.7 g of 2-(3,4-diethoxyphenyl)-4-(3-methoxycarbonyl-4-trifluoromethanesulfonyloxyphenyl) thiazole as a white powder.

M.p.: 112°–113° C.

Example 458

In 5 ml of dimethylformamide was dissolved 600 mg of 2-(3,4-diethoxyphenyl)-4-(3-carboxy-4-methoxymethoxyphenyl)thiazole. Thereto was added 56 mg of sodium hydride and 290 mg of 1-bromononane. The mixture was stirred at room temperature for 14 hours. The solvent was removed by distillation. To the residue were added 80 ml of dichloromethane and 30 ml of a 10% aqueous sodium hydroxide solution, and phase separation was conducted. The dichloromethane portion was washed with 20 ml of a saturated aqueous sodium chloride solution, dried and subjected to distillation to remove the solvent. The residue was subjected to silica gel column chromatography. There was obtained, from the dichloromethane layer, 340 mg of 2-(3,4-diethoxyphenyl)-4-(3-nonyloxycarbonyl-4-methoxymethoxyphenyl)thiazole as a colorless oily substance.

Properties: NMR[61)]

In the same procedure as in Example 458 were obtained the compounds of Examples 382–385, 390, 398, 404, 407, 415, 443, 444, 445, 447–450 and 452, by using respective starting materials.

Example 459

In a mixed solvent consisting of 2 ml of dimethylformamide and 0.2 ml of water were dissolved 200 mg of 2-(3,4-diethoxyphenyl)-4-chloromethylthiazole, 73 mg of 2-acetylpyrrole, 200 mg of sodium iodide and 200 mg of sodium hydroxide. The solution was stirred at 80° C. for 4 hours. The reaction mixture was subjected to distillation to remove the solvent. To the residue were added 30 ml of dichloromethane and 20 ml of water, and phase separation was conducted. The organic layer was washed with 15 ml of a saturated aqueous sodium chloride solution, dried and subjected to distillation to remove the solvent. The residue was recrystallized from methanol to obtain 60 mg of 2-(3,4-diethoxyphenyl)-4-(2-acetyl-1-pyrrolyl)methylthizaole as white acicular crystals.

M.p.: 123°–124° C.

Example 460

In 5 ml of dimethyl sulfoxide were dissolved 1 g of 2-(3,4-diethoxyphenyl)-4-(3-methoxycarbonyl-4-trifluoromethylsulfonyloxyphenyl)thiazole and 0.73 g of 1-(2-aminoethyl)piperidine. The mixture was stirred at 80° C. for 5 hours. To the reaction mixture were added 40 ml of ethyl acetate and 20 ml of water, and phase separation was conducted. The organic layer was washed with 15 ml of a saturated aqueous sodium chloride solution, dried and subjected to distillation to remove the solvent. The residue was purified by silica gel column chromatography (elutant: dichloromethane/methanol =49/1 by v/v) and dissolved in diethyl ether. The solution was mixed with hydrochloric acid-methanol to obtain a hydrochloride. The hydrochloride was recrystallized from diethyl ether to obtain 330 mg of 2-(3,4-diethoxyphenyl)-4-{3-methoxycarbonyl-4-[2-(1-piperidinyl)ethylamino]phenyl}thiazole dihydrochloride as a yellow powder.

M.p.: 93°–94° C.

The compounds of Examples 389, 403, 433, 434 and 442 were obtained in the same procedure as in Example 460, by using respective starting materials.

Example 461

In 20 ml of ethanol was dissolved 340 mg of 2-(3,4-diethoxyphenyl)-4-(3-nonyloxycarbonyl-4-methoxymethoxyphenyl)thiazole. Thereto was added 2 ml of 10% hydrochloric acid, and the mixture was refluxed for 20 minutes. The solvent was removed by distillation. To the residue were added 40 ml of dichloromethane and 20 ml of water, and phase separation was conducted. The organic layer was washed with 15 ml of a saturated aqueous sodium chloride solution, dried and subjected to distillation to remove the solvent. The residue was recrystallized from ethanol to obtain 245 mg of 2-(3,4-diethoxyphenyl)-4-(3-nonyloxycarbonyl-4-hydroxyphenyl)thiazole as a white powder.

M.p.: 67°–68° C.

In the same procedure as in Example 461 were obtained the compounds of Examples 379, 380, 382–385, 395, 396, 411, 412, 417, 421–435, 445 and 451 by using respective starting materials.

Example 462

In a mixed solvent consisting of 50 ml of methanol and 5 ml of water were suspended 1 g of 2-(3,4-diethoxyphenyl)-4-(3-methoxycarbonyl-4-hydroxy-5-allylphenyl)thiazole, 50 mg of palladium acetate [$Pd(OAc)_2$] and 230 mg of copper acetate [$Cu(OAc)2.H_2O$]. The suspension was stirred in an oxygen atmosphere at 50° C. for 6 hours. 50 mg of palladium acetate was further added. After 10 hours, 50 mg of palladium acetate was furthermore added. After 14 hours, when no solid starting materials in the reaction mixture were visible, the reaction mixture was filtered. The liltrate was concentrated. The residue was purified by silica gel column chromatography (eluent: dichloromethane/hexane =1/1 by v/v) and recrystallized from methanol-dichloromethane to obtain 230 mg of 2-(3,4- 1 diethoxyphenyl)-4-(2-methyl-7-methoxycarbonyl-5-benzofuryl)thiazole.

Light brown prismatic

M.p.: 144°–145° C.

NMR[62)]

Example 463

In 20 ml of methanol was dissolved 1 g of 2-(3,4-diethoxyphenyl)-4-[3-methoxymethoxymethoxycarbonyl-4-methoxymethoxy-5-(2-methyl-2-propenyl)phenyl] thiazole. Into the solution being stirred under ice-cooling was blown ozone. After 1 hour, 0.5 ml of methyl sulfide was added. The mixture was stirred at the same temperature for 30 minutes. The solvent was removed from the reaction mixture by distillation. To the residue were added 50 ml of dichloromethane and 25 ml of water. The organic layer was separated, washed with 15 ml of a saturated aqueous sodium chloride solution, dried and subjected to distillation to remove the solvent. The residue was purified by silica gel column chromatography (eluent: dichloromethane/n-hexane =2/3 by v/v) to obtain 500 mg of 2-(3,4-diethoxyphenyl)-4-(3-methoxymethoxycarbonyl-4-methoxymethoxy-5-acetylmethylphenyl)thiazole as a colorless oily substance.

Properties: NMR[64)]

The compound of Example 450 was obtained in the same procedure as in Example 463, by using starting materials.

Example 464

In 15 ml of ethanol was dissolved 220 mg of 2-(3,4-diethoxyphenyl)-4-(3-methoxymethoxycarbonyl-4-methoxymethoxy-5-acetylmethylphenyl)thiazole. Thereto was added 1 ml of 10% hydrochloric acid, and the mixture was refluxed for 2 hours with heating. The solvent was removed by distillation. To the residue were added 20 ml of ethyl acetate and 10 ml of water, and phase separation was conducted. The organic layer was washed with 10 ml of a saturated aqueous sodium chloride solution, dried and subjected to distillation to remove the solvent. The residue was purified by silica gel column chromatography (eluent: chloroform/methanol =99/1 by v/v) and recrystallized from an n-hexane-ethyl acetate mixed solvent to obtain 2-(3,4-diethoxyphenyl)-4-(3-carboxy-4-hydroxy-5-acetylmethyl) thiazole as a white powder.

In the same procedure as in Example 467 were obtained the compounds of Examples 379–385, 389, 391, 394–396, 399, 403, 411–414, 416–418, 421–435, 445 and 451 by using respective starting materials.

Example 465

In 40 ml of o-dichlorobenzene was dissolved, with heating, 2 g of 2-(3,4-diethoxyphenyl)-4-[3-carboxy-4-hydroxy-5-(2-methyl-2-propenyl)phenyl]-thiazole. Thereto were added about 10 mg of iodine and 1.5 g of potassium iodide (ground in-a mortar), and the mixture was refluxed for 14 hours with heating. The reaction mixture was mixed with 30 ml of water and phase separation was conducted. The organic layer was mixed with 30 ml of ethyl acetate. The mixture was washed with 20 ml of a saturated aqueous sodium chloride solution, dried and subjected to distillation to remove the solvent. The residue was purified by silica gel column chromatography (eluent: dichloromethane) and recrystallized from diisopropyl ether to obtain 1 g of 2-(3,4-diethoxyphenyl)-4-(2,2-dimethyl-7-carboxy-2,3-dihydrobenzofuran-5-yl)thiazole as white powdery crystals.

M.p.: 106°–107° C.

Example 466

In a mixed solvent consisting of 100 ml of tetrahydrofuran and 40 ml of water was dissolved 3.7 g of 2-(3,4-diethoxyphenyl)-4-[3-methoxymethoxycarbonyl-4-methoxymethoxy-5-(1-propenyl)phenyl]thiazole. To the solution were added 100 mg of osmium tetroxide ($OsO_4$) and 5.6 g of sodium periodate ($NaIO_4$), and the mixture was stirred at room temperature for 14 hours. The reaction mixture was filtered. The filtrate was concentrated to a ⅓ volume. To the concentrate was added 100 ml of ethyl acetate, and phase separation was conducted. The organic layer was washed with 40 ml of a saturated aqueous sodium chloride solution, dried and subjected to distillation to remove the solvent. The residue was purified by silica gel column chromatography (elutant: dichloromethane) to obtain 600 mg of 2-(3,4-diethoxyphenyl)-4-(3-methoxymethoxycarbonYl-4-methoxymethoxy-5-formylphenyl)thiazole (compound A) and 1.28 g of 2-(3,4-diethoxyphenyl)-4-[3-methoxymethoxy-carbonyl-4-methoxymethoxy-5-(1,2-dihydroxypropyl)-phenyl]thiazole (compound B). The 2-(3,4-diethoxy-phenyl)-4-[3-methoxymethoxycarbonyl-4-methoxymethoxy-5-(1,2-dihydroxypropyl)phenyl]thiazole (compound B) was dissolved in 40 ml of methanol. To the solution were added 5 g of sodium periodate ($NaIO_4$) and 10 ml of water, and the mixture was stirred at room temperature for 14 hours. The solvent was removed from the reaction mixture by distillation. The residue was mixed with 80 ml of ethyl acetate and 40 ml of water, and phase separation was conducted. The organic layer was washed with 20 ml of a saturated aqueous sodium chloride solution, dried and subjected to distillation to remove the solvent. The residue was combined with 600 mg of the above-obtained 2-(3,4-diethoxyphenyl)-4-(3-methoxy-methoxycarbonyl-4-methoxymethoxy-5-formylphenyl)thiazole (compound A). The mixture was recrystallized from ethanol to obtain 1.6 g of 2-(3,4-diethoxyphenyl)-4-(3-methoxymethoxycarbonyl-4-methoxy-methoxy-5-formyl-phenyl)thiazole as white acicular crystals.

M.p.: 113°–114° C.

The compound of Example 417 was obtained in the same procedure as in Example 466 by using starting materials.

The compounds of Examples 467–509, shown in Table 14 were obtained in the same procedures as in Example 1 and Example 138, by using respective starting materials.

TABLE 14

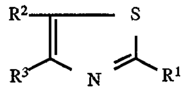

| Example No. | $R^1$ | $R^2$ | $R^3$ | Crystal form (recrystallization solvent) | M.p. (°C.) (salt form) |
|---|---|---|---|---|---|
| 467 | 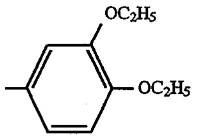 | H | 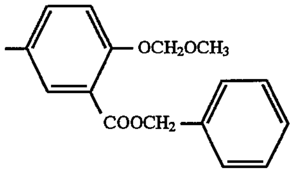 | Yellow oily | NMR[67] (—) |
| 468 | " | H | 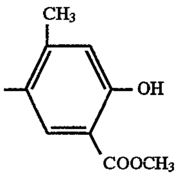 | Reddish brown acicular (ethyl acetate) | 122–124 (—) |
| 469 | " | H | 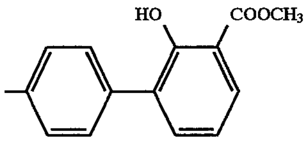 | Light yellow acicular (ethyl acetate-n-hexane) | 166–167 (—) |
| 470 | " | H | 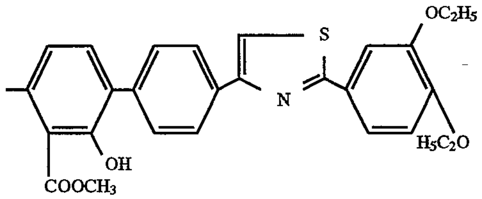 | White acicular (ethyl acetate) | NMR[68] (—) |
| 471 | " | H | 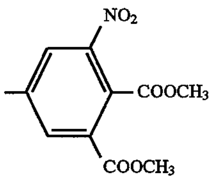 | Light brown solid | NMR[69] (—) |
| 472 | 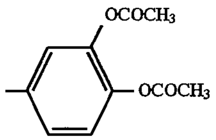 | H | 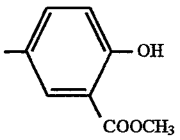 | White acicular (ethyl acetate-n-hexane) | 167–168 (—) |
| 473 | 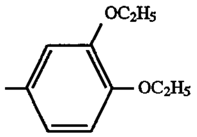 | H | 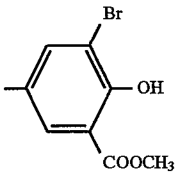 | White powder (ethanol) | 175–176 (—) |

TABLE 14-continued
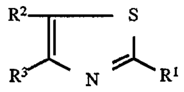
| Example No. | $R^1$ | $R^2$ | $R^3$ | Crystal form (recrystallization solvent) | M.p. (°C.) (salt form) |
|---|---|---|---|---|---|
| 474 | " | H | 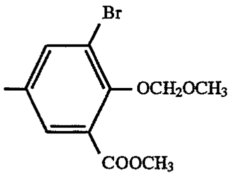 | Light yellow acicular (ethyl acetate-n-hexane) | 106–107 (—) |
| 475 | " | H | 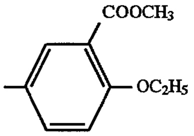 | Light yellow acicular (diisopropyl ether) | 89–90 (—) |
| 476 | " | H | 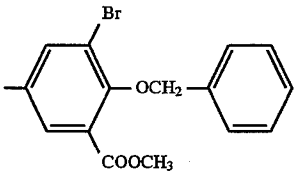 | White acicular (diethyl ether) | 103–105 (—) |
| 477 | " | H | 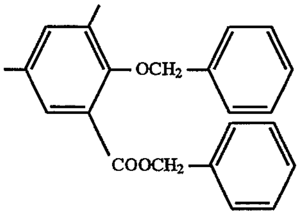 | White acicular (diethyl ether) | 107–108 (—) |
| 478 | " | H | 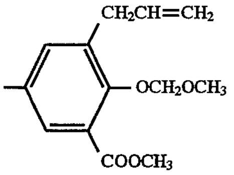 | Colorless oily | NMR[70] (—) |
| 479 | " | H | 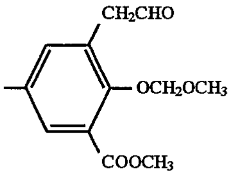 | Colorless oily | NMR[71] (—) |
| 480 | " | H | 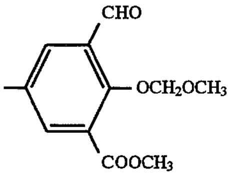 | Colorless oily | NMR[72] (—) |

TABLE 14-continued
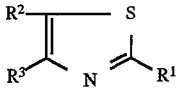
| Example No. | R¹ | R² | R³ | Crystal form (recrystallization solvent) | M.p. (°C.) (salt form) |
|---|---|---|---|---|---|
| 481 | " | H | 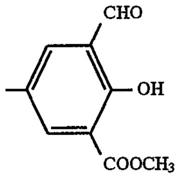 | Yellow granular (dichloromethane-ether) | 179–181 (—) |
| 482 | " | H | 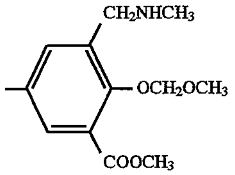 | Colorless oily | NMR[73] (—) |
| 483 | " | H | 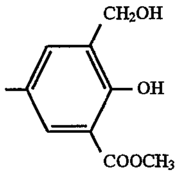 | Yellow solid | NMR[74] (—) |
| 484 | " | H | 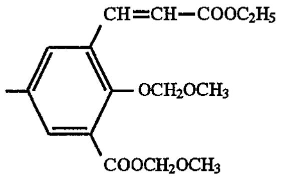 | Yellow powder (ethanol) | 94–96 (—) |
| 485 | " | H | 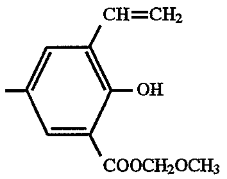 | Colorless oily | NMR[75] |
| 486 | " | H | 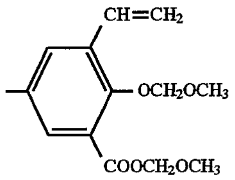 | | NMR[76] |
| 487 | " | H | 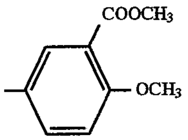 | White acicular (diisopropyl ether) | 92–93 (—) |
| 488 | " | H | 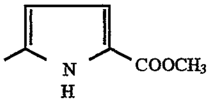 | White acicular (ethanol) | 125.8–127.8 |
| 489 | " | H | 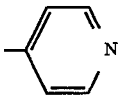 | Yellow acicular (ethanol) | 226.5–229 (—) |

TABLE 14-continued

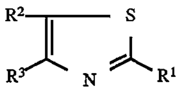

| Example No. | $R^1$ | $R^2$ | $R^3$ | Crystal form (recrystallization solvent) | M.p. (°C.) (salt form) |
|---|---|---|---|---|---|
| 490 | " | H | 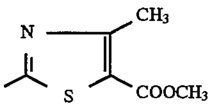 | White acicular (ethanol) | 152–154 (—) |
| 491 | " | H | 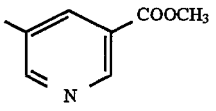 | Yellow powder (ethanol) | 172.4–175.6 (HBr) |
| 492 | " | H | 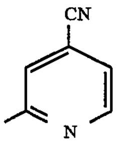 | Yellow powder (ethanol) | 237.2–238 (—) |
| 493 | " | H | 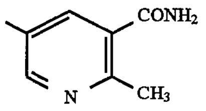 | | NMR[77] (—) |
| 494 | " | H | 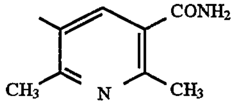 | Gray powder (ethanol-diemthylformamide) | 272–277 |
| 495 | " | H | 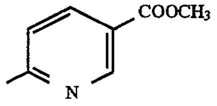 | Yellow powder (ethanol) | 215–215.8 (—) |
| 496 | " | H | 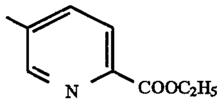 | Yellow powder (ethanol) | 204–205.4 (HBr) |
| 497 | " | H | 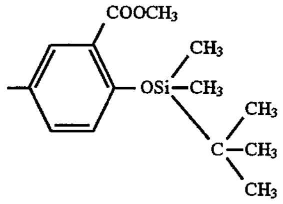 | Colorless oily | NMR[78] |
| 498 | " | H | 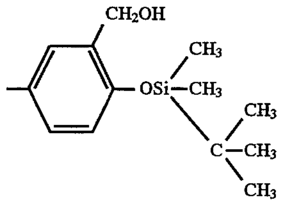 | White prismatic (ethyl acetate-n-hexane) | 1.01.3–103 (—) |
| 499 | " | H | 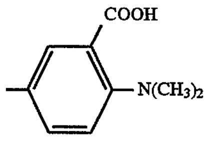 | White powder (acetone) | 107–110 (—) |

TABLE 14-continued
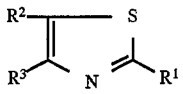
| Example No. | $R^1$ | $R^2$ | $R^3$ | Crystal form (recrystallization solvent) | M.p. (°C.) (salt form) |
|---|---|---|---|---|---|
| 500 | " | H | 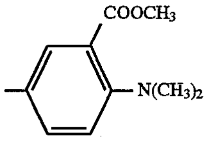 | Yellow oily | NMR[79)] |
| 501 | " | H | 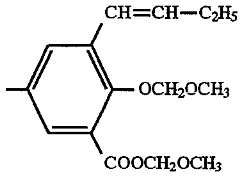 | | |
| 502 | " | H | 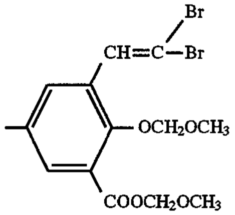 | | |
| 503 | " | H | 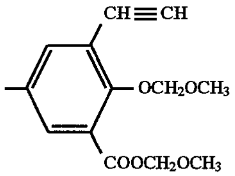 | | |
| 504 | " | H | 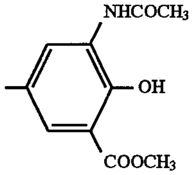 | White acicular (ethyl acetate) | 197–198 (—) |
| 505 | " | H | 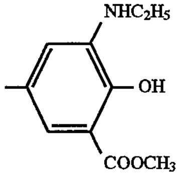 | | |
| 506 | " | H | 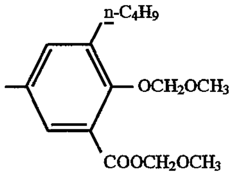 | | |
| 507 | " | H | 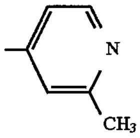 | | NMR[80)] (—) |

TABLE 14-continued

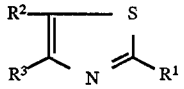

| Example No. | $R^1$ | $R^2$ | $R^3$ | Crystal form (recrystallization solvent) | M.p. (°C.) (salt form) |
|---|---|---|---|---|---|
| 508 | " | H | 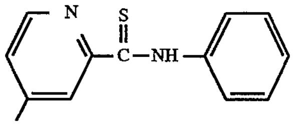 | | NMR[81] (—) |
| 509 | " | H | 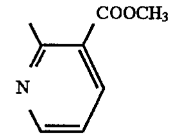 | | NMR[82] (HBr) |

Example 510

In 30 ml of methanol was dissolved 500 mg of 2-(3,4-diethoxyphenyl)-4-(3-methoxycarbonyl-4-methoxy-methoxy-5-formylphenyl)thiazole. Thereto was added 3 ml of a 30% methylamine solution. The mixture was stirred at room temperature for 14 hours and at 70° C. for 1 hour. Thereto was added 530 ml of sodium boron hydride with stirring under ice- cooling. The mixture was stirred at room temperature for 3 hours. The solvent was removed from the reaction mixture by distillation. The residue was mixed with 40 ml of ethyl acetate and 20 ml of water, and phase separation was conducted. The organic layer was washed with 10 ml of a saturated aqueous sodium chloride solution, dried and subjected to distillation to remove the solvent. The residue was subjected to silica gel chromatography (eluent: dichloromethane/methanol =49/1 by v/v). From the eluate was obtained 150 mg of 2-(3,4-diethoxyphenyl)-4-(3-methoxycarbonyl-4-methoxymethoxy-5-methylaminomethyl-phenyl)thiazole.

Colorless oily

Properties: NMR[73]

The compound of Example 402 was obtained in the same procedure as in Example 510, using starting materials.

Example 511

In 20 ml of methanol was suspended 300 mg of 2-(3,4-diethoxyphenyl)-4-(3-methoxycarbonyl-4-hydroxy-5-formylphenyl)thiazole with stirring. Threto was added 26.5 mg of sodium boron hydride at 0° C. The mixture was stirred at room temperature for 1 hour. 26.5 mg of sodium boron hydride was further added, and the resulting mixture was stirred at the same temperature for 1 hour. The solvent was removed from the reaction mixture by distillation. To the residue were added 30 ml of dichloromethane and 15 ml of water, and phase separation was conducted. The organic layer was washed with 10 ml of a saturated aqueous sodium chloride solution, dried and subjected to distillation to remove the solvent to obtain 300 mg of 2-(3,4-diethoxyphenyl)-4-(3-methoxycarbonyl-4-hydroxy-5-hydroxymethylphenyl)-thiazole.

Yellow solid

Properties: NMR[74]

The compounds of Examples 397, 412, 423, 445 and 498 were obtained in the same procedure as in Example 511, by using respective starting materials.

Example 512

500 mg of 2-(3,4-diethoxyphenyl)-4-(3-methoxymethoxycarbonyl-4-methoxymethoxy-5-formylphenyl)-thiazole was added to 20 ml of a solution of a newly prepared Wittig reagent (triethyl phosphonoacetate: 270 mg, sodium hydride: 48 mg) in tetrahydrofuran. The mixture was stirred at room temperature for 4 hours. The solvent was removed from the reaction mixture by distillation. To the residue were added 20 ml of ethyl acetate and 15 ml of water, and phase separation was conducted. The organic layer was washed with 10 ml of a saturated aqueous sodium chloride solution, dried and subjected to distillation to remove the solvent. The residue was recrystallized from ethanol to obtain 380 mg of 2-(3,4-diethoxyphenyl)-4-[3-methoxymethoxycarbonyl-4-methoxymethoxy-5-(2-ethoxycarbonylvinyl)phenyl]thiazole.

Yellow powder

M.p.: 94°–96° C.

The compounds of Examples 478, 485, 486, 501 and 501 were obtained in the same procedure as in Example 512, by using respective starting materials.

Example 513

535 mg of methyltriphenylphosphonium bromide was suspended in 10 ml of tetrahydrofuran with stirring. Thereto was added 190 mg of potassium tert-butoxide at −5° C., and the mixture was stirred at the same temperature for 1 hour. Thereto was added 500 mg of 2-(3,4-diethoxyphenyl)-4-(3-methoxycarbonyl-4-methoxymethoxy-5-formylphenyl) thiazole. The mixture was stirred at the same temperature for 2 hours and at room temperature for 1 hour. To the reaction mixture were added 30 ml of ethyl acetate and 20 ml of water, and phase separation was conducted. The organic layer was washed with 20 ml of a saturated aqueous sodium chloride solution, dried and subjected to distillation to remove the solvent. The residue was purified by silica gel column chromatography (eluent: dichloromethane/n-hexane=2/1 by v/v) to obtain 240 mg of 2-(3,4-diethoxyphenyl)-4-(3-methoxymethoxycarbonyl-4-hydroxy-5-vinylphenyl)thiazole (A) and 120 mg of 2-(3,4-diethoxyphenyl)-4-(3-methoxymethoxycarbonyl-4-methoxymethoxy-5-vinylphenyl)-thiazole (B).

NMR data of compound (A):

$^1$H-NMR ($CDCl_3$) δ: 1.49 (3H, t, J=7.0Hz), 1.51 (3H, t, J=7.0Hz), 3.58 (3H, s), 3.95 (3H, s), 4.15 (2H, q, J=7.0Hz), 4.22 (2H, q, J=7.0Hz), 5.08 (2H, s), 5.43 (1H, dd, J=1.1, 11.1lHz), 5.89 (1H, dd, J=17.7Hz), 6.92 (1H, d, J=8.4Hz), 7.17 (1H, dd, J=11.1, 17.7Hz), 7.43 (1H, s), 7.54 (1H, dd, J=2.1, 8.4Hz), 7.61 (1H, d, J=2.1Hz), 8.29 (2H, d, J=1.3Hz).

NMR data of compound (B):

$^1$H-NMR ($CDCl_3$) δ: 1.49 (3H, t, J=7.0Hz), 1.51 (3H, t, J=7.0Hz), 3.58 (3H, s), 3.59 (3H, s), 4.15 (2H, q, J=7.0Hz), 4.22 (2H, q, J=7.0Hz), 5.10 (2H, s), 5.43 (1H, dd, J=1.1, 11.1Hz), 5.51 (2H, s), 5.89 (1H, dd, J=1.1, 17.1Hz), 6.92 (1H, d, J=8.4Hz), 7.18 (1H, dd, J=11.1, 17.7Hz), 7.43 (1H, s), 7.54 (1H, dd, J=2.1, 8.4Hz), 7.61 (1H, d, J=2.1Hz), 8.29 (2H, d, J=1.3Hz).

Example 514

In 10 ml of ethanol was dissolved 350 mg of 2-(3,4-diethoxyphenyl)-4-[3-methoxymethoxycarbonyl-4-methoxymethoxy-5-(2-ethoxycarbonylvinyl)phenyl] thiazole. Thereto was added 0.2 ml of 10% hydrochloric acid. The mixture was stirred at 60° C. for 1 hour with heating. Thereto was added 1 ml of 10% sodium hydroxide. The mixture was refluxed for 4 hours with heating. The solvent was removed from the reaction mixture by distillation. The residue was mixed with 15 ml of water. The mixture was made weakly acidic with 10% hydrochloric acid and extracted with 40 ml of hot ethyl acetate. The organic layer was washed with 15 ml of a saturated aqueous sodium chloride solution, dried and subject to distillation to remove the solvent. The residue was recrystallized from ethyl acetate to obtain 170 mg of 2-(3,4-diethoxyphenyl)-4-[3-carboxy-4-hydroxy-5-(2-carboxyvinyl)phenyl] thiazole.

Yellow powder

M.p.: 260°–261° C.

Example 515

In 20 ml of methanol was dissolved 150 mg of 2-(3,4-diethoxyphenyl)-4-(3-methoxycarbonyl-4-methoxymethoxy-5-methylaminomethylphenyl)thiazole. Thereto was added 0.2 ml of 10% hydrochloric acid. The mixture was stirred at 60° C. for 30 minutes. 2 ml of 10% sodium hydroxide was added, and the mixture was refluxed for 1 hour with heating. The reaction mixture was made neutral with 10% hydrochloric acid and the solvent was removed by distillation. The residue was mixed with ethanol. The insoluble was collected by filtration, washed with water, dried and recrystallized from dimethylformamide to obtain 35 mg of 2-(3,4-diethoxyphenyl-4-(3-carboxy-4-hydroxy-5-methylaminomethylphenyl)thiazole.

Light brown granular

M.p.: 271°–273° C.

Example 516

A mixture of 500 mg of 2-(3,4-diethoxyphenyl)-4-(4-cyano-pyridyl)thiazole, 20 ml of ethanol and 17 ml of a 4% aqueous sodium hydroxide solution was refluxed for 16 hours with heating. The reaction mixture was allowed to stand. Then, 200 ml of water was added thereto. The mixture was extracted with 80 ml of dichromethane two times. The aqueous layer was made acidic (pH=about 3) with concentrated hydrochloric acid and extracted with 150 ml of ethyl acetate three times. The ethyl acetate layer was dried over anhydrous sodium sulfate and concentrated. The residue was recrystallized from ethyl acetate to obtain 290 mg of 2-(3,4-diethoxyphenyl)-4-(4-carboxy-2-pyridyl)thiazole.

White acicular crystals

M.p.: 236.2°–237.2° C.

Example 517

5.23 g of imidazole and 4.85 g of tertbutyldimethylchlorosilane were added, in this order, to a suspension of 4.02 g of 2-(3,4-diethoxyphenyl)-4-(3-methoxycarbonyl-4-hydroxyphenyl)thiazole in 60 ml of dimethylformamide at room temperature. The mixture was stirred at the same temperature for 4 hours. To the reaction mixture were added 100 ml of ice water and 200 ml of ethyl acetate. The organic layer was separated, washed with 100 ml of water and 50 ml of a saturated aqueous sodium chloride solution in this order, dried over anhydrous magnesium sulfate and subjected to distillation to remove the solvent. The residue was purified by silica gel column chromatography (eluent: n-hexane/ethyl acetate =10/1) to obtain 5.14 g of 2-(3,4-diethoxyphenyl)-4-(3-methoxycarbonyl-4-tertbutyldimethylsilyloxyphenyl)thiazole.

Colorless oily substance

Properties

Example 518

548 mg of lithium aluminum hydride was added to a solution of 5.43 g of 2-(3,4-diethoxyphenyl)-4-(3-methoxycarbonyl-4-tert-butyldimethylsilyloxyphenyl)-thiazole in 100 ml of tetrahydrofuran, with ice-cooling. The mixture was stirred at the same temperature for 7 hours. To the reaction mixture were added 1.1 ml of water and 3 g of sodium sulfate. The resulting mixture was filtered through Celite. The filtrate was subjected to distillation to remove the solvent. To the residue were added 200 ml of ethyl acetate and 50 ml of water. The mixture was neutralized with 5N hydrochloric acid. The insoluble was removed by filtration. The filtrate was subjected to phase separation. The organic layer was washed with 50 ml of water, dried over anhydrous magnesium sulfate and subjected to distillation to remove the solvent. The residue was purified by silica gel column chromatography (eluent: n-hexane/ethyl acetate=10/1 by v/v) and recrystallized from ethyl acetate-n-hexane to obtain 1.23 g of 2-(3,4-diethoxyphenyl)-4-(3-hydroxymethyl-4-tert-butyldimethylsilyloxyphenyl)thiazole.

White prismatic crystals

M.p.: 101.3°–103° C.

The compounds of Examples 397, 412, 423, 445 and 483 were obtained in the same procedure as in Example 518, by using respective starting materials.

Example 519

The following compound was obtained in the same procedures as in Examples 1 and 138, by using starting materials. 2-(3,4-Diethoxyphenyl)-4-[3-carboxy-4-hydroxy-5-(1-isobutenyl)phenyl]thiazole Properties: 1H-NMR (DMSO-$d_6$) δ: 1.38 (3H, t, J=6.9Hz), 1.40 (3H, t, J=6.9Hz), 1.86 (3H, s), 1.95 (3H, s), 4.12 (2B, q, J=6.9Hz), 4.15 (2B, q, J=6.9Hz), 6.33 (1H, brs), 7.09 (1H, d, J=8.7Hz), 7.48–7.62 (2H, m), 7.93 (1H, s), 7.95 (1H, d, J=2.1Hz), 8.31 (1H, d, J=2.1Hz).

Example 520

The following compounds were obtained in the same procedures as in Examples 1 and 138, by using respective starting materials.

4[-(3,4-Diethoxyphenyl)-4-thiazolyl]- pyridinium-1-oxide

Properties: 1H-NMR (DMSO-$d_6$) δ: 1.35 (3H, t, J=6.9Hz), 1.37 (3H, t, J=6.9Hz), 4.07 (4H, m), 7.07 (1H, d, J=8.3Hz), 7.52 (1H, dd, J=2.0Hz, 8.3Hz), 7.58 (1H, d, J=2.0Hz), 8.03 (2H, d, J=7.2Hz), 8.29 (2H, d, J=7.2Hz), 8.33 (1H, s).

2-(3,4-Diethoxyphenyl)-4-(2-cyano-4-pyridinium) thiazole

Properties: $^1$H-NMR (DMSO-$d_6$) δ: 1.36 (3H, t, J=6.9Hz), 1.38 (3H, t, J=6.9Hz), 4.08–4.23 (4H, m), 7.08 (1H, d, J=8.3Hz), 7.55–7.61 (2H, m), 8.32 (1H, dd, J=1.3Hz, 5.2Hz), 8.64 (2H, s), 8.84 (1H, d, J=5.2Hz).

NMR data of the compounds of Examples 417, 423, 425, 444, 446–449, 452, 467, 470, 471, 478–480, 482, 483,485, 486, 493, 497, 500 and 507–509 (NMR[58])–NMR[82]))

NMR[58]): Compound of Example 417

$^1$H-NMR (DMSO-$d_6$) δ: 1.38 (3H, t, J=7.0Hz), 1.40 (3H, t, J=7.0Hz), 2.22 (3H, s), 3.87 (2H, s), 4.08 (2H, q, J=7.0Hz), 4.16 (2H, q, J=7.0Hz), 7.10 (1H, d, J=8.2Hz), 7.48–7.60 (2H, m), 7.99 (1H, s), 8.08 (1H, d, J=2.3Hz), 8.38 (1H, d, J=2.3Hz).

NMR[59]): Compound of Example 423

$^1$H-NMR (DMSO-$d_6$) δ: 1.38 (3H, t, J=6.9Hz), 1.40 (3H, t, J=6.9Hz), 4.11 (2H, q, J=6.9Hz), 4.15 (2H, q, J=6.9Hz), 4.60 (2H, s), 7.08 (1H, d, J=8.9Hz), 7.45–7.63 (2H, m), 7.77 (1H, s), 8.06 (1H, d, J=2.2Hz), 8.34 (1H, d, J=2.2Hz).

NMR[60]): Compound of Example 425

$^1$H-NMR ($CDCl_3$) δ: 1.48 (3H, t, J=7.0Hz), 1.50 (3H, t, J=7.0Hz), 2.78 (2H, t, J=6.7Hz), 3.09 (2H, t, J=6.7Hz), 4.07–4.30 (4H, m), 6.91 (1H, d, J=8.3Hz), 7.52 (1H, d, J=8.3Hz), 7.60 (1H, brs), 8.02 (1H, brs), 8.38 (1H, brs).

NMR[61]): Compound of Example 444

$^1$-NMR ($CDCl_3$) δ: 0.08–1.00 (3H, m), 1.00–1.67 (18H, m), 1.67–1.95 (2H, m), 3.54 (3H, s), 4.16 (2H, q, J=7.0Hz), 4.23 (2H, q, J=7.0Hz), 4.35 (2H, t, J=6.6Hz), 5.30 (2H, S), 6.92 (1H, d, 7.27 (1H, d, J=8.7Hz), 7.36 (1H, s), 7.53 dd, J=2.0Hz, 8.4Hz), 7.62 (1H, d, J=2.0Hz), 8.08 (1H, dd, J=2.3Hz, 8.7Hz), 8.35 (1H, J=2.3Hz).

NMR[62]): Compound of Example 446

$^1$H-NMR ($CDCl_3$) δ: 1.50 (3H, t, J=7.0Hz), 1.52 (3H, t, J=7.0Hz), 2.55 (3H, d, J=0.9Hz), 4.04 (3H, s), 4.16 q, J=7.0Hz), 4.23 (2H, q, J=7.0Hz), 6.50 (1H, d, J=1.0Hz), 6.93 (1H, d, J=8.4Hz), 7.45 (1H, s), 7.55 (1H, dd, J=2.1Hz, 8.4Hz), 7.64 (1H, d, J=2.1Hz), 8.34 (1H, d, J=1.8Hz), 8.42 (1H, d, J=1.8Hz).

NMR[63]): Compound of Example 447

$^1$H-NMR ($CDCl_3$) δ: 1.49 (3H, t, J=7.0Hz), 1.51 (3H, t, J=7.0Hz), 1.78 (3H, s), 3.54 (2H, s), 3.59 (3H, s), 4.16 (2H, q, J=7.0Hz), 4.22 (2H, q, J=7.0Hz), 4.71 (1H, brs), 4.90 (1H, brs), 5.09 (2H, s), 5.51 (2H, s), 6.92 (1H, d, J=8.4Hz), 7.40 (1H, s), 7.53 (1H, dd, J=2.1Hz, 8.4Hz), 7.61 (1H, d, J=2.1Hz), 7.98 (1H, d, J=2.4Hz), 8.34 (1H, d, J=2.4Hz).

NMR[64]): Compound of Example 448

$^1$H-NMR ($CDCl_3$) δ: 1.49 (3H, t, J=7.0Hz), 1.51 (3H, t, J=7.0Hz), 2.24 (3H, s), 3.56 (3H, s), 3.59 (3H, s), 3.95 (2H, S), 4.16 (2H, q, J=7.0Hz), 4.22 (2H, q, J=7.0Hz), 5.09 (2H, S), 5.50 (2H, S), 6.92 (1H, d, J=8.4Hz), 7.42 (1H, S), 7.52 (1H, dd, J=2.1Hz, 8.4Hz), 7.60 (1H, d, J=2.1Hz), 8.01 (1H, d, J=2.3Hz), 8.39 (1H, d, J=2.3Hz).

NMR[65]): Compound of Example 449

$^1$H-NMR ($CDCl_3$) δ: 1.50 (3H, t, J=7.0Hz), 1.51 (3H, t, J=7.0Hz), 1.97 (3H, dd, J=1.6Hz, 6.6Hz), 3.58 (3H, s), 3.59 (3H, s), 4.16 (2H, q, J=7.0Hz), 4.22 (2H, q, J=7.0Hz), 5.09 (2H, s), 5.50 (2H; s), 6.38 (1H, dd, J=15.9Hz, 6.6Hz), 6.83 (1H, d, J=15.9Hz), 6.93 (1H, d, J=8.4Hz), 7.42 (1H, s), 7.55 (1H, dd, J=2.1Hz, 8.4Hz), 7.61 (1H, d, J=2.1Hz), 8.23 (1H, d, J=2.2Hz), 8.27 (1H, d, J=2.2Hz).

NMR[66]): Compound of Example 450

$^1$H-NMR ($CDCl_3$) δ: 1.16 (1.5H, d, J=6.3Hz), 1.22 (1.5H, d, J=6.3Hz), 1.43–1.57 (6H, m), 3.59 (3H, s), 3.62 (3H, s), 4.05–4.36 (4H, m), 5.07–5.28 (2H, m), 5.30 (2H, s), 5.50 (2H, s), 6.93 (1H, d, J=8.4Hz), 7.45 (1H, s), 7.54 (1H, dd, J=2.1Hz, 8.4Hz), 7.61 (1H, d, J=2.1Bz), 8.21 (0.5H, d, J=2.3Hz), 8.32 (0.5H, d, J=2.3Hz), 8.48 (1H, m),

NMR[67]): Compound of Example 467

$^1$H-NMR ($CDCl_3$) δ: 1.49 (3H, t, J=7.0Hz), 1.50 (3H, t, J=7.0Hz), 3.49 (3H, s), 4.17 (2H, q, J=7.0Hz), 4.19 q, J=7.0Hz), 5.28 (2H, s), 5.40 (2H, s), 6.91 (1H, d, J=8.4Hz), 7.22–7.70 (9H, m), 8.08 (1H, dd, J=2.4Hz, 8.7Hz), 8.40 (1H, d, J=2.4Hz).

NMR[68]): Compound of Example 470

$^1$H-NMR ($CDCl_3$) δ: 1.44–1.67 (12H, m), 4.04 (3H, s), 4.10–4.33 (8H, m), 6.92 (2H, d, J=8.4Hz), 7.37 (1H, s), 7.46 (1H, s), 7.52–7.63 (3H, m), 7.66 (1H, d, J=2.0Hz), 7.75 (2H, d, J=8.4Hz), 8.08 (2H, d, J=8.4Hz), 8.20 (1H, d, J=2.2Hz), 8.46 (1H, d, J=2.2Hz), 11.43 (1H, s).

NMR[69]): Compound of Example 471

$^1$H-NMR ($CDCl_3$) δ: 1.50 (3H, t, J=7.0Hz), 1.53 (3H, t, J=7.0Hz), 2.42 (3H, s), 3.96 (3H, s), 4.17 (2H, q, J=7.0Hz), 4.23 (2H, q, J=7.0Hz), 6.94 (1H, d, J=8.4Hz), 7.54 (1H, dd, J=2.1Hz, 8.4Hz), 7.59 (1H, s), 7.60 (1H, d, J=2.1Hz), 8.76 (1H, d, J=2.3Hz), 8.80 (1H, d, J=2.3Hz).

NMR[70]): Compound of Example 478

$^1$H-NMR ($CDCl_3$) δ: 1.49 (3H, t, J=7.0Hz), 1.51 (3H, t, J=7.0Hz), 3.59 (3H, s), 3.59 (2H, d, J=6.3Hz), 3.94 s), 4.16 (2H, q, J=7.0Hz), 4.22 (2H, q, J=7.0Hz), 5.08 (2H, S), 5.07–5.17 (1H, m), 5.17–5.27 (1H, m), 5.96–6.16 (1H, m), 6.92 (1H, d, J=8.4Hz), 7.40 (1H, s), 7.54 (1H, dd, J=2.1Hz, 8.4Hz), 7.60 (1H, d, J=2.1Hz), 7.98 (1H, d, J=2.4Hz), 8.27 (1H, d, J=2.4Hz).

NMR[71]): Compound of Example 479

$^1$H-NMR ($CDCl_3$) δ: 1.48 (3H, t, J=7.0Hz), 1.51 (3H, t, J=7.0Hz), 3.55 (3H, s), 3.89 (2H, d, J=1.7Hz), 3.94 (3H, s), 4.15 (2H, q, J=7.0Hz), 4.21 (2H, q, J=7.0Hz), 5.09 (2H, s), 6.91 (1H, d, J=8.4Hz), 7.43 (1H, s), 7.52 (1H, dd, J=2.1Hz, 8.4Hz), 7.59 (1H, d, J=2.1Hz), 8.04 (1H, d, J=2.3Hz), 8.36 (1H, d, J=2.3Hz), 9.79 (1H, t, J=1.7Hz).

NMR[72]): Compound of Example 480

$^1$H-NMR ($CDCl_3$) δ: 1.50 (3H, t, J=7.0Hz), 1.52 (3H, t, J=7.0Hz), 3.60 (3H, s), 3.98 (3H, s), 4.16 (2H, q, J=7.0Hz), 4.23 (2H, q, J=7.0Hz), 5.22 (2H, s), 6.92 (1H, d, J=8.4Hz), 7.50 (1H, s), 7.54 (1H, dd, J=2.1Hz, 8.4Hz), 7.60 (1H, d, J=2.1Hz), 8.57 (1H, d, J=2.5Hz), 8.73 (1H, d, J=2.5Hz), 10.50 (1H, s).

NMR[73]): Compound of Example 482

$^1$H-NMR ($CDCl_3$) δ: 1.49 (1H, t, J=7.0Hz), 1.51 (3H, t, J=7.0Hz), 2.50 (3H, s), 3.60 (3H, s), 3.92 (2H, s), 3.94 (3H, s), 4.15 (2H, q, J=7.0Hz), 4.22 (2H, q, J=7.0Hz), 5.12 (2H, s), 6.92 (1H, d, J=8.4Hz), 7.44 (1H, s), 7.54 (1H, dd, J=2.1Hz, 8.4Hz), 7.60 (1H, d, J=2.1Hz), 8.13 (1H, d, J=2.4Hz), 8.37 (1H, d, J=2.4Hz).

NMR[74]): Compound of Example 483

$^1$H-NMR ($CDCl_3$) δ: 1.50 (3H, t, J=7.0Hz), 1.52 (3H, t, J=7.0Hz), 2.41 (1H, t, J=6.6Hz), 4.01 (3H, s), 4.16 (2H, q, J=7.0Hz), 4.23 (2H, q, J=7.0Hz), 4.82 (2H, d, J=6.6Hz), 6.93 (1H, d, J=8.4Hz), 7.34 (1H, s), 7.55 (1H, dd, J=2.0Hz, 8.4Hz), 7.60 (1H, d, J=2.0Hz), 8.10 (1H, d, J=2.3Hz), 8.40 (1H, d, J=2.3Hz), 11.38 (1H, s).

NMR[75]): Compound of Example 485

$^1$H-NMR ($CDCl_3$ ) δ: 1.49 (3H, t, J=7.0Hz), 1.51 (3H, t, J=7.0Hz), 3.58 (3H, s), 3.95 (3H, s), 4.15 (2H, q, J=7.0Hz), 4.22 (2H, q, J=7.0Hz), 5.08 (2H, s), 5.43 (1H, dd, J=1.1Hz, 11.1Hz), 5.89 (1H, dd, J=1.1Hz, 17.7Hz), 6.92 (1H, d, J=8.4Hz), 7.17 (1H, dd, J=11.1Hz, 17.1Hz), 7.43 (1H, s), 7.54 (1H, dd, J=2.1Hz, 8.4Hz), 7.61 (1H, d, J=2.1Hz), 8.27 (2H, d, J=1.3Hz).

NMR[76)]: Compound of Example 486

$^1$H-NMR ($CDCl_3$) δ: 1.49 (3H, t, J=7.0Hz), 1.51 (3H, t, J=7.0Hz), 3.58 (3H, s), 3.59 (3H, s), 4.15 (2H, q, J=7.0Hz), 4.22 (2H, q, J=7.0Hz), 5.10 (2H, s), 5.43 (1H, dd, J=1.1Hz, 11.1Hz), 5.51 (2H, s), 5.89 (1H, dd, J=1.1Hz, 17.7Hz), 6.92 (1H, d, J=8.4Hz), 7.18 (1H, dd, J=11.1Hz, 17.7Hz), 7.43 (1H, s), 7.54 (1H, dd, J=2.1Hz, 8.4Hz), 7.61 (1H, d, J=2.1Hz), 8.29 (2H, d, J=1.3Hz).

NMR[77)]: Compound of Example 493

$^1$H-NMR (DMSO-d6) δ: 1.35 (3H, t, J=6.9Hz), 1.37 (3H, t, J=6.9Hz), 2.72 (3H, s), 4.11 (4H, m), 7.09 (1H, d, J=9.0Hz), 7.57 (1H, dd, J=2.2Hz, 9.0Hz), 7.60 (1H, d, J=2.2Hz), 7.89 (1H, brs), 8.22 brs), 8.44 (1H, s), 8.70 (1H, d, J=2.0Hz), 9.27 (1H, d, J=2.0Hz).

NMR[78)]: Compound of Example 497

$^1$H-NMR ($CDCl_3$) δ: 0.24 (6H, s), 1.03 (9H, s), 1.49 (3H, t, J=7.0Hz), 1.51 (3H, t, J=7.0Hz), 3.91 (3H, s), 4.15 (2H, q, J=7.0Hz), 4.22 (2H, q, J=7.0Hz), 6.91 (1H, d, J=8.3Hz), 6.95 (1H, d, J=8.5Hz), 7.34 (1H, s), 7.51 (1H, dd, J=2.0Hz, 8.3Hz), 7.62 (1H, d, J=2.0Hz), 8.03 (1H, dd, J=2.4Hz, 8.5Hz), 8.34 (1H, d, J=2.4Hz).

NMR[79)]: Compound of Example 500

$^1$H-NMR ($CDCl_3$) δ: 1.49 (3H, t, J=7.0Hz), 1.51 (3H, t, J=7.0Hz), 2.91 (6H, S), 3.94 (3H, S), 4.15 (2H, q, J=7.0Hz), 4.22 (2H, q, J=7.0Hz), 6.91 (1H, d, J=8.4Hz), 6.99 (1H, d, J=8.8Hz), 7.28 (1H, s), 7.52 (1H, dd, J=2.0Hz, 8.4Hz), 7.62 (1H, d, J=2.0Hz), 7.97 (1H, dd, J=2.2Ez, 8.8Hz), 8.25 (1H, d, J=2.2Hz).

NMR[88)]: Compound of Example 507

$^1$H-NMR ($CDCl_3$) δ: 1.49 (3H, t, J=7.0Hz), 1.51 (3H, t, J=6.9Hz), 2.63 (3H, s), 4.10–4.27 (4H, m), 6.89 (1H, d, J=8.4Hz), 7.48 (1H, dd, J=2.1Hz, 8.4Hz), 7.59–7.64 (3H, m), 7.74 (1H, s), 8.53 (1H, d, J=5.2Hz).

NMR[81)]: Compound of Example 508

$^1$H-NMR ($CDCl_3$) δ: 1.45 (3H, t, J=7.0Hz), 1.49 (3H, t, J=7.0Hz), 4.09 (2H, q, J=7.0Hz), 4.17 (2H, q, J=7.0Hz), 6.89 (1H, d, J=8.4Hz), 7.25–7.32 (1H, m), 7.42–7.46 (2H, m), 7.49 (1H, dd, J=2.2Hz, 8.4Hz), 7.61 (1H, d, J=2.2Hz), 7.81 (1H, s), 8.08–8.15 (3H, m), 8.57 (1H, dd, J=0.6Hz, 5.0Hz), 9.20 (1H, dd, J=0.6Hz, 1.5Hz), 12.11 (1H, brs).

NMR[82)]: Compound of Example 509

$^1$H-NMR ($CDCl_3$) δ: 1.47 (3H, t, J=7.0Hz), 1.50 (3H, t, J=7.0Hz), 3.81 (3H, s), 4.10–4.24 (4H, m), 6.93 (1H, d, J=8.4Hz), 7.46–7.55 (3H, m), 8.00 (1H, dd, J=1.6Hz, 7.8Hz), 8.21 (1H, s), 8.74–8.76 (1H, m).

Example 521

The following compounds were obtained in the same procedures as in Examples 1 and 147, by using respective starting materials.

5-Ethoxycarbonyl-2-(α-bromoacetyl)pyrazine and 3,4-diethoxythiobenzamide were subjected to the same reaction as in Example 1 and then to the same hydrolysis as in Example 147 to obtain 2-(3,4-diethoxyphenyl)-4-(5-carboxy-2-pyrazyl)thiazole.

4-Ethoxycarbonyl-2-(α-bromoacetyl)pyrimidine and 3,4-diethoxythiobenzamide were subjected to the same reaction as in Example 1 and then to the same hydrolysis as in Example 147 to obtain 2-(3,4-diethoxyphenyl)-4-(4-carboxy-2-pyrimidyl)thiazole.

5-Ethoxycarbonyl-2-(α-bromoacetyl)pyrimidine and 3,4-diethoxythiobenzamide were subjected to the same reaction as in Example 1 and then to the same hydrolysis as in Example 147 to obtain 2-(3,4-diethoxyphenyl)-4-(5-carboxy-2-pyrimidyl)thiazole.

6-Ethoxycarbonyl-2-(α-bromoacetyl)pyrazine and 3,4-diethoxythiobenzamide were subjected to the same reaction as in Example 1 and then to the same hydrolysis as in Example 147 to obtain 2-(3,4-diethoxyphenyl)-4-(6-carboxy-2-pyrazyl)thiazole.

4-Ethoxycarbonyl-2-(α-bromoacetyl)pyrrole and 3,4-diethoxythiobenzamide were subjected to the same reaction as in Example 1 and then to the same hydrolysis as in Example 147 to obtain 2-(3,4-diethoxyphenyl)-4-(4-carboxy-2-pyrrolyl)thiazole.

4-Ethoxycarbonyl-2-(α-bromoacetyl)furan and 3,4-diethoxythiobenzamide were subjected to the same reaction as in Example 1 and then to the same hydrolysis as in Example 147 to obtain 2-(3,4-diethoxyphenyl)-4-(4-carboxy-2-furyl)thiazole.

5-Ethoxycarbonyl-3-(α-bromoacetyl)furan and 3,4-diethoxythiobenzamide were subjected to the same reaction as in Example 1 and then to the same hydrolysis as in Example 147 to obtain 2-(3,4-diethoxyphenyl)-4-(5-carboxy-3-furyl)thiazole.

4-Ethoxycarbonyl-2-(α-bromoacetyl)thiophene and 3,4-diethoxythiobenzamide were subjected to the same reaction as in Example 1 and then to the same hydrolysis as in Example 147 to obtain 2-(3,4-diethoxyphenyl)-4-(4-carboxy-3-thienyl)thiazole.

5-Ethoxycarbonyl-3-(α-bromoacetyl)thiophene and 3,4-diethoxythiobenzamide were subjected to the same reaction as in Example 1 and then to the same hydrolysis as in Example 147 to obtain 2-(3,4-diethoxyphenyl)-4-(5-carboxy-3-thienyl)thiazole.

5-Ethoxycarbonyl-2-(α-bromoacetyl)thiazole and 3,4-diethoxythiobenzamide were subjected to the same reaction as in Example 1 and then to the same hydrolysis as in Example 147 to obtain 2-(3,4-diethoxyphenyl)-4-(5-carboxy-2-thiazolyl)thiazole.

Preparation Example 1

| | |
|---|---|
| 2-(3,4-Dimethoxyphenyl)-4-(3,4-dihydroxycarbostyril-6-yl)thiazole | 5 mg |
| Starch | 132 mg |
| Magnesium stearate | 18 mg |
| Lactose | 45 mg |
| Total | 200 mg |

Tablets each containing the above components in the above amounts were produced according to an ordinary method.

Preparation Example 2

| | |
|---|---|
| 2-(3,4-Dimethoxyphenyl)-4-(2-oxo-benzoxazol-5-yl)thiazole | 500 mg |
| Polyethylene glycol (m.w.: 4000) | 0.3 g |
| Sodium chloride | 0.9 g |
| Polyoxyethylene sorbitan monoleate | 0.4 g |
| Sodium metabisulfite | 0.1 g |
| Methylparaben | 0.18 g |
| Propylparaben | 0.02 g |
| Distilled water for injection | 100 ml |

The above parabens, sodium metabisulfite and sodium chloride were dissolved in the above distilled water with stirring at 80° C. The solution was cooled to 40° C. Therein were dissolved the present compound, the polyethylene glycol and the polyoxyethylene sorbitan monoleate in this order. To the solution was added the distilled water for injection to obtain a desired final volume. The resulting solution was filtered through an appropriate filter paper and sterilized. 1 ml of the thus prepared solution was filled into each ampul to prepare an injection.

PHARMACOLOGICAL TESTS

The pharmacological tests for present compounds were conducted according to the following methods.

(1) Activity for inhibiting the generation of superoxide radical ($O_2^-$) in human neutrophilic leukocytes Human neutrophilic leukocytes were prepared in accordance with the method of M. Markert et al. (Methods in Enzymology, vol. 105; pp. 358–365, 1984). That is, a whole blood obtained from a healthy adult and treated by anticoagulation method was subjected to a dextranhypotonic treatment to obtain leukocyte cells. The leukocyte cells were then subjected to a density gradient ultracentrifugation by Ficoll-Paque to obtain a neutrophilic leukocyte fraction.

$O_2^-$ generation was examined by the ferricytochrome C method in accordance with the method of B. N. Cronstein et al. [Journal of Experimental Medicine, vol. 158, pp. 1160–1177 (1983)]. That is, $1\times10^{-6}$ cell of neutrophilic leukocytes were stimulated with $3\times10^{-7}$M of N-formyl-L-methionyl-L-leucyl-L-phenylalanine (FMLP) at 37° C. in the presence of 1.3 mg/ml of ferricytochrome C and 5 μg/ml of cytochalasin B in a Hepes-buffered Hank's solution (pH 7.4); the amount of ferrocytochrome C formed by 4 minutes of reduction was determined by measuing an absorbance at a wavelength of 550 nm using a spectrophotometer; an absorbance in the presence of 25.1 μg/ml of superoxide dismutase (SOD) was also measured; the difference of the two absorbances was taken as the amount of superoxide radical ($O_2^-$) generated. Each test compound was dissolved in dimethyl sulfoxide (DMSO); the solution was added to neutrophilic leukocytes before the addition of FMLP; then, the neutrophilic leukocytes were pre-incubated at 37° C. By using the amount of superoxide radical ($O_2^-$) generated when the test compound solution was added and the amount of superoxide radical ($O_2^-$) generated when only the solvent (DMSO) was added, a ratio of inhibition (%) was calculated, and the activity for inhibiting superoxide radical ($O_2^-$) generation was expressed as 50% inhibitory concentration ($IC_{50}$).

TEST COMPOUNDS 1. 2-(3-Pyridyl)-4-phenylthiazole-¼ ferrous chloride salt
2. 2-(3,4-Dimethoxyphenyl)-4-phenylthiazole
3. 2,4-Di(3-pyridyl)thiazole
4. 2-(3-pyridyl)-4-methyl-5-ethoxycarbonylthiazole hydrochloride
5. 2-(2,4-Dimethoxyphenyl)-4-(3,4-dihydrocarbostyril-6-yl) thiazole
6. 2-(2-Pyridon-3-yl)-4-phenylthiazole
7. 2-(3,4-Dimethoxyphenyl)-4-(3,4-dihydrocarbostyril-6-yl) thiazole
8. 2-(3,4-Dimethoxyphenyl)-4-(3,4-dihydroxyphenyl)-thiazole hydrochloride
9. 2-(4-Pyridyl)-4-(3,4-dihydroxyphenyl)thiazole hydrochloride
10. 2-(3-Thienyl)-4-(3,4-dihydroxyphenyl)thiazole
11. 2-(2-Thfenyl)-4-(3,4-dihydroxyphenyl)thiazole
12. 2-(4-Oxo-1,4-dihydroquinolin-3-yl)-4-(3,4-dihydroxyphenyl)thiazole
13. 2-(Pyrazin-2-yl)-4-(3,4-dihydroxyphenyl)thiazole
14. 2-(3,4-Dihydroxyphenyl)-4-(3,4-dihydrocarbostyril-6-yl)thiazole hydrobromide
15. 2-(Carbostyril-3-yl)-4-(3,4-dihydroxyphenyl)-thiazole
16. 2-(Pyrrol-2-yl)-4-(3,4-dihydroxyphenyl)thiazole
17. 2-(3,4-Dimethoxyphenyl)-4-(4-methyl-2H-1,4-benzothiazin-3(4H)-on-6-yl)thiazole
18. 2-(3,4-Dimethoxyphenyl)-4-(3-hydroxy-4-pentyloxyphenyl)-thiazole
19. 2-(3,4-Dimethoxyphenyl)-4-(4-methylsulfonylphenyl) thiazole
20. 2-Phenyl-4-(3,4-dihydroxyphenyl)thiazole hydrochloride
21. 2-(3,4,5-Trimethoxyphenyl)-4-(3,4-dihydroxyphenyl)-thiazole hydrochloride
22. 2-(3,4-Methylenedioxyphenyl)-4-(3,4-dihydroxyphenyl)-thiazole
23. 2-(3,4-Dimethoxyphenyl)-4-(carbostyril-6-yl)-thiazole
24. 2-(3,4-Dimethoxyphenyl)-4-(7-hydroxy-3,4-dihydrocarbostyril-6-yl)thiazole
25. 2-(3,4-Dimethoxyphenyl)-4-(2-oxyindol-5-yl)thiazole
26. 2-(3,4-Dihydrocarbostyril-6-yl)-4-(3,4-dihydroxyphenyl)-thiazole hydrochloride
27. 2-(3,4-Dimethoxyphenyt)-4-(3-oxo-3,4-dihydro-2H-1,4-benzoxazin-6-yl)thiazole
28. 2-(3,4-Dimethoxyphenyl)-4-(3,4-dihydro-2H-1,4-benzoxazin-6-yl)thiazole hydrochloride
29. 2-(3,4-Dimethoxyphenyl)-4-(2-oxobenzimidazol-5-yl) thiazole
30. 2-(3,4-Dimethoxyphenyl)-4-(3-oxo-4-methyl-3,4-dihydro-2H-1,4-benzoxazin-6-yl)thiazole
31. 2-(3,4-Dimethoxyphenyl)-4-(10-acetylphenothiazin-2-yl)thiazole
32. 2,4-Di(3,4-dimethoxyphenyl)thiazole
33. 2-(3,4-Dimethoxyphenyl)-4-(3-acetylamino-4-hydroxyphenyl)-thiazole
34. 2-(3,4-Dimethoxyphenyl)-4-(3,4-dihydrocarbostyril-7-yl)thiazole
35. 2-(3,4-Dimethoxyphenyl)-4-(2-oxobenzothiazol-6-yl) thiazole
36. 2-(3,4-Dimethoxyphenyl)-4-(2-oxobenzoxazol-5-yl) thiazole
37. 2-(3,4-Dimethoxyphenyl)-4-(3-amino-4-hydroxyphenyl)thiazole dihydrochloride
38. 2-(3,4-Dimethoxyphenyl)-4-(1-methyl-3,4-dihydrocarbo-styril-7-yl)thiazole
39. 2-(3,4-Dimethoxyphenyl)-4-(3,5-dihydroxyphenyl)-thiazole
40. 2-(3,4-Dimethoxyphenyl)-4-(2,5-dihydroxyphenyl)-thiazole
41. 2-(3,4-Dimethoxyphenyl)-4-(2,6-dihydroxyphenyl)-thiazole
42. 2-(3,4-Dimethoxyphehyl)-4-(2-oxo-3-methylbenzothiazol-6-yl)thiazole
43. 2-(3,4-Dimethoxyphenyl)-4-(3-nitro-4-acetylaminophenyl)thiazole
44. 2-(3,4-Dimethoxyphenyl)-4-(1,3-dimethyl-2-oxobenzimidazol-5-yl)thiazole
45. 2-(3,4-Dimethoxyphenyl)-4-(2,4-dihydroxyphenyl)-thiazole
46. 2-(3,4-Dimethoxyphenyl)-4-(3-nitro-4-chlorophenyl)-thiazole
47. 2-(3,4-Dimethoxyphenyl)-5-(3,4-dihydrocarbostyril-6-yl)thiazole
48. 2-(3,4-Dimethoxyphenyl)-4-(3,4-diacetylaminophenyl) thiazole
49. 2-(3,4-Dimethoxyphenyl)-4-(2-oxo-3-methylbenzoxazol-5-yl)thiazole
50. 2-(3,4-Dimethoxyphenyl)-4-(3-nitrophenyl)thiazole
51. 2-(3,4-Dimethoxyphenyl)-4-(3,5-diamino-4-hydroxyphenyl)thiazole 52. 2-(3,4-Dimethoxyphenyl)-4-(3,5-dinitro-4-hydroxyphenyl)thiazole
53. 2-(3-Methoxy-4-methylthiophenyl)-4-(3,4-dihydrocarbo-styril-6-yl)thiazole
54. 2-(3-Methoxy-4-methylsulfinylphenyl)-4-(3,4-dihydrocarbo-styril-6-yl)thiazole
55. 2-(3,4-Dimethoxyphenyl)-4-(2-oxobenzoxazol -6-yl) thiazole
56. 2-(3-Pyridyl)-4-(4-fluorophenyl)thiazole-⅓ $FeCl_2$ salt
57. 2-(3,4-Dimethoxyphenyl)-4-(2,3-dioxo-1,2,3,4-tetrahydro-quinoxalin-6-yl)thiazole
58. 2-(3,4-Dimethoxybenzoyl)-4-(3,4-dihydrocarbostyril-6-yl)thiazole
59. 2-(3,4-Diethoxyphenyl)-4-(3,4-dihydrocarbostyril-6-yl) thiazole
60. 2-(3,4-Dimethoxyphenyl)-4-(2-pyridyl)thiazole hydrochloride
61. 4-(3,5-Dihydroxyphenyl)-2-(3,4-diethoxyphenyl)-thiazole
62. 4-(3-Carboxy-4-hydroxyphenyl)-2-(3,4-diethoxy-phenyl)thiazole
63. 4-(4-Hydroxysulfonyloxyphenyl)-2-(3,4-dimethoxyphenyl)thiazole
64. 4-(4-Hydroxyphenyl)-2-(3,4-diethoxyphenyl)thiazole
65. 4-(3-Acetylamino-4-hydroxyphenyl)-2-(3,4-diethoxyphenyl)thiazole
66. 4-(4-Hydroxy-3-aminophenyl)-2-(3,4-diethoxyphenyl) thiazole dihydrochloride
67. 4-(4-Cyanophenyl)-2-(3,4-diethoxyphenyl)thiazole
68. 4-(3,4-Dihydrocarbostyril-6-yl)-2-(4-methoxy-3-propoxy-phenyl)thiazole
69. 4-(4-Amidinophenyl)-2-(3,4-diethoxyphenyl)thiazole hydrochloride
70. 4-(2,4,6-Trihydroxyphenyl)-2-(3,4-dimethoxyphenyl) thiazole
71. 4-(3,5-Diaminophenyl)-2-(3,4-dimethoxyphenyl) thiazole dihydrochloride
72. 4-(4-Aminophenyl)-2-(3,4-diethoxyphenyl)thiazole hydrochloride
73. 4-[1-Hydroxy-1-(3,4-dimethoxyphenyl)methyl]-2-(3,4-diethoxyphenyl)thiazole
74. 4-[4-Methoxy-3-(4-ethyl-1-piperazinyl)phenyl]-2-(3,4-dihydroxyphenyl)thiazole trihydrochloride
75. 4-(4-Chlorophenyl)-2-(3,4-diethoxyphenyl)thiazole
76. 4-(3,4-Diacetyloxyphenyl)-2-(3-pyridyl)thiazole
77. Methyl 4-[2-(3,4-dimethoxyphenyl)thiazol-4-yl]phenyl-β-D-glucopyranosidouronate
78. 2-(3,4-Diethoxyphenyl)-4-[4-(2,3,4,6-tetra-0-acetyl-β-D-glucopyranosyloxy)phenyl]thiazole
79. 4-(3,5-Diacetyloxyphenyl)-2-(3,4-diethoxyphenyl) thiazole
80. 4-(4-Hydroxy-3-methoxycarbonylphenyl)-2-(3,4-diethoxyphenyl)thiazole
81. 4-(4-Methoxycarbonylmethoxy-3-methoxycarbonylphenyl)-2-(3,4-diethoxyphenyl)thiazole
82. 4-(4-Hydroxy-3-carbamoylphenyl)-2-(3,4-diethoxyphenyl)thiazole
83. 4-(3-Carboxy-4-hydroxy-5-allylphenyl)-2-(3,4-diethoxyphenyl)thiazole
84. 4-{3-Carboxy-4-hydroxy-5-(2-methyl-2-propenyl)-phenyl}-2-(3,4-diethoxyphenyl)thiazole
85. 4-(3-Carboxy-4-hydroxy-5-methylphenyl)-2-(3,4-diethoxyphenyl)thiazole
86. 4-(3-Methoxycarbonyl-4-hydroxyphenyl)-2-(3-methoxy-4-ethoxyphenyl)thiazole
87. 4-(3-Carboxyphenyl)-2-(3,4-diethoxyphenyl)thiazole
88. 4-(3-Carboxy-4-hydroxyphenyl)-2-(3-methoxy-4-ethoxyphenyl)thiazole
89. 4-(3-Amino-4-hydroxy-5-methoxycarbonylphenyl)-2-(3,4-diethoxyphenyl)thiazole
90. 4-(3-Carboxy-4-hydroxy-5-propylphenyl)-2-(3,4-diethoxyphenyl)thiazole
91. 4-(3-Carboxy-6-hydroxyphenyl)-2-(3,4-diethoxyphenyl)thiazole
92. 4-(3-Carboxy-4-hydroxyphenyl)-2-(3-ethoxy-4-methoxyphenyl)thiazole
93. 4-(3-Carboxy-4-hydroxy-5-isobutylphenyl)-2-(3,4-diethoxyphenyl)thiazole
94. 3-{3-Carboxy-4-hydroxy-5-(2-hydroxyethyl)phenyl}-2-(3,4-diethoxyphenyl)thiazole
95. 4-(3-Carboxy-4-amino-6-hydroxyphenyl)-2-(3,4-diethoxyphenyl)thiazole
96. 4-(3-Carboxy-4-aminophenyl)-2-(3,4-diethoxyphenyl)-thiazole
97. 4-(3-Carboxy-4-acetyloxyphenyl)-2-(3,4-diethoxyphenyl)-2-(3,4-diethoxyphenyl)thiazole
98. 4-(3-Ethyl-4-hydroxyphenyl)-2-(3,4-Diethoxyphenyl) thiazole
99. 4-(3-Carboxy-4-hydroxyphenyl)-2-(3,4-diethoxyphenyl)-5-methylthiazole
100. 4-(3-Carboxy-4,6-dihydroxyphenyl)-2-(3,4-diethoxyphenyl)thiazole
101. 4-(3-Methoxycarbonyl-5-nitro-6-hydroxyphenyl)-2-(3,4-diethoxyphenyl)thiazole
102. 4-(3-Methoxycarbonyl-5-amino-6-hydroxyphenyl)-2-(3,4-diethoxyphenyl)thiazole
103. 4-(3-Carboxy-5-allyl-6-hydroxyphenyl)-2-(3,4-diethoxy-phenyl)thiazole
104. 4-(3-Carboxy-6-hydroxyphenyl)-2-(3-ethoxy-4-methoxy-phenyl)thiazole
105. 4-(3-Carboxy-4-hydroxyphenyl)-2-(3,4-dimethoxyphenyl)thiazole (a compound mentioned in Example 3 of Japanese Patent Publication No. 15935/1971)
106. 4-(3-Carboxy-4-hydroxyphenyl)-2-phenylthiazole (a compound mentioned in Example 2 of Japanese Patent Publication No. 15935/1971)
107. 4-(3-Carboxy-4-methoxyphenyl)-2-phenylthiazole (a compound mentioned in Example 4. of Japanese Patent Publication No. 15935/1971)
108. 4-(3-Carboxy-4-methoxyphenyl)-2-benzylthiazole (a compound mentioned in Example 9 of Japanese Patent Publication No. 15935/1971)
109. 4-(3-Carboxyphenyl)-2-(4-chlorophenyl)thiazole (a compound included in Japanese Patent Publication No. 15935/1971)
110. 4-(3-Carboxy-5-hydroxyphenyl)-2-(3,4-diethoxyphenyl)thiazole (a compound included in Japanese Patent Publication No. 15935/1971)
111. 4-(3-Carboxy-4-hydroxyphenyl)-2-(3,4-dibutoxyphenyl)thiazole (a compound included in Japanese Patent Publication No. 15935/1971)
112. 4-(3-Carboxy-6-methoxyphenyl)-2-(3,4-diethoxyphenyl)thiazole (a compound included in Japanese Patent Publication No. 15935/1971)
113. 4-(2-Hydroxy-3-amino-5-carboxyphenyl)-2-(3,4-diethoxy-phenyl)thiazole hydrochloride
114. 4-(2-Hydroxy-3-propyl-5-carboxyphenyl)-2-(3,4-diethoxy-phenyl)thiazole
115. 4-(6-Carboxy-2-pyridyl)-2-(3,4-diethoxyphenyl)-thiazole
116. 2-(3,4-Diethoxyphenyl)-4-phenylthiazole
117. 2-(3,4-Diethoxyphenyl)-4-{3-methoxycarbonyl-4-[2-(1-piperidinyl)ethylamino]phenyl}thiazole dihydrochloride 118. 2-(3,4-Diethoxyphenyl)-4-[4-hydroxy-3-(2-dimethylaminoethoxycarbonyl)phenyl]thiazole trihydrochloride 119. 2-(3,4-Diethoxyphenyl)-4-(2-carboxy-5-pyrrolyl)-thiazole 120. 2-(3,4-Diethoxyphenyl)-4-(4-hydroxy-3-n-nonyloxy-carbonylphenyl)thiazole 121. 2-(3,4-Diethoxyphenyl)-4-(2-methoxycarbonyl-5-furyl)thiazole 122. 2-(3,4-Diethoxyphenyl)-4-(2-carboxy-5-furyl)-thiazole 123. 2-(3,4-Diethoxyphenyl)-4-(2-dimethylaminocarbonyl-6-pyridyl)thiazole 124. 2-(3,4-Diethoxyphenyl)-4-(2-acetyl-1-pyrrolyl)-methylthiazole 125. 2-(3,4-Diethoxyphenyl)-4-(3-carboxy-4-methoxyphenyl)thiazole 126. 2-(3,4-Diethoxyphenyl)-4-(3-carboxy-4-hydroxy-5-ethylphenyl)thiazole 127. 2-(3,4-Diethoxyphenyl)-4-(2-hydroxymethyl-6-pyrrolidyl)thiazole 128. 2-(3,4-Diethoxyphenyl)-4-[2-(4-methyl-1-piperazinyl) carbonyl)-6-pyridyl]thiazole 129. 2-(3,4-Diethoxyphenyl)-4-(2-carboxy-5-thienyl)-thiazole 130. 2-(3,4-Diethoxyphenyl)-4-(2-methyl-7-carboxy-5-benzofuryl)thiazole 131. 2-(3,4-Diethoxyphenyl)-4-(4-ethoxycarbonyl-2-thiazolyl)thiazole 132. 2-(3,4-Diethoxyphenyl)-4-(4-carboxy-2-thiazolyl)-thiazole 133. 2-(3,4-Diethoxyphenyl)-4-(4-hydroxy-3-hydroxymethylphenyl)thiazole 134. 2-(3,4-Diethoxyphenyl)-4-(4-ethoxy-3-carboxyphenyl) thiazole 135. 2-(3,4-Diethoxyphenyl)-4-(3-carboxy-5-pyridyl)-thiazole hydrochloride 136. 2-(3,4-Diethoxyphenyl)-4-(3-n-butoxycarbonyl-4-n-butoxyphenyl)thiazole.

137. 2-(3,4-Diethoxyphenyl)-4-(3-carboxy-4-n-butoxyphenyl)thiazole 138. 2-(3,4-Diethoxyphenyl)-4-(3-carboxy-4-n-propoxyphenyl)thiazole 139. 2-(3,4-Diethoxyphenyl)-4-(2,2-dimethyl-7-carboxy-2, 3-dihydrobenzofuran-5-yl)thiazole 140. 2-(3,4-Diethoxyphenyl)-4-[3-carboxy-4-hydroxy-5-(1-propenyl)phenyl]thiazole 141. 2-(3,4-Diethoxyphenyl)-4-(2-methyl-3-carboxy-5-pyridyl)thiazole 142. 2-(3,4-Diethoxyphenyl)-4-(3-carboxy-4-hydroxy-5-formylphenyl)thiazole 143. 2-(3,4-Diethoxyphenyl)-4-(3-carboxy-6-pyridyl)-thiazole 144. 2-(3,4-Diethoxyphenyl)-4-(2-carboxy-5-pyridyl)-thiazole 145. 2-(3,4-Diethoxyphenyl)-4-(3-carboxy-4-hydroxy-5-bromophenyl)thiazole 146. 2-(3,4-Diethoxyphenyl)-4-(3-carboxy-4-dimethylaminophenyl)thiazole 147. 2-(3,4-Diethoxyphenyl)-4-(3-carboxy-4-hydroxy-5-vinylphenyl)thiazole The results are shown in Table 15. In Table are shown the results of the comparative test between present compounds (test compound Nos. 62, 87,,88, 91, 92 and 104) and prior art comounds.

TABLE 15

| Test compound (No.) | $IC_{50}$ (μM) |
|---|---|
| 1 | 1 |
| 2 | 0.08 |
| 3 | 1 |
| 4 | 0.5 |
| 5 | 0.3 |
| 6 | 0.7 |
| 7 | 0.3 |
| 8 | 0.05 |
| 9 | 0.5 |
| 10 | 0.4 |
| 11 | 0.3 |
| 12 | 1 |
| 13 | 0.4 |
| 14 | 1 |
| 15 | 0.3 |
| 16 | 0.5 |
| 17 | 0.3 |
| 18 | 1 |
| 19 | 0.5 |
| 20 | 0.4 |
| 21 | 0.5 |
| 22 | 0.3 |
| 23 | 0.4 |
| 24 | 0.3 |
| 25 | 1 |
| 26 | 0.8 |
| 27 | 1 |
| 28 | 1 |
| 29 | 0.07 |
| 30 | 0.05 |
| 31 | 0.1 |
| 32 | 0.08 |
| 33 | 0.04 |
| 34 | 1 |
| 35 | 0.05 |
| 36 | 0.03 |
| 37 | 0.07 |
| 38 | 0.5 |
| 39 | 0.01 |
| 40 | 0.03 |
| 41 | 0.2 |
| 42 | 0.08 |
| 43 | 0.4 |
| 44 | 0.04 |
| 45 | 0.3 |
| 46 | 1 |
| 47 | 1 |
| 48 | 1 |
| 49 | 0.07 |
| 50 | 0.4 |
| 51 | 0.03 |
| 52 | 0.2 |
| 53 | 0.4 |
| 54 | 0.8 |
| 55 | 0.07 |
| 56 | 1 |
| 57 | 0.3 |
| 58 | 1.0 |
| 59 | 0.08 |
| 60 | 0.05 |
| 61 | 0.003 |
| 62 | 0.01 |
| 63 | 0.03 |
| 64 | 0.04 |
| 65 | 0.06 |
| 66 | 0.06 |
| 67 | 0.07 |
| 68 | 0.08 |
| 69 | 0.1 |
| 70 | 0.2 |
| 71 | 0.2 |
| 72 | 0.2 |
| 73 | 0.2 |
| 74 | 0.3 |
| 75 | 0.6 |
| 76 | 0.6 |

TABLE 15-continued

| Test compound (No.) | $IC_{50}$ (μM) |
|---|---|
| 77 | 0.8 |
| 78 | 1 |
| 79 | 0.0013 |
| 80 | 0.01 |
| 81 | 0.026 |
| 82 | 0.06 |
| 83 | 0.04 |
| 84 | 0.02 |
| 85 | 0.08 |
| 86 | 0.033 |
| 87 | 0.0048 |
| 88 | 0.1 |
| 89 | 0.007 |
| 90 | 0.008 |
| 91 | 0.023 |
| 82 | 0.02 |
| 93 | 0.012 |
| 94 | 0.18 |
| 95 | 0.0087 |
| 96 | 0.023 |
| 97 | 0.1 |
| 98 | 0.083 |
| 99 | 0.72 |
| 100 | 0.048 |
| 101 | 0.01 |
| 102 | 0.069 |
| 103 | 0.094 |
| 104 | 0.034 |
| 113 | 0.025 |
| 114 | 0.1 |
| 115 | 0.08 |
| 116 | 0.37 |
| 117 | 0.46 |
| 118 | 0.56 |
| 119 | 0.024 |
| 120 | 0.49 |
| 121 | 0.038 |
| 122 | 0.019 |
| 123 | 0.38 |
| 124 | 0.12 |
| 125 | 0.19 |
| 126 | 0.014 |
| 127 | 0.02 |
| 128 | 0.58 |
| 129 | 0.082 |
| 130 | 0.24 |
| 131 | 0.19 |
| 132 | 0.05 |
| 133 | 0.0092 |
| 134 | 0.13 |
| 135 | 0.035 |
| 136 | 0.13 |
| 137 | 0.11 |
| 138 | 0.14 |
| 139 | 0.1 |
| 140 | 0.0047 |
| 141 | 0.094 |
| 142 | 0.12 |
| 143 | 0.27 |
| 144 | 0.035 |
| 145 | 0.11 |
| 146 | 0.11 |
| 147 | 0.01 |

TABLE 16

| Test compound (No.) | $IC_{50}$ (μM) |
|---|---|
| Present compound | |
| 62 | 0.01 |

TABLE 16-continued

| Test compound (No.) | $IC_{50}$ (μM) |
|---|---|
| 87 | 0.0048 |
| 88 | 0.1 |
| 91 | 0.023 |
| 92 | 0.02 |
| 104 | 0.034 |
| Prior art compound | |
| 105 | 1.0 |
| 106 | NE |
| 107 | NE |
| 108 | NE |
| 109 | NE |
| 110 | 0.66 |
| 111 | 8.3 |
| 112 | 8.7 |

NE: Abbreviation of "not effective"

(2) Activity for inhibiting the generation of venticular arrhythmia in rat heart when the coronary artery was closed and then blood was reperfused There were used male rats of Spaque Dawley (SD) strain (7–10 week old, body weight: 250–350 g). Each test compound was administered at a dose of 33 μl/kg in a form dissolved in a physiological saline solution. Each rat was anesthesized with pentobarbital and thoracotomized under artifical respiration; the descending branch before left coronary artery was ligated with a piece of silk string for 10 minutes; then, the blood was reperfused and observation was made for 10 minutes. The incidence of venticular arrhythmia was examined using a standard four-legs secondary induced cardiograph. A test compound was intravenously administered at a dose of 1 mg/kg 5 minutes before the ligature of the coronary artery.

The results on the test compound-administered group and the physiological saline solution-administered group as a control are shown in Table 17.

TABLE 17

| Test compound | Duration of ventricular fibrillation when blood reperfused (sec) | Motality (%) |
|---|---|---|
| No. 37 | 16.6 | 20 |
| Control group (physiological saline solution) | 89.9 | 60 |

(3) Activity for inhibiting the renal disturbances appearing when kidney was in ischemia and then blood was reperfused In this test were used male rats of SD strain (body weight: about 250 g) which had been fasted for 18 hours. Each test compound was administered at a dose of 1 ml/kg of body weight, in a 20% or 40% solution dissolved in DMF. The right kidney of each rat was enucleated; the artery blood circulation in the left kidney was shut down for 60 minutes; then, the blood was reperfused. Each test compound was intravenously administered at a dose of 3 mg/kg 15 minutes before reperfusion, and blood drawing was made from each rat 24 hours and 4 hours after reperfusion to measure blood plasma creatinine (mg/100 ml) using a cratinine test kit manufactured by Wako Pure Chemical Industries, Ltd. and calculate "Mean±S.E."therefrom.

The results are shown in Table 18

TABLE 18

| Test compound | 24 hours | 48 hours |
|---|---|---|
| Control (20% DMF) | 3.64 ± 0.44 | 3.37 ± 0.77 |
| No. 8 | 2.21 ± 0.19 | 2.04 ± 0.40 |
| Control (40% DMF) | 3.30 ± 0.38 | 3.37 ± 0.72 |
| No. 33 | 2.63 ± 0.47 | 1.76 ± 0.18 |

1 (4) Activity for inhibiting the heart muscle necrosis in rat caused by clogging of the coronary artery and subsequent blood reperfusion Male rats of SD strain (7–10 week old, 250–350 g) were used in this test. The activity of creatine phosphokinase (CPK) in tissue was used as an indication of heart muscle necrosis.

A test compound was dissolved in a small amount of 1N aqueous NaOH solution, then diluted with a physiological saline solution, and administered at a dose of 1 ml/kg of body weight. Each rat was anesthetized with pentobarbital and thoracotomized under artificial respiration; the descending branch before left coronary artery was ligated with a piece of silk string for 12 minutes; then, the blood was reperfused. Thereafter, the thoracotomized chest was closed and the rat was waken from anesthesia. 2 hours after reperfusion, the heart was enucleated under anesthesia; only the ischemic area was homogenized; and the activity of CPK contained therein was measured. The test compound was intravenously administered at a dose of 6 mg/kg 5 minutes before ligature of the coronary artery.

The results on the NaOH/physiological saline solution-administered group as a control and the compound-administered group are shown in Table 19.

TABLE 19

| | n | Activity of creatine phosphokinase in tissue (U/mg of protein) Mean ± S.E. |
|---|---|---|
| Control group | | 14.86 ± 0.89 |
| Test compound No. | 62 | 19.53 ± 1.56* |

*: $p < 0.05$ 2-way ANOVA ANALYSIS (comparison with control group)
n: Number of tests The reduction in CPK activity in tissue was inhibited significantly. Hence, it is considered that the present compound inhibited the disturbances of cell functions in heart caused by ischemia and subsequent reperfusion.

We claim:

1. A thiazole derivative of the general formula,

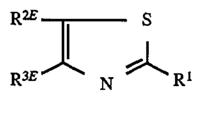

wherein:

$R^1$ represents a phenyl group which may have, as substituents on the phenyl ring, 1–5 groups selected from the group consisting of an alkoxy group, a tri-lower alkyl group-substituted silyloxy group, a lower alkyl group, a hydroxyl group, a lower alkenyloxy group, a lower alkylthio group, a phenyl group which may have a group selected from the group consisting of a thiazolyl group having, as a substituent on the thiazolyl ring, a phenyl group which may have a lower alkoxy group on the phenyl ring, a carboxyl group and a hydroxyl group, a lower alkylsulfinyl group, a lower alkylsulfonyl group, a halogen atom, a nitro group, a group of the formula,

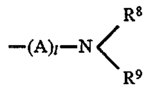

(wherein A represents a lower alkylene group or a group

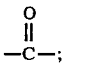

represents 0 or 1; and $R^8$ and $R^9$, which may be the same or different, each represent a hydrogen atom, a lower alkyl group, a lower alkanoyl group, an amino-lower alkyl group which may have a lower alkyl group as a substituent, or a piperidinyl-lower alkyl group; further $R^8$ and $R^9$ as well as the adjacent nitrogen atom being bonded thereto, together with or without another nitrogen atom or oxygen atom may form a five- to six-membered saturated or unsaturated heterocyclic group; said five- to six-membered heterocyclic group may have a lower alkanoyl group or a lower alkyl group as a substituent), a lower alkanoyl group, a lower alkanoyloxy group, a lower alkoxycarbonyl group, a cyano group, a tetrahydropyranyloxy group which may have 1–4 substituents, selected from the group consisting of a hydroxyl group, a lower alkoxycarbonyl group, a phenyl-lower alkoxy group, a hydroxyl group- or lower alkanoyloxy group-substituted lower alkyl group and a lower alkanoyloxy group, an amidino group, a hydroxysulfonyloxy group, a lower alkoxycarbonyl-substituted lower alkoxy group, a carboxy-substituted lower alkoxy group, a mercapto group, a lower alkoxy-substituted lower alkoxy group, a lower alkyl group having hydroxyl groups, a lower alkenyl group, an aminothiocarbonyloxy group which may have a lower alkyl group as a substituent, an aminocarbonylthio group which may have a lower alkyl group as a substituent, a lower alkanoyl-substituted lower alkyl group, a carboxy group, a group of the formula,

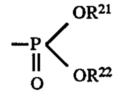

(wherein $R^{21}$ and $R^{22}$, which may be the same or different each represent a hydrogen atom or a lower alkyl group), a phenyl-lower alkoxycarbonyl group, a lower alkynyl group, a lower alkoxycarbonyl-substituted lower alkyl group, a carboxy-substituted lower alkyl group, a lower alkoxycarbonyl-substituted alkenyl group, a carboxy-substituted lower alkenyl group, a lower alkyl-sulfonyloxy group, which may have a halogen atom, a lower alkoxy-substituted lower alkoxycarbonyl group, a lower alkenyl group having halogen atoms and a phenyl-lower alkoxy group; and a phenyl group having a lower alkylenedioxy group;

$R^{2E}$ represents a hydrogen atom; and $R^{3E}$ represents a 5- to 15-membered monocyclic, bicyclic or tricyclic heterocyclic residual group having 1 to 2 hetero atoms selected from the group consisting of a nitrogen atom, an oxygen atom and a sulfur atom, and said heterocyclic residual group may have 1 to 3 substituents selected from the group consisting of an oxo group, an alkyl group, a benzoyl group, a lower alkanoyl group, a hydroxyl group, a carboxy group, a lower alkoxycarbonyl group, a lower alkylthio group, a group of the formula,

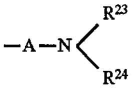

(wherein A is a lower alkylene group or a group

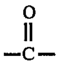

and; $R^{23}$ and $R^{24}$, which may be the same or different, each represent a hydrogen atom or a lower alkyl group; further $R^{23}$ and $R^{24}$ as well as the adjacent nitrogen atom being bonded thereto, together with or without another nitrogen atom or oxygen atom may form a five- to six-membered saturated heterocyclic group; and said five- to six-membered heterocyclic group may have a lower alkyl group as a substituent), a cyano group, a lower alkyl group having hydroxy groups, a phenylaminothiocarbonyl group and an amino-lower alkoxycarbonyl group which may have a lower alkyl group as a substituent; or a salt thereof;

provided that $R^{3E}$ is not an unsubstituted pyrazinyl group;

provided further that $R^3$ is not a 3-hydroxy-2,5-dioxo-3-pyrrolinyl group;

provided further that when $R^{3E}$ is a julolidine or tetrahydroquinoline group, which may have a $C_1$–$C_6$ alkyl group, then $R_1$ is not a group of the formula:

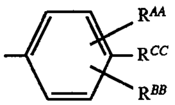

(wherein $R^{CC}$ is a hydroxyl group, mono- or di- $C_1$–$C_6$ alkylated amino group; and each of $R^{AA}$ and $R^{BB}$, which may be the same or different, is a hydrogen atom, a $C_1$–$C_6$ alkoxy group which may be substituted by a carboxyl group, or a $C_1$–$C_6$ alkyl group) which may be substituted by a carboxyl group; and provided further that $R^{3E}$ is not a substituted or unsubstituted cumarinyl group or a substituted or unsubstituted 5,6-benzocumarinyl group.

2. The thiazole derivative of claim 1, wherein $R^1$ i phenyl group which may have from 1–3 substituents selected the group consisting of an alkoxy group and a hydroxyl grou a salt thereof.

3. The thiazole derivative of claim 2, wherein $R^1$ i phenyl group which may have from 1–3 lower alkoxy groups as substituents, or a salt thereof.

4. The thiazole derivative of claim 3, wherein the heterocyclic residual group of $R^{3E}$ is pyrrolidinyl, piperid piperazinyl, morpholino, pyridyl, 1,2,5–6-tetrahydropyridyl thienyl, quinolyl, 1–4-dihydroquinolyl, benzothiazolyl, pyr pyrimidyl, pyridazylthienyl, pyrrolyl, carbostyryl, 3–4-dih carbostyryl, 1,2,3,4-tetrahydroquinolyl, indolyl, isoindoly indolinyl, benzoimidazolyl, benzooxazolyl, imidazolidnyl, isoquinolyl, quinazolidinyl, quinoxalinyl, cinnolinyl, phthalazinyl, carbazolyl, acrydinyl, chromanyl, isoindoliny isochromanyl, pyrazolyl, imidazolyl, pyrazolidinyl, phenothiazinyl, benzofuryl, 2,3-dihyrobenzo(b) furyl, benzothienyl, phenoxthiinyl, phenoxazinyl, 4H-chromenyl, 1H-indazolyl, phenazinyl, xanthenyl, thianthrenyl, isoindolinyl, imidazolinyl, 2-pyrrolinyl, furyl, oxazolyl, isooxazolyl, thiazolyl, isothiazolyl, pyranyl, pyrazolidinyl, 2-pyrazoli quinuclidinyl, 1–4-benzoxazinyl, 3,4-dihydro-2H-1,4-benzoxazinyl, 3,4-dihydro-2H-1,4-benzothiazinyl, 1,4-benzothiazinyl, 1,2,3,4-tetrahydroquinoxalinyl, 1,3-dithiadihydronaphthalenyl, phenanthridinyl, 1,4-dithianaphthalenyl, dibenzo(b,e)azepine or 6,11-dihydro-5H-dibenzo(b,e)azepine, or a salt thereof.

5. The thiazole derivative of claim 4, wherein the heterocyclic residual group is a pyridyl group, or a salt thereof.

6. The thiazole derivative according to claim 1, wherein $R^1$ is a phenyl group which may have from 1 to 3 lower alkoxy groups as substituents; $R^{3E}$ is a pyridyl or furyl heterocyclic residual group which may have 1 to 3 substituents selected from the group consisting of an oxo group, an alkyl group, a benzoyl group, a lower alkanoyl group, a hydroxyl group, a carboxy group, a lower alkoxycarbonyl group, a lower alkylthio group, a group of the formula:

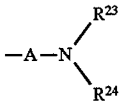

(wherein A is the same as defined above; $R^{23}$ and $R^{24}$ which may be the same or different, each represents a hydrogen atom or a lower alkyl group; further $R^{23}$ and $R^{24}$, as well as the adjacent nitrogen atom being bonded thereto, together with or without another nitrogen atom or oxygen atom may form a five- to six-membered saturated heterocyclic group which may have a lower alkyl group as a substituent), a cyano group, a lower alkyl group having hydroxyl groups, a phenylaminothiocarbonyl group and an amino-lower alkoxycarbonyl group which may have a lower alkyl group as a substituent; or a salt thereof.

7. The thiazole derivative according to claim 6, wherein $R^{3E}$ is a pyridyl or furyl heterocyclic residual group which may have 1 to 3 substituents selected from the group consisting of a carboxy group, a hydroxyl group, a lower alkoxycarbonyl group and a lower alkyl group having hydroxyl groups; or a salt thereof.

8. The thiazole derivative according to claim 7, wherein $R^{3E}$ is a pyridyl group which may have 1 to 3 substituents selected from the group consisting of a carboxy group, a hydroxyl group, a lower alkoxycarbonyl group and a lower alkyl group having hydroxyl groups; or a salt thereof.

9. 2-(3,4-Diethoxyphenyl)-4-(2-carboxy-6-pyridyl)-thiazole.

10. A superoxide radical inhibitor comprising as the active ingredient a thiazole derivative or a salt thereof of claim 1 and a pharmaceutically acceptable carrier.

11. A superoxide radical inhibitor comprising as the active ingredient 2-(3,4-diethoxyphenyl)-4-(2-carboxy-6-pyridyl) thiazole and a pharmaceutically acceptable carrier.

* * * * *

UNITED STATES PATENT AND TRADEMARK OFFICE
CERTIFICATE OF CORRECTION

PATENT NO. : 5,643,932 
DATED : July 1, 1997
INVENTOR(S) : Masatoshi Chihiro et al.

It is certified that error appears in the above-indentified patent and that said Letters Patent is hereby corrected as shown below:

Title page, delete "[22] Filed: May 19, 1995" and insert

--[22] PCT Filed: Nov. 29, 1991
[86] PCT No.: PCT/JP91/01659
§371 Date: July 29, 1992
§102(e) Date: July 29, 1992
[87] PCT Pub. No.: WO92/09586
PCT Pub. Date: --

Claim 1, column 256, line 16, before "represents" insert --ℓ--;

Column 257, line 43, "group) which" should read --group which--;

line 44, "group; and" should read --group); and--.

Claim 2, column 257, line 48, "$R^1$ i" should read --$R^1$ is a--;

line 50, "grou" should read --group, or--.

Claim 3, column 257, line 52, "$R^1$ i" should read --$R^1$ is a--.

Claim 4, column 257, line 56, "piperid" should read --piperidinyl, --;

line 57, insert --,-- after "1,2,5-6-tetrahydropyridyl";

line 58, "pyr" should read --pyrazyl,--;

UNITED STATES PATENT AND TRADEMARK OFFICE

CERTIFICATE OF CORRECTION

PATENT NO. : 5,643,932 Page 2 of 2

DATED : July 1, 1997

INVENTOR(S) : Masatoshi Chihiro et al.

It is certified that error appears in the above-indentified patent and that said Letters Patent is hereby corrected as shown below:

line 59, "carbostyril, 3-4-dih" should read --carbostyril, 3-4-dihydro- --;

line 60, "isoindoly" should read --isoindolyl, --;

line 63, "isoindoliny" should read --isoindolinyl, --;

column 258, line 7, "2-pyrazoli" should read --2-pyrazolinyl,--;

lines 9-10, "1,3-dithiadihydronaphthalenyl" should read --1,3-dithia-2,4-dihydronaphthalenyl--.

Signed and Sealed this

First Day of June, 1999

*Attest:*

Q. TODD DICKINSON

*Attesting Officer* *Acting Commissioner of Patents and Trademarks*